United States Patent
Ge et al.

(10) Patent No.: US 10,087,458 B2
(45) Date of Patent: Oct. 2, 2018

(54) MANIPULATING BS1 FOR PLANT SEED YIELD

(71) Applicant: The Samuel Roberts Noble Foundation, Inc., Ardmore, OK (US)

(72) Inventors: Liangfa Ge, Ardmore, OK (US); Rujin Chen, Ardmore, OK (US)

(73) Assignee: Noble Research Institute, LLC, Ardmore, OK (US)

( * ) Notice: Subject to any disclaimer, the term of this patent is extended or adjusted under 35 U.S.C. 154(b) by 178 days.

(21) Appl. No.: 14/861,980

(22) Filed: Sep. 22, 2015

(65) Prior Publication Data

US 2016/0201076 A1    Jul. 14, 2016

Related U.S. Application Data

(60) Provisional application No. 62/055,498, filed on Sep. 25, 2014.

(51) Int. Cl.
*A01H 5/00* (2018.01)
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8247* (2013.01)

(58) Field of Classification Search
None
See application file for complete search history.

(56) References Cited

PUBLICATIONS

Xia et al. (Frontiers in Plant Science, 8:1-11, 2017).*
White (PNAS, 103:13238-13243; 2006).*
Young et al. (NCBI, Genbank Sequence Accession No. KEH43800; Published Jun. 18, 2014).*
Hakata et al. (Biosci. Biotechnol. Biochem., 76:2129-2134, 2012).*
Bai et al., "Origin and evolutionary analysis of the plant—specific TIFY transcription factor family," *Genomics*, 98:128-136, 2011.
Chen et al., "Control of dissected leaf morphology by a Cys(2)His(2) zinc finger transcription factor in the model legume *Medicago truncatula*," *Proc Natl Acad Sci U S A*, 107:10754-10759, 2010.
Cheng et al., "Reverse genetics in *Medicago truncatula* using Tnt1 insertion mutants," *Methods Mol Biol*, 678:179-190, 2011.
Choi et al., "A sequence-based genetic map of *Medicago truncatula* and comparison of marker colinearity with *M. sativa*,". *Genetics*, 166:1463-1502, 2004.
Cuellar Perez et al., "The non-JAZ TIFY protein TIFY8 from *Arabidopsis thaliana* is a transcriptional repressor," *PLOS ONE*, 9:e84891, 2014.
Horiguchi et al., "The transcription factor AtGRF5 and the transcription coactivator AN3 regulate cell proliferation in leaf primordia of *Arabidopsis thaliana*," *Plant J*, 43:68-78, 2005.
Horiguchi et al., "ANGUSTIFOLIA3 plays roles in adaxia/abaxial patterning and growth in leaf morphogenesis," *Plant Cell Physiol*, 52:112-124, 2011.
Kawade et al., "ANGUSTIFOLIA3 signaling coordinates proliferation between clonally distinct cells in leaves," *Curr Biol*, 23:788-792, 2013.
Kim et al., "A transcriptional coactivator, AtGIF1, is involved in regulating leaf growth and morphology in *Arabidopsis*," *Proc Natl Acad Sci U S A*, 101:13374-13379, 2004.
"*Medicago truncatula* Genome Project v4.0," available at: http://jcvi.org/medicago/, retrieved Dec. 12, 2016.
Pauwels et al,. "NINJA connects the co-repressor TOPLESS to jasmonate signalling," *Nature*, 464:788-791, 2010.
Peng, J. et al., "Regulation of compound leaf development in *Medicago truncatula* by fused compound leaf1, a class M KNOX gene," *Plant Cell*, 23:3929-3943, 2011.
Vanholme et al., "The tify family previously known as ZIM," *Trends Plant Sci*, 12:239-244, 2007.
Vercruyssen et al., "ANGUSTIFOLIA3 binds to SWI/SNF chromatin remodeling complexes to regulate transcription during *Arabidopsis* leaf development," *Plant Cell*, 26:210-229, 2014.
Wang et al,."Control of compound leaf development by Floricaula/Leafy ortholog Single Leaflet1 in *Medicago truncatula*," *Plant Physiol*, 146:1759-1772, 2008.
White et al., "Peapod regulates lamina size and curvature in *Arabidopsis*," *Proc Natl Acad Sci U S A*, 103:13238-13243, 2006.
Young et al., "The *Medicago* genome provides insight into the evolution of rhizobial symbioses," *Nature*, 480:520-524, 2011.

* cited by examiner

*Primary Examiner* — Vinod Kumar
(74) *Attorney, Agent, or Firm* — Dentons US LLP

(57) ABSTRACT

The present invention provides methods for increasing plant seed yield or seed size through reduced expression of a BS1 gene. Also provided are plants with increased seed yield or seed size comprising reduced expression of a BS1 gene produced by such methods.

10 Claims, 22 Drawing Sheets

Specification includes a Sequence Listing.

a b c l

MANIPULATING BS1 FOR PLANT SEED YIELD

This application claims the priority of U.S. Provisional Application Ser. No. 62/055,498, filed Sep. 25, 2014, the entire disclosure of which is incorporated herein by reference.

BACKGROUND OF THE INVENTION

Field of the Invention

The present invention relates generally to the field of molecular biology. More specifically, the invention relates to plant genes involved in plant morphology and methods of use thereof.

INCORPORATION OF SEQUENCE LISTING

The sequence listing that is contained in the file named "NBLE090US-revised_ST25.txt", which is 252 kilobytes as measured in Microsoft Windows operating system and was created on Mar. 31, 2016, is filed electronically herewith and incorporated herein by reference.

BACKGROUND OF THE INVENTION

Genetic modification of plants has, in combination with conventional breeding programs, led to significant increases in agricultural yield over the last decades. Genetically modified plants may be selected for a single agronomic trait, for example by expression of a single enzyme coding sequence (e.g., enzymes that provide herbicide resistance). Genetic manipulation of genes involved in plant growth and yield may enable increased production of valuable commercial crops, resulting in benefits in agriculture and development of alternate energy sources such as biofuels. Accordingly, methods capable of increasing seed yield and/or seed size through gene regulation are described.

SUMMARY OF THE INVENTION

In one aspect, the invention provides a method of increasing seed yield comprising reducing expression of a BS1 gene in a plant, wherein the seed yield of the plant is increased when compared to a plant that lacks the reduced expression. In one embodiment, the BS1 gene is a gene set forth in Table 1. In another embodiment, the plant is a dicotyledonous plant, such as a plant selected from the group consisting of *Arabidopsis thaliana*, *Arabidopsis lyrata*, *Carica papaya*, *Ricinus communis*, *Cucumis sativus*, *Prunus persica*, *Vitis vinifera*, *Manihot esculenta*, *Citrus sinensis*, *Eutrema salsugineum*, *Citrus clementina*, *Capsella rubella*, *Aquilegia coerulea*, *Malus domestica*, *Linum usitatissimum*, *Eucalyptus grandis*, *Solanum lycopersicum*, *Solanum tuberosum*, *Gossypium raimondii*, *Populus trichocarpa*, *Phaseolus vulgaris*, *Solanum lycopersicum*, *Theobroma cacao*, *Conradina grandiflora*, *Mimulus guttatus*, *Brassica rapa*, *Boechera stricta*, *Arachis hypogaea*, *Medicago truncatula*, *Medicago sativa*, *Glycine max*, cotton, carrot, canola, tomato, potato, alfalfa, grape, clover, poplar, willow, eucalyptus, hemp, a *Lotus* sp., a *Vinca* sp., a *Nicotiana* sp., a *Vitis* sp., or a *Ricinus* sp. In other embodiments, the plant has altered morphology when compared to a plant that lacks the increased expression, such as increased plant biomass or increased seed yield. In another embodiment, reducing expression of the BS1 gene comprises use of an antisense or RNAi construct targeting the BS1 gene, or mutation of the BS1 gene.

In another aspect, the invention provides a plant comprising reduced expression of a BS1 gene, wherein the seed yield of the plant is increased when compared to a plant that lacks the reduced expression. In certain embodiments, the invention also provides a seed that produces such a plant, or a seed produced by such a plant. In another embodiment, the invention also provides a DNA-containing plant part of such a plant, which may be further defined a protoplast, cell, meristem, root, leaf, node, pistil, anther, flower, seed, embryo, stalk or petiole.

In another aspect, the invention provides a plant comprising reduced expression of a BS1 gene, wherein the seed yield of the plant is increased when compared to a plant that lacks the reduced expression. In certain embodiments, the invention also provides a seed that produces such a plant or a seed produced by such a plant. In another embodiment, the invention also provides a DNA-containing plant part of such a plant, which may be further defined a protoplast, cell, meristem, root, leaf, node, pistil, anther, flower, seed, embryo, stalk or petiole In another aspect, the invention provides a method of producing a plant comprising increased seed yield, the method comprising: (a) obtaining a plant comprising reduced expression of a BS1 gene, wherein the seed yield of the plant is increased when compared to a plant that lacks the reduced expression; (b) growing said plant under plant growth conditions to produce plant tissue from the plant; (c) crossing said plant with itself or another, distinct plant to produce progeny plants; and (d) selecting a progeny plant comprising reduced expression of a BS1 gene, wherein said progeny plant comprises increased seed yield when compared to a plant that lacks the reduced expression.

In another aspect, the invention provides a transgenic plant comprising a selected DNA, wherein the selected DNA down regulates a cell proliferation factor, wherein said down-regulation increases seed yield or seed size. In an embodiment, the selected DNA comprises a BS1 sequence, such as set forth in Table 1. In another embodiment, the selected DNA is an antisense or RNAi construct. In another embodiment, the transgenic plant is further defined as a legume or an R0 transgenic plant. In another embodiment, the transgenic plant is further defined as a progeny plant of any generation of an R0 transgenic plant, wherein the transgenic plant has inherited the selected DNA from the R0 transgenic plant.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

BRIEF DESCRIPTION OF THE SEQUENCE LISTING

SEQ ID NOs:1-2—DNA sequences of the forward and reverse primers for genotyping and cloning BS1 in *Medicago truncatula*.

SEQ ID NOs:3-4—DNA sequence of the forward and reverse primers for amplification of the deletion border in *Medicago truncatula*.

SEQ ID NOs:5-6—DNA sequence of primers for amplification of the BS1 genomic sequence in *Medicago truncatula*.

SEQ ID NOs:7-10—DNA sequence of primers for genotyping for PPD in *Arabidopsis thaliana*.

SEQ ID NOs:11-14—DNA sequence of primers for genotyping for AN3 in *Arabidopsis thaliana*.

SEQ ID NOs:15-21—DNA sequence of primers for performing tail PCR of the deletion ends of BS1 in *M. truncatula*.

SEQ ID NOs:22-45—DNA sequence of primers for performing qRT-PCR.

SEQ ID NOs:46-60—DNA sequence of primers for construct components.

SEQ ID NOs:61-68—DNA sequence of primers for performing ChIP-qPCR.

SEQ ID NOs:69-118—DNA sequences of BS1 genes listed in Table 1.

SEQ ID NOs:119-168—Protein sequences of BS1 genes listed in Table 1.

SEQ ID NOs:169-170—genomic DNA sequences of additional orthologs of *M. sativa* BS1.

SEQ ID NOs:171-172—Protein sequences of additional orthologs of *M. sativa* BS1.

Figure 9:
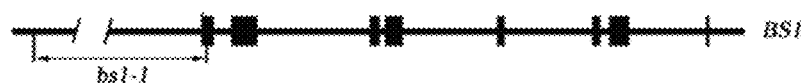
FIG. 9: Shows that BS1 encodes a conserved transcription regulator. a, Map-based cloning leads to identifying a deletion at the bs1 locus. b, Reverse transcription polymerase chain reaction (RT-PCR) analysis shows lack of transcripts of the BS1 gene in the bs1-1 mutant, in contrast to wild-type plants. The expression of an ACTIN gene is present in both wild type and the bs1-1 mutant, serving as an internal control. c, Tissue-specific RT-PCR analysis shows that the BS1 gene is expressed in all major organs, including root, stem, shoot apical meristem (SAM), stipule, leaf, flower, and seed pod. The ACTIN gene is used as an internal control. d-g, Nuclear localization of BS1-GFP. d, e, Transient expression of 35S::BS1-GFP shows nuclear localization of the fusion protein in tobacco leaves. f, g, As a control, free GFP was localized to cytoplasm in tobacco. Shown are confocal images of GFP (d, f) and overlays with Normaski images (e, g). h-k, RNA in situ hybridization shows that BS1 gene is expressed in SAM and leaf primordia as early as P0 in vegetative shoot buds (h) and in petals, carpel, and developing embryo in flowers (j). A sense probe was used as negative controls in neighboring sections (i, k). l, Alignments of BS1 (SEQ ID NO:167) and BS1 homologs from alfalfa (*Medicago sativa*; MsBS1; SEQ ID NO:168), soybean (*Glycine max*; GmBS1 (SEQ ID NO:162) and GmBS2; SEQ ID NO:163) and *Lotus japonicus* (LjBS1; SEQ ID NO:173) show highly conserved PPD, TIFY and CC2 domains (underlined).
Figure 9:
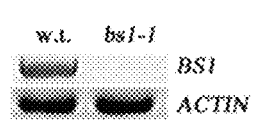
Figure 9:
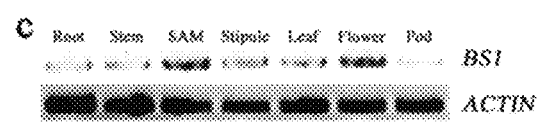
Figure 9:
Figure 9:
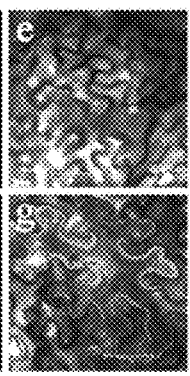
Figure 9:
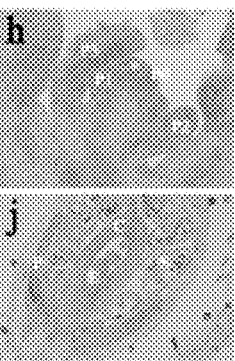
Figure 9:
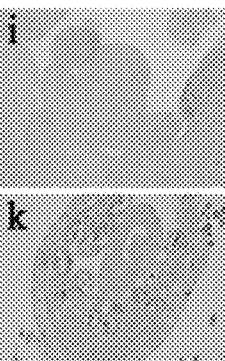
Figure 9:
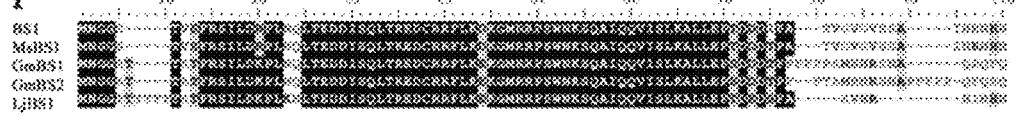
Figure 9:
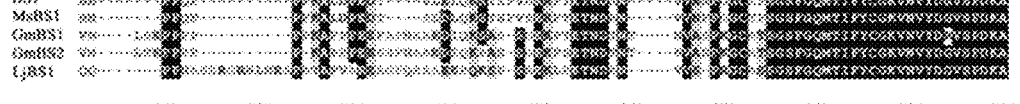
Figure 9:
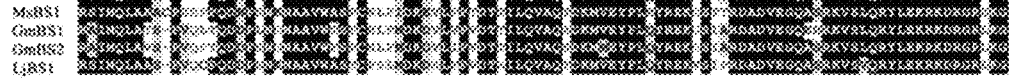

SEQ ID NO:173—*Lotus japonicus* BS1 LjBS1 polypeptide sequence (FIG. 9(*l*))

SEQ ID NO:174—GmBS1 mRNA fragment (FIG. 18A)

SEQ ID NO:175—amiR-GmBS mRNA fragment (FIG. 18A)

SEQ ID NO:176—GmBS2 mRNA fragment (FIG. 18B)

SEQ ID NO:177—amiR-GmBS mRNA fragment (FIG. 18B)

DETAILED DESCRIPTION OF THE INVENTION

The present invention provides a method of increasing the seed yield in a plant by reducing or eliminating expression of a BS1 gene. Plants of the present invention that exhibit reduced expression of a BS1 gene demonstrate beneficial traits including increased seed yield, increased seed size and weight, increased pod size, increased leaf size, and increased plant biomass when compared to a plant that lacks the reduced expression.

The size of plant lateral organs such as seeds and leaves is controlled by a plant's genetic make-up and also by the environmental conditions under which plants are grown. Plant lateral organs are primary sources of food and feed and as such, methods for increasing these would be beneficial. To facilitate an improvement in crop yield, the inventors provide for the first time a conserved BIG SEEDS1 (BS1)

regulatory module that controls plant organ size in *Medicago truncatula*, soybean (*Glycine max*), and *Arabidopsis thaliana*. BS1 encodes a plant-specific transcription regulator that determines lateral organ growth by negatively targeting factors that mediate cell proliferation. By downregulating BS1 orthologs in soybean (*Glycine max*) using microRNA (miRNA), the inventors have been able to significantly increase seed size and weight in these plants, thus providing a powerful strategy for increasing soybean seed yield. Thus, the present invention comprises methods for reducing or eliminating expression of a BS1 gene in a plant comprising introducing into the plant a nucleic acid sequence that when expressed in the plant produces reduces or eliminates expression of a BS1 gene. Such a sequence may comprise a nucleic acid sequence such as a dsRNA or miRNA and may result in increased seed yield or seed size in the plant.

Thus, in one embodiment, a plant in accordance with the invention having increased seed yield or seed size may comprise reduced expression of a BS1 gene sequence, such as a sequence set forth herein in Table 1. In another embodiment, a plant with increased seed yield or seed size may lack expression of a BS1 gene sequence, such as a sequence set forth herein in Table 1. In another embodiment, a plant in accordance with the invention having increased seed yield or seed size may comprise reduced expression of a BS1 gene, such as a gene set forth in Table 1. In other embodiments, the invention provides primers which may be useful for detection or amplification of a sequence as described herein. Such sequences are set forth herein as SEQ ID NOs: 1-68. In another embodiment, such primers may be useful for detecting the presence of absence of a gene or sequence of the invention. In accordance with the invention, nucleic acid and/or protein sequences may share sequence identity at the nucleic acid or amino acid level. For example, such sequences may share 100%, 99%, 98%, 97%, 96%, 95%, 94%, 93%, 92%, 91%, 90%, 89%, 88%, 87%, 86%, 85%, 84%, 83%, 82%, 81%, 80% sequence identity, or the like.

Without being limited to a particular theory, a plant useful for the present invention may be a plant as set forth in Table 1, for instance displaying reduced Bs1 expression with increased seed yield or seed size. In an embodiment, a plant in accordance with the invention may be a dicot, for example *Arabidopsis thaliana*, *Arabidopsis lyrata*, *Carica papaya*, *Ricinus communis*, *Cucumis sativus*, *Prunus persica*, *Vitis vinifera*, *Manihot esculenta*, *Citrus sinensis*, *Eutrema salsugineum*, *Citrus clementina*, *Capsella rubella*, *Aquilegia coerulea*, *Malus domestica*, *Linum usitatissimum*, *Eucalyptus grandis*, *Solanum tuberosum*, *Gossypium raimondii*, *Populus trichocarpa*, *Phaseolus vulgaris*, *Solanum lycopersicum*, *Theobroma cacao*, *Conradina grandiflora*, *Mimulus guttatus*, *Brassica rapa*, *Boechera stricta*, *Arachis hypogaea*, *Medicago trunculata*, *Medicago sativa*, *Glycine max*, cotton, carrot, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp.

TABLE 1

BS1 genes in different plant species.

| Species Name | Gene Name | SEQ ID NO (DNA) | SEQ ID NO (protein) |
| --- | --- | --- | --- |
| Arabidopsis lyrata | AlBS1 | 69 | 119 |
| Arabidopsis lyrata | AlBS2 | 70 | 120 |
| Carica papaya | CpBS1 | 71 | 121 |
| Ricinus communis | RcBS1 | 72 | 122 |
| Ricinus communis | RcBS2 | 73 | 123 |
| Cucumis sativus | CsBS1 | 74 | 124 |
| Prunus persica | PpBS1 | 75 | 125 |
| Vitis vinifera | VvBS1 | 76 | 126 |
| Vitis vinifera | VvBS2 | 77 | 127 |
| Manihot esculenta | MeBS1 | 78 | 128 |
| Manihot esculenta | MeBS2 | 79 | 129 |
| VManihot esculenta | MeBS3 | 80 | 130 |
| Citrus sinensis | CsBS1 | 81 | 131 |
| Citrus sinensis | CsBS2 | 82 | 132 |
| Arabidopsis thaliana | AtPPD1 | 83 | 133 |
| Arabidopsis thaliana | AtPPD2 | 84 | 134 |
| Eutrema salsugineum | EsBS1 | 85 | 135 |
| Citrus clementina | CcBS1 | 86 | 136 |
| Citrus clementina | CcBS2 | 87 | 137 |
| Capsella rubella | CrBS1 | 88 | 138 |
| Capsella rubella | CrBS2 | 89 | 139 |
| Aquilegia coerulea | AcBS1 | 90 | 140 |
| Malus domestica | MdBS1 | 91 | 141 |
| Malus domestica | MdBS2 | 92 | 142 |
| Linum usitatissimum | LuBS1 | 93 | 143 |
| Linum usitatissimum | LuBS2 | 94 | 144 |
| Eucalyptus grandis | EgBS1 | 95 | 145 |
| Solanum tuberosum | StBS1 | 96 | 146 |
| Solanum tuberosum | StBS2 | 97 | 147 |
| Gossypium raimondii | GrBS1 | 98 | 148 |
| Gossypium raimondii | GrBS2 | 99 | 149 |
| Gossypium raimondii | GrBS3 | 100 | 150 |
| Populus trichocarpa | PtBS1 | 101 | 151 |
| Populus trichocarpa | PtBS2 | 102 | 152 |
| Phaseolus vulgaris | PvBS1 | 103 | 153 |
| Solanum lycopersicum | SlBS1 | 104 | 154 |
| Solanum lycopersicum | SlBS2 | 105 | 155 |
| Theobroma cacao | TcBS1 | 106 | 156 |
| Theobroma cacao | TcBS2 | 107 | 157 |
| Conradina grandiflora | CgBS1 | 108 | 158 |
| Conradina grandiflora | CgBS2 | 109 | 159 |
| Mimulus guttatus | MgBS1 | 110 | 160 |
| Mimulus guttatus | MgBS2 | 111 | 161 |
| Glycine max | GmBS1 | 112 | 162 |
| Glycine max | GmBS2 | 113 | 163 |
| Brassica rapa | BrBS1 | 114 | 164 |
| Brassica rapa | BrBS2 | 115 | 165 |
| Boechera stricta | BsBS1 | 116 | 166 |
| Medicago truncatula | MtBS1 | 117 | 167 |
| Medicago sativa | MsBS1 | 118 | 168 |
| Medicago sativa | MsBS2 | 169 | 171 |
| Medicago sativa | MsBS3 | 170 | 172 |

I. Nucleic Acids, Polypeptides and Plant Transformation Constructs

Certain embodiments of the current invention concern isolated nucleic acid sequences comprising a BS1 coding sequence, set forth herein in Table 1. The invention also provides sequences complementary to such sequences. Also provided are primers for detecting or amplifying a sequence in accordance with the invention, which are set forth herein as SEQ ID NOs:1-68. Complements to any nucleic acid sequences described herein are also provided.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs that can be used to determine "identity" between two sequences may include but are in no way limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul et al., NCBI NLM NIH, Bethesda, Md. 20894; Altschul et al., 1990). The well known Smith Waterman algorithm can also be used to determine identity.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison are known in the art and may include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes," or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The nucleic acids provided herein may be from any source, e.g., identified as naturally occurring in a plant, or synthesized, e.g., by mutagenesis of a sequence set forth herein. In an embodiment, the naturally occurring sequence may be from any plant. In certain embodiments, the plant may be a dicotyledonous plant, for example, *Arabidopsis thaliana, Arabidopsis lyrata, Carica papaya, Ricinus communis, Cucumis sativus, Prunus persica, Vitis vinifera, Manihot esculenta, Citrus sinensis, Eutrema salsugineum, Citrus clementina, Capsella rubella, Aquilegia coerulea, Malus domestica, Linum usitatissimum, Eucalyptus grandis, Solanum tuberosum, Gossypium raimondii, Populus trichocarpa, Phaseolus vulgaris, Solanum lycopersicum, Theobroma cacao, Conradina grandiflora, Mimulus guttatus, Brassica rapa, Boechera stricta, Arachis hypogaea, Medicago trunculata, Medicago sativa, Glycine max*, cotton, carrot, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp. or the like Coding sequences, such as a BS1 coding sequence, or complements thereof, may be provided in a recombinant vector or construct operably linked to a heterologous promoter functional in plants, in either sense or antisense orientation. Expression constructs may also be provided comprising these sequences, including antisense oligonucleotides thereof. In one embodiment, such a recombinant vector or construct may encode an RNA molecule such as a miRNA that reduces or eliminates the expression of a gene involved in cell proliferation in the plant, such as a BS1 gene. In other embodiments, plants and plant cells transformed with the sequences may be provided. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

The choice of any additional elements used in conjunction with the BS1 sequences may depend on the purpose of the transformation. One of the major purposes of transformation of crop plants is to add commercially desirable, agronomically important traits to the plant, as described herein. Such traits may include, but are not limited to increased seed yield, increased seed size and weight, increased pod size, increased leaf size, and increased plant biomass, pesticide resistance, herbicide tolerance, drought tolerance, and the like.

Vectors or constructs used for plant transformation may include, for example, plasmids, cosmids, YACs (yeast artificial chromosomes), BACs (bacterial artificial chromosomes) or any other suitable cloning system known in the art, as well as fragments of DNA therefrom. Thus, when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. In an embodiment, introduction of such a construct into a plant may result in increased expression of a particular gene in the plant. In another embodiment, introduction of such a construct may result in reduction or elimination of expression of a particular gene. Preferred components likely to be included with vectors used in the current invention are as follows.

A. Regulatory Elements

As used herein, "gene suppression" or "reduced expression" or "decreased expression" may refer to any of the well-known methods for reducing the levels of protein produced as a result of gene transcription to mRNA and subsequent translation of the mRNA. Gene suppression also refers to the reduction of protein expression from a gene or a coding sequence including posttranscriptional gene suppression and transcriptional suppression. Posttranscriptional gene suppression is mediated by homology between all or a part of an mRNA molecule transcribed from a gene or coding sequence targeted for suppression and the corresponding double stranded RNA used for suppression, and refers to the substantial and measurable reduction of the amount of mRNA in the cell. The transcribed RNA can be in the sense orientation, in the anti-sense orientation, or in both orientations. Transcriptional suppression is mediated by the presence in the cell of a nucleic acid molecule such as a double-stranded RNA (dsRNA) exhibiting substantial sequence identity to a desired DNA sequence or the complement thereof. Such suppression may be effective against a native plant gene associated with a trait, or a gene that may be introduced into the plant.

Post-transcriptional gene suppression by anti-sense or sense oriented RNA to regulate gene expression in plant cells is disclosed in, for example, U.S. Pat. Nos. 5,107,065, 5,759,829, 5,283,184, and 5,231,020. The use of dsRNA or miRNA to suppress genes in plants is disclosed in WO 99/53050, WO 99/49029, U.S. Patent Application Publication No. 2003/0175965, and 2003/0061626, U.S. patent application Ser. No. 10/465,800, and U.S. Pat. Nos. 6,506,559, and 6,326,193.

A preferred method of posttranscriptional gene suppression in plants employs both sense-oriented and anti-sense-oriented, transcribed RNA which is stabilized, e.g., as a hairpin and stem and loop structure. A preferred DNA construct for effecting post transcriptional gene suppression may be one which encodes an RNA exhibiting an anti-sense orientation exhibiting substantial identity to a segment of a gene targeted for suppression. Such a sequence may be linked to a second segment encoding an RNA exhibiting substantial complementarity to the first segment. Such a construct would be expected to form a stem and loop structure by hybridization of the first segment with the second segment and a loop structure from the nucleotide sequences linking the two segments (see WO94/01550, WO98/05770, US 2002/0048814, and US 2003/0018993). In particular embodiments, the present invention thus provides methods of reducing or eliminating expression of a BS1 gene through expression of a dsRNA or miRNA targeting a BS1 gene in the plant, as well as plants produced by such methods.

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. Any suitable promoters known in the art may be used to express a nucleic acid sequence in accordance with the invention in a plant. In an embodiment, such a nucleic acid sequence may encode an RNA molecule such as a miRNA or dsRNA that results in reduction or elimination of expression of a BS1 gene in a plant. In an embodiment of the invention, the CaMV35S promoter or a native promoter may be used to express an RNA molecule that results in reduction or elimination of expression of a BS1 gene in a plant.

The DNA sequence between the transcription initiation site and the start of the coding sequence, i.e., the untranslated leader sequence, can also influence gene expression. One may thus wish to employ a particular leader sequence with a transformation construct of the invention. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of nucleic acid sequences targeting a BS1 gene in a plant.

It is envisioned that nucleic acid sequences targeting a BS1 gene may be introduced under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters, which have higher activity in roots.

B. Transcription Terminating Sequences

Transformation constructs prepared in accordance with the invention may include a 3' end DNA sequence that acts as a signal to terminate transcription and allow for the polyadenylation of the mRNA produced by coding sequences operably linked to a promoter. In one embodiment of the invention, the native terminator of a BS1 sequence may be used. Alternatively, a heterologous 3' end may enhance the expression of sense or antisense BS1 sequences. Examples of such sequences that may be used in this context include those from the nopaline synthase gene of *Agrobacterium tumefaciens* (nos 3' end) (Bevan et al., 1983), the terminator sequence for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., β-glucuronidase 'GUS,' green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the invention may be in the alteration of plant phenotypes by genetic transformation with nucleic acid molecules, such as miRNA or dsRNA molecules, which are complementary to a BS1 coding sequence. Such nucleic acid molecules may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. Genetic Transformation

Additionally provided herein are transgenic plants transformed with a recombinant vector as described herein encoding or producing a BS1 sequence, or a sequence modulating expression thereof. In an embodiment, a recombinant vector as described herein may encode a dsRNA or miRNA complementary to a BS1 sequence.

In one embodiment, the disclosure provides a transgenic plant or plant cell comprising a polynucleotide molecule or a recombinant DNA construct as described herein, wherein the polynucleotide molecule or recombinant DNA construct encodes or produces a BS1 sequence, or a variant or homologue thereof. In an embodiment, the polynucleotide molecule or a recombinant DNA construct may result in the downregulation or elimination of BS1 expression in the plant. The disclosure therefore also provides progeny of these plants, vegetative, propagative, and reproductive parts of the plants comprising a transgene encoding a BS1 sequence. In an embodiment, a plant in accordance with the present disclosure comprises increased seed yield or seed size relative to a plant not comprising such a polynucleotide molecule or DNA construct.

Suitable methods for transformation of plant or other cells for use with the current invention are believed to include virtually any method by which DNA can be introduced into a cell, such as by direct delivery of DNA, by *Agrobacterium*-mediated transformation (U.S. Pat. No. 5,591,616 and U.S. Pat. No. 5,563,055; both specifically incorporated herein by reference) by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present invention comprising reduced or eliminated BS1 expression can be of any species. In some embodiments, the transgenic plant is a dicotyledonous plant, for example an agronomically important plant such as soybean, *Medicago truncatula*, a poplar, a willow, a *eucalyptus*, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or an *Arabidopsis* species. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell.

Also contemplated herein is a plant genetically engineered to exhibit reduced expression of a BS1, wherein the BS1 comprises a protein product of a sequence set forth in Table 1, wherein the protein product (e.g. a polypeptide) alters plant morphology. In an embodiment, the plant may lack expression of a BS1 gene. In an embodiment, the altered plant morphology may be increased seed yield, increased seed size, increased leaf size, or increased biomass. Such plants are described in the Examples, and may be useful, e.g., as commercial plants, due to their increased plant size and seed number.

The plants of these embodiments having decreased or a lack of expression of BS1 may be of any species. The species may be any monocotyledonous or dicotyledonous plant, such as those described herein. One of skill in the art will recognize that the present invention may be applied to plants of other species by employing methods described herein and others known in the art.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

The expression of a gene product is often determined by evaluating the phenotypic results of its expression. These assays also may take many forms including but not limited to analyzing changes in the chemical composition, morphology, or physiological properties of the plant. Chemical composition may be altered, for instance, by expression of genes encoding enzymes or storage proteins which change amino acid composition and may be detected by amino acid analysis, or by enzymes that change starch quantity which may be analyzed by near infrared reflectance spectrometry. Morphological changes may include, for instance, larger seeds, larger seed pods, larger leaves, greater stature, thicker stalks, and altered leaf-stem ratio, among others. Most often changes in response of plants or plant parts to imposed treatments are evaluated under carefully controlled conditions termed bioassays.

IV. Evaluation of Increased Seed Production or Size

A plant useful for the present invention may be an $R_0$ transgenic plant. Alternatively, the plant may be a progeny plant of any generation of an $R_0$ transgenic plant, where the transgenic plant has the nucleic acid sequence from the $R_0$ transgenic plant.

Plants in accordance with the invention exhibiting reduced or a lack of BS1 expression may also be used to produce increased seed size or numbers, increased plant biomass, for example by obtaining the above-identified plant comprising reduced or a lack of BS1 expression, growing said plant under plant growth conditions to produce plant tissue from the plant; and preparing biomass from said plant tissue. The increased seed production or biomass can be subsequently used for any purpose, for example for food or commodity products, or to produce biofuel.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected nucleic acid sequence producing a dsRNA or miRNA targeting a BS1 coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

Expression: The combination of intracellular processes, including transcription and translation, undergone by a coding DNA molecule such as a structural gene to produce a polypeptide. A plant in accordance with the invention may exhibit altered expression of a gene set forth herein. Such altered expression may include increased expression, decreased expression, or complete absence of expression.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. The sequence may also be altered, i.e. mutated, with respect to the native regulatory sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Plant Materials

Homozygous big seeds1-1 (bs1-1; M477), bs1-2 (FN 1860-III) and bs1-3 (FN 2876) mutants were isolated from a fast neutron bombardment (FNB)-induced deletion mutant collection of *Medicago truncatula* cv. Jemalong A17 background. The bs1-1 allele was backcrossed to wild type (A17). BC1 mutant and its descendants were used for phenotypic characterization. F2 mapping populations were generated from crosses between bs1-1 and a polymorphic ecotype *M. truncatula* cv. Jemalong A20. A total of 518 individuals (432 wild-type like and 86 mutants) was used in a bulk segregant and fine mapping analyses to construct a linkage map of the bs1 locus. *Arabidopsis thaliana* Δppd (CS16548) and an3-1 (CS241) mutant lines were obtained from the *Arabidopsis* Stock Center at Ohio State University. AN3pro::uidA line was described previously (Horiguchi et al., *Plant J* 43:68-78, 2005).

Example 2

Isolation and Phenotypic Analysis of bs1 Mutant

From a forward genetic screen of mutants with an increased seed size from a fast neutron bombardment (FNB)-induced deletion mutant collection of *Medicago*

*truncatula* (cv. Jemalong A17) (Peng et al., *Plant Cell* 23:3929-3943, 2011; Chen et al., *Proc Natl Acad Sci USA* 107:10754-10759, 2010), a unique mutant named big seeds1 (bs1) was isolated. The bs1 mutant exhibited large seeds, seed pods, and leaves, along with several other phenotypes compared with wild-type plants (FIG. 1*a-g*). To measure leaf and seed parameters, digital images of leaves and seeds were obtained using a high-resolution scanner (EPSON PERFECTION V700 PHOTO, EPISON) and analyzed using ImageJ and Tomato Analyzer (Brewer et al., *Plant Physiology* 141:15-25, 2006). To accurately measure bs1-1 mutant leaves, leaves were flattened by carefully cutting the leaf margin before scanning.

Figure 1:
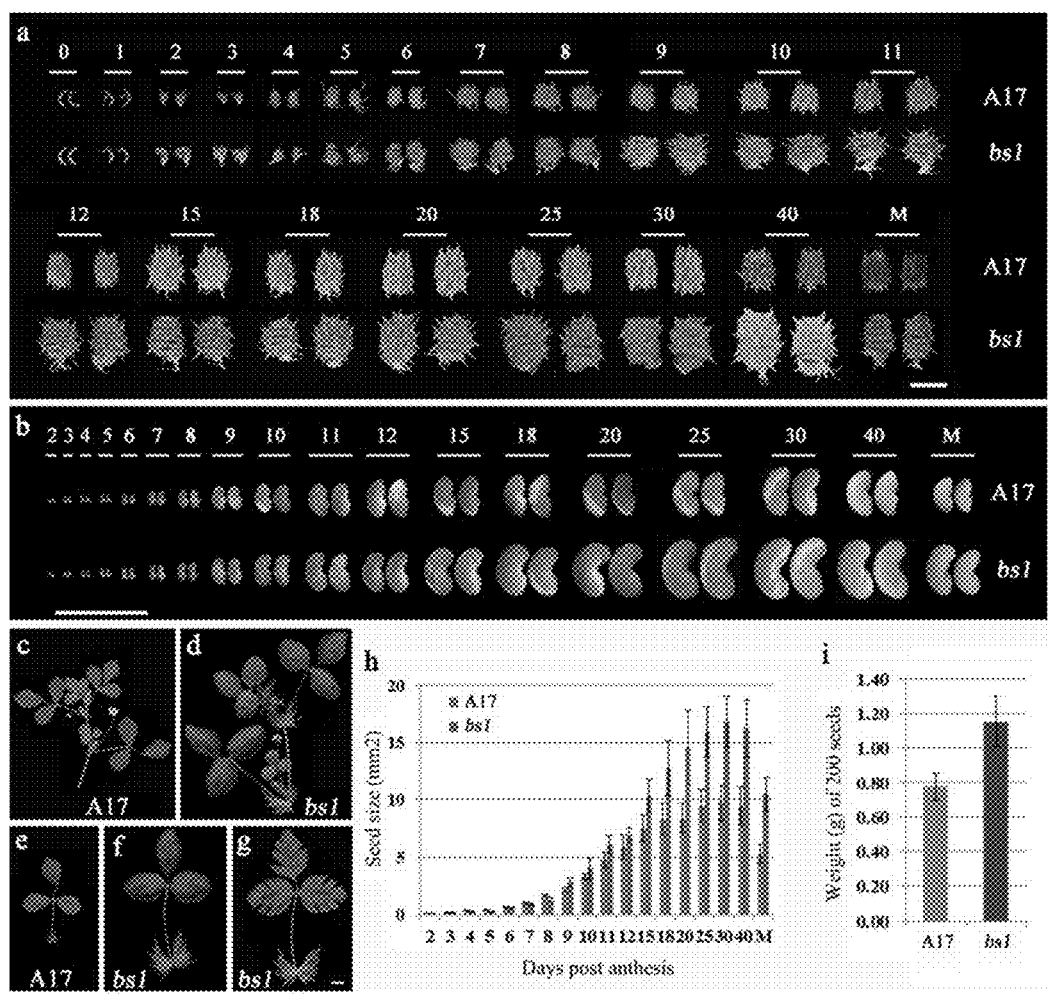
FIG. 1: Shows that BS1 negatively regulates growth of lateral organs, including leaves, seeds, and seed pods in *Medicago truncatula*. (a, b) Seed pods (a) and seeds (b) of wild type (top) and bs1-1 mutant (bottom) at different days post anthesis (dpa; numbers on top of horizontal lines; M, mature). Two representative images are shown for each time point. (c, d) Shoots of two-month old wild-type (c) and bs1-1 mutant (d). (e-g), Compound leaves of wild-type (e) and bs1-1 mutant (f, g). (g), The dome-shaped leaflets in (f) are flattened by introducing cuts at the margins. (h), Measurements of seed sizes over time (dpa). Data are means±s.d. for n=12. i, Measurements of seed weights (grams per 200 seeds). Data are means±s.d. for n=3. M, mature organ. Scale bars, 1 cm.

Time-course experiments show that developing seeds 11 DPA (days post anthesis) and older were significantly larger in the bs1 mutant than in wild-type plants (FIG. 1*a*, *b*, and *h*). Seed pods were already larger at earlier stages of development in the mutant (FIG. 1*a*). Maturation of seeds and seed pods appeared to be slightly delayed in the bs1 mutant compared with wild-type plants (FIG. 1*a*, *b*). In line with an increase in seed size, mature seeds were more than 20% heavier in the bs1 mutant than wild-type (FIG. 1*i*).

Figure 2:
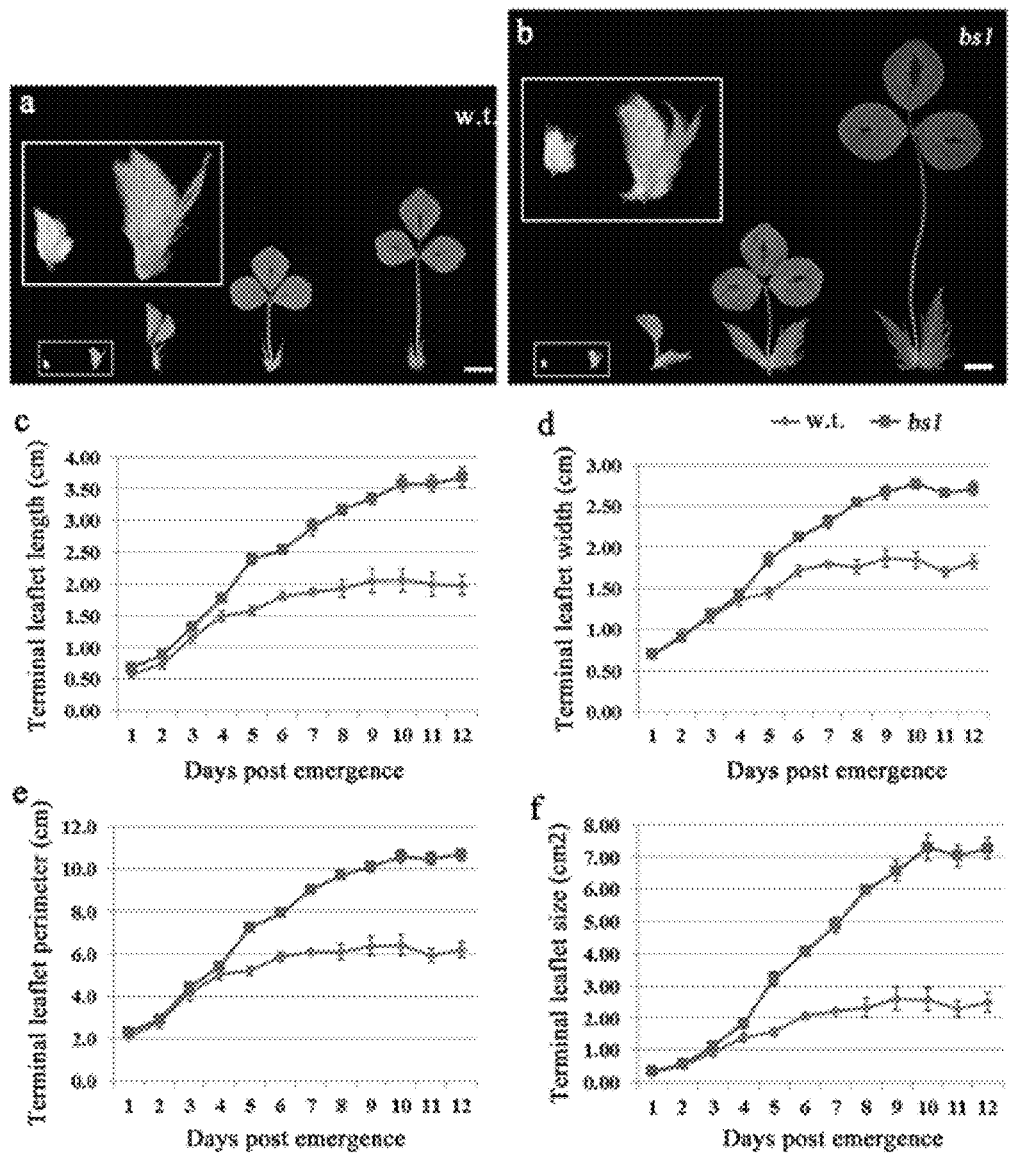
FIG. 2: Shows a time course analysis of leaf phenotypes of *Medicago* bs1-1 mutant. a, b, Leaf morphology of six week-old wild type (A17; a) and bs1-1 mutant (b). Shown are compound leaves dissected sequentially from the shoot apex to the base of the stem (left to right). c-f, Measurements of terminal leaflet length (c), width (d), perimeter (e) and area (f) of compound leaves during a 12-day time course. Shown are means±s.d. for n=6.

In the bs1 mutant, both terminal and lateral leaflets of its trifoliate leaves were dramatically increased in length, width, perimeter, and size compared with wild-type counterparts (FIG. 1*c-g*; FIG. 2*a*, *b*). In addition, the shape of leaflets was also altered. Leaflets of the bs1 mutant had a dome-shaped curvature, in contrast to the flat leaflets of wild-type plants. The dome-shaped leaflets could be flattened by introducing cuts in the edges (FIG. 1*e-g*). Petioles of the bs1 mutant were longer than wild-type petioles (FIG. 2*a*, *b*). Further, the size of stipules was increased by more than 10 times in the bs1 mutant compared with wild-type stipules (FIG. 1*c-g*; FIG. 2*a*, *b*).

Figure 3:
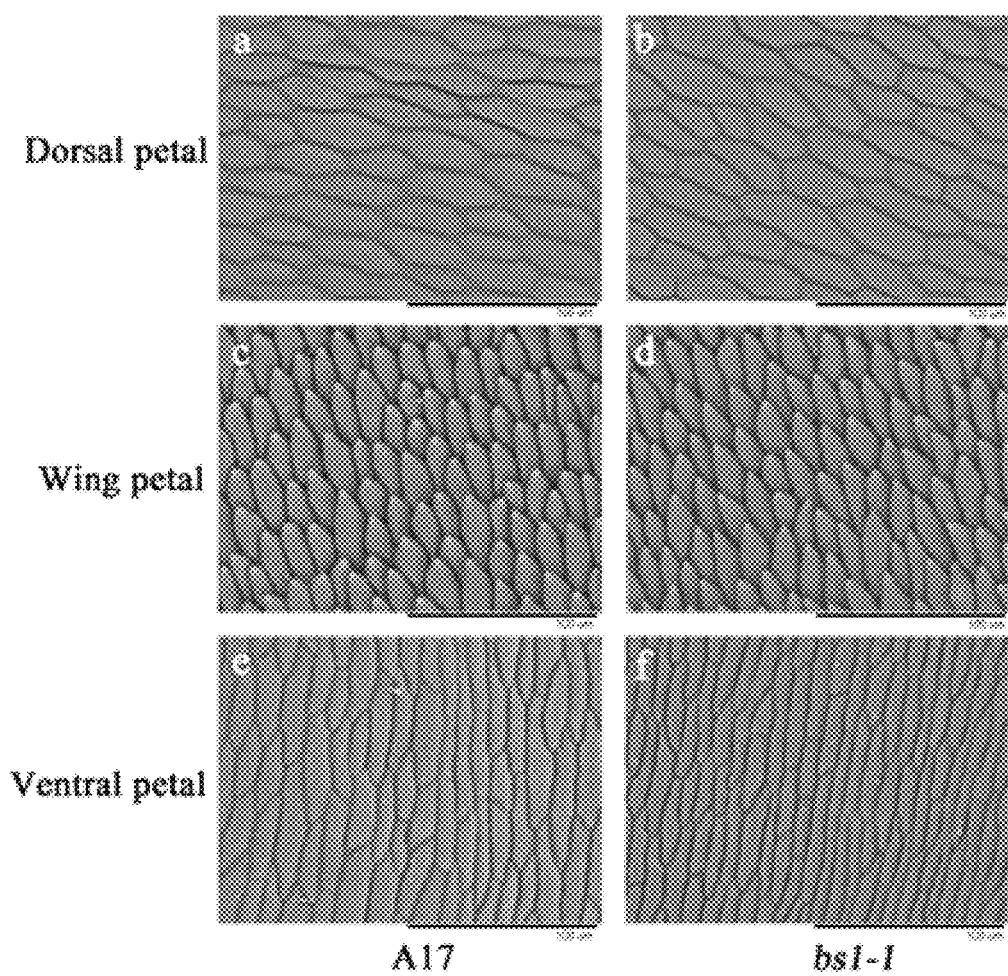
FIG. 3: Shows a scanning electron microscopic (SEM) images of petals. a-f, Shown are images of dorsal (a, b), wing (c, d) and ventral (e, f) petals of wild type (a, c, e) and bs1-1 mutant (b, d, f). Scale bars, 100 um.
Figure 4:
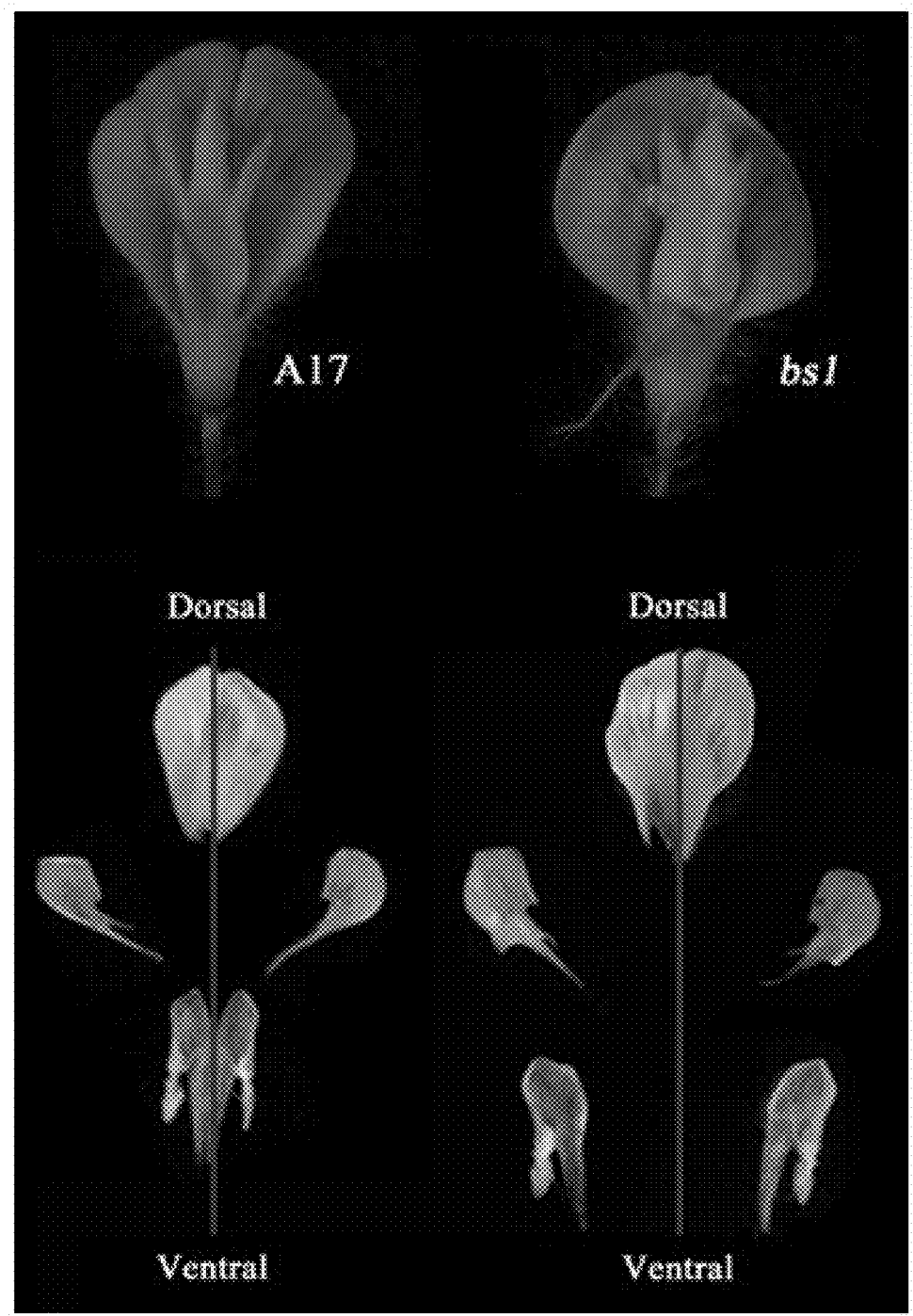
FIG. 4: Shows *Medicago* bs1 mutant exhibits altered floral patterning. Shown are flowers (top panels) and dissected petals (bottom panels) of wild type (A17; left panels) and bs1-1 mutant (right panels).
Figure 5:
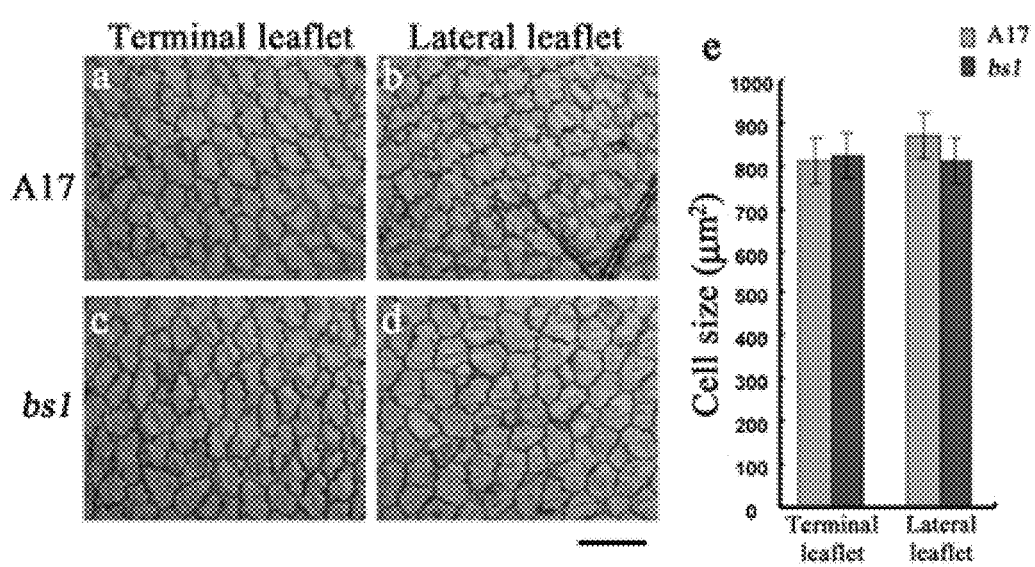
FIG. 5: Shows measurements of leaf epidermal cell size. a, Epidermal peels of terminal and lateral leaflets of compound leaves of six week-old wild type and bs1-1 mutant. b, Measurements of leaf epidermal cells of wild-type (A17) and bs1-1 mutant. Shown are means±s.d. for n=60. Scale bar, 100 um.

Although the size and identity of floral organs was not altered in the bs1 mutant, floral patterning was altered (FIGS. 3 and 4). As a member of the Papilionoideae subfamily of legumes (Fabaceae), *M. truncatula* produces flowers resembling those of garden pea (*Pisum sativum*) with three types of petals: one dorsal petal with bilateral symmetry, two asymmetric wing petals, and one symmetric ventral petal derived from fusion of two ventral petal primordia during early floral development (FIG. 4) (Wang et al., *Plant Physiol* 146:1759-1772, 2008). In the bs1 mutant, the ventral petal primordia failed to fuse together, resulting in two separate ventral petals with an acquired internal asymmetry (FIG. 4).

An increase in organ size may result from an increase in cell proliferation and/or cell expansion, two successive processes contributing to the final organ size (Hepworth, et al., *Curr Opin Plant Biol* 17:36-42, 2014; Gonzalez, et al., *Plant Physiol* 153:1261-1279, 2010). Measurements show that epidermal cells of fully-expanded leaves were similar in size between the bs1 mutant and wild-type plants, suggesting that cell proliferation rather than cell expansion is altered in the bs1 mutant (FIG. 5*a-e*). Leaf primordia are initiated from the periphery of the shoot apical meristem (SAM) and initially consist of cells that undergo coordinated division without changes in cell size. As the leaf grows, cells at the distal tip cease dividing and differentiate, resulting in a cell cycle arrest front moving from the tip to base. Eventually, all cells cease dividing and the leaf reaches its final size (Nath et al., *Science* 299:1404-1407, 2003; Donnelly et al., *Developmental Biology* 215:407-419, 1999; Poethig et al., *Planta* 165:170-184 1985).

To further examine the developmental processes affected in the bs1 mutant, leaf development was followed over time. For the time lapse analysis of leaf size, the youngest emerging leaf of six-week-old plants was labeled and imaged daily during a 12-day time course. For the time lapse analysis of seed size, flowers were labeled and seed pods were collected at different time points after anthesis. Seeds were carefully removed from seed pods and imaged. To measure seed weight, wild type (A17) and the bs1-1 mutant, and soybean seeds were weighed on a digital balance. Fresh weights of fully-expanded leaves from six-week-old plants were also measured using a digital balance.

In the first 4 days after emerging from the shoot apex, young leaves (P5; P for plastochron) of both wild-type and the bs1 mutant similarly expanded along the proximodistal (length) and mediolateral (width) axes (FIG. 2*c-f*). The expansion of wild-type leaves along the length and width axes reached a plateau approximately 2 days later (FIG. 2*c-f*). By contrast, leaves of the bs1 mutant continuously expanded and did not reach a plateau until approximately 6 days later (FIG. 2*c-f*). These results show that the enlarged organ phenotype of the bs1 mutant was caused by prolonged cell proliferation. This is consistent with the observation that seed and seed pod maturation was delayed in the bs1 mutant (FIG. 1*a*, *b*).

Example 3

Forage Quality Analysis of Bs1 Mutant

Wild-type and the bs1-1 mutant plants were grown in 1-gallon pots in the greenhouse. Arial portions of three-month-old plants were harvested and dried in a 50° C. oven for three days. The samples were then ground in a Thomas-Wiley model 4 Laboratory Mill (Lehman Scientific, Wrightsville, Pa.) with 1-mm sieves. Acid detergent fiber (ADF) and neutral detergent fiber (NDF) were estimated by standard protocols (Reddy et al., *Proc Natl Acad Sci USA* 102:16573-16578, 2005). To determine NDF, 0.5 grams of ground samples were transferred to a F57 ANKOM filter bag (ANKOM Technology, Fairport, N.Y.) and heated at 100° C. for 1 h in an ANKOM Fiber Analyzer. The samples were washed in near-boiling water, dried at 100° C. for 2 h, and weighed to determine fiber loss. To determine ADF, the material remaining after NDF analysis was incubated in an acid detergent solution (2% cetyltrimethylammonium bromide in 0.5M $H_2SO_4$) for 1 h, filtered and rinsed sequentially with near-boiling water and acetone, and dried at 100° C. for 2 h to determine fiber loss.

Figure 6:
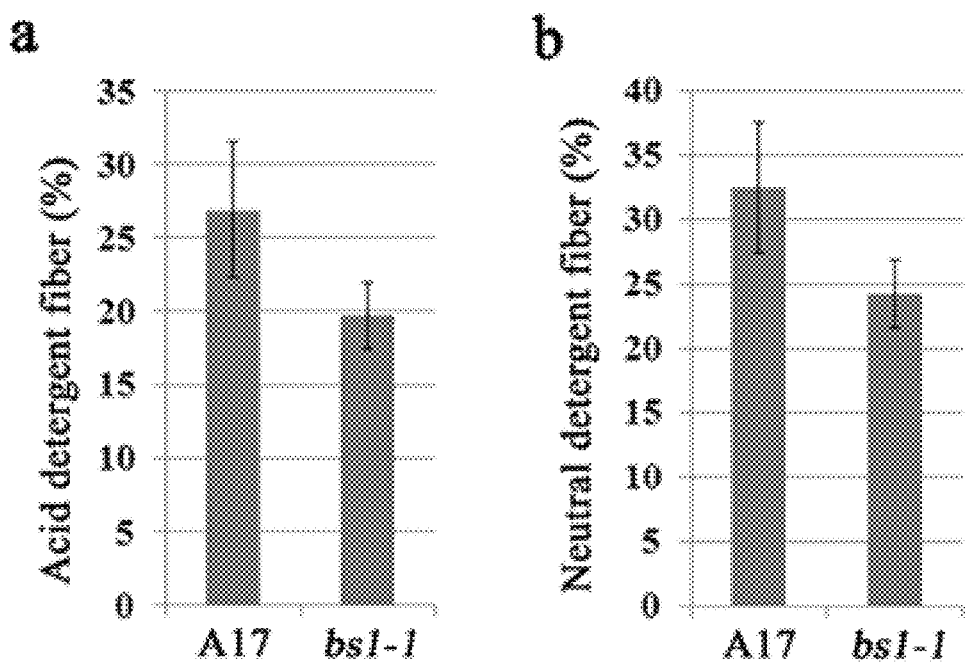
FIG. 6: Shows forage quality analysis. a, Acid detergent fiber (ADF); b, Neutral detergent fiber (NDF) of three month-old wild type (A17) and bs1-1 mutant. Shown are means±s.d., n=40.

Forage quality analyses showed that acid detergent fiber (ADF) and neutral detergent fiber (NDF) were significantly decreased in three-month-old bs1-1 mutant compared with wild-type plants (FIG. 6). These results show that an increase in cell proliferation and leaf growth due to loss-of-function of BS1 improved the forage quality of the plants.

Example 4

Mapping of BS1

Figure 7:
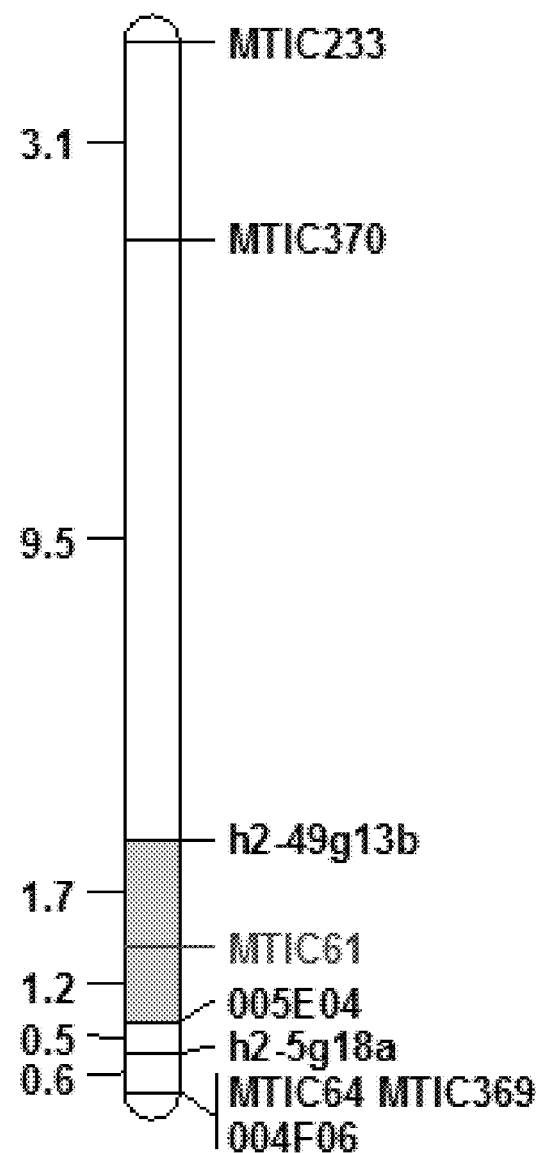
FIG. 7: Shows a genetic map position of the bs1 locus on chromosome 1 measured based on the recombination frequency analysis of 86 bs1-1 mutant plants from a F2 mapping population of 518 individuals.

Total genomic DNA was isolated from fresh leaf tissues of individual plants grown in the greenhouse using the CTAB method (Saghai-Maroof et al., *Proc Natl Acad Sci USA* 81:8014-8018, 1984). PCR amplification and PCR products separation using a Li-Cor 4300 DNA sequencer were carried out as previously described (Yu et al., *Theor Appl Genet* 113:308-320, 2006). A total of 267 SSR (simple sequence repeat) markers distributed across the eight chromosomes of *M. truncatula* (available at medicago.org/genome/downloads.php) were used to construct the linkage map using a bulked-extreme and recessive-class approach as previously described (Zhang et al., *Proc Natl Acad Sci USA* 91:8675-8679, 1994). Two bulked DNA samples from 15 mutant plants were made each by pooling equal amounts of DNA samples prepared from individual plants. DNA samples from polymorphic wild-type plants (*M. truncatula* cv. Jemalong A17 and Jemalong A20) were included in the analysis to validate SSR markers. Recombination between markers and the big seeds1 locus was calculated using the maximum likelihood estimator, $r=(N1+N2/2)/N$, where N is the total number of mutant plants, N1 is the number of recombinant homozygotes and N2 is the number of recombinant heterozygotes. The recombination ratio variance was given by $Vr=r(1-r)/2N$. The Kosambi mapping function was used to estimate the genetic distances between the markers and the big seeds1 locus and the recombination ratio was converted to map distance in centiMorgans (Koornneef et al., *Heredity* 74:265-272, 1983). A bulk segregant analysis revealed that 20 SSR markers located on chromosome 1 showed co-segregation with the big seeds1 locus. Segregation data obtained from the mutant plants were used in the color map method (Kiss et al., *Acta Biol Acad Sci Hung* 19:125-142, 1998), which employed a comparison of graphical genotypes for mapping. According to the *Medicago truncatula* genetic map (available at medicago.org/genome/map.php), recombination frequencies were calculated with 9 of the 20 SSR markers using 86 mutant plants and determined map positions of these markers. Based on this analysis, the big seeds1 locus was mapped to a region on chromosome 1 flanked by SSR markers, h2-49g13b and 005E04, and tightly linked to the SSR marker, MTIC61 (Table 2 and FIGS. 7 and 8*a*) (Choi et al., *Genetics* 166:1463-1502, 2004).

TABLE 2

Recombination frequency and genetic distance between bs1 and molecular markers on chromosome 1.

| Marker | Recombination frequencies (±s.d.) | Genetic distance (cM ± s.d.) |
| --- | --- | --- |
| MTIC233 | 0.139 ± 0.026 | 14.3 ± 0.029 |
| MTIC370 | 0.110 ± 0.023 | 11.2 ± 0.025 |
| h2-49g13b | 0.017 ± 0.010 | 1.7 ± 0.010 |
| MTIC61 | 0.0 ± 0.0 | 0.0 ± 0.0 |
| 005E 04 | 0.011 ± 0.008 | 1.2 ± 0.008 |
| h2-5g18a | 0.017 ± 0.010 | 1.7 ± 0.010 |
| MTIC64 | 0.023 ± 0.012 | 2.3 ± 0.012 |
| MTIC369 | 0.023 ± 0.012 | 2.3 ± 0.012 |
| 004F06 | 0.023 ± 0.012 | 2.3 ± 0.012 |

Example 5

Cloning of BS1

Due to the presence of sequence gaps in the mapped region (FIG. 8*b*), alternative approaches were used to clone the gene. First, the transcript profiles in vegetative shoot buds and young leaves were compared between wild type and the mutant. *Medicago truncatula* transcriptome analysis was performed as previously described (Tadege et al., *Plant Cell* 23:2125-2142, 2011; Uppalapati et al., *Plant Cell* 24:353-370, 2012). Total RNA was isolated from vegetative shoot buds and young leaves of six week-old plants using the RNeasy Plant Mini Kit (Qiagen). Three biological replicates for wild-type (A17) and the bs1-1 mutant were analyzed using Affymetrix *Medicago* GeneChip (Affymetrix). Probe labelling, hybridization and scanning were carried out according to manufacturer's instructions. Raw data were normalized with Robust Multichip Average (Irizarry et al., *Nucleic acids research* 31:e15, 2003). Presence and absence calls of probesets were obtained using dCHIP. Probesets with expression ratios of bs1-1/A17 greater than 2 or less than 0.5 were selected and analyzed for differentially expressed genes between A17 and bs1-1 using associative analyses (Dozmorov et al., *Bioinformatics* 19:204-211, 2003).

Figure 8:
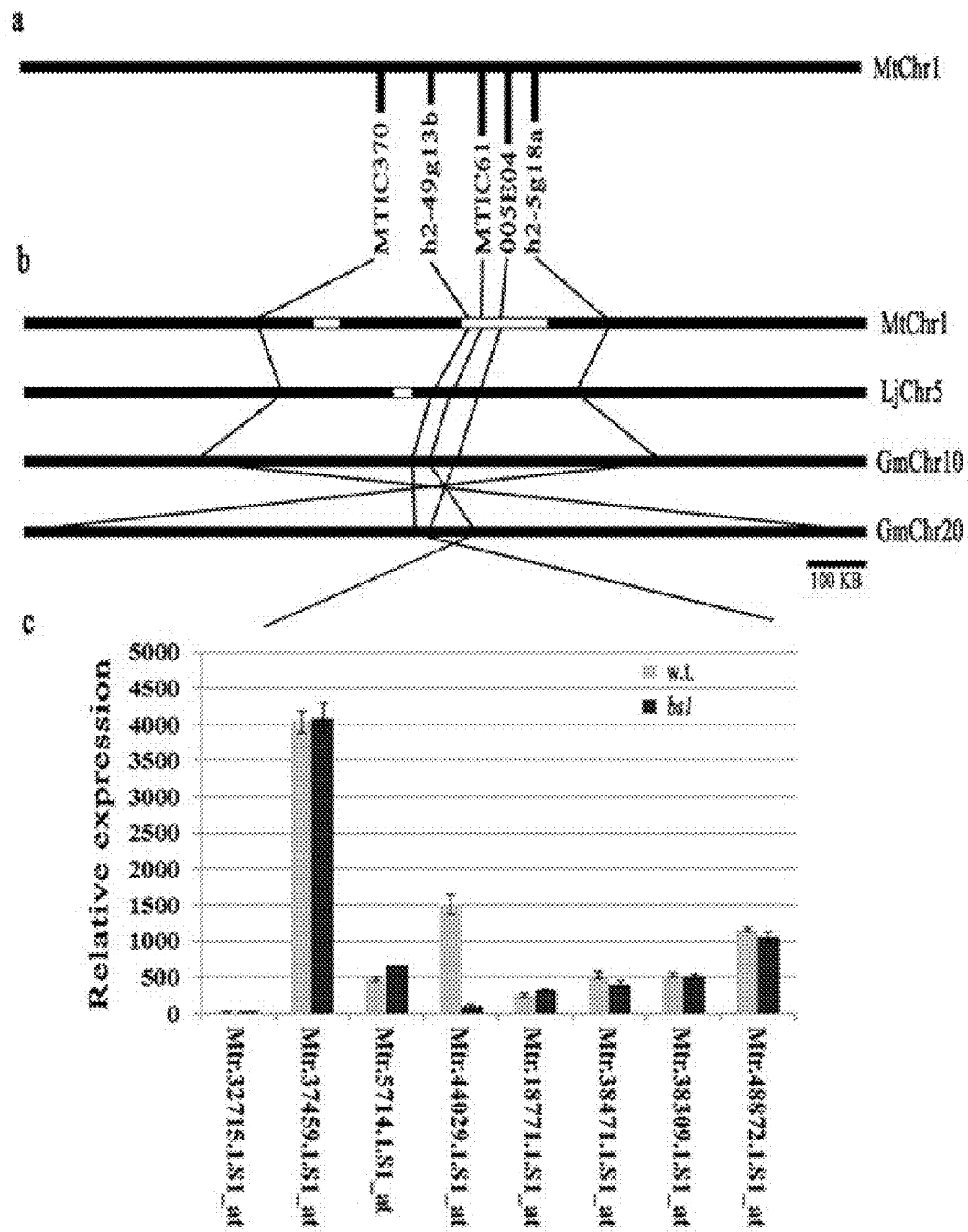
FIG. 8: Shows map-based cloning of *Medicago* BS1 gene. a, Mapping of the *Medicago* bs1 locus on chromosome 1. An F2 mapping population of 518 individuals consisting of 86 mutant plants and 432 wild-type-like plants was analyzed. b, Synteny analysis of chromosome 1 of *M. truncatula*, chromosome 5 of *Lotus japonicus* and chromosomes 10 and 20 of soybean (*Glycine max*) at the bs1 locus. c, Relative expression levels of *Medicago* microarray probesets mapped to the bs1 syntenic region. In contrast to other microarray probesets in the region, the expression level of Mtr.44029.1.S1_at was significantly downregulated in the bs1-1 mutant compared with wild type. Shown are means±s.d., n=3.

The microarray approach revealed that several probesets, which match to unanchored BAC (bacterial artificial chromosome) sequences containing the flanking h2-49g13b and 005E 04 markers (available at medicago.org/genome/downloads.php), were similarly expressed in the mutant and wild-type plants, suggesting that their sequences are intact in the mutant (FIG. 8*c*). Next, genome analysis identified that a region on chromosome 5 in *Lotus japonicus* and regions on chromosomes 10 and 20 in soybean (*Glycine max*), two closely-related species, are syntenic to the mapped BS1 region (FIG. 8*b*). Using the syntenic sequences, one microarray probeset, Mtr.44029.1.S1_at, was mapped to the syntenic location and was found to be significantly down-regulated in both shoot buds and young leaves of the bs1 mutant compared with wild-type plants (FIG. 8*c, d*). Reverse transcription (RT)-PCR amplification detected the corresponding transcript in wild-type plants but not in the bs1 mutant (FIG. 9*b*), suggesting that Mtr.44029.1.S1_at was deleted in the mutant. The deletion borders were recovered using PCR-based chromosomal walking and thermal asymmetric interlaced (TAIL)-PCR (FIG. 9*a*). Sequencing results showed that the right deletion border occurred in the first exon at 398 bp downstream from the translation initiation codon ATG of the candidate gene. However, the left border did not match to any available sequences and was likely located in the gap region.

Example 6

Confirmation of BS1 Candidate Gene

Figure 10:
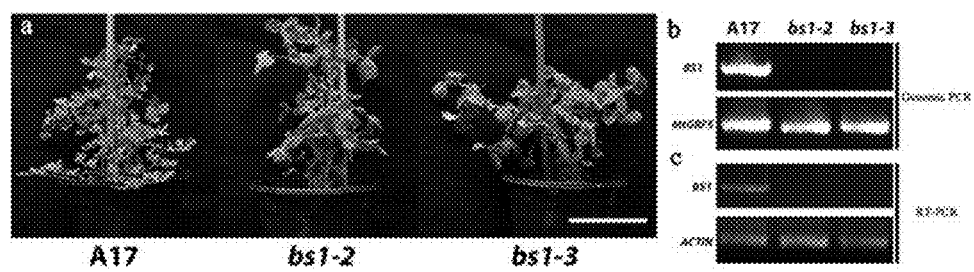
FIG. 10: Shows analysis of *Medicago* bs1-2 and bs1-3 alleles. a, Phenotype of six-week-old wild type (A17), bs1-2 and bs1-3 alleles. b, c, Genomic PCR (b) and RT-PCR (c) analysis of the bs1-2 and bs1-3 mutants, showing deletion and lack of gene expression of the BS1 gene, respectively. *Medicago* GRF5 and ACTIN genes were used as internal controls. Scale bar, 10 cm.
Figure 11:
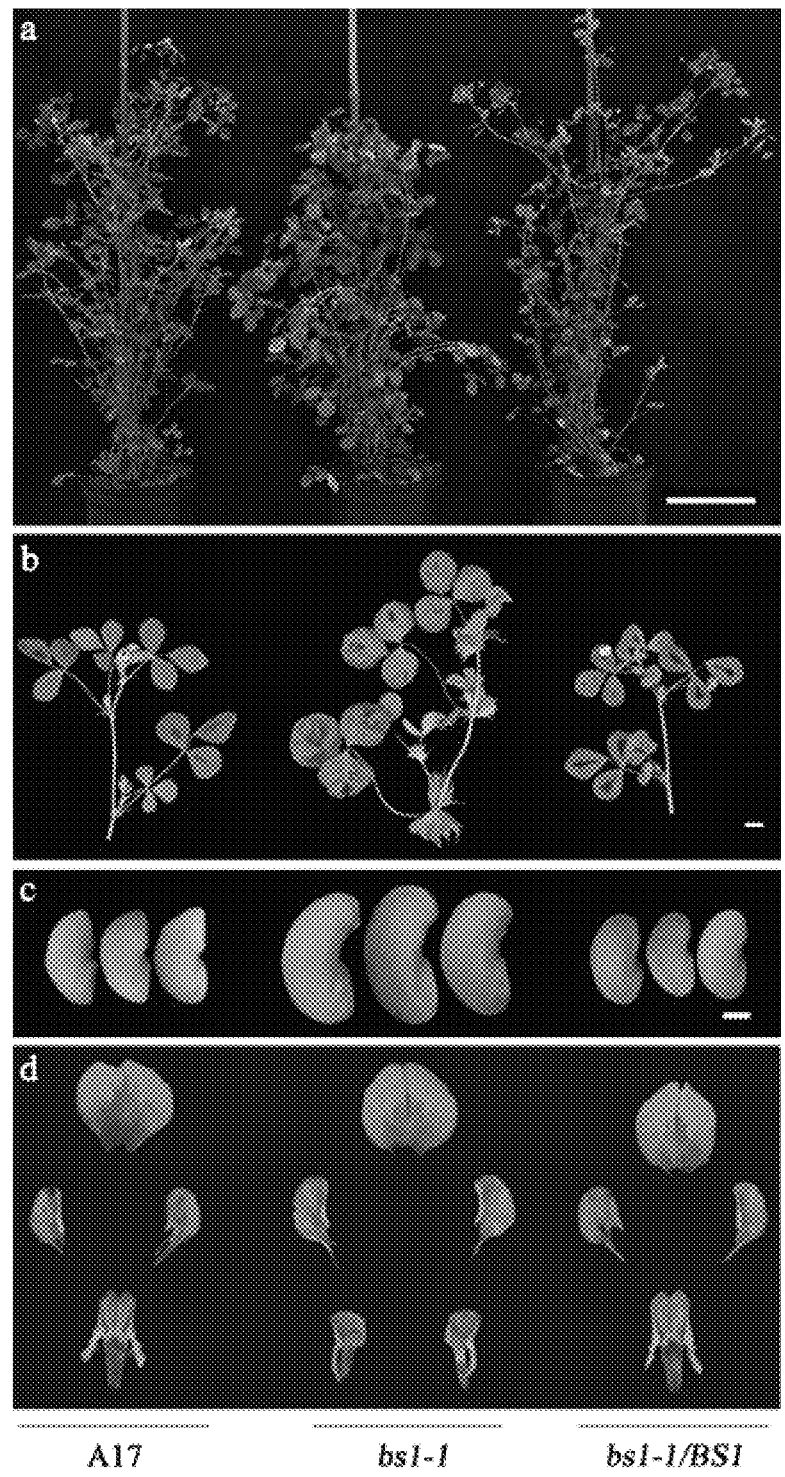
FIG. 11: Shows functional complementation of bs1-1 mutant. Introduction of the BS1 coding sequence under the control of its own promoter rescued bs1-1 mutant phenotypes. Shown are representative images of plants (a), leaves (b), seeds (c) and flowers (d) of wild type (A17), bs1-1 mutant and bs1-1 mutant transformed with BS1pro::BS1 (BS1). Scale bars, 10 cm for a, 1 cm for b, 1 mm for c.

To confirm the candidate gene, two additional alleles named bs1-2 (FN 1860) and bs1-3 (FN 2876) were isolated from the FNB mutant collection (FIG. 10*a*). Genomic PCR and RT-PCR showed that the candidate BS1 locus was completely deleted in both alleles (FIG. 10*b, c*). In addition, introducing the BS1 coding sequence under the control of its own promoter completely rescued the bs1 mutant phenotypes, confirming that Mtr.44029.1.S1_at corresponds to BS1 (FIG. 11*a-d*). Sequence analysis shows that BS1 encodes a protein of 331 amino acids in length, belonging to the group II of the TIFY family of plant-specific transcription factors and regulators (FIG. 9*h*) (Bai et al., *Genomics* 98:128-136, 2011; Vanholme et al., *Trends Plant Sci* 12:239-244, 2007). When transiently expressed in tobacco leaves or stably expressed in *Arabidopsis thaliana*, BS1-GFP fusion proteins were localized to the nucleus, in contrast to free GFP that exhibited cytoplasmic localization (FIGS. 9*c-f* and 12). The GFP signal was imaged, using the Leica SP2 laser confocal microscope as previously described (Ge et al., *Plant Physiol* 164:216-228, 2014; Peng et al., *Plant Cell* 23:3929-3943, 2011). Database searches and PCR amplification identified BS1 homologous sequences from diverse eudicot species such as alfalfa (*M. sativa*), *L. japonicas*, soybean (*G. max*), tomato (*Solanum lycopersicum*) and potato (*Solanum tuberosum* L.). However, no homologous sequences were identified from monocot species including rice and maize (FIG. 9*l*).

Example 7

Expression Analysis of BS1

Reverse transcription was performed using Qiagen SuperScript II Kit (Qiagen). Quantitative PCR was conducted on 7900HT Fast Real-Time PCR system (Applied Biosystems) as previously described (Ge et al., *Plant Physiol* 164:216-228, 2014). RT-PCR analyses showed that BS1 was expressed in all major organs including seeds, seed pods, flowers, shoot buds, and leaves (FIG. 9g). RNA in situ hybridization was performed as previously described (Ge et al., *Plant Physiol* 164:216-228, 2014), with minor modifications. The BS1 riboprobes correspond to a 751-bp sequence from the BS1 coding region. Eight micrometer sections from shoot apices of 2-4-week-old seedlings and flowers were processed and hybridized with digoxigenin-labeled sense and antisense probes. RNA in situ hybridization showed that BS1 transcripts were present in the shoot apical meristem (SAM), leaf primordia as early as P0 and lamina tissues (FIG. 9h, i). In reproductive tissues, BS1 transcripts were detected in petal primordia, carpel and embryos (FIG. 9j, k).

Example 8

Analysis of Transcript Profiles of bs1 and Wild Type Plants

Figure 13:
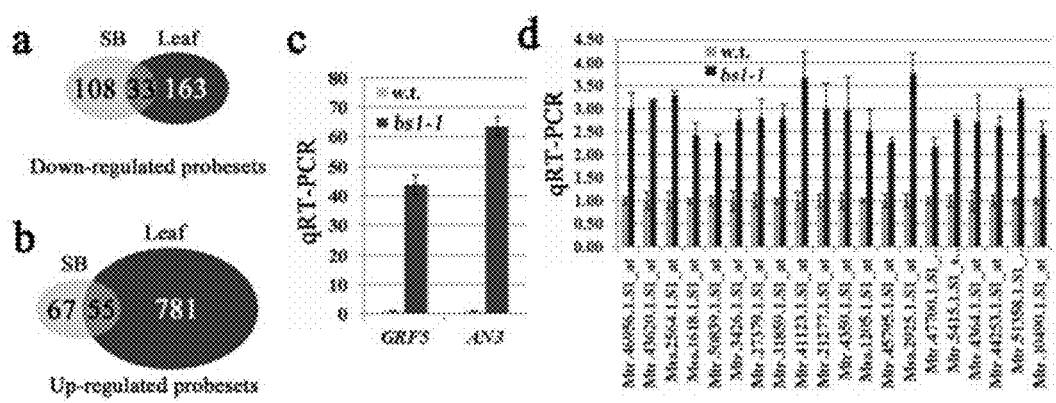
FIG. 13: Shows that BS1 negatively regulates cell proliferation. a, Microarray analyses show that 141 and 196 genes were downregulated in vegetative shoot buds (SB) and young leaves (Leaf), respectively, of the bs1-1 mutant compared with wild-type, with 33 overlapping genes. b, Microarray analyses also show that 142 and 796 genes were upregulated in vegetative shoot buds and young leaves, respectively, of the bs1-1 mutant compared with wild-type, with 55 overlapping genes. A larger number of genes is upregulated than those downregulated in young leaves, but in vegetative shoot buds, of the loss-of-function bs1-1 mutant compared with wild-type plants. c, Quantitative RT-PCR analysis shows that *Medicago* GRF5 and AN3 (also called GIF1) were significantly upregulated in young leaves of the bs1-1 mutant compared with wild-type, consistent with the microarray analysis. A *Medicago* ACTIN gene was used as the internal control. d, qRT-PCR analysis also confirms that a large number of cell cycle-related genes was also highly upregulated in expanding leaves of the bs1-1 mutant compared with wild-type plants. Data are shown as means±s.d. for n=3.

To dissect the mechanisms by which BS1 regulates cell proliferation, transcript profiles were analyzed in both vegetative shoot buds and young leaves of wild type and the bs1 mutant (FIG. 13a). A large number of core cell cycle (CCC) genes were significantly upregulated in young leaves, but not in the shoot buds of the bs1 mutant compared with wild-type (Table 3), consistent with an increase in cell proliferation observed in bs1 mutant leaves.

Figure 12:
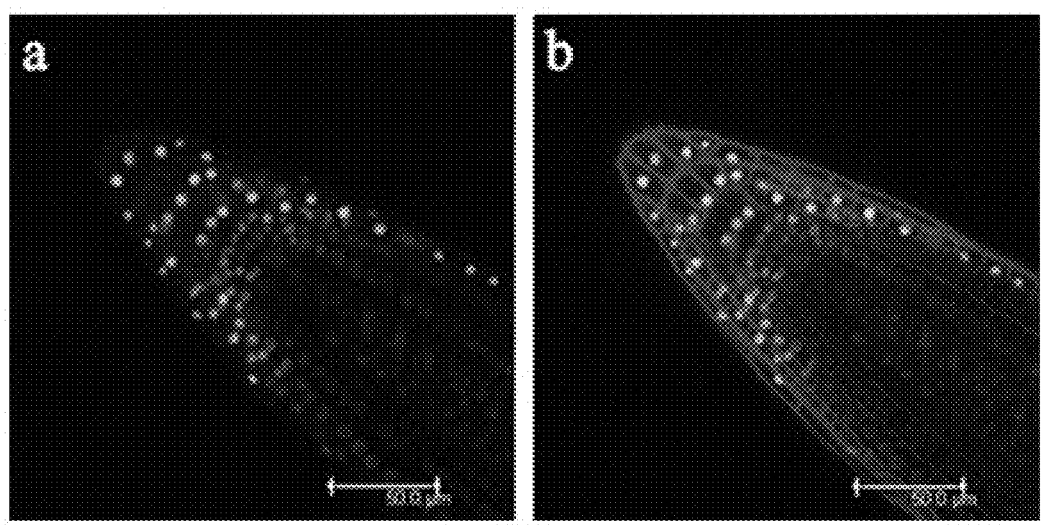
FIG. 12: Shows nuclear localization of BS1-GFP. 35S::BS1-GFP was stably expressed in *Arabidopsis thaliana* plants. Shown are a confocol image of GFP (a) and an overlay with a confocal image of propidium iodide staining outlining root tip cells (b). Scale bars, 50 um.
Figure 14:
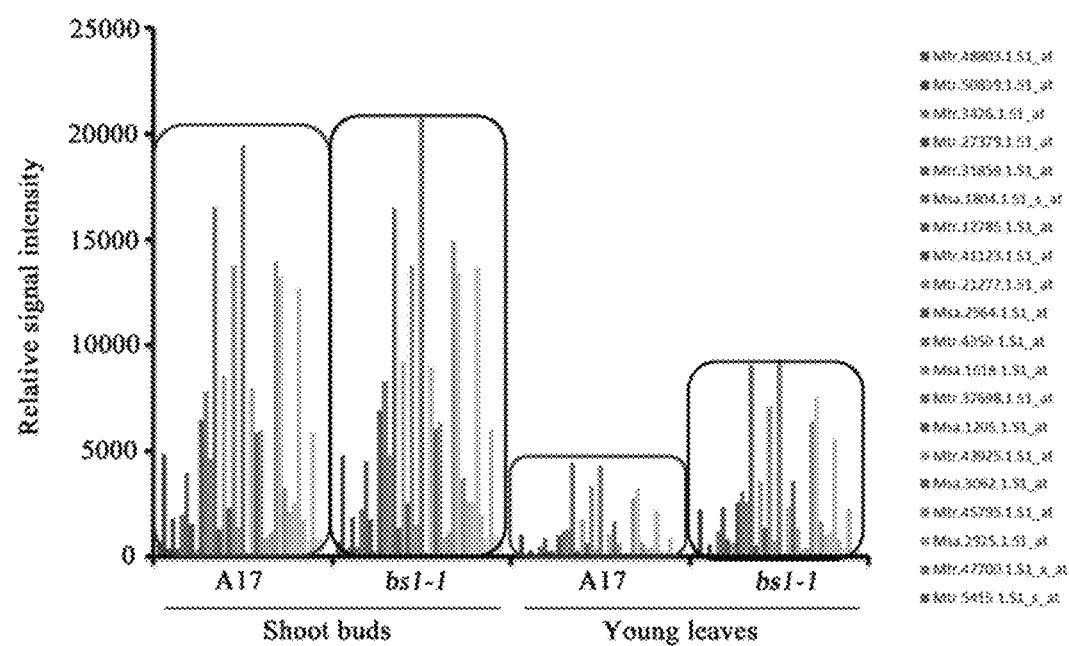
FIG. 14: Shows transcript profile analysis of cell cycle-related genes in the bs1-1 mutant. Microarray-based expression profiling analysis of cell cycle-related genes in vegetative shoot buds and young leaves of wild-type and bs1-1 mutant. Downregulation of cell cycle genes as indicated by the relative signal intensity was significantly less promoted in young leaves of the bs1-1 mutant than were in wild-type plants.

Comparisons of transcript levels between shoot buds and young leaves show that the expression of CCC genes was dramatically downregulated in leaf tissues of both wild-type and the bs1 mutant plants (FIG. 12). However, the downregulation of CCC genes was significantly less in the bs1 mutant than in wild-type plants (FIG. 14), indicating an insufficient suppression of CCC gene expression in expanding leaves of the bs1 mutant.

The expression levels of all known organ size regulatory genes from the transcript profiling data were examined. Interestingly, five probesets related to cell proliferation were most significantly upregulated in bs1 leaves, three of which were also upregulated in bs1 shoot buds, compared with wild-type plants (Table 4). These microarray probesets are related to *Arabidopsis* Growth Regulating Factor5 (GRF5) and GRF-Interacting Factor1 (GIF1, also known as ANGUSTIFOLIA3 or AN3). GRF5 and GIF1 are interacting transcription factor and co-activator, respectively; and, AN3 is known to regulate transcription of GRF5 (Horiguchi et al., *Plant J* 43:68-78, 2005; Kim et al., *Proc Natl Acad Sci USA* 101:13374-13379, 2004; Vercruyssen et al., *Plant Cell* 26:210-229, 2014; Kawade et al., *Curr Biol* 23:788-792, 2013; Horiguchi et al., *Plant Cell Physiol* 52:112-124, 2011). Overexpression of either gene increases leaf size and alters leaf shape, resembling the bs1 leaf phenotypes.

Using the available *Medicago* sequence (Mt4.0v1) (Young et al., *Nature*, 2011), two GRF5 probesets were mapped to Medtr8g020560 (MtGRF5) and one GIF1 probeset to Medtr1g080590 (MtGIF1; Table 4). Quantitative RT-PCR confirms that MtGRF5 and MtGIF1 were significantly upregulated in leaves of the bs1-1 mutant compared with wild-type plants (FIG. 13b).

TABLE 3

Upregulation of core cell cycle genes in the bs1 mutant.

| | Fold changes (bs1/A17) | | | *Arabidopsis* homologs | |
| --- | --- | --- | --- | --- | --- |
| Probesets | Shoot buds | Young leaves | Medicago gene | Locus | Gene |
| Mtr.27379.1.S1_at | 1.05 | 2.02 | AC235748_1029.1 | At5g43080.1 | CYCA3;1 |
| Mtr.29458.1.S1_at | 1.02 | 1.68 | AC235748_1029.1 | At5g43080.1 | CYCA3;1 |
| Mtr.5292.1.S1_at | 1.05 | 1.79 | contig__57417_1.1 | At5g43080.1 | CYCA3;1 |
| Mtr.31859.1.S1_at | 1.14 | 2.39 | | At1g16330.1 | CYCB3;1 |
| Msa.1804.1.S1_s_at | 1.12 | 2.52 | | At4g34160.1 | CYCD3;1 |
| Mtr.12785.1.S1_at | 1.15 | 2.63 | contig__83623_1.1 | At4g34160.1 | CYCD3;1 |
| Msa.913.1.S1_at | 1.05 | 1.62 | contig__85803_1.1 | At3g54180.1 | CDKB1;1 |
| Mtr.38989.1.S1_at | 0.97 | 1.81 | contig__85803_1.1 | At3g54180.1 | CDKB1;1 |
| Mtr.27402.1.S1_at | 1.10 | 1.53 | Medtr1g011470.1 | At5g11300.1 | CYCA2;2 |
| Mtr.50839.1.S1_at | 0.98 | 2.14 | Medtr1g075610.1 | At1g20930.1 | CDKB2;2 |
| Mtr.32437.1.S1_at | 1.02 | 1.58 | | At2g36010.3 | E2Fa |
| Mtr.3426.1.S1_at | 1.11 | 2.11 | Medtr2g102530.1 | At1g15570.1 | CYCA2;3 |
| Mtr.41123.1.S1_at | 1.14 | 3.11 | Medtr3g102310.1 | At3g50070.1 | CYCD3;3 |
| Mtr.11388.1.S1_at | 1.10 | 1.80 | Medtr4g052000.1 | At5g22220.1 | E2Fb |
| Mtr.42269.1.S1_at | 1.13 | 1.70 | | At5g22220.1 | E2Fb |
| Mtr.16199.1.S1_at | 0.82 | 1.51 | Medtr4g086450.1 | At1g49620.1 | KRP7 |
| Mtr.17064.1.S1_s_at | 1.12 | 2.12 | Medtr4g106540.2 | At3g48160.2 | DEL1 |
| Mtr.21277.1.S1_at | 0.78 | 2.32 | Medtr5g015670.1 | At4g37630.1 | CYCD5;1 |
| Msa.3007.1.S1_at | 1.13 | 1.60 | Medtr5g023790.1 | At1g20610.1 | CYCB2;3 |
| Mtr.32176.1.S1_at | 1.08 | 1.83 | Medtr5g088980.1 | At3g11520.1 | CYCB1;3 |
| Mtr.4712.1.S1_s_at | 1.05 | 1.79 | Medtr7g089080.1 | At5g06150.1 | CYCB1;2 |
| Mtr.31360.1.S1_at | 1.05 | 1.79 | Medtr7g089080.1 | At5g06150.1 | CYCB1;2 |
| Mtr.24738.1.S1_at | 1.03 | 1.98 | Medtr8g074000.1 | At4g35620.1 | CYCB2;2 |
| Mtr.32067.1.S1_s_at | 0.94 | 1.51 | | At4g35620.1 | CYCB2;2 |
| Mtr.31170.1.S1_at | 1.10 | 1.61 | | At1g76310.1 | CYCB2;4 |
| Mtr.33796.1.S1_at | 1.11 | 1.64 | | At1g76310.1 | CYCB2;4 |
| Mtr.33796.1.S1_s_at | 1.04 | 1.77 | | At1g76310.1 | CYCB2;4 |
| Mtr.39505.1.S1_at | 1.07 | 1.99 | Medtr8g095930.1 | At1g44110.1 | CYCA1;1 |

TABLE 4

Upregulation of organ size regulatory genes in the bs1 mutant.

| Probesets | Fold Changes (bs1/A17) | | Medicago gene | Arabidopsis homolog | |
| --- | --- | --- | --- | --- | --- |
| | Shoot buds | Young leaves | | Locus | Gene |
| Mtr.29046.1.S1_at | 1.765826218 | 31.91493284 | Medtr1g080590.1 | At5g28640.1 | GIF1 |
| Mtr.50542.1.S1_at | 3.440737167 | 11.289024 | Medtr8g020550.1 | At3g13960.1 | GRF5 |
| Mtr.39218.1.S1_at | 1.481458133 | 10.1833997 | | At5g28640.1 | GIF1 |
| Mtr.50543.1.S1_at | 3.286545681 | 7.359077706 | Medtr8g020560.1 | At3g13960.1 | GRF5 |
| Mtr.13651.1.S1_at | 0.937787251 | 4.382843705 | contig_237721_1.1 | At3g13960.1 | GRF5 |

Example 9

Plasmids and Plant Transformation

BS1 promoter was cloned into the SacI and NcoI sites of pCAMBIA3301 to generate the BS1pro::uidA reporter construct. To generate the complementation construct, the uidA (GUS) reporter gene was replaced by the BS1 cDNA at the NcoI and BstEII sites. To generate the BS1 overexpression construct, the BS1 cDNA without the stop codon was first cloned into pENTRY-D (Invitrogen), according to the manufacture's instructions, and then was cloned into the pMDC83 gateway destination vector, using LR reaction. To silence soybean BS1 orthologs, an artificial microRNA (pre-amiR) was designed to target both GmBS1 and GmBS2, using Web MicroRNA Designer (WMD, available at wmd3.weigelworld.org/cgi-bin/webapp.cgi). The soybean native microRNA319 backbone was used to generate pre-amiR. Using overlapping PCR, pre-amiR was generated and cloned into the pTF101 vector (Paz et al., Plant Cell Rep 25:206-213, 2006). To generate BS1 and PPD2 yeast two hybrid bait constructs, BS1 and PPD2 cDNAs were cloned into the NdeI and SalI sites of pGBKT7 vector. To generate the M. truncatula MYC2 prey construct, MtMYC2 cDNA was cloned into the NdeI and BamHI sites of pGADT7 vector. To generate the bait constructs for M. truncatula JAZ3 and JAZ3-JAZ domain, the full-length CDS and the JAZ domain of MtJAZ3 were first cloned into pENTRY-D (Invitrogen), and then cloned into the pGBKT7-GATEWAY vector, using LR reactions. M. truncatula NINJA and Arabidopsis MYC2 prey constructs were cloned into the pGADT7-GATEWAY vector, using the gateway cloning strategy. Medicago (R108), soybean (G. max cv. Williams 82) and Arabidopsis (Columbia-0) were transformed as previously described (Paz et al., Plant Cell Rep 25:206-213, 2006; Wang et al., Plant Physiol 146:1759-1772, 2008). Primers used in this study are listed in Table 5.

TABLE 5

List of primers (SEQ ID NOs: 1-68).

| Name | Sequence | Usage |
| --- | --- | --- |
| BS1-F | CACCATGAACGGCGGAAGCACCG | Genotyping and cloning |
| BS1-R | CTAGTCTCAGGTTTTAGCATTC | Genotyping and cloning |
| BS1 Deletion Border-F | CTTCTTGGGACATGCTGTGCAGCCT | Amplification of deletion border |
| BS1 Deletion Border-R | TTTCCGTGGGTCTCTCAGCAACAGGT | Amplification of deletion border |
| BS1 N Terminal-R | TCTTGCCCTTCGATCTTCCC | Amplification of genomic sequence |
| BS1 C Terminal-F | CTTGAAAAGCGAAAGGACAGG | Amplification of genomic sequence |
| PPD-Deletion-F1 | TGTTCTGATATCTACAGGTCAC | Genotyping |
| PPD-Deletion-R1 | GAAGATGATCTTCGATCACACG | Genotyping |
| PPD-Deletion-F2 | GATTCTCCAAGATCAGCTGAG | Genotyping |
| PPD-Deletion-R2 | GTAACTGATTTATCGTTCACTAGC | Genotyping |
| AN3-Deletion-F1 | ATAACACACACACAGAGATACAC | Genotyping |
| AN3-Deletion-R1 | ACCTGTTGGATATGATCAGAGG | Genotyping |
| AN3-Deletion-F2 | AGCAACAAGCGACTCAACAGC | Genotyping |
| AN3-Deletion-R2 | CTACTTCTTCTGCTGCTGCTG | Genotyping |
| BS1 Tail1 | TCTCTCAGCAACAGGTGAAGTGG | Tail PCR |

TABLE 5-continued

List of primers (SEQ ID NOs: 1-68).

| Name | Sequence | Usage |
|---|---|---|
| BS1 Tail2 | GTTCCAAAGCAGTATCTTCGGG | Tail PCR |
| BS1 Tail3 | GGGATATCATCGTCGGTAGG | Tail PCR |
| BS1 Promoter-Tail1 | GAGTTGGTTAAGAGGTCTGTCGAGG | Tail PCR |
| BS1 Promoter-Tail2 | GGAAACGGTGCTTCCGCCGTTC | Tail PCR |
| BS1 Promoter-Tail3 | AGTGTTGTGTATGATTCACCAAGG | Tail PCR |
| BS1 Promoter-Tail4 | GATGGGTTTCTTGTACTTCAAACC | Tail PCR |
| MtACTIN-Q-F | GCAGATGCTGAGGATATTCAACC | qRT-PCR |
| MtACTIN-Q-R | CTTCGTCACCAACATAGGCATCC | qRT-PCR |
| MtGRF5-Q-F | GAACACCTATTCCACCAGATCT | qRT-PCR |
| MtGRF5-Q-R | CAGTACTTTGAGTCTGGATATGCT | qRT-PCR |
| MtAN3-Q-F | GTGCTGAGAACCAATCAAGGCT | qRT-PCR |
| MtAN3-Q-R | CTGCTGTTGAAGCTGTTGAGCAT | qRT-PCR |
| MtH4-Q-F | AAGGGTGGTGCAAAGCGTCATCGC | qRT-PCR |
| MtH4-Q-R | TGTTCAGTGTAAGTGACAGCATCACG | qRT-PCR |
| MtCYCD;3 QRT-F | TCTTGGATGGAAGATGAATCCAGC | qRT-PCR |
| MtCYCD;3 QRT-R | ACATGAACCATTGTAGCAGTTGCC | qRT-PCR |
| MtCYCD;1 QRT-F | GGGAAGACGATGATAATGATGATGAAGG | qRT-PCR |
| MtCYCD;1 QRT-R | GAGTCAAAGTTCATCACATTTTTCAGATCG | qRT-PCR |
| GmGIG1-QRT-F | CCTCAAAGAAAAAGGGATGCG | qRT-PCR |
| GmGIG1-QRT-R | CAGATTTCTGAATGTCTTCAGC | qRT-PCR |
| GmGIG-QRT-F | CCTTCCGACGATGATACTCC | qRT-PCR |
| GmGIG-QRT-R | GTCATTTGCCCAAATGATCCAC | qRT-PCR |
| GmACTIN-QRT-F | ACTGGAATGGTGAAGGCAGG | qRT-PCR |
| GmACTIN-QRT-R | CATTGTAAAATGTGTGATGCCAG | qRT-PCR |
| GmGIF1-1-QRT-F | TGCCTACTACCCCAACAACG | qRT-PCR |
| GmGIF1-1-QRT-R | GTCCACTAGAAGGATACTGACC | qRT-PCR |
| GmH4 QRT-F | AGGGTATCACGAAACCTGCG | qRT-PCR |
| GmH4 QRT-R | TCCAAAACCGTAGAGGGTCC | qRT-PCR |
| GmCYCD3 QRT-F | GTGAATTTGACCAAGCAGAGG | qRT-PCR |
| GmCYCD3 QRT-R | CACTCCACGGCTTCTATGCG | qRT-PCR |
| MtJAZ3-F | CACCATGCAGTGGTCATTTTCAAATAAGG | Construct |
| MtJAZ3-R | TCTAATCACTTCCATACATGTTCTTC | Construct |
| MtJAZ3 JAZ domain-F | CACCATGCCAAGGGGAGGTTCAAGTAGC | Construct |
| MtMYC2-F | CACCATGAATCTTTGGAGCGACGATAACTC | Construct |
| MtMYC2-R | TTGAACATCCCCGACTTTAGAGG | Construct |
| MtNINJA-F | CACCATGGAGGACGATAGCGGGCTTG | Construct |
| MtNINJA-R | ACTGTGAGAAGAGGAACCAAGATTACC | Construct |
| MYC2-F | CACCATGACTGATTACCGGCTACAACC | Construct |

TABLE 5-continued

List of primers (SEQ ID NOs: 1-68).

| Name | Sequence | Usage |
|---|---|---|
| MYC2-R | ACCGATTTTTGAAATCAAACTTGCTC | Construct |
| Gm319A-F | TTTCGGATCCTTTACTAGTACTACCCCACC | Construct |
| Gm319A-R | TTTCCTGCAGCTAAAACATTCCTCCAACTGTG | Construct |
| aMiGmBS-R1 | GATATCGTTGCGGTGACACGTTTACCTTAGGGTCTTCAACG | Construct |
| aMiGmBS-F1 | GGTAAACGTGTCACCGCAACGATATCTCATGGGTGACAGTAAGATTC | Construct |
| aMiGmBS-R2 | AAGTGTCATTGCAACGATATAGTACAGGAAACTTAAGATTCAATTTG | Construct |
| aMiGmBS-F2 | TATATCGTTGCAATGACACTTTTTTCCTTTTGTCTCTTACTTCTTC | Construct |
| GIF1 Promoter Frag-A-F | GTATGACTCGTCACGTGACC | CHIP-PCR |
| GIF1 Promoter Frag-A-R | TCTGTCTCTCTCTCTTTCCTC | CHIP-PCR |
| GIF1 Promoter Frag-B-F | GTTCTAGGGAACTAGTTATGCC | CHIP-PCR |
| GIF1 Promoter Frag-B-R | GAGAGGTCACATCTAGATGCG | CHIP-PCR |
| GIF1 Promoter Frag-C-F | GCATAGAAACACTATTGGTTTGG | CHIP-PCR |
| GIF1 Promoter Frag-C-R | GTTAAACCCTCTTGTAGATGTGG | CHIP-PCR |
| GIF1 Promoter Frag-D-F | AGTAAAATGTATACGATACAACAC | CHIP-PCR |
| GIF1 Promoter Frag-D-R | CTTTTAAAGACCGCTTCTGTCC | CHIP-PCR |

Example 10

BS1 Orthologs in *Arabidopsis*

The extent of functional conservation of BS1/GRF5/AN3 in *A. thaliana* was evaluated. BS1 is related to two tandem-repeat genes, At4g14713 (PPD1) and At4g14720 (PPD2) in *Arabidopsis*. In ppd1 ppd2 deletion mutant (Δppd), leaves are dome-shaped and larger than wild-type (FIG. 15a) (White et al., *Proc Natl Acad Sci USA* 103, 13238-13243, 2006). Siliques of the Δppd mutant were wider at the top and shorter in length than wild-type siliques (FIG. 15b, c, h) (White et al., *Proc Natl Acad Sci USA* 103, 13238-13243, 2006). However, the seed size was normal in the Δppd mutant, suggesting partially diverged function of PPD genes in reproductive development in *Arabidopsis*. Single ppd mutants displayed weaker phenotypes than the double deletion mutant due to a functional redundancy (FIG. 16a, b). Overexpression of the *Medicago* BS1 gene (35S::BS1) rescued the phenotypes of Δppd and ppd2 mutants (FIG. 16a-d), confirming that BS1 and PPDs are functional orthologs. PPDs have been reported to play a role in secondary cell cycle arrest by negatively regulating proliferation of dispersed meristematic cells (DMCs) in leaves. By contrast, GRF5 and GIF1 (AN3) are known to play a role in primary cell cycle arrest in *Arabidopsis* leaves (Horiguchi et al., *Plant J* 43:68-78, 2005; Kim et al., *Proc Natl Acad Sci USA* 101:13374-13379, 2004).

Example 11

Complementation Analysis in *Arabidopsis*

To further examine the role of PPDs, the AN3pro::uidA reporter was introduced into the Δppd mutant by crossing. Histochemical staining shows that the GUS activity was greatly upregulated in siliques of the Δppd mutant, compared with that of wild-type plants (FIG. 15i-l). Furthermore, the silique and leaf phenotypes of the Δppd mutant was restored to wild type- and an3-like phenotypes, respectively, in Δppd an3 double mutant (FIG. 15a-c, h); the epistatic interaction confirms that AN3 (GIF1) acts downstream of PPDs in controlling leaf expansion and silique shape. These results demonstrate a novel and conserved role of BS1/PPDs in regulating lateral organ size and shape in *Medicago* and *Arabidopsis* through negatively regulating AN3 expression.

Example 12

Evaluation of BS1 Protein Interactions

As a group II member of the TIFY family of proteins, BS1 and its orthologs do not contain DNA-binding domains. Some TIFY family members are known to interact with the adaptor protein, NINJA, which, in turn, interacts with the transcription co-repressors, TOPLESS (TPL) and TOPLESS-RELATED PROTEINs (TPRs), via its ERF-associated amphiphilic repressor (EAR) domain (Cuellar Perez et al., *PLoS One* 9:e84891, 2014; Pauwels et al., *Nature* 464:788-791, 2010).

Bait and prey constructs were co-transformed into the yeast two hybrid strain GOLD (Clontech), using Frozen-EZ Yeast Transformation II Kit (Zymo Research). Protein-protein interactions were tested on the SD medium containing X-a-Gal (40 ng/ml) and Aureobasidin A (125 ng/ml), without leucine, tryptophan, adenine and histidine.

Figure 15:
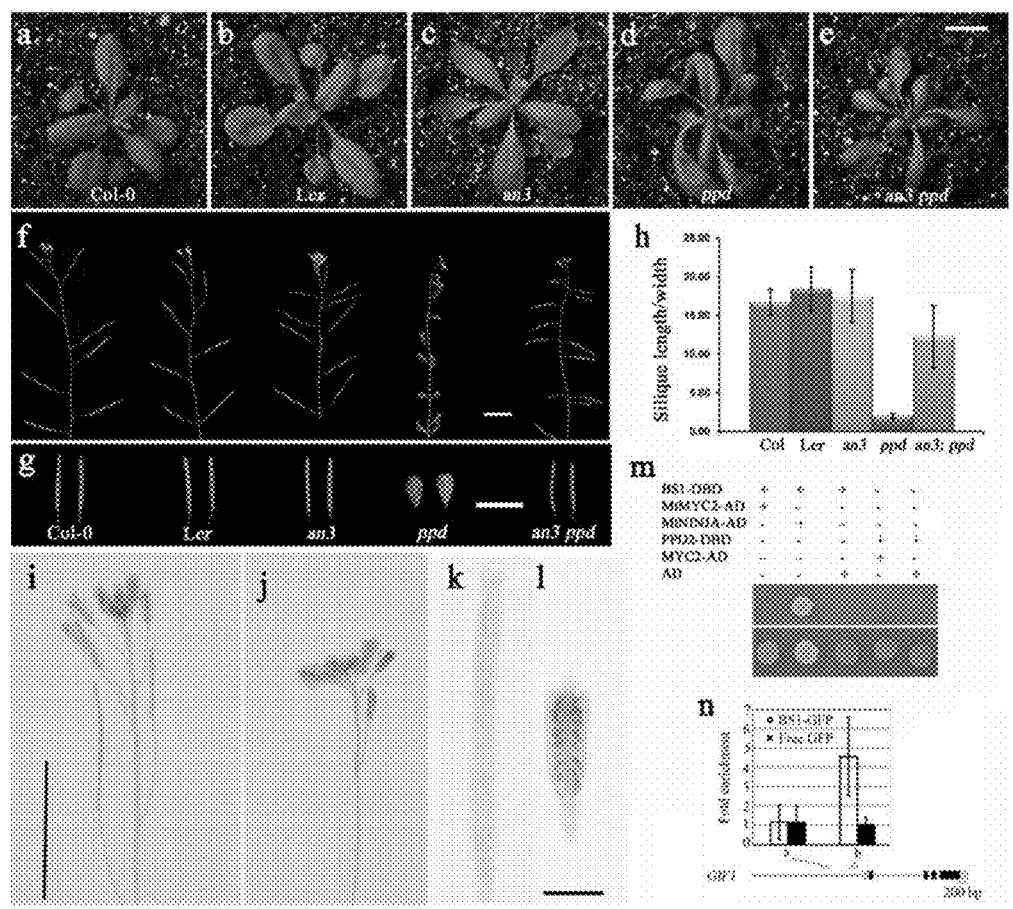
FIG. 15: Shows a conserved function of BS1/PPD in lateral organ development through negative regulation of AN3 (GIF1) gene expression. a-e, Three week-old wild-type (Col-0 and Ler), an3/gif1, Δppd and an3 Δppd mutants, showing epistatic interactions of an3 and ppd. f, Silique phenotypes of the Δppd mutant were largely restored to the wild-type level in an3 Δppd double mutant. g, Close-up views of siliques of wild-type plants and an3/gif1, Δppd and an3 Δppd mutants. h, Measurements of silique length and width ratios. Data are shown as means±s.d. for n=20. i-l, Histochemical analysis of GIF1pro::uidA reporter activities in wild-type plants (i, k) and Δppd mutant (j, l), showing higher reporter activities in expanding siliques of the Δppd mutant than wild-type plants. k, l, Close-up views of GIF1pro::uidA reporter activities in expanding siliques and seeds of wild-type and the Δppd mutant. m, Yeast one-hybrid assays. Shown are interactions between *Medicago* BS1 and NINJA, but not with MYC2. Similarly, *Arabidopsis* PPD did not interact with MYC2. n, Chromatin immunoprecipitation coupled with quantitative PCR (ChIP-qPCR) shows enrichment of GIF1/AN3 promoter sequences in BS1-GFP chromatin samples. *Arabidopsis* plants that overexpress BS1-GFP (35S::BS1-GFP) and free GFP (35S::GFP) were used. Shown are means±s.d. for n=3.
Figure 16:
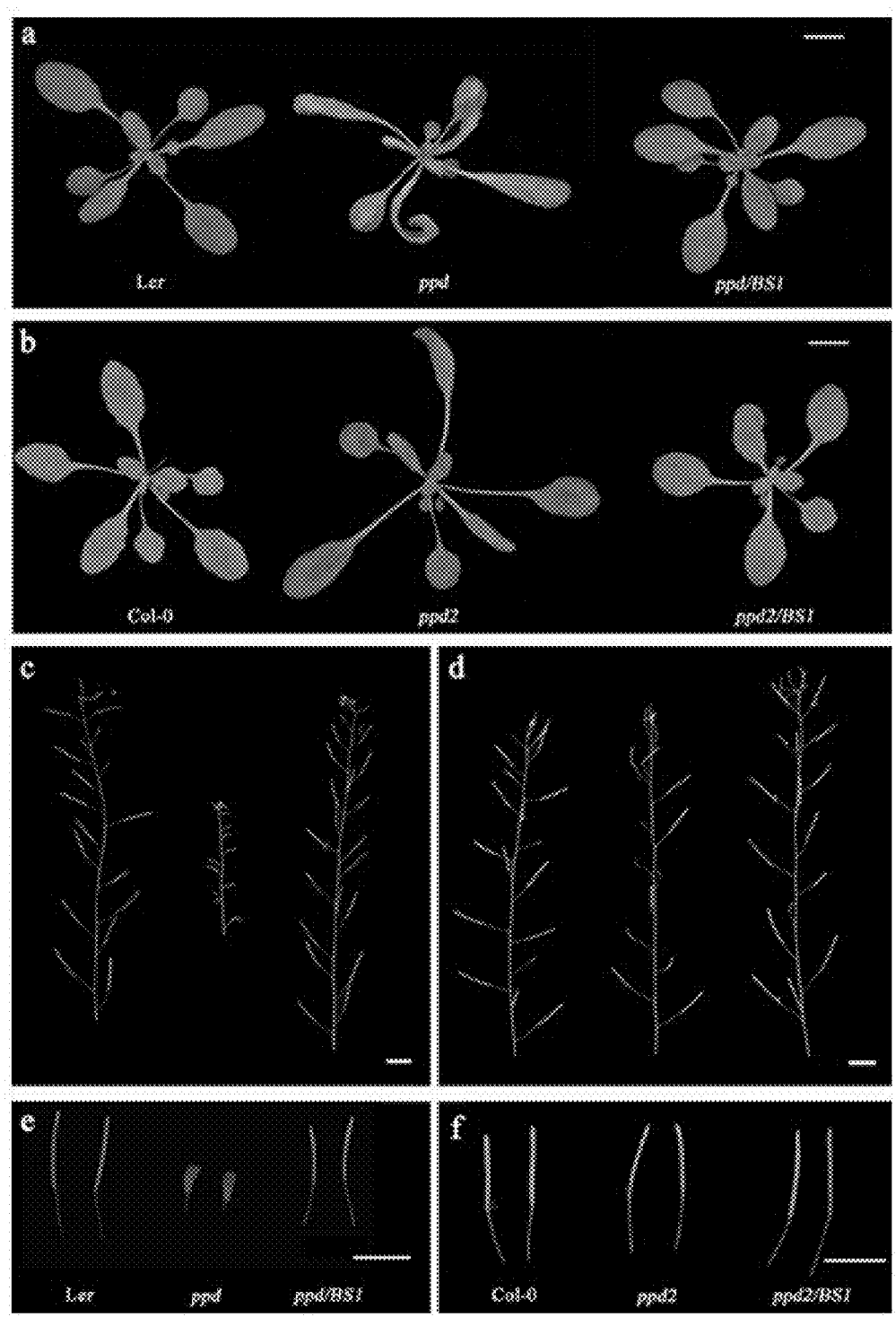
FIG. 16: Shows functional complementation of *Arabidopsis* ppd mutants by *Medicago* BS1 gene. *Arabidopsis* ppd (ppd1 ppd2 double) and ppd2 single mutants were transformed with 35S::BS1. a, b, Representative images of wild type (Ler and Col-0), ppd, ppd/BS1, ppd2 and ppd2/BS1 plants. c, d, Representative images of inflorescence stems of wild type (Ler and Col-0), ppd, ppd/BS1, ppd2 and ppd2/BS1. e, f, Close-up views of siliques. Scale bars, 1 cm.
Figure 17:
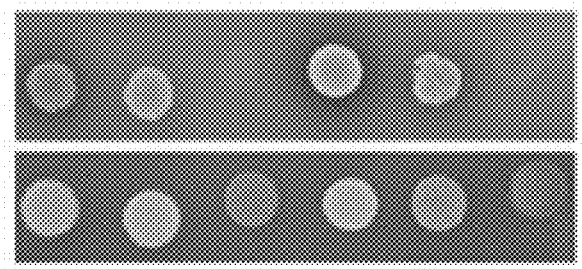
FIG. 17: Shows yeast two-hybrid assays. Shown are interactions between *Medicago* JAZ3 and MYC2, and NINJA, but not with the empty vector. The JAZ domain of the *Medicago* JAZ3 protein is sufficient for the interactions.

Using yeast two-hybrid assays, we show that BS1 interacted strongly with NINJA, but not with MYC2, a transcription factor involved in jasmonic acid (JA) signaling25 (FIG. 15m). Similarly, PPD2 also did not interact with MYC2 (FIG. 15m). As a control, *Medicago* JAZ3 was shown to interact strongly with both MYC2 and NINJA via its JAZ domain (FIG. 17). These results suggest that BS1/PPD forms a repressor complex with NINJA and TPL to negatively control expression of specific downstream targets such as GIF1 (AN3)18. To confirm this in vivo, chromatin immunoprecipitation coupled was performed with quantitative PCR (ChIP-qPCR), using *Arabidopsis* plants overexpressing BS1-GFP. Because 35S::BS1-GFP completely rescued the Δppd mutant phenotypes, this suggests that the fusion protein is functional. ChIP-qPCR results show that GIF1 (AN3) promoter sequences were specifically enriched in the BS1-GFP chromatin (FIG. 15n), supporting that GIF1 (AN3) is a direct downstream target of BS1.

Example 13

Downregulation of BS1 in Soybean

Figure 18:
FIG. 18: Shows artificial microRNA (amiR) targeting GmBS1 and GmBS2. A (SEQ ID NOs:174-175), B (SEQ ID NOs:176-177), amiR targeting the soybean BS orthologs GmBS1 (A) and GmBS2 (B) was designed using the MicroRNA Designer. Shown are the microRNA and its target sequences of the GmBS1 and GmBS2 genes, and the associated hybridization energy. C, D, Native soybean miR319 backbone was used for the construction of amiR-GmBS by replacing the miR319 sequence with the designed microRNA sequence (underlined). The secondary structures of the native soybean miR319 backbone and amiR-GmBS were generated by the mfold Server.
Figure 19:
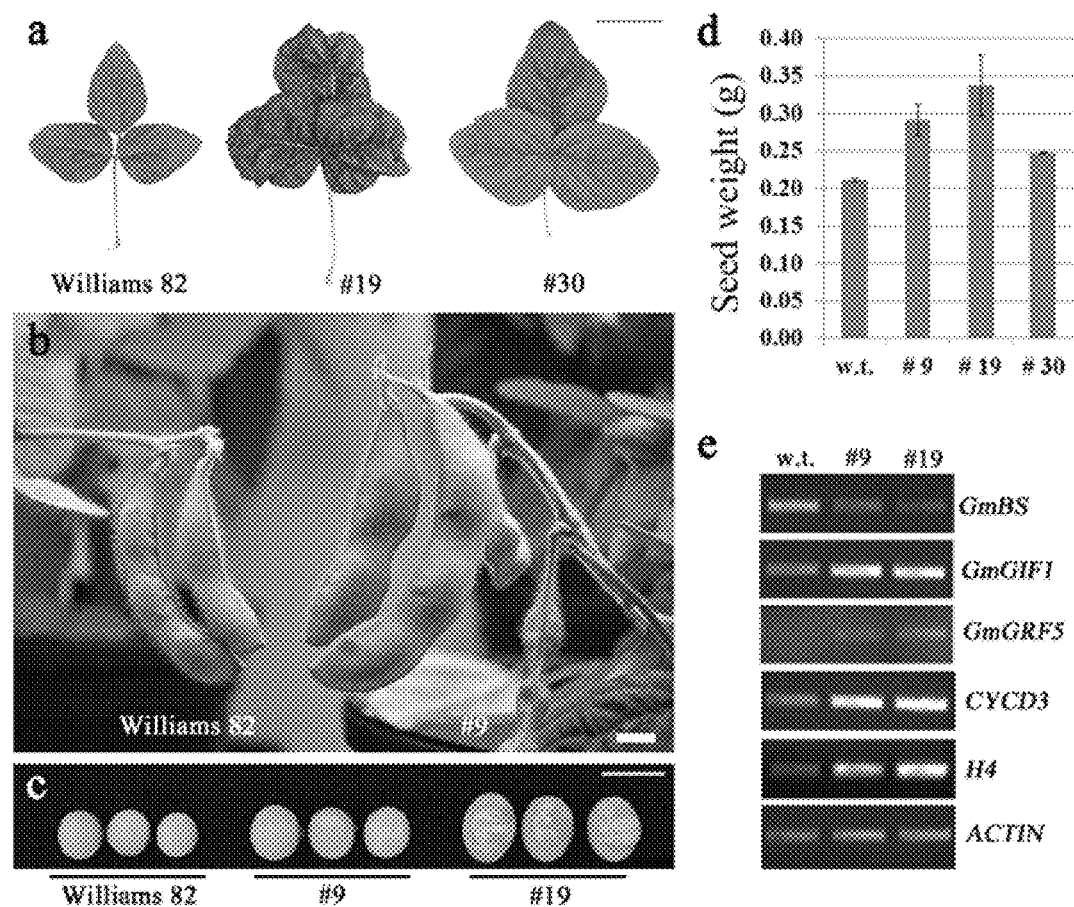
FIG. 19: Shows that soybean BS1 orthologs negatively regulate lateral organ growth. a-c, Representative images of leaves (a), seed pods (b), and seeds (c) of wild type (Williams 82) and transgenic soybean lines that overexpress an artificial microRNA targeting a highly conserved coding sequence of the soybean BS1 orthologs, GmBS1 and GmBS2, showing enlarged leaves, seed pods, and seeds. (d). Measurements of seed weights (grams). (e), RT-PCR analysis of gene expression in young leaves, showing that GmBS genes were greatly downregulated in independent transgenic lines (#9 and #19), compared with wild type. On the other hand, the expression of soybean GIF1, GRF5, CYCD3 and HISTONE4 (H4) genes was greatly upregulated in the transgenic lines. A soybean ACTIN gene was used as the internal loading control. Scale bars, 10 cm for a, 1 cm for b, c.

Because of the functional conservation seen in *Medicago* and *Arabidopsis*, downregulation of BS1 orthologs in soybean (*G. max* cv. Williams 82) was attempted. Based on genome syntenies and sequence similarities, we isolated two soybean BS1 orthologs named GmBS1 (Glyma10g38970) and GmBS2 (Glyma20g28840) (FIG. 9l). To downregulate their expression, an artificial microRNA was designed to target a highly conserved coding sequence of GmBS1 and GmBS2 (FIG. 18). RT-PCR analyses show that GmBS gene expression was significantly downregulated in three out of five independent transgenic soybean plants transformed with the artificial microRNA under the control of 35S promoter (35S::pre-amiR). Consistent with this, these transgenic plants (lines #9, #19 and #30) displayed dramatically increased sizes and weights of seeds, seed pods and leaves compared with wild-type plants (FIG. 18). Gene expression analysis shows that soybean GRF5, AN3, and several cell cycle-related genes such as CYCD3 and HISTONE4 were all upregulated in the transgenic plants, similar to the bs1 mutants (FIG. 19).

Taken together, the results show that downregulation of the soybean BS1 orthologues results in plants with significantly enlarged lateral organs, including seeds, seed pods and leaves similar to the *Medicago* bs1 mutants, confirming a conserved molecular mechanism in controlling plant organ size and shape in multiple species. In addition, our work presents an effective strategy to increase soybean seed yield. Soybean is a major crop worldwide. Identification of the BS1/AN3/GRF5 module in the control of plant organ size from multiple species provides novel opportunities to develop an optimal strategy for improving crop yield.

Example 14

Seed Amino Acid Contents of Wild Type and Transgenic Soybean Lines

Figure 20:
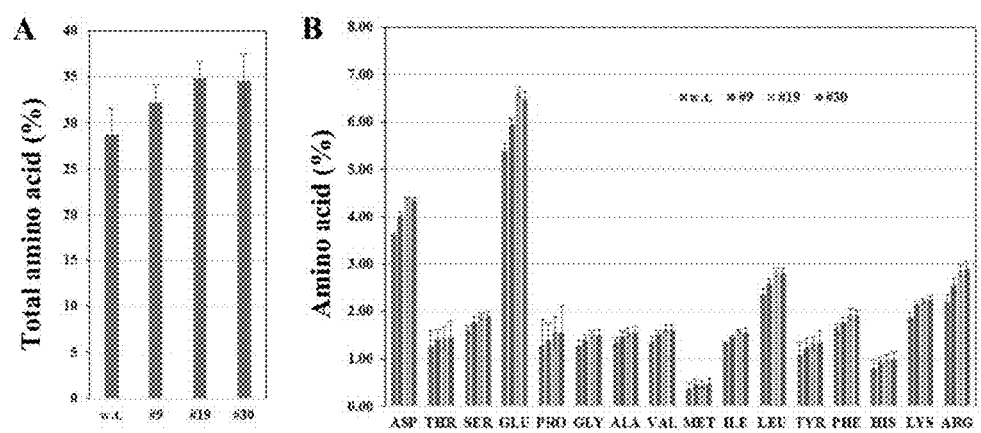
FIG. 20: Measurements of seed amino acid contents in wild type and three independent transgenic soybean lines. A. Total seed amino acid contents (%; w/w) of wild type (w.t.) and the transgenic lines (#9, #19 and #30). B. Seed amino acid contents (%; w/w) of wild type and three transgenic lines. Five biological replicates were measured. Shown are means±s.d.

The amino acid content of dried soybean seeds from wild type (w.t.; Williams 82) and the three independent transgenic lines (#9, #19 and #30) in which the BIG SEEDS1 gene is downregulated was measured. For each line, five biological replicates were determined with one seed for each measurements. 16 amino acids (Asp, Thr, Ser, Gly, Pro, Gly, Ala, Val, Met, Ile, Leu, Tyr, Phe, His, Lys and Arg) were measured using a HITACHI L8900 Amino Acid Analyzer (http://www.aaaservicelab.comcastbiz.net/index.html), with proline (Pro) and lysine (Lys) measured as hydroxyproline and hydroxylysine, respectively. No deleterious effects on total amino acid or individual amino acid contents were detected in the transgenic soybean lines when compared with wild type plants (FIG. 20A). The results show, however, that in the transgenic lines #19 and #30, total seed amino acid and individual amino acid contents were significantly increased compared to wild type plants (FIG. 20B; Student's t-test, p<0.05, n=5). In the transgenic line #9, total seed amino acid, and ASP, THR, SER, GLU, PRO, GLY, ALA, VAL, MET, TYR, HIS, LYS and ARG were also increased (FIG. 20B; Student's t-test, p<0.1, n=5) compared to wild type plants.

Example 15

Figure 21:
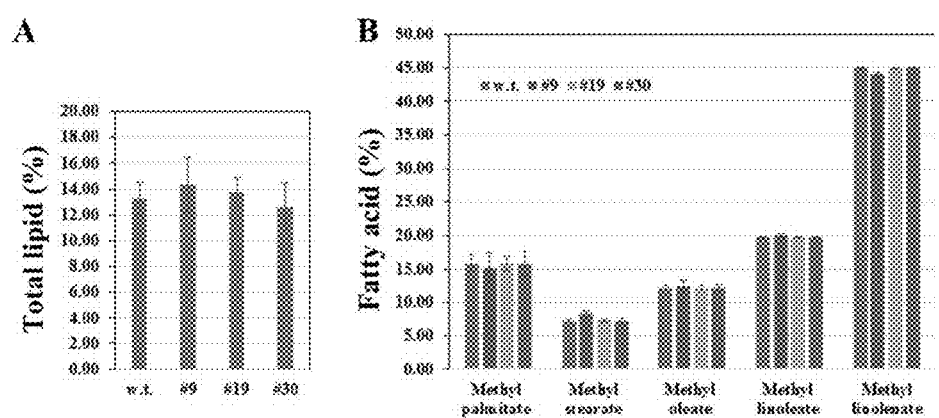
FIG. 21: Measurements of total seed lipid and five major fatty acids in wild type and three independent transgenic soybean lines. A. Total seed lipid contents (%; w/w) of wild type (w.t.) and three transgenic lines (#9, #19 and #30). B. Five major seed fatty acid contents in the total lipid (%; w/w) of wild type (w.t.) and three transgenic lines (#9, #19 and #30). Five biological replicates were measured. Shown are means±s.d.

Seed Amino Acid Contents of Wild Type and Transgenic Soybean Lines Measurements of Seed Lipid Contents of Wild Type and Transgenic Soybean Lines Total seed lipid and fatty aid content was measured of dried soybean seeds from wild type (w.t.; Williams 82) and the three independent transgenic lines (#9, #19 and #30), in which the BIG SEEDS1 gene is downregulated, using GC-MS (gas chromatography-mass spectrometry) by the Noble Foundation Analytical Chemistry Core Facility. Five biological replicates were measured with one seed for each measurements. Five major seed fatty acids were measured as Methyl Palmitate, Methyl Stearate, Methyl Oleate, Methyl Linoleate and Methyl Linolenate, respectively. No deleterious effects on total seed lipid and fatty acid contents were detected in the transgenic lines compared with wild type plants (FIGS. 21A, 21B).

Example 16

Measurements of Leaf Stem Ratios of *Medicago truncatula* bs1 Mutant Plants

Figure 22:
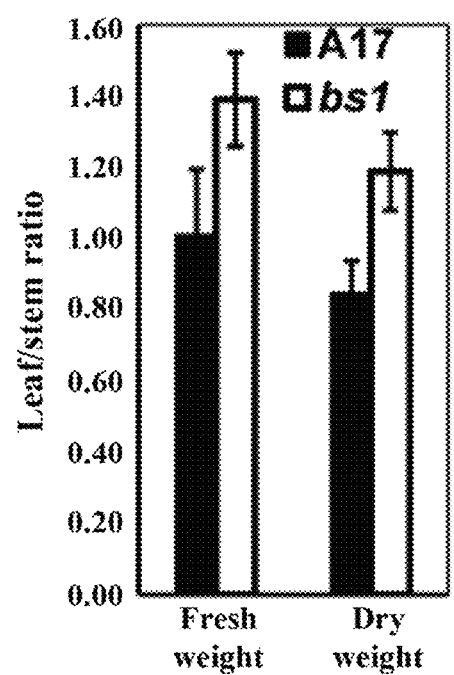
FIG. 22: Measurements of leaf stem ratios of *Medicago truncatula* wild type and bs1 mutant plants. Fresh and dry weights of dissected leaves and stems from two-months-old wild type (A17) and mutant (bs1) plants were determined. Ten biological replicates were measured. Shown are means±s.d.

Forage quality analyses show that mutations of the *Medicago truncatula* BIG SEEDS1 gene significantly increased the forage quality of the mutant plants. To confirm whether this was be due to an increase in the leaf stem ratio of the mutant, the leaf stem ratios of two-months-old wild type (Jemalong A17) and bs1 mutant plants were measured. FIG. 22 shows that the leaf stem ratios based on fresh weights or dry weights were significantly increased in the bs1 mutant compared to wild type plant (Student's t-test, p<0.05, n=10).

Example 17

Identification of Alfalfa (*Medicago sativa*) BIG SEEDS1 Orthologous Sequences and their Use In order to introduce the *Medicago truncatula* bs1 mutant phenotype into alfalfa (*Medicago sativa*) for improvements of its forage quality, a total of three potential alfalfa BIG SEEDS1 orthologous sequences were identified based on their high degree of sequence similarity with the *M. truncatula* BIG SEEDS1 sequence of SEQ ID NO:117, using the available alfalfa genome sequences. These genes are designated as MsBs1 (Table 1; SEQ ID NOs:118, 168 for nucleotide and predicted protein sequences, respectively), MsBS2 (Table 1; SEQ ID NOs:169, 171 for genomic nucleotide and predicted protein sequences, respectively) and MsBS3 (Table 1; SEQ ID NOs:170, 172 for genomic nucleotide and predicted protein sequences, respectively). Expression of MsBs1, MsBS2, and/or MsBS3 may be altered in *M. sativa* to achieve beneficial agronomic qualities such as increased seed yield, increased plant biomass, enhanced forage quality, altered seed amino acid content etc.

What is claimed is:

1. A method of improving forage quality of a forage plant comprising:
   (a) transforming forage plants with an antisense or RNAi construct that targets a BS1 (BIG SEEDS 1) gene to reduce expression of the protein encoded by said BS1 gene of said forage plants, or mutating the BS1 gene of said forage plants using fast neutron bombardment that reduces or eliminates the expression of the protein encoded by the BS1 gene of said forage plants; and
   (b) selecting a transformed or mutated forage plant from step (a), wherein said selected transformed forage plant exhibits said reduced expression of the protein encoded by said BS1 gene, wherein said mutated forage plant exhibits said reduction or elimination of the protein expressed by said BS1 gene, wherein said selected transformed forage plant or said selected mutated forage plant exhibits improved forage quality as compared to a control or wild type plant of the same forage plant species that is not transformed with said construct or does not contain said mutated BS1 gene, wherein said improvement in said forage quality comprises decrease in acid detergent fiber (ADF) and neutral detergent fiber (NDF) as compared to said control or wild type plant of the same forage plant species, and wherein the protein encoded by said BS1 gene in said forage plants has 95% amino acid sequence identity to the amino acid sequence of SEQ ID NO: 167.

2. The method of claim 1, wherein the BS1 gene encodes a protein comprising an amino acid sequence having at least 96% amino acid sequence identity to the amino acid sequence of SEQ ID NO: 167.

3. The method of claim 1, wherein the forage plant is a dicotyledonous plant.

4. The method of claim 3, wherein the dicotyledonous forage plant is *Medicago trunculata* or *Medicago sativa*.

5. The method of claim 1, wherein the selected transformed or mutated forage plant further exhibits increased plant biomass when compared to a control or wild type forage plant of the same forage plant species that is not transformed with said construct or does not contain said mutated BS1 gene.

6. The method of claim 1, wherein the selected transformed or mutated forage plant further exhibits increased seed yield when compared to a control or wild type forage plant of the same forage plant species that is not transformed with said construct or does not contain said mutated BS1 gene.

7. The method of claim 1 further comprising:
   (c) growing said selected transformed forage plant or said selected mutated forage plant of step (b) under plant growth conditions;
   (d) crossing said selected transformed forage plant or said selected mutated forage plant from step (c) with itself or another, distinct forage plant of the same forage plant species to produce progeny forage plants; and
   (e) selecting a transformed progeny forage plant or mutated progeny forage plant from step d) comprising reduced or eliminated expression of the protein encoded by said BS1 gene, wherein said forage progeny plant comprises said improved forage quality when compared to a control or wild type forage plant of the same forage plant species that is not transformed with said construct or does not contain said mutated BS1 gene.

8. The method of claim 1, wherein the BS1 gene encodes a protein comprising an amino acid sequence having at least 97% amino acid sequence identity to the amino acid sequence of SEQ ID NO: 167.

9. The method of claim 7, wherein the BS1 gene encodes a protein comprising an amino acid sequence having at least 96% amino acid sequence identity to the amino acid sequence of SEQ ID NO: 167.

10. The method of claim 7, wherein the BS1 gene encodes a protein comprising an amino acid sequence having at least 97% amino acid sequence identity to the amino acid sequence of SEQ ID NO: 167.

* * * * *

SEQUENCE LISTING

<160> NUMBER OF SEQ ID NOS: 177

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
caccatgaac ggcggaagca ccg                                               23

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ctagtctcag gttttagcat tc                                                22

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
cttcttggga catgctgtgc agcct                                             25

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
tttccgtggg tctctcagca acaggt                                            26

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tcttgccctt cgatcttccc                                                   20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
cttgaaaagc gaaaggacag g                                                 21

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
tgttctgata tctacaggtc ac                                              22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gaagatgatc ttcgatcaca cg                                              22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gattctccaa gatcagctga g                                               21

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gtaactgatt tatcgttcac tagc                                            24

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
ataacacaca cacagagata cac                                             23

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
acctgttgga tatgatcaga gg                                              22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
agcaacaagc gactcaacag c                                               21
```

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctacttcttc tgctgctgct g                                          21

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tctctcagca acaggtgaag tgg                                        23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gttccaaagc agtatcttcg gg                                         22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gggatatcat cgtcggtagg                                            20

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gagttggtta agaggtctgt cgagg                                      25

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ggaaacggtg cttccgccgt tc                                         22

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
agtgttgtgt atgattcacc aagg                                      24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
gatgggtttc ttgtacttca aacc                                      24

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
gcagatgctg aggatattca acc                                       23

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
cttcgtcacc aacataggca tcc                                       23

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gaacacctat tccaccagat ct                                        22

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
cagtactttg agtctggata tgct                                      24

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gtgctgagaa ccaatcaagg ct                                        22

<210> SEQ ID NO 27

```
<211> LENGTH: 23
<212> TYPE: DNA
<213> ORGANISM: Artificial Sequence
<220> FEATURE:
<223> OTHER INFORMATION: Primer

<400> SEQUENCE: 27
ctgctgttga agctgttgag cat                                            23

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
aagggtggtg caaagcgtca tcgc                                           24

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
tgttcagtgt aagtgacagc atcacg                                         26

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
tcttggatgg aagatgaatc cagc                                           24

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
acatgaacca ttgtagcagt tgcc                                           24

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
gggaagacga tgataatgat gatgaagg                                       28

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
```
gagtcaaagt tcatcacatt tttcagatcg                                30

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
cctcaaagaa aagggatgc g                                          21

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
cagatttctg aatgtcttca gc                                        22

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ccttccgacg atgatactcc                                           20

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
gtcatttgcc caaatgatcc ac                                        22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
actggaatgg tgaaggcagg                                           20

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
cattgtaaaa tgtgtgatgc cag                                       23

<210> SEQ ID NO 40
<211> LENGTH: 20
<212> TYPE: DNA

```
<213> ORGANISM: Artificial Sequence
<220> FEATURE:
<223> OTHER INFORMATION: Primer

<400> SEQUENCE: 40
tgcctactac cccaacaacg                                          20

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
gtccactaga aggatactga cc                                       22

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
agggtatcac gaaacctgcg                                          20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
tccaaaaccg tagagggtcc                                          20

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gtgaatttga ccaagcagag g                                        21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cactccacgg cttctatgcg                                          20

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
caccatgcag tggtcatttt caaataagg                                29
```

<210> SEQ ID NO 47
<211> LENGTH: 26
<212> TYPE: DNA
<213> ORGANISM: Artificial Sequence
<220> FEATURE:
<223> OTHER INFORMATION: Primer

<400> SEQUENCE: 47
tctaatcact tccatacatg ttcttc                                          26

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
caccatgcca aggggaggtt caagtagc                                        28

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
caccatgaat ctttggagcg acgataactc                                      30

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
ttgaacatcc ccgactttag agg                                             23

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
caccatggag gacgatagcg ggcttg                                          26

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
actgtgagaa gaggaaccaa gattacc                                         27

<210> SEQ ID NO 53
<211> LENGTH: 27
<212> TYPE: DNA
<213> ORGANISM: Artificial Sequence
<220> FEATURE:

<223> OTHER INFORMATION: Primer

<400> SEQUENCE: 53
caccatgact gattaccggc tacaacc                        27

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
accgattttt gaaatcaaac ttgctc                         26

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
tttcggatcc tttactagta ctaccccacc                     30

<210> SEQ ID NO 56
<211> LENGTH: 32
<212> TYPE: DNA
<213> ORGANISM: Artificial Sequence
<220> FEATURE:
<223> OTHER INFORMATION: Primer

<400> SEQUENCE: 56
tttcctgcag ctaaaacatt cctccaactg tg                  32

<210> SEQ ID NO 57
<211> LENGTH: 41
<212> TYPE: DNA
<213> ORGANISM: Artificial Sequence
<220> FEATURE:
<223> OTHER INFORMATION: Primer

<400> SEQUENCE: 57
gatatcgttg cggtgacacg tttaccttag ggtcttcaac g        41

<210> SEQ ID NO 58
<211> LENGTH: 47
<212> TYPE: DNA
<213> ORGANISM: Artificial Sequence
<220> FEATURE:
<223> OTHER INFORMATION: Primer

<400> SEQUENCE: 58
ggtaaacgtg tcaccgcaac gatatctcat gggtgacagt aagattc  47

<210> SEQ ID NO 59
<211> LENGTH: 47
<212> TYPE: DNA
<213> ORGANISM: Artificial Sequence
<220> FEATURE:
<223> OTHER INFORMATION: Primer

<400> SEQUENCE: 59
aagtgtcatt gcaacgatat agtacaggaa acttaagatt caatttg  47

<210> SEQ ID NO 60
<211> LENGTH: 46
<212> TYPE: DNA
<213> ORGANISM: Artificial Sequence
<220> FEATURE:
<223> OTHER INFORMATION: Primer

<400> SEQUENCE: 60
tatatcgttg caatgacact tttttccttt tgtctcttac ttcttc        46

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gtatgactcg tcacgtgacc        20

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
tctgtctctc tctctttcct c        21

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
gttctaggga actagttatg cc        22

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
gagaggtcac atctagatgc g        21

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
gcatagaaac actattggtt tgg        23

<210> SEQ ID NO 66
<211> LENGTH: 23
<212> TYPE: DNA
<220> FEATURE:
<223> OTHER INFORMATION: Primer

<400> SEQUENCE: 66
gttaaaccct cttgtagatg tgg                                            23

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
agtaaaatgt atacgataca acac                                           24

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
cttttaaaga ccgcttctgt cc                                             22

<210> SEQ ID NO 69
<211> LENGTH: 975
<212> TYPE: DNA
<213> ORGANISM: Arabidopsis lyrata

<400> SEQUENCE: 69
atggatgttg gagtgtctcc ggcgaagtct atacttgaga aacctctgaa actgctcact     60
gaagaggaca tttctcagct tactcgcgaa gattgccgca aattcctcaa agagaaagga    120
atgcgcaggc cttcgtggaa caaatctcag gcgatccaac aagttttatc ccttaaagct    180
ctctacgagc ctggagacga ttccggcgcc ggaatcctcc gcaagatcct cgtttctcag    240
ccgtcaaatc cgcctcgcgt ttcaacaacg ttgattgagc aagcaacga gctcgaagct    300 tgtggcaaga ttctggagga tgacggctcg tgccatagaa gggattctcc aagatcagct    360
gagttttctg gcaattctgg tcagtttgtt gcggataaag atggccacaa gcctgtttcc    420
cccagcagaa gcccagctga acaagtgcg ccggttgggc aaatgacgat attctacagt    480
ggcaaagtga atgtatatga tggagtacca cctaaaaagg cgcggtcaat catgcacttt    540
gcagctaatc caattgattt gcctgaaaat ggtatttttg cttctagtag aatgatttcg    600
aagcccatga gtaaagagaa gatggtggag cctcccccaat atggccttga aaagacagct    660
gcttctcgtg attccgatgt ggagggtcag gcgaacagaa aagtgtcgtt gcaaagatat    720
cttgaaaagc ggaaagacag aagatttttct aagaccaaga aggctccagg agttgcgtcc    780
tctagcttgg agatgtttct gaatcgtcag ccacggatga acgctgcata ttcacaaaac    840
cttagcggca cagggctctg cgagtcacct gaaaatcaaa caaaaagccc gaatctctca    900
gttgatctaa acagtgatct aaacagtgaa ggtatgaaca agcatttgtt aaatggttcc    960
aacgatctcc cttaa                                                    975

<210> SEQ ID NO 70
<211> LENGTH: 939
<212> TYPE: DNA
<213> ORGANISM: Arabidopsis lyrata

<400> SEQUENCE: 70
atggatgtcg gagtttcgtc ggcgaagtct atacttgcga agccactgaa gctactcact     60

```
gaagaagaca tttctcagct cactcgcgaa gactgccgta aattcctcaa agacaaagga      120
atgcgaaggc cttcgtggaa caaatctcag gcgatccagc aagttttatc cctcaaagct      180
ctctttgagc ccggtgacga ttccggcgcc ggtatcctcc gcaagatcca cgtttctcag      240
ccggcaaatc cgcctcgcgt tacaacaact aacgagcttg agagtgtgg ccggaatcct       300 tttcaggaag atgacggccc atgccacaga agggattctc caaaatcagc tgagttttcc      360
ggcggttctg ctcagtatgc agcggagaaa gatacctgca aagcccagc tgaaacgagt       420 gcgctggttg ggcaaatggc gattttctat agtggcaaag tgaatgtgta tgatggagta      480
ccacctgaaa aggcccggtc aattatgcac tttgcagcca atccaattga tttgcctgaa      540
aatggtattt ttgcttcgag tagaatgatt tcaaagcgca taagtaaaga aagatggtg       600 gaacttcccc aaaatggcct tgagaaggcg aattttctc gtgattctga tatggaggt       660 caggcgaaca gaaaggtgtc tttgcaaaga tatcgtgaga agcggaaaga cagaaaattc      720
tcaaaggcta aaagtgtcc aggagttgcg tcctctagct tggagatgtt tctgaatcgt       780
cagccacgga tgaacgctgc atattcacaa aaccttggct gcacaggatc tccactgcaa      840
agcgagtcac ctgaaaacca gacaaaaagt cccaatcttt cagttgatct aaacagtgaa      900
ggtaagaaga gaatcatatg gagagctttg ttaaaatag                             939

<210> SEQ ID NO 71
<211> LENGTH: 939
<212> TYPE: DNA
<213> ORGANISM: Carica papaya

<400> SEQUENCE: 71
atggcggctc acctgacacg tgtcgtcaca ggaatgcgta gaccatcttg gaacaaatcg       60
caggcgatcc agcaagttat ttcccttaag gctctcctcg aaaccaccga tgattccggt      120
gccggagctc ttcgtaagat cctcgttct ccccagaaa cgactcctcg cgtaacttca       180
tctccagttg attcagtgaa ggagttgggt gctggagcc aaatttcccc gcctgcggac      240
gagaatggtc cttaccggcg aaaaagtcct cagaaatctg cagagttggg ttgcaggcca      300
gtaggtgaag cagataccaa aacctcatct cccagaagtc caggagaagc aaatgcgctg      360
gttgggcaga tgaccatttt ttactgtggc aaggtgaatg tgtatgatgg agtgcccct       420 gataaggcac aagcaatcat gcaccttgcc gcaagtccgc tagatttccc tcaagatgac      480
gccattggtg ggaatacagt acctaggtcc tttccgtgcc atttgcagat gagtgacaaa      540
cacgcctttg ttcctcccag tgcagttatc tctcagacaa tgcaaacaga gaaggttctg      600
gaataccctc agcaacaccg ggagaaggga ataacactc gtgagcctga tttagaaggt       660
caagcaaaca gaaaggtgtt attgcagaga tacctcgaaa gcggaaggga caggggaga       720 ttttttaagg ttaaaagag tacaggagta acttcctccg ggttggagat gtatttgagt      780
catcaagtga ggccaaatac ctcaactgga caatcaagtg ggagtggcac aaactctcca      840
ccccaacctg gattgccaca catctcacat agctcagctg acaaccagat aaaacatggc      900
agcttgtctg ttgatcttaa cgacgaaggt acaatgtaa                             939

<210> SEQ ID NO 72
<211> LENGTH: 1008
<212> TYPE: DNA
<213> ORGANISM: Ricinus communis

<400> SEQUENCE: 72
```

```
atggacgccg gagtgacgtc gttcaggtca atactagata aaccccctaac tcagctaact    60
gaagaagaca tttctcaact cacacgcgaa gattgccgca aatacctcaa agaaaaagga   120
atgcgaagac cttcatggaa caaatcgcaa gcgatccagc aagtgatttc tctaaaagca   180
cttcttgaaa ctagtgaaga ttccggtgcc ggtgctctcc gtagaatctt agtttctaaa   240
cctccggtta cttcaaattc tgttgattca gctaaggaac caagtgatag caacaataat   300
aacttactag atgagacagc tcctcatgat tctcccaaat ctcctcctcc ggcgccatcg   360
ttggattgtc cactggaaga ggcagataat aaagtcattt cttcaagaag tcctggtgca   420
acagatgggt tggtcgggca aatgacgatt ttctattgtg gaaaggtgaa tgtttatgat   480
ggagtcccac ccgataaggc ccaggcgatc atgcatcttg cagcgactcc aattcactca   540
cctttagacg atccaattcg tagacctgta tttgcttttc cgtatcattt acagacccca   600
agtgacaaac atgtctttgt tccttctaat gctgcaattt ctccaaccac accaacagag   660
aaggtgacag aatattctca gcagtgtagg gagaaaggaa atgtaactta tgatcatgat   720
gtagagggtc aagcaaaccg aaaaatgtca ttgcagagat atctggagaa gaaaaaggat   780
aggggaagat tcaagggtag gaaaaattta gggcctaatt cgtctagctt ggatgcatat   840
ttgaaccatc aaatgaggac acatatctca aacgagcaat caaccaggag cagtacaagc   900
tctccaaccc agcctggagt gccacatact tcgagtaact cggccgaaga tcagctgaag   960
actgccagtt ttgctgttga tcttaatgaa gatgtccaag aaccttga    1008
```

<210> SEQ ID NO 73
<211> LENGTH: 813
<212> TYPE: DNA
<213> ORGANISM: Ricinus communis

<400> SEQUENCE: 73

```
atgtcgccgg aatctaagac catgcaaacg ggagatataa tttcccggtc aaatctagac    60
aaacctcttc accaactcac tgaagatgac attgctcagc tcactcgcga agattgccgc   120
agatacctca agacaaaagg catgagaagg ccgtcgtgga caaatcgca ggcaatacag   180
caagtcatct ctctcaaagc gctacttgaa acggcgccgg attcaaacga agttcctaaa   240
agaagactct acattcccca tcctcataat gtcccccttc atcatcgcat aacagattgg   300
tcagatcacg cacaagcaat aatgcagctg gctgcatgcc cactctcttt gtctggagat   360
acttcatctg atgcaattcc agcattacgg cccattccga gccagttgga agctccaggt   420
gtcaaaacat ctcttagtcc tatgtttgtc tatccaaccc agcagacagg gaaagtggca   480
gaacactgcc atctgcctaa ggaagaaagc aacttattcc atgaagacaa cctagaaggc   540
cgaacaagta gaaaagcatc agtgcagaga tatcttgaga acgaaaaga caggttcaag   600
aacaagagaa aggtggcaat gccttcttca gacatccact taaaccattg cgtgagagat   660
gagttctcaa atgatcaatg gaatctaacg gaggcatgct ttgctaccca gcccagacca   720
tctcaaacac ctatccaatg cagcactgtt gcttatacag aaaagcatac taatctctct   780
gctgatctca atggcaaagg tgacataggc taa    813
```

<210> SEQ ID NO 74
<211> LENGTH: 1011
<212> TYPE: DNA
<213> ORGANISM: Cucumis sativus

<400> SEQUENCE: 74

```
atgagtgccg gtgcggcgac gttccggtct atactcgaca aaccccctcaa ccagttgacg    60
```

```
gaggatgaca tttcgcagct cactcgagag gattgtcgca atacctaaa  agaaaaagga    120 atgcggcggc cctcttggaa caaatctcag gcgatccagc aggttatttc tcttaaagca    180
ttgcttgagc cttgtgatga ttccggcgcc ggcgctctca ggaaggtcgt cgtttcgcct    240
cggataaatt caaatcaagg tgattcaccc aaagaaccga gtgatgatgc tcaggttaca    300
atgtcagttg atgaatctgc ttatagcaat gtggagactg cgaaatctac tcctgaggat    360
cccccggttg aaccagagaa caatgttact agtcccagag atcaatacga tacaaatgga    420
gtggatggcc aaatgacaat tttctattgt ggcaaggtga atgtgtatga tggagttcca    480
ccagataagg cgtgggcaat catgcatctt gcagctagtc caattcattt ccctcagaat    540
catcccatga gtggaactgc tgcatgtcag tctccaccat gtcttttgca gacttccagt    600
gacagagatg actttcttcc tcctagtgct accatctatc gaaatgtgca cacagagaag    660
ttgggtgagc accctcagca gcagcagcat gcaaagggga ccagtatgcg ggattctgat    720
gttgagggtc aggcgagtcg gaaagtttca ttacagagat atcttgaaaa gcgaaaggac    780
aggggaaggt taaagaacaa gaaaaataca ggattgtctt ctcctagcct ggagggatat    840
atgaaccatc aaatgaggac gcacatatcc aataagaatt taggtcaaat tgtgacgagc    900
tctttatccc caactggagt agcaaaagcc ttcgttggac cagctgacaa tcagccaaaa    960
cttgcatgtt tttctgtcga ccttaatgtc aaagatatcc aggagtgctg a            1011

<210> SEQ ID NO 75
<211> LENGTH: 1002
<212> TYPE: DNA
<213> ORGANISM: Prunus persica

<400> SEQUENCE: 75
atgaacgcca ccacgacgtc gttccgctcc attctcgaga agcccctcaa ccagctcaca    60
gaggacgaca tttctcagct cacccgcgaa gactgccgca atacctcaa  agaaaaagga   120 atgcggaggc cttcgtggaa caaatcgcag gcgatccagc aagttatttc cctcaaggct   180
ctgctggagc ccaacgacga taccggcgcc ggagcgctca gacgattgt  cgtttcgcct   240 cataccacca ccccgcgcgc ggcttcgaat tcagccggtt cggccaagga agcgagtgcc   300
gatgtccagg tttccgtgtc agccgacgaa ccggtgccgt atcagaaacc ggttcaggag   360
gaccggccag ccgatgccga tacgaaggcc atcagtccaa gaaatcagtg tacaactgat   420
gcatcagtta ggcaaatgac aattttctac tgcggcaagg tgaatgtata tgatggagtg   480
ccacctgata aggcacgggc aatcatgcac cttgcagcaa ggcccaacca tttgcctctg   540
gacaatcaat ttggtggtac tgcggcacta agatccttac gatgccaatt tcagactgcc   600
ggagacaaag atggctttct ccctccgagt gccacattct ctcaggccat gcaaacagag   660
aagatcggtg aatatactca gcagtactgg gagaaaggga acagcactcg agatcctgat   720
gcagagggcc aggcaagcag aaaagtctcg tggagagat  atcgtgaaaa gcgaaaggac   780
aggggaagat taaagattaa gaaaaatatt ggatcgagtt ctagcttgga ggtctttttg   840
aatcatcaac ttaggacaca tacctcaaat ggtaattcaa gtcagagtgg cacaagctct   900
ccaccccagc ctgggctgct acaaacagct gacaatcagc caaagagtct gtgtcttccc   960
gttgacctaa atgacaagga tatcctggaa cgccgaactt ga                     1002

<210> SEQ ID NO 76
<211> LENGTH: 1026
<212> TYPE: DNA
```

<213> ORGANISM: Vitis vinifera

<400> SEQUENCE: 76

```
atgtcgccgg agaatgccaa tatccggtca ctgctcgata aaccgcttca ccagctcact      60
gaagacgaca tttctcagct cactcgcgaa gattgccgca aatacctcaa agaaaaagga     120
atgcgaaggc cgtcctggaa caaatctcag gcgatccagc aagtgatctc gctaaagacg     180
cttctcgaaa cgacgtcgga ttgcggcggc ggagatgccg ccggagctcg gaagaagctc     240
tttgttcctc caccggaaaa tcagcatcgt gtccctttga ctcggatctc tgtgtcggat     300
gaagaatcgg ttccgtatca gcgacaagat cccccgaaac cgatatttc cggcgataca     360
gaggcccacc ttttggcggc ggcggatagt gactccattc ctccaagaac cttggatgca     420
atgaatgggc cagcaggaca gatgacaatt ttctactgtg ggaaggtgaa cgtttatgat     480
gatgtgtcta tggataaggc aaaagcaata atgcagcttg ctgcaagctc acttcatttg     540
catcaggaag ctccatgtga tggaactcca gaattactgc ctttctcatg ccatttacgg     600
gctgcaagtg ttaaaatagg cccaagttct cctacagtga tctacccaac attgcaaaca     660
gtgaaaatga cagaaaattg tcagctgcac agagaagaaa gcaacatatt tcgtgaagac     720
aaccaccctg ctgcagaagt tccaacaagc agaaaagcat cagtgcaaag atatcttgag     780
aagcgaaaag acaggtttaa aagcaagaaa agaggaggaa tgccttcatc tgctggctta     840
gacatctact taaaccatcg ggtgggggat cagataccaa atgatcagtc aaaccagagt     900
gatgcatgct ccctttccca ctgcagagca caccacatcc ctaccccatg cagcttggtc     960
gagaatatga caaagcatac taatctctct gctgatctca atatcaaaga tgtccaagag    1020
cattga                                                                1026
```

<210> SEQ ID NO 77
<211> LENGTH: 978
<212> TYPE: DNA
<213> ORGANISM: Vitis vinifera

<400> SEQUENCE: 77

```
atgaatcccg gcgtcaccac tctccgctct atactggaca aacccctca cgaactcacc      60
gaagaagaca tttctcagct cactcgtgaa gattgtcgca aatacctcaa agaaaaagga     120
atgcgtcgtc cttcctggaa caaatcgcag gcgatccagc aggttatttc gcttaaatcg     180
ttgctcgaaa ccagtgaggg cagcggtgcc ggagttttga ggaagatcac cgattcaccg     240
ccggcggaaa atctacctcc ggttacctcc aattcagctg attcaggcaa ggagctgagt     300
gctgatatcc agatctcagt atcagctgat gaactggttc cccttccgcc aaaagatcat     360
catccagaat ccaccccttc tggcgaatta gccagccggc ctccagaggc agacaccaag     420
catacttgtc ccagaagtcc aggtgcaaca aattgtttgg ttgggcagat gacaattttc     480
tactgtggaa aggtgaatgt gtatgatgga gttccagatg ataaggcaca agcaatcatg     540
catcttgcag caagcccatt ccatttgcct tcagatgacc cctttagtgg tgctgctatg     600
ctttgctcct ctccatgcca tttgcatact gccaatgtta acatggcca tattcctcct     660
cgagccatgg tttctcagac tatgcaaaca gatgttgaag gtcaggttga cagaaaatta     720
tcattgcaaa gatatttcga aaagcgaaaa gacagattta gagcaggaa aaaatagga     780
ctaccttctg gtagcttgga gatgtatgtg aaccatcaag caaggacaca acccctcgaat    840
gggcaatcaa gccggagtgg cacaagctct ccacccccagc atggattgtc gcacaccctg    900
tgcagctcag ctgacaacca tacaaagaat ttcactcctt ttgttgatct aaacagtaaa    960
```

```
gatatccaag aaagttga                                                   978
```

<210> SEQ ID NO 78
<211> LENGTH: 672
<212> TYPE: DNA
<213> ORGANISM: Manihot esculenta

<400> SEQUENCE: 78

```
atggacgccg gtgtcacggc attccggtcg atactcgaca aaccccctcac acagcttact    60
gaagaagaca tttcccagct cacccgcgaa gattgccgca atacctcaa agaaaaagga    120
atgcggagac cttcttggaa caaatcacaa gcgatccagc aagtaatctc cctcaaagca    180
ctccttgaaa ctagtgaaga ttccggcgcc ggtgctctcc ggaaaatctt agtttccaaa    240
ccaccggcta cttcaatttc gattgattca attaaggaac cgagtgatac aaataatatc    300
gcaatttcgg ggtctgcaga tgagacggct ccttgccggc aaaatgattc tccaaaatcc    360
cctcctccgg gaccgttgga ttgccaagct gaagaggcag ataataaagc cattgcttcc    420
agaagtcctg gtgcaacaga tggattggtc aggcaaatga caattttcta ttgcggcaag    480
gtgaatgtgt atgatggagt cccacctgat aaggcccagg caatcatgca tcttgcagca    540
agtccaattc agtctcatct ggatgatcca attcatagac ctgcattttc atttccatgt    600
cattttcaga ccccaagtga caaacatggc tttcttcatc ctaatgctgc atttgtccat    660
gccactctaa ca                                                        672
```

<210> SEQ ID NO 79
<211> LENGTH: 1026
<212> TYPE: DNA
<213> ORGANISM: Manihot esculenta

<400> SEQUENCE: 79

```
atgcagccgg gagagaccat ttcgcggtct cctcttgaca aacccattca ccaactcact    60
gaagatgaca tttctcagct cactcgcgaa gattgccgga gatacctaaa agaaaaaggc   120
atgagacggc cttcgtggaa caaatcgcag gcagtccagc aggtgatctc tctcaaaacg   180
cttctcgaag cgacaccgga tactcggaga aagctctaca ttccccgtcc agataaccct   240
catcgtgccc ctgcaaattc ctctgtttca gtgaaggaaa cgagccccga taaacagatc   300
tccgcatcgc ctgaggaacc tgttccgttt ccacgacatg atcccacaaa gcatgattct   360
catgtagatc tcccggcccg tctcgttgcc accgataatg actcggtttc cccgaggatt   420
aagaccacag caaatgagcc tgtaggacag atgacaattt ttattgtgg gaaggttaac    480
atttatgatg atgtaccaag agacaaggca caagcaataa tgcagcttgc tgcatatcca   540
ctctcatttt ctctggaaac ttcgtctgat acagttccag cattatggcc cattccaagc   600
cgactggaaa gtccaggtgt caaagcagcg cctatttcgc ctatgttgat cttttcctgcc   660
ctgcagacag gtaaagtggc cgataattgt gagctgccca gggaagagag caacatgtca   720
catgaagaca gcctagaagg cccagcaagt agaaaagcat cagtacagag atatcttgaa   780
aagcgaaaag acaggttcaa gaacaagaga aaggtggcaa tgccttcatc tgctagctcg   840
gacatgaact tcaattatcg agaaggagat caattctcaa atgatcaatg aaccttagt    900
ggtgcattct cttctcctca acccagacca cctcaaatgc caacacaatg cagctcggtt   960
gagaatacag caaacattc ctatctcccct gctgatctca atggcagaga tatacaagaa   1020
tgttga                                                              1026
```

<210> SEQ ID NO 80
<211> LENGTH: 1020
<212> TYPE: DNA
<213> ORGANISM: Manihot esculenta

<400> SEQUENCE: 80

```
atggacgccg gcgtcacgtc attccggtcg atactcgaga aacccctcac tcagctcact      60
gaagaagaca tttctcagct cactcgcgag gattgccgca aatacctcaa ggaaaaagga     120
atgcggagac cttcctggaa caaatcacaa gcgatccagc aagtaatctc cctcaaagct     180
cttcttgaac ctagtgaaga ttccggtgcc ggtgctctga aaaaatctt ggtttccaaa      240
ccaccggcta cttcaaattc ggttcattca attaaggagc ccagtgatac caataacaac     300
gcgatttcgg gtctgcaga tgagactgct ccgagtcggc aaaacgactc tccaaaagct      360
actcctccag ggccgttaga ttcccaaccg ggagagaccg ataataaaga cagtgccacc     420
agatgtaatg atgcagcaga tggattggtt gggcaaatga caattttcta ttgtggaaag     480
gtgaatgtgt atgatggaat ccctcctgat aaggcccaga caatcatgca tcttgcagca     540
agtcgaattc aattacctct ggatgatcca actcgtagac ctgcattttc atttccatgt     600
cattttcaga tcccaagtga caaacatggt tttattcctc cgaatgctgc agtctttcaa     660
tctactcaaa cagaaaagat gaaagaatac tctcatccgt gtaaggacaa agcaaacata     720
tctcttgaac ctgatgtaga gggtcaagca acagaagag tgtcattgca gagatatctg      780
gagaagaaaa aagataggg aagatttaag ggcaggaaaa atacagggcc cacttcttct      840
agcttggagg tgtatttgaa ccatcatgtg aggatgcata cctcaagtga acaaacaacc     900
aggagcagca aagctctcc atcccagcct ggagtaccac ctaccttgtg tagctcagct      960
gaggatcagt caaagatttc ctgttttct gttgatctta tgaagtatt ggactgttga     1020
```

<210> SEQ ID NO 81
<211> LENGTH: 981
<212> TYPE: DNA
<213> ORGANISM: Citrus sinensis

<400> SEQUENCE: 81

```
atgtcaccgg gagagacggt ttcccggtcg ctacttgaca agcctctcca ccagctcact      60
gaagatgaca tttctcaggt cactcgtgaa gattgtcgcc gatacctcaa agaaaaaggc     120
atgaggaggc catcgtggaa caaatcgcag gcgatccagc aagtgatctg cctcaagacg     180
ctgcttgaaa caacgacgga taccgaggcc actgaggcac gaaggaaact ctacagtgtc     240
ccttcacatt cggctgttac agttaaggaa acatgtgaac cggctccttg tcggcgtcag     300
gatgccccca tgcctgattt ttcaggcgac tcttctagtc gacttgcagc tgacagtgaa     360
tctatttctc ccagaactac agtagcagca aaggaggcag taggacagat gacaatcttt     420
tacagtggaa aggtgaatgt ctacgatgat atgccgagtg agaaggcaca agcaattctg     480
cagcttgctg caagcccact ccctctatca cagaaagctc catcagatgg aacaacagga     540
ctacagtctg ttccgtgcca cttgcaaact gcaggtatca atgtaggccc aagttctccg     600
gtgatcttcc caacgttaca aacagtgaaa gtggtgaaaa actgtcagct tccctgggaa     660
gaaagcaaca tttctcatga agacagcttt gatgggccaa ccagcagaaa agcatcggtg     720
cagagatacc gggagaagcg gaaagacagg tttaagaaca agagaaagat agcaatgcct     780
tcatccagta gtctggacgt ctacttaaac cgctgggtgg agatcagtt tgcaaatgag     840
caattgaatc ctagtgatgt ttgctctact cttcaaagca ggccatctca gacatctcct     900
```

```
ggatgtggtg tggttgagaa tttggcaaat gtttccaatc ttcctgtgga tcctaatgac      960
aaagatgtca cggaaaactg a                                               981
```

<210> SEQ ID NO 82
<211> LENGTH: 1032
<212> TYPE: DNA
<213> ORGANISM: Citrus sinensis

<400> SEQUENCE: 82

```
atggacgtgg acggtggcgt gacgtcgtgc cggtcaatac tcgagaaacc tctcagtcag       60
ctcactgaag aggacattac gcagctcaca cgcgaagatt gccgcaaatt tctcaaggag      120
aaaggaatgc gcaggccatc gtggaacaaa tcgcaggcga tccagcaggt gatctctctc      180
aaagctttgc tcgagtccag cggcgattcc ggctcaggtg ttttacgcag agtactcgtc      240
tcgcctccgg aaagtatgcc gccgcgcgtg aatgtgactt caaattcagc tgatttagta      300
aaggaaccga ccatctcagt ttctggagac caaaacagtg catataggcg aagtaccct       360 cgcaactgtg ctgttgatgc agataacaag accatctcta acagaaatcc ctgtgaagca      420
aatgggtcca tagggcagat gacgattttc tattgtggca aggtgaacgt gtacgaagga      480
gtgccaactg ataaggcaca ggagattatg caccttgcag caactccaat tgattttcc       540 cagaacggtt catttggtgg aattacggca tagggccaa ttccatgcca tttacaagtg       600
acaagcaaca gacatgtgtc tctcctctt cgtcctgctg ccatgatctc tcagttcatg       660
caaacaggga agatagcaga ttattctcag gagtataggg agaaagcgat tagtactcat      720
gactctgatg tggatggtca ggttaaccga aaagtctcgt tgcagaggta tcttgaaaag      780
cgaaaagaca ggggaaggtt tttcaaggga aagaaaaata caggaccaac tcctagtttg      840
gagatgtacc tgaaccatcc ggggaagaca catgcctcca atggacaaca gagccagagc      900
aacacaagct ctccgaccca gcctgagttg tccaacacat tggggacctc cccagacaac      960
caggcaaaga ctgtcatgct tccggttgat ctcaacaatg aaggtagtct aagaagttct     1020
attcatgaat ga                                                         1032
```

<210> SEQ ID NO 83
<211> LENGTH: 942
<212> TYPE: DNA
<213> ORGANISM: Arabidopsis thaliana

<400> SEQUENCE: 83

```
atggatgtcg gagtttcacc ggcgaagtct atacttgcga aacctctgaa gctactcact       60
gaagaggaca tttctcagct cactcgcgaa gactgccgca aattcctcaa agacaaagga      120
atgcgaagac cgtcgtggaa caaatctcag gcgatccagc aagttttatc tcttaaagct      180
ctctatgagc ctggagacga ttccggcgcc ggtatcttcc gcaagatcct cgtttctcag      240
ccagtaaatc cgcctcgcgt cacaacaacg ttgattgagc aagcaacga gctgaagct       300 tgtggccggg tttcttatcc ggaagataac ggcgcgtgcc atagaatgga ttctccaaga      360
tcagctgagt tttccggtgg gtctggtcac tttgtatccg agaaagatgg ccacaagacg      420
actatttctc ccagaagccc agctgaaaca agtgagctcg ttgggcaaat gacgatattc      480
tatagtggaa aagtgaatgt gtatgatgga ataccacctg aaaaggcccg gtcaatcatg      540
cactttgcag ccaatccaat tgatttgcct gaaaacggta ttttgcttc cagtagaatg      600 atttcaaagc tcataagtaa agagaagatg atggaacttc cccaaaaagg ccttgagaag      660
```

| gcgaattctt ctcgtgattc tggtatggag ggccaggcga acagaaaggt atctttgcaa | 720 |
| agatatcgtg aaaagcggaa agacagaaaa ttctcaaagg ccaaaaagtg tccaggagtt | 780 |
| gcgtcctcta gcttggagat gtttctgaat tgtcagccac ggatgaaagc tgcatattcg | 840 |
| caaaacctag gctgcaccgg atctccactg catagccagt cacctgaaag ccagacaaaa | 900 |
| agtcccaatc tttcagttga tctaaacagt gaaggcattt aa | 942 |

<210> SEQ ID NO 84
<211> LENGTH: 948
<212> TYPE: DNA
<213> ORGANISM: Arabidopsis thaliana

<400> SEQUENCE: 84

| atggatgtag gagttactac ggcgaagtct atacttgaga agcctctgaa gcttctcact | 60 |
| gaagaagaca tttctcagct tactcgcgaa gattgccgca aattcctcaa agagaaagga | 120 |
| atgcgcaggc cttcgtggaa taaatctcag gcgatccagc aagttttatc tcttaaagct | 180 |
| ctctatgaac ctggagatga ttccggcgcc ggaatcctcc gcaagatcct tgtttctcag | 240 |
| ccgccaaatc cgcctcgcgt tacaacaacg ttgattgagc aaggaacga gctcgaagct | 300 |
| tgtggaagga ttccttttaca ggaagatgat ggtgcgtgcc atagaaggga ttctccaaga | 360 |
| tcagctgagt tttctggtag ttctggtcag tttgttgcgg ataaagatag ccacaagact | 420 |
| gtttctgttt cccccagaag cccagctgaa acaaatgcgg tggttgggca aatgacgata | 480 |
| ttttatagtg gcaaagtgaa tgtatatgat ggagtaccac ctgaaaaggc ccggtctatc | 540 |
| atgcattttg cagccaatcc aattgatttg cctgaaaatg gtattttgc ttctagtaga | 600 |
| atgatttcga aacccatgag taagagaag atggtggagc ttccccaata tggacttgaa | 660 |
| aaggcacctg cttctcgtga ttctgatgtt gagggtcagg cgaacagaaa agtatcgttg | 720 |
| caaagatatc ttgaaaagcg gaaagacaga agattttcta agaccaagaa ggctccagga | 780 |
| gttgcgtcct ctagcttgga gatgtttctg aatcgtcagc cacggatgaa cgctgcatat | 840 |
| tcacaaaacc ttagtggcac agggcattgc gagtcacctg aaaatcaaac aaaaagtccc | 900 |
| aatatctcag ttgatctaaa cagtgatcta aacagcgaag ataattaa | 948 |

<210> SEQ ID NO 85
<211> LENGTH: 969
<212> TYPE: DNA
<213> ORGANISM: Eutrema salsugineum

<400> SEQUENCE: 85

| atggatgtta atgtgtcttc ggccaagtct atacttgaga agcctcttaa gcttctcact | 60 |
| gaagaggaca tttctcagct cactcgcgaa gattgccgga aatttctcaa ggagaaagga | 120 |
| atgcgcaggc cttcttggaa caaatctcag gcgatccagc aagttctctc tctcaaagct | 180 |
| ctctttgagc ccggcgacga ttccggcgcc ggaatcctcc gcaagatcct cgtttctcag | 240 |
| cctccgattc cgcctcgtgt gataacaacg ccgccgattg agccaagcaa caacgagctt | 300 |
| ggagcttgtg gccggattcc ttttcaggaa gatgacggct catgccacag gagagattct | 360 |
| ccaagatcag ctgagttttc cggtggtggt tctggtcatt ttgtagctga aaagagagc | 420 |
| tacaagacag tctctcccag cagaagcccg gcagaaacaa gtgcgatggt tgggcaaatg | 480 |
| acgattttct atagtgggaa agtgaatgtg tatgatggag taccacctga aaaggcgcgg | 540 |
| tcaatcatgc acttagcagc caaccccgatg gatttgcctg aaaatggcat ttttgcttct | 600 |
| agtagaatga tttccaggcc catgagtaaa gagaagatgg tggaacatcc ccattacggc | 660 |

```
cttgaaaagg caaatgcttc tcgtgattct gatgtggaga gtcaggcgaa cagaaaagtg      720
tcgttgcaaa gatatcttga aaagcggaaa gatagaagat tctccaagac caagaaggct      780
ccaggagttg catcgtctag cttggagatg tatctgaatc gtcagccacg gatgaacgct      840
gctgcatttt cacaaaacct tggctgcaca ggagagcccc acacgttctg tgagtcacct      900
gaaaatcaga caaaaagtcc taatctctca gttgatctga acagtgatct aaacagtgaa      960
gatatttaa                                                              969
```

<210> SEQ ID NO 86
<211> LENGTH: 1023
<212> TYPE: DNA
<213> ORGANISM: Citrus clementina

<400> SEQUENCE: 86

```
atggacgtgg acggtggcgt gacgtcgtgc cggtcaatac tcgagaaacc tctcagtcag       60
ctcactgaag aggacattac gcagctcaca cgcgaagatt gccgcaaatt tctcaaggag      120
aaaggaatgc gcagaccatc gtggaacaaa tcgcaggcga tccagcaggt gatctctctc      180
aaagctttgc tcgagtccag cggcgattcc ggctcaggtg ttttacgcag agtactcgtc      240
tcgcctccgg aaagtatgcc gccgcgcgtg aatgtgactt caaattcagc tgatttagta      300
aaggaaccga ccatctcagt ttctggagac caaaacagtg cgtataggcg aagtacccct      360
cgcaactgtg ctgttgatgc agataacaag accatctcta acagatccct aaatccctgt      420
gaagcaaatg ggtccatagg gcagatgacg attttctatt gtggcaaggt gaacgtgtac      480
gaaggagtgc caactgataa ggcacaggag attatgcacc ttgcagcaac tccaattgat      540
ttttcccaga acggttcatt tggtggaatt acggcatata gggccattcc atgccattta      600
caagtgacaa gcaacagaca tgtgtctctc cctcttcgtc ctgctgccat gatctctcag      660
ttcatgcaaa cagggaagat agcagattat tctcaggagt atagggagaa agcgattagt      720
actcatgact ctgatgtgga tggtcaggtt aaccgaaaag tctcgttgca gaggtatctt      780
gaaaagcgga aagacagggg aaggttttc aagggaaaga aaaatacagg accaactcct      840
agtttggaga tgtacctgaa ccatccgggg aagacacatg cctccaatgg acaacagagc      900
cagagcaaca caagctctcc gacccagcct gagttgtcca acacattggg gacctcccca      960
gacaaccagg cgaagactgt catgcttccg gttgatctca acaatgaaga tattcaagac     1020
tga                                                                   1023
```

<210> SEQ ID NO 87
<211> LENGTH: 981
<212> TYPE: DNA
<213> ORGANISM: Citrus clementina

<400> SEQUENCE: 87

```
atgtcaccgg agagacggt tcccggtcg ctacttgaca agcctctcca ccagctcact       60
gaagatgaca tttctcaggt cactcgtgaa gattgtcgcc gatacctcaa agaaaaaggc      120
atgaggaggc catcgtggaa caaatcgcag gcgatccagc aagtgatctg cctcaagacg      180
ctgcttgaaa caacgacgga taccgaggcc actgaggcac gaaggaaact ctacagtgtc      240
ccttcacatt cggctgttac agttaaggaa acatgtgaac cggctccttg tcggcgtcag      300
gatgccccca tgcctgattt ttcaggcgac tcttctagtc gacttgcagc tgacagtgaa      360
tctatttctc ccagaactac agtagcagca aaggaggcag taggacagat gacaatcttt      420
```

```
tacagtggaa aggtgaatgt ctacgatgat atgccgagtg agaaggcaca agcaattctg    480
cagcttgctg caagcccact ccctctatca cagaaagctc catcagatgg aacaacagga    540
ctacagtctg ttccgtgcca cttgcaaact gcaggtatca atgtaggccc aagttctccg    600
gtgatcttcc caacgttaca aacagtgaaa gtggtggaaa actgtcagct ccctgggaa     660 gaaagcaaca tttctcatga agacagcttt gatgggccaa ccagcagaaa agcatcggtg    720
cagagatacc gggagaagcg gaaagacagg tttaagaaca agagaaagat agcaatgcct    780
tcatccagta gtctggacgt ctacttaaac cgctgggtgg agatcagtt tgcaaatgag     840 caattgaatc ctagtgatgt ttgctctact cttcaaagca ggccatctca gacatctcct    900
ggatgtggtg tggttgagaa tttggcaaat gtttccaatc ttcctgtgga tcctaatgac    960
aaagatgtca cggaaaactg a                                              981
```

<210> SEQ ID NO 88
<211> LENGTH: 936
<212> TYPE: DNA
<213> ORGANISM: Capsella rubella

<400> SEQUENCE: 88

```
atggaggatg taggagtgtc aacggcgaag tctatacttg cgaagcctct taagctactc    60
actgaagatg acatttctca gctcactcgc gaagactgcc gcaaattcct caaagagaaa    120
ggaatgcgca ggccttcgtg gaacaaatct caggcgatcc agcaagtttt atcacttaaa    180
gctctctttg agcccggcga cgattccggc gccggtatcc tccgcaagat cctcgtttct    240
cagccgccaa ttccgcctcg tgtcacaaca acgtcgactg agctaagcaa cgagctcgaa    300
gcttgtggcc ggattcctcc atttcaggaa gatgatggtc cctgccatag aagggattct    360
ccaagatcag ctgagttttc cggtggttct gctcattatc cagctgagaa agataccaac    420
aagactgtct ccctcagaag cccagctgaa actaatgcgc tggttgggca atgacgata    480 ttctatagtg ggaaagtgaa tgtgtatgat ggagtaccat ctgagaaggc ccagtcaatc    540
atgcactttg cagcaaatcc agttgacttg cctgcaaatg gtatcttttc ttctagttgt    600
atgcccatga gtaaagagaa gatggtgaa cttccccaaa ttggccttga gagggtgaat     660
tcttctcgtg atttttgatat ggaaggtcag gcaaacagga agatgtcgtt gcaaagatat    720
cgtgaaaagc ggaaggacag aagattcctt aaagccaaaa agtctccagg agttgcgtcc    780
tcgagcttgg aaatgtttct aaatcgtcag ccacgaatga atgctgcata ctcacaaaac    840
cttggccaca caagatcttc actgcagagc gagtcacctg aaaaccaaag aaaaagtccc    900
aatctatcag ttgatctaaa cagtgaagat atttaa                              936
```

<210> SEQ ID NO 89
<211> LENGTH: 813
<212> TYPE: DNA
<213> ORGANISM: Capsella rubella

<400> SEQUENCE: 89

```
atggatgttg gagtatctcc ggcgaagtct atacttgcga agcctctgaa actgttgact    60
gaagaggaca tttctcagct cactcgcgaa gattgtcgca aattcctcaa agagaaagga    120
atgcgcaggc cttcatggaa caaatctcag gcgatccagc aagtttatc ccttaaagct     180 ctctttgagc ctggcgacga ttccggcgcc ggaatcctcc gtaagatcct cgtttctcag    240
ccgtcaattc cgcctccggt tacatcaact tcgattgagc aagtagcga gctcgaagct     300 tgtggtagga atccttttca agaagatgaa ggtccttgcc atagaaggga ttctccaaga    360
```

```
tcagctgagt tttccggtgg ttctgctcag tttgtagctg agaaagatag cttaaagaca    420
gtttccccca gaagtccagc tgaaacaagt ccgctggttg acaaatgac gatattctat     480 agtggaaaag tgaaagtata tgatggagta ccacctgaaa aggcgcggtc aatcatgcac    540
tttgcagcta atccaattga ttttcctgaa aatggtattt ttgcctctag tagaatgatt    600
tcgaagccca tgagtaaaga aagatggtg gatcttcccc aatatggcct tgaaaaggcc    660
actgcttctc gtgattctga tgtggagggt caagcgaaca gaaagtgtc attgcaaaga    720 taccttgata gcggaaaga caggtgcgtt aaggaacag ccgttgttgc aataatgttg     780
tgtacacact tgcgcttatt ccaaaatcgc tga                                 813

<210> SEQ ID NO 90
<211> LENGTH: 1044
<212> TYPE: DNA
<213> ORGANISM: Aquilegia coerulea

<400> SEQUENCE: 90
atgaaacctg acgagacagt ttcccggtca ccacttgata aacctttgtt tcaacttact    60
gatgaagata tttcacagct cactcgtgaa gattgccgga aatttctcag agacaaaggt    120
atgagacgtc cttcatggaa caaatctcag gcgattgaac aagtgatctc acttaaaacg    180
ttgctagaac caagaacgga atctgacaca atgccaccg aatccggca gaaattactt      240 gtttctcggc tagaaaattc tacccaagta cctttaaatg caagacaaa tgcctcaaat    300 ttaaagacat ctgttcaggc aataaactcc ggggaagccg atattcatgg tgacaggccg    360
tgtcgggtcc ctgttccagt ccctgacgat aacacaatca ctgttccagt ccctgacaat    420
aacatcactt catccagaaa cctgaactcc accaatggac tggttggtca gatgacaatt    480
ttctactgcg gcaaggtgat cgtctacgat ggtatgcctg ctgagaaggc acatgcaatc    540
atgaaatttg caggaagcca tatcaatgtg cctgaggatt cttccaccagc tggagctgca  600 gtaattcaat cctttgcatg ccaattacag gcagcatcca tcagacatgg acttgctttc    660
ccgtcagcgg tctctccacc cttgcacaat gtggtagccg atacttctca gcattgcagg    720
gaggaagtga cagtttctcg tgaagttgaa cccgagggtc cagtgagtag aaaagcatct    780
gtacaaagat attggagaa gcgaaaagac aggggggcggt ttaagaacaa gcgaagata    840 gagtcatctt ctagcttaga gatatacttg aaccatcaac tggggatca gtaccttaat     900 gagaaatcaa gtcagagcag gcatgttcc ccaccccaac ctagagcacc acacactccc    960
actcgttgca gttcagttga gaaccaggtc acaaatgtcg tgttctccat tgatctcaat   1020
gataacgatg ttcgggaagg ctga                                           1044

<210> SEQ ID NO 91
<211> LENGTH: 1098
<212> TYPE: DNA
<213> ORGANISM: Malus domestica

<400> SEQUENCE: 91
atgaacgccg ccaccacgac gtttccctcc attctcgrga agccccttaa ccagctcacc    60
gaggatgaca tttcccagct cacccgcgaa gactgccgca gtacctcaa agaaaaagga   120 atgcggcggc cctcttggaa caaatctcag gcgatccagc aggttatttc cctcaaggcg   180
ctgctggagc caacgaaga ttccggcgcc ggagctctca gaaagattgt cgtttcggct    240
cagacgacca ccgccaccac ccagcgtgcg gcttcgaatt ccgctgattc agctaaggaa   300
```

```
gcgagcgccg atgtccaggc ttcagtgtcc gcagacgaac cagcgacgca tccgagaaat    360
gaacggccga atcggttccc cgaggatccg ccggtcgatg cggataccgc ggccatcagt    420
cccagaaatc agtgtacaac tgatgcatta gttcggcaaa tgacaatttt ctacagtggc    480
aaggtgaatg tatatgatgg agtgccacct gataaggtaa atgaagcttt ctatttgaat    540
ggagaccttg agataagcct tccaatgcag cgatatatgg atttgcaggc acgggcaatc    600
ctgcactttg cagcagggcc caaccatctg cttctggaca atcaatttgg tggtgctgca    660
gcagaaaggt ccttasggtg ccaatatcag actgcgggcg ataaagatgg cccttttccct   720 cctagtgcaa caatttctca atcaatgcaa acagggaagt tcggcgaata tacacagcag    780
tactgggaga aagggaacag cactcgtgat cctgatgcag agggtcaggc cagcagaaaa    840
gtctcgttgc agagataccg tgaaaagcga aaagacagag aaagattaaa gataaagaaa    900
aatagtggag cgaattctag cttggaggtt tacttgaatc atcaactcag gacacatacc    960
tcaaatggta attcaagtca gagtggcaca agctctccac cccaacctgg gctgctgcag   1020
acagctgaaa atcagccaaa gatccgctgt cttcctgttg acctaaacga gaaggatatc   1080
ctggaacgcc aagcttaa                                                  1098

<210> SEQ ID NO 92
<211> LENGTH: 1401
<212> TYPE: DNA
<213> ORGANISM: Malus domestica

<400> SEQUENCE: 92
atgaacgccc ccacgacgac gtttcgctcc attctcgaga agccsctcaa tcagctcacc     60
gaggatgaca tttcccagct cacccgcgaa gactgccgca atacctcaa agaaaaaggc    120 gatccagcag gttatttcgc tcaaggcgct gctggagccc aacgacgatt ccggcgccgg    180
agctctcaga aagattgtcg ttttgcctca tacgaccacc gccaccaccc agcgcgtcag    240
tactttcgta tgtgcttgtt tcccgagaaa ttmaaaacgg gagagaaaat tacagcggct    300
tcgaattccg ctgattcagc taaggaagtg agccccgatg tccaggcttc tgtgtccgct    360
gacgaattgg cgccgcatcc gagaaatgaa ccgcccaaac cagctcccga ggacccaccg    420
gtctatgcgg ataccacggc catcagtctc aggcttatct tttctccatg ggtcatggct    480
tatgcttggg ttgattacat acgtattaaa ggtttaactg aagtgacgtt gcggttagga    540
tgcatattct ctgtgttcct taagacgggt atgaagccaa aaaatcattg tacaactgat    600
gcatcagtta gtaaaatgac aattttctac agcggcaagg tgaatgtata tgatggagtg    660
ccacctgata aggtaaatga agctttctct ttgaatggag accwtgagat aagccttcca    720
atgcagggat atatggattt gcaggcacgg gcaatcctgc accttgcagc agggcccaac    780
catttgcttt tggacaatca atttggtggt gctgcagcag caagatcctt acattgccaa    840
tttcagactg caggcgataa agatggcctt ttccttccta gtgcaacaat ttctcaggca    900
atgcaaacag gtaactttac agagaaggtc rgtaatata cacagcagta ctgggagaaa    960
gggaacaaca ctcgtgatcc tgatgcagag ggtcaggcga acagaaaagt ctcgttgcag   1020
agataccgtg aaaagcgaaa agacaggaa aaattaaaga ttaagaaaaa tattggatcg   1080
aatactagct tggaggttta cttgaatcgt caactcagga yacatacctc aaatggtaat   1140
tcaagtcagt atggcacaag ctctccaccc caacctgagc tgctacagac agctgaaaat   1200
cagccaaggt tccgctgtct tcctgttgac ctaaacgaga agggtagatt ggatgccgaa   1260
ttctgttatg tgatgaaaaa tcgcggtcgc ggctcagttg gtgcatcgga aaaatgtatt   1320
```
actttccggc ttactctgca gttttaggt tccactttta aagagcctct ttgggcagag    1380
cttcaatcta gtttcctata g                                             1401

<210> SEQ ID NO 93
<211> LENGTH: 1278
<212> TYPE: DNA
<213> ORGANISM: Linum usitatissimum

<400> SEQUENCE: 93
atgcagcctg ctgtcggcga taccgcttcc cgttccccgc ttgacaagcc gctccaccag     60
ctaaccgaag atgacatttc tcagctcact cgagaggatt gccgcagatt cctcaaagag    120
aaagggatga aaggccgtc gtggaacaaa tcgcaggcaa tccagcaggt gatctcgctc    180
aaaaccctac ttgaaccgcc gccggagtcc gaagacggcc aacctccacg gaggcgctac    240
attccccgta cggctaacac gtatcgtgcc cctgcaactc caaatcccgc tgtttcagtg    300
agagtatccg ccgttgatac tccgatctct gcccctcccg atgattctgc accctatcgc    360
cggcatgatc ctccttttgaa tgattttccg gcgagtaact ctcttcctcc tgctccggtt    420
ccggctgtac atcacgctgc cataaaagag aacggttccg tctctcccag gagtacaggt    480
caagttaatg aacaacatgg gcagatgaca atatttttact gtgggaaggt gaatgtctat    540
gatgatatgc cgagagataa ggctcgagtt attctgcagc ttgctgcaag tcctgtcccc    600
ttgacacagg atggcacatc tgatgctagt caacctgcat ggcccttccc cggtcaaacg    660
gaaactcatg gtgctaaagc tgctcaaacg tcatcagctc tgcccttttc ttccctgcaa    720 actgaaaaact gtcttatttt gagggacaac tgccatttca ctcctgaagg caaccaagaa    780
ggccctgcaa gcagaaaagc gtccgtgcag agatatcttg agaagcggaa agacaggttc    840
aagcacaaga gaaaagtggc aatgcctaca tcagctaatt tagacatcta cttaaacaac    900
cgggtgggcg atcaagtctc aaatgaacca tggggctcaa ctgatacttg ctcctctcct    960
caatctatac atccccagcg ctgcatttct gctgagaaca cagcaaagca ctccattctc   1020
gctgctgatc tcgctcccaa aggtttatcg gttttctgta tgcacgagaa tgttaagcgc   1080
tgtgaggata aaggcataaa acaaaactct ggcagcaat tcagtatttt aggccacgtc   1140
aacactctgt cacccatccg aagcgagtgg gttcgaggaa ggtatttggt tgttggttcc   1200
ttcctggtta gaattcctaa acatgtagta tatacaacat gttgtagagc aatgtcgcgg   1260
ttatctcttc tgggctaa                                                  1278

<210> SEQ ID NO 94
<211> LENGTH: 1134
<212> TYPE: DNA
<213> ORGANISM: Linum usitatissimum

<400> SEQUENCE: 94
atgcagcctg ctgtcggcga taccgcttcc cgttccccgc tcgacaagcc tctccaccag     60
ctaaccgaag atgacatttc tcagctcact cgagaagatt gccgcagatt cctcaaagag    120
aaagggatga aaggccgtc gtggaacaaa tcgcaggcaa tccagcaggt gatctcgctc    180
aaaaccctac ttgaaccgcc gccggagtcc gaagacggcc aagctccacg gaggcgctac    240
attccccgta cggataacac gtatcgtgcc cctgcaactc caaatcctgc tgtttcagtg    300
aaagtatccg ccgttgatac tccgatctct gcgcctcccg atgattctgc gccctatcgc    360
cggcatgatc ctcctctgaa tgattttccg gcgagtaact ctgcattgga ctttcttcac    420

| | |
|---|---|
| tgcccattaa accatctgtt gttgcgaatg cttagcatga gtacaggtca agttaatgag | 480 |
| caacatgggc agatgacaat attttactgt gggaaggtga acgtctatga tgatatgccg | 540 |
| agagataagg ctcgagttat tctgcagctt gctgcaagtc ctgtcccctt gacacaggat | 600 |
| ggcgcatctg atgctagtca gcctgcatgg cccttccccg gtcaaacgga aactcatggt | 660 |
| gctaaagcag ctcaaacgtc atcagctctg cccttttctt ccctgcaaac tgaaggcccg | 720 |
| gcaagcagaa aagcgtccgt gcagagatac cttgagaaac ggaaagacag gttcaagcac | 780 |
| aagagaaaag tggcaatgcc tacatcagct aatttagaca tctacttaaa caaccgggtg | 840 |
| ggcgatcaag tctcaaatga accatggggc tcaactgata cttgctcctc tcctcaatct | 900 |
| atacatcccc agcgctgcat ttctgctgag aacacagcaa tgcactccat tctcgctgct | 960 |
| gatcttgctc ccaaaggttt atccgttttc tgtgttagct tttcaacttg ctgtttgaac | 1020 |
| aaacttgaca atgcatattc acggaacccct tgcgtcattc caatttggcc tgacgaggac | 1080 |
| tgtatttttcc aattttactg ttttgtgttc aatgctgaag aaactgcata ttga | 1134 |

<210> SEQ ID NO 95
<211> LENGTH: 924
<212> TYPE: DNA
<213> ORGANISM: Eucalyptus grandis

<400> SEQUENCE: 95

| | |
|---|---|
| atgacgtcgc tccgctgcat cctcgacaaa cccctcaacc agctcacgga ggacgacatc | 60 |
| tcgcagctca cccgcgagga ttgccgcaaa ttcctcaagg acaaagggat gaggaggccg | 120 |
| tcgtggaaca atcccaggc gatccagcag gtcatctcgc tcaaggcgct gctcgagggc | 180 |
| cccgaggacg acgattccgg cgccaggacg ctgcggaaga tcgtcgtctc gtccgcggag | 240 |
| aatccaccgc cgcgggctaa ctcgaactcg aactcgcccg actcggcgaa ggaggtgagc | 300 |
| cctggcgcca gcgtgtcgga attcgcggac gaggccgcgc cgtatcggcg gaaggatccg | 360 |
| ccggagccgg cgccggcgcc tcatggagat gcggcagctt cggctggggc cgaccaggag | 420 |
| agaaatgcgg ttagtcccag aaatgttggt gccggagagg ttacactggg gcaaatgaca | 480 |
| attttctact gtggcaaggt gaatgtttat gacagagtgt ctcctgacaa ggcaaggaca | 540 |
| atcatgcaac ttgcatctgg tccaatccct ttgccgctgg atgattcatc aaatggaagt | 600 |
| gcagcaattt ggtcattccc ttgtcacatg caggccaata ctgacaactt gtgtctatta | 660 |
| cctccaagag caatggtctc tcataccaca caaacagaca tggaaggtca tatgaatcga | 720 |
| agagttcggc tgcagaagta cttttgacaag cgaaaggaca gggggagatt taagtcaagg | 780 |
| aaagatgccg gaccagcctc ttcaggcttg gagatgttct tgatgaacca aataagggtg | 840 |
| cctgttccag atggacaatt gagtaaaaat gcgataacct gtgcaccaca acctgggatg | 900 |
| gcccacggca aaaatagtcc ctaa | 924 |

<210> SEQ ID NO 96
<211> LENGTH: 1059
<212> TYPE: DNA
<213> ORGANISM: Solanum tuberosum

<400> SEQUENCE: 96

| | |
|---|---|
| atgccgccgg aagaaacagt ttccaagtca cctctcgata aacctctcaa tcaactcact | 60 |
| gacgatgaca tttctcagct cacacgcgaa gactgccgtc gttacctcaa acaaaaagga | 120 |
| atgagaaagc cgtcatggaa taaatcacag gcgattcagc aagttatatc gttgaaggct | 180 |
| ctcctcgagc cggatactga cgccggaact cggaagaaac ttcacattcc tcgtgcagat | 240 |

```
actcatgtcc agagcgggaa aaatacctat ggcgaacctt ctgaaccagt gcctgataga        300
agaaatcagc aggacagacc tgatctttcc agtcatatta ctgcccttcc ggtcgctgtt        360
gtggataatt cagctccttc tagaacaata ggttcagcag ataaaccagt aggacaaatg        420
acaatcttct atagaggcaa ggtgaatgtc tatgatgatg tgcctgccga caaggcacaa        480
aaaatcatgt gtcttgcttc aagccctctt tgtgtgcctt cagaaactcc atcgaatgcc        540
actgtagcag ctcgacattc agcatgctgc ttacaagctg caaatagtaa actacgccta        600
gatactaata ttgtaccgac tattcaaaca gtgaaaatga gtgaggtttc tcgagttcct        660
atagaagaaa gcaaccgctt atacaatgat aatcctgaag cagtggagag ccccgcaagc        720
aggaaagcat cagtacaaag atatcttgag aagcgaaaag aaaggttcaa gtggaagaga        780
aaggtagaaa caacttcatc agctagcttg gatatctatt taagtgatcg aattgggact        840
cgtacgccaa gtgactatgc aagtggggct gatctttgct tcacacccca cattacacct        900
acaggaagtg gtcctataca agacaatatt cagatgaatc ccactttttc tagtgatctc        960
aatgacagag agagtgaatg tcggaaactg aatggttggg gatgcacacc agatttctgt       1020
ttttgtcttg aaatgttcag aggccacatc atgttctag                              1059

<210> SEQ ID NO 97
<211> LENGTH: 1020
<212> TYPE: DNA
<213> ORGANISM: Solanum tuberosum

<400> SEQUENCE: 97
atgtcgctgg aagaaactgt ttacaagtct cctctggata aaccgctcta cctacttacc         60
gatgacgaca tttctcagct cactcgcgaa gattgccgac gttatcttaa agctaaagga        120
atgagaaaac cgtcatggaa taaatcacag gcgattcagc aggtgatatc actgaaggcg        180
ttgttagaga cgacgccgga ctccgacacc ggtcagcgga aaaggcgtca cattcctcgc        240
ccagacacca gtttacagcg agtccagaaa gaaacgggca tcgatgcaga atttgctgaa        300
tcggctgaag aaatggtgcc gtacggtaga aaacttccca ataaacctga tctttccggc        360
aataaggctg caggttctgt tgccgttgtc aataacttaa ctccttctag aaccacagat        420
tcgggaaatg catcagcagg tcaattgata atcttctatt gtggcaaggt gaatgtgtat        480
gatgatgtac ctgctgaaaa ggcacaagca atcattcatc ttgctgcaag cccactctttt       540 gtgccttcag aaactccatt ggatgctacc agagcagctc aacattccga atgccatttg        600
caatctgcaa atgttaaaat gggtccagat tctcctatgg tgctcatgcc aaccatgcaa        660
acagggagaa taactgaagt gactcgcctg catttggagg gaagcaacac tttctatgag        720
gacaattctg aatcagtgaa ccacgtaagc agaaaagcat tactggaaag atatcgtgag        780
aagcggaaag acaggttcaa gagaaagatg ggaatgcctt catctgctag cttggacatc        840
tatttgaacc atcgaaccgg aaatcatacc ccaagtgagc tctcaagtag gagcaacact        900
tgttccccgc ctgctattag attatctgtt gcacctgctc caagtggttc aatggataac        960
attctccaaa tggatgccaa tgcttctggt tttctcgacg acaaagatgg taaagagtga       1020

<210> SEQ ID NO 98
<211> LENGTH: 1038
<212> TYPE: DNA
<213> ORGANISM: Gossypium raimondii

<400> SEQUENCE: 98
```

```
atgtcaacgg gagaaatggt ttcccggtca cctctataca agcctctcaa ccagctcacc    60
gaggatgaca tttctcaggt cactcgcgaa gattgccgcc gttacctcaa agaaaaaggg   120
atgcggagac cttcgtggaa caaatcgcag gcgattcagc aggtcatctc actgaaaact   180
cttctagaaa cgacatcgga ttctgacggt gtcaaagctt ccaagaaact tcacgttccc   240
ttcccccaca atccgcctcg tttcgtttct gattcaaccg ttcaaccgaa tgaaacgaca   300
cggcataaag ggatctcggt cccgctaaac gaatccgttc ctcgcatccg ttcagatccc   360
tcggaattca aattttccgg cggaaattcc gttcaaaccg ccgtctctgc taatgattct   420
gtttctccaa gatctgcgag tgtagccaaa gagccttcag acagatgaca aatttttat    480
tgtgggaaag tgaatgtcta tgataatata cctggtcgta aggcggaagc aatcttgcag   540
tttgctgcaa gcccagtctc atttcttcag gaaactctag ttgatcaaag gaccacgcca   600
ttgtccattc catgccatgt acaggctgca ggtgataaag taagccaacg ttcaccaggg   660
gttgtattgt catcaatgca agcagtgaag gttgcagaaa actgtcaatt tcctcgagag   720
gattgcaatg tatcttatga agatagcctt gaaggtccca ctagcagaaa cgcattgttg   780
caaagatatc ttgagaaaaa gaaagacagg tttaagaaca agagaaaatt ggcaacatct   840
tcatctcgta cctagacat ctacttgaat caaatggggg atcagttctc aaatgagcag   900
tcgaagcaaa gtgaatcata ttcttctact caagctcgac cacctcacac gccactttgg   960
tgcagctcca tggaaaatct tcccaagatt gccaatgtca ctactcatcc tgatggcaaa  1020
gatatattcg aagtatga                                                 1038
```

<210> SEQ ID NO 99
<211> LENGTH: 1098
<212> TYPE: DNA
<213> ORGANISM: Gossypium raimondii

<400> SEQUENCE: 99

```
atggaggctg gggtaacgac gacggcgact acaacagcgt cgttcagttc gatacttgat    60
aaaccctca gccaactaac cgaagaagac atttctcaac tcactcgcga agactgtcgc   120
aaattcctca agaaaaagg aatgcgtagg ccgtcatgga acaaatcgca ggcgatccag   180
caagtgattt cgttcaaggc gttgttggaa agcaacgaag attccggcgc cggagctcgc   240
cggaaaatcc ttgtttgtcc accaccgtca cattttcctc cgcaaaatgc ggtagcttca   300
aattctggtg agtcagtaaa agaagcagtc tttggagaag aagaaagcct gtacggccaa   360
aaagatcttt ctttgaaagc tgctccggtg gtgcagatga attgtcaggg cggtgacacg   420
gatgacaaga ctctttcgcc tagtttaggc tctccacggg agtattcaaa attgcctggc   480
agaagtcaat gtgaaacaaa tgagttgggt gggcaaatga caatttttta ctgtggaaag   540
atcaatgtgt acgatggtgt accacttgct aaggcacgag caatcatgca cctggcagct   600
tctcctattg attttcctca gggcaatcta tgtaatcaaa atggtgcctt taggtccttt   660
ctgggtcatg tacaagaagc cgaagacaaa acgaccttta cttcatctat tgctttgaac   720
ttgaattctc ataccatgca cactgagaag atgacagaat atcagcagca gtttagggga   780
aaagcaaaca tcagtcgtga ttctgatgta gatggacagg tgagcagaaa agaatcattg   840
cagcgatatc ttgaaaagcg aaaagacagg ggaagattct ttaaaggcag gaaaaatgca   900
ggacaagctt tgtctagctc ggagatgtac ctgaaccatc agataagagc tcactactta   960
aatggacaaa caaaccagag cagaacaagt tctccaccac agtctggagt gccacatgca  1020
ttttatagct cagctgacaa ccaagagctt gtgaattttt ctgtagatct caatgatgaa  1080
```
ggtggtcaag aacactga 1098

<210> SEQ ID NO 100
<211> LENGTH: 1026
<212> TYPE: DNA
<213> ORGANISM: Gossypium raimondii

<400> SEQUENCE: 100

| | |
|---|---|
| atgtctccgg gagaaacggt ctcccggtca cctctagaca agcctctgaa ccagcttact | 60 |
| gaggatgaca tttctcaggt cactcgcgaa gattgccgcc gttacctcaa agaaaaaggg | 120 |
| atgcggagac cgtcttggaa caaatcgcag gcgattcagc aggtgatctc gttgaaaact | 180 |
| cttctagaaa cgacgtctga ttccgacgcc gttgaagctc ggaagaaact ttaccctccc | 240 |
| tgcccggaat atccgcctcg cgtgcgtgtc gtttctgatt caaacgttct accgagggaa | 300 |
| atgacaccga taacgggat attggttcca gtttccgaat ccgttccttg cccccattca | 360 |
| aatccctcga atccgatttt tccggcgac aattctggcc gaacggtcat ctccggaaat | 420 |
| gattctgttt ctccaagaat tgcaggtgca gcaaaagagc cagcaggaca gatgacaatc | 480 |
| ttttactgtg ggaaagtgaa tgtctatgat gatatgcctg ttgtaaggc tgaagcaatc | 540 |
| atgcagcttg ctgcaagccc agtctcattt cctcacgaaa ttctagctga tcaaaggtcc | 600 |
| acaccatggt ccattccatg ccattccag gctgcaagtg tcaaaacaat cccatgttca | 660 |
| caaatggtta tattgccacc tcagcaaaca gaaaactgtc aatttcctcg agaagagagc | 720 |
| aatgcatctc ttgaagacag ccttgaagga cctactagca gaaaagcatt ggtgcaaaga | 780 |
| tatcttgaga agaagaaaga caggtttaag aacaagagaa agttggcaat gtcttcatct | 840 |
| ccgaccttag acatctactt aaatcaagtg ggagatcagt tttcaaatga gcagttgaaa | 900 |
| caaagtgaac catattattc tccccaagca gaagtgcacc gcatgcctct tgagtgcagc | 960 |
| tccattgaaa atgttgcaaa gattccccgc cttactactg atggaaaaga tgcattcaag | 1020 |
| atatga | 1026 |

<210> SEQ ID NO 101
<211> LENGTH: 1128
<212> TYPE: DNA
<213> ORGANISM: Populus trichocarpa

<400> SEQUENCE: 101

| | |
|---|---|
| atgcaaccgg gagagacagt ttcccggtca gctctagaaa accccttca ccaactaacc | 60 |
| gaagatgaca tttctcagct cactcgcgaa gattgccgcc gttacctcaa agaaaaaggt | 120 |
| atgagaaggc cgtcgtggaa caaatcgcag gcaatacagc aagtgatttc actcaagaca | 180 |
| ctcctagaaa cgacgccgga gacagaatct ccaaggcgac gactctacat tccccctcct | 240 |
| gataaccctc gcgtgccccc tgcaaattcc tctgtctcgg tgggggggaga aagtgccgat | 300 |
| gcaccgatct tggtgtcagc tgaggagtta gtgccgtccc ggcaaccgca tcccccgaat | 360 |
| cccgttgttc ccgctgatcc tccgccgccg gtgtttgtcg ctgccaccga aaatgattcg | 420 |
| gtttctccaa gaactacagg ggcggcaaaa gaatcagcag acagatgac aattttttac | 480 |
| tgtgggaagg taaacgtcta tgataatgta ccgagagata aggcacaagt aataatgcat | 540 |
| cttgctgcaa gcccatttgc tccacctcag gaagcttctt caaatgtaat tccagcacta | 600 |
| tggcctattc catgtcaatt ggaaactcca ggtgtcaaag caactccaaa ttccactgtg | 660 |
| gtgatcttcc caaacctgcc aacagtgaaa ggcgcggatg atggtcagct tccccaggaa | 720 |

| | |
|---|---|
| gaaagcaaca tagctcgcga agacaaccta gaaggctcaa caagcagaaa agcatccttg | 780 |
| caaagatatt tagagaagaa gaaagacagg ttaaagaaca agagaaaggt ggcaatgact | 840 |
| tctgctagcg tagacatcta cttaaaccat cgggttggag atcaaatctc gaatgatcat | 900 |
| tggaacctaa atgatgcctg ctcatctccc cagcctagac ctcctcaaac gcctaataga | 960 |
| tgcaactcta ttgacaattt agcaaaaaat ggcagccttt cagctgacct taatgaaaaa | 1020 |
| ggatatgcac aaaagcgttt actgcagttc agcttgtggt tctttactga aagtgctgaa | 1080 |
| tggaagagat gcaacacact tttgaatgtt attgaaaata catgttaa | 1128 |

<210> SEQ ID NO 102
<211> LENGTH: 1365
<212> TYPE: DNA
<213> ORGANISM: Populus trichocarpa

<400> SEQUENCE: 102

| | |
|---|---|
| atgaaaagga aatcaagact tgtaaaatgt aaactaagag acaaggtgaa gtttcaagtg | 60 |
| agacgccgcg acacaaacgc ctcccctctt cctccacgca tctctcactc tcctgcccat | 120 |
| tctcccagaa ccttgtcacc ccttgaagta caacatattc accaaaatac cactcgaagg | 180 |
| tgtaaaatca cactaaatcg ctccggtaac cgatcaccgg acccaaaatc aaacaccatg | 240 |
| cagccgggag agacagtttt ccggtcagct ctggacaaac ccctacacca gctaacagaa | 300 |
| gatgatattt ctcaggtcac tcgcgaagat tgccgccgtt acctcaaaga aaaaggtatg | 360 |
| agaaggccgt cgtggaacaa atcgcaggca atacagcaag tgatttcact caaaacactc | 420 |
| ctggaagcga cgccggagac tgaatctcca aggcgacgac tctacattcc ccgccctcct | 480 |
| cctcatcctc ctgataatac tcctcgtgtg cgtttctctg ccgtccctcc aaattcctct | 540 |
| gtttcagaga gggagcaag tgctgaaacg ccgatctcgg tgccagccga ggagccagtt | 600 |
| ccgtgccggc aacacgatcc tccaaatccc gatgatcctg ccgatcctct gcctcctgtc | 660 |
| catgccgccg tcaccgagaa tgcttcggtt tcaccaagaa ctacaggcat ggcagaagaa | 720 |
| tcagcaggac agatgacaat tttttactgt gggaaggtaa acgtctatga tgatgtaccg | 780 |
| ggagacaagg cgcaagcaat aatgcatctt gctgcaagcc catttgctcc acctcaggat | 840 |
| gcttcttcag atgtaattcc tacattaagg cctttacaat gccagttaga cactccaggt | 900 |
| gtcaaagctg ctccaaattc aattgtggcg aactttccaa ccctgccaac agtgaaaggg | 960 |
| gcagatagtg gtcagcttct ctgggaagaa agcaacatag ctcgtgaaga caacctagaa | 1020 |
| ggctctacaa gcagaaaagc atccttacaa agatattttg agaagaagaa agacaggttc | 1080 |
| aagaacaaga gaaaggtggc agtgccttct gctagcttgg acgtcttctt aagccatctg | 1140 |
| gttggagatc aaatctcaaa tgatcattgg aacctaaatg atgcctgctc ccttcccaa | 1200 |
| cccaggcctc cccaaacgcc taaccggtgc aactctgttg acaatgtagc aaaaaatggc | 1260 |
| atcctcaaag ctgaccttaa caacaaaggt gatgcagatt tatcttgttg tcttgactttt | 1320 |
| agttccaagc agattaatgc gtggtgctta tgcttgggat gttga | 1365 |

<210> SEQ ID NO 103
<211> LENGTH: 1008
<212> TYPE: DNA
<213> ORGANISM: Phaseolus vulgaris

<400> SEQUENCE: 103

| | |
|---|---|
| atgaacgccg gcggaaccgc caccttccga tccatcctgg acaagcccct gaaccagctc | 60 |
| acggaggatg acatttctca gctcactcgc gaggactgtc gcagattcct caaagaaaaa | 120 |

```
gggatgcgca ggccttcatg gaacaaatcg gaggcgatcc aacaggtcat ttccctcaaa      180
gcgcttctcg aaccttccga cgatgattct cctcctcatc ctcccccccat gcaccaccat     240 cctcatgcgc ctcaacctca agccaatttg actcaacctc cgcctaaggt ccctcctcct     300
gaagaacccg cttttcacgc cgtcgacgac attcagaaat ctgcctcttc tggggaaaaa     360
cctacggaga ctaatgacac caacaccaac gccaacgttg ctagcccag agggtgtgca      420 actagtggat catttggcca aatgacaatt ttctattgtg gtaaggtgaa cgtctatgat     480
ggagtctcac ctgataaggc acgagcaatc atgcagcttg ctgcaagtcc tgtccacttt    540
actcaggatg atcctttaca tggaaatgca tcagtttggt cttctccttg tcacttaccg    600
atggataagg atgtcctcat ccctgttgat acaacaatcc ttaaggttgc tcaagcagat    660
aagatggtgg aatatcctct gcaatacaga gacaaaggga gcttaaatcg tgatgctgat   720
atagatggtc aagcaagcag aaaaatgtcg ttgcagcgat atcgtgaaaa gcgtaaggac   780 agggaagat ttaaaggcaa gaaattgact gcaataactt catctaactt cgagatgtat    840
ttgaaccttc cagtgaaggt ccatgcctca aatgggaatt caagccgtag tagcactagc    900
tctccaccac agcctagact gcctctagtt tccagtggtt cagctgacaa ccagctcaaa    960
gttgcccttc ccattgatct caatgacaaa gatgttcaag aatgctaa                 1008

<210> SEQ ID NO 104
<211> LENGTH: 960
<212> TYPE: DNA
<213> ORGANISM: Solanum lycopersicum

<400> SEQUENCE: 104
atgccgccgg aagaaacagt ttccaagtca cctctcgata aacctctcaa tcagctcact     60
gacgatgaca tttctcagct cactcgcgaa gactgccgcc gttacctcaa acaaaaagga    120
atgagaaagc cgtcatggaa taaatcacag gcgattcagc aagttatatc gttgaaggct    180
ctcctcgagc cggatactga cgccggaagt cggaagaaac ttcacattcc tcgtgcagat    240
actcatgtcc agagagggaa aaataccact ggcgaacctt ctgaaccagt gcctgataga    300
agaaatcagc aagataaacc tgatcttccc aatcatagca ctgcccttcc ggtcactgtt    360
gttgacaatt cagctccttc tagaactata ggttcagcag ataaaccagt aggacaaatg    420
acaatcttct atagaggcaa ggtgaatgtc tatgatgatg tgcctgctga caaggcacaa    480
aaaatcatgt gtcttgcttc aagccctctt tgtatgcctt cagaaactcc atcgaatgcc    540
actgcagcag ctcgacattc agcatactgc ttacaagctg caaatagtaa actacgccta    600
gatactgtga aaatgagtga ggtttctcga gttcctatag aagaaagcaa ccgcttatgc    660
aatgataatc ctggagcagt ggagagcccc gcaagcagga agcatcagt acaaagatat    720 cttgagaagc gaaaagaaag gttcaagtgg aagagaaagg tagaaacaac ttcatcagct    780
aacttggata tctatttaag cgatcgaatt gggacttgtt caccaagtga ctatgcaagt    840
ggggctgatc ttagcttccc accccacatt acacctacag gaagtggtcc tatacaagac    900
aacattcaga tgaatcccac cttttctagt ggtctcaatg acagagatgt tagaaagtga    960

<210> SEQ ID NO 105
<211> LENGTH: 1020
<212> TYPE: DNA
<213> ORGANISM: Solanum lycopersicum

<400> SEQUENCE: 105
```

```
atgtcgctgg aacaaactgt ttacaagtct cctctggaca aaccgcttta cctacttacc    60
gatgacgaca tttctcagct cactcgcgaa gattgccgac gttttcttaa agctaaagga   120
atgagaaagc cgtcatggaa taaatcacag gcgattcagc aggtgatttc actgaaggcg   180
ttgtttgaga cgacgccgga atccgacacc ggtcagcgga aaaagcgtca cattcctcgc   240
ccggacacta gtttacagcg agtccagaaa gaaacgagta tcgatgcaga atttgctgaa   300
tcggctgaag aaacggtgcc gtacggtaga aaacctccca ataaacctga tctttccggc   360
gacaaagctg caagtgctgt tgccgttgtc aataacttag ctccttctag aaccacagat   420
tcaggaaatg catcatcagg tcaattgaca atcttctatt gtggcaaggt gaatgtgtat   480
gatgatgtac ctgctgaaaa ggcagaagca atcatgcatc ttgctgcaag cccactcttt   540
gtcccttcag aaactccatt ggatgctaac agagcagctc aacattccga atgccatttg   600
caagctgcaa atgttaaact gggtcaagat tctcctatgg tgttcatgcc aaccatgcaa   660
acagggaaaa taactgaagt tactcgcctg catttggagg aaagcaacac ttcctatgaa   720
gacaatcctg aagcagtgaa ccacgtaagc aggaaagcat tactggaaag atatcgtgag   780
aagcggaaag acaggttcaa gagaaagatg ggaatgcctt catctgctag cttggacatc   840
tatttgaacc atcgaaccat aaatcatacc caaagcgagc tctcaagtag gagcaacact   900
tgttccccgc ccgcaattag attatctgct gcgcctgctc caagtggttc aatggataac   960
attctccaaa tggatgccaa tgcttctggt tttctcgacg acaaagatgg taaagagtga  1020
```

<210> SEQ ID NO 106
<211> LENGTH: 1281
<212> TYPE: DNA
<213> ORGANISM: Theobroma cacao

<400> SEQUENCE: 106

```
atgacatttc tcaggtcact cgcgaagatt gccgccgtta cctcaaagaa aaaggtctct    60
ctctttcttt gcatcttttt gtgtttcttt tgcatatttt cttatgtaaa agtgcgtacg   120
cgttgcattt ctagttttct tttttgttgt tctttgcgtg tagggatgcg gagaccgtcg   180
tggaacaaat cgcaggctat tcagcaggtg atctcgctga aaacgctcct tgaaacaacg   240
tcggattcgg acgccgtcga agcttgcaag aaactccaca ttccctgccc tgaaaatccg   300
cctcgtgtcg tttctgattc aacggttcta gtgaatgaaa cgacacagca taacggaaat   360
tcggccccag tcaacgaatc tgttccttgt ccccgtccag atccctctaa atccgacttt   420
tcaggcgata ttcgggccg taacgccatc tctggaaatg actctgtttc tccaagaact   480
gcaggagctg ctaaagagca agcaggacag atgacaattt tttactgtgg ggaagtgaat   540
gtctatgatg atatgcctgg ttgtaaggcg caagcaatct tgcagcttgc tgcaagtcca   600
cttttcactat ctcaggaaac tgcagctgat caaagcagag caccatggtc tgttccatgc   660
cagttacaag ctgcaggtgt caagataagc ccatgttcac caatggttat attgccatca   720
ccgcaaacag taaaggtggc agaaaactgt cagtttcctt gggaagagag caatatatct   780
cgtgaagaca gccttgaagg tcccagtagc agaaaagcat tggtacaaag atatcttgag   840
aggaagaaag acaggtttaa gaacaagaga agttggcaa cgtcttcatc tcctacctta   900
gacatctaca taaatcaagt gggagatcag tttgcaaatg agcagttgaa gccaagtgaa   960
ccatattctt cttcccaaac acgaccgcct tacacacccc ttcggtgcaa ctccattgag  1020
aatgtcccaa agattgccag tcttgctact catcctgatg ccaaagcttc caacagctgg  1080
aaaggaagcc tggttgtggc ttctcttatc tggacaatat tcctgcggct ttatcatatg  1140
```

```
aagtctcaaa ctagttacgc tagtttagtc ataaagttcc ctgtcagttt caacatattt    1200
caactgcctg tactgatgac cagcaaaaat gcatcatatt tatacagtca acaggtgtca    1260
ctagatgtat atgaaatatg a                                              1281
```

<210> SEQ ID NO 107
<211> LENGTH: 1065
<212> TYPE: DNA
<213> ORGANISM: Theobroma cacao

<400> SEQUENCE: 107

```
atggaggcgg gggtagcgac gacgacgaca acgacggagt cgtttaggtc gatacttgat     60
aaacccctca gccaactaac agaagaagac atttctcagc tcactcggga agattgtcga    120
aaattcctca aggaaaaagg aatgcggagg ccgtcgtgga acaaatcgca ggcgatccag    180
caagtaattt cactcaaggc gttgttggag agcaacgaag attccggcgc cggagctatc    240
cggaagatcc tcgtttctcc accatcaccg tcagtgcctc cgcaaaatgc agcggcgcgt    300
gtggcttcca attcatgtga ttcagtaaaa gaagcggttg tcggagaaga aggaagcccg    360
tatcggcgaa agatcctcc tttgaaacct tctccggtgg gggagataaa ttgccttggc    420
ggtgacacgg ataacaagaa tctctctcct agaagtccat gtgaatcaaa tgagttgggt    480
gggcaaatga caatttccta ctgtggaaag gtcaatgtgt atgatggagt accacttgat    540
aaggcacggg caatcatgca tctggcagcg actcctattg attttcctca ggacaatcaa    600
tgtagtggaa atgcagccct taggtccttt atgtgccatg tccaagcagt cggtgacaaa    660
aatggccttg ttgcttctac tgccttgaac tctcatacca tgcaaacaga aagttgaca    720 gaatatcagc atcagtttag ggaaaaagga aatatcgctc gtgacgctga tgtagatggg    780
caggtgaaca gaaaagtatc attgcagaga tatcgtgaaa agcgaaaaga caggggaaga    840 tttttttaagg gcaggaagaa tacaggacaa gcttcctcta gcttggagat gtacctgaac    900
catcagataa gaactcacaa ctcaaatgga caatcaagcc ggagcagcac gggttctcca    960
ccacagtctg gattgccaca tgcatttttgt agctcagctg acaaccaagc aaaacttgtg   1020
aatctttctg tagatctcaa tgacaaaagt gttcaagaac actga                    1065
```

<210> SEQ ID NO 108
<211> LENGTH: 939
<212> TYPE: DNA
<213> ORGANISM: Conradina grandiflora

<400> SEQUENCE: 108

```
atggaggatg taggagtgtc aacggcgaag tctatacttg cgaagcctct taagctactc     60
actgaagatg acatttctca gctcactcgc gaagactgcc gcaaattcct caagagaaa    120 ggaatgcgca ggccttcgtg gaacaaatct caggcgatcc agcaagtttt atcacttaaa    180
gctctctttg agcccggcga cgattccggc gccggtatcc tccgcaagat cctcgttct    240 cagccgccaa ttccgcctcg tgtcacaaca acttcgactg agctaagcaa cgagctcgaa    300
gcttgtggcc ggattcctcc ttttcaggaa gatgatggtc cctgccatag aagggattct    360
ccaagatcag ctgagttttc cggtggttct gctcattatc agctgagaa agataccaac    420 aagactgtct ccctcagaag cccagctgaa actaatgcgc tggttggaca aatgacgata    480
ttctatagtg ggaaagtgaa tgtgtatgat ggagtaccat ctgagaaggc ccagtcaatc    540
atgcactttg cagccaatcc agttgacttg cctgcaaatg gtatcttttc ttctagttgt    600
```

```
atgcccatga gtaaagagaa gatggtggaa cttccccaaa ttggccttga gagggtgaat      660
tcttctcgtg attttgatat ggaaggtcat gcaaacagga agatgtcgtt gcaaagatat      720
cgtgaaaagc ggaaggacag aagattcctt aaagccaaaa agtctccagg agttgcgtcc      780
tcgagcttgg aaatgtttct aaatcgtcag ccacgaatga atgctgcata ctcacaaaac      840
cttggccaca caagatcctc actgcagagc gagtcacctg aaaacccaag aaaaagtccc      900
aatctatcag ttgatctaaa cagtgaagca gatatttaa                             939

<210> SEQ ID NO 109
<211> LENGTH: 942
<212> TYPE: DNA
<213> ORGANISM: Conradina grandiflora

<400> SEQUENCE: 109
atggatgttg gagtctctcc ggcgaagtct atacttgcga agcctctgaa actgttgact       60
gaagaggaca tttctcagct cactcgcgaa gattgtcgca aattcctcaa agagaaagga      120
atgcgcaggc cttcatggaa caaatctcag gcgatccagc aagttttatc ccttaaagct      180
ctctttgagc ctggcgacga ttccggcgcc ggaatcctcc gtaagatcct cgtttctcag      240
ccgtcaattc cgcctccggt tacatcaact tcgattgagc aagtagcga gctcgaagct       300 tgtggtagga atccttttca agaagatgaa ggtccttgcc atagaaggga ttctccaaga      360
tcagctgagt tttccggtgg ttctgctcag tttgtagctg agaaagatag cttaaagaca      420
gtttccccca gaagtccagc tgaaacaagt ccgctggttg acaaatgac aatattctat       480 agtgaaaaag tgaaagtata tgatggagta ccacctgaaa aggcgcggtc aatcatgcat      540
tttgcagcta atccaattga tttgcctgaa atggtatttt tgcctctag tagaatgatt       600 tcgaagccca tgagtaaaga gaagatggtg gatcttcccc aatatggcct tgaaaaggcc      660
actgcttctc gtgattctga tgtggagggt caagcgaaca gaaaagtgtc attgcaaaga      720
taccttgata gcggaaagga cagaagattc tccaaaacca aaaaggctcc aggagttgca      780
tcatctagct tggacatgtt tctgaatcgt cagccacgga tgaatgctgc atattcacaa      840
aaccttagcg gcgcagggct ctgcgagtca cctgagaacc agacaaaaag ttcaaatctc      900
tcagttgatc taaacagcga tctaaacagt gaagatctgt aa                         942

<210> SEQ ID NO 110
<211> LENGTH: 1017
<212> TYPE: DNA
<213> ORGANISM: Mimulus guttatus

<400> SEQUENCE: 110
atgcagccgg aagtcaccgc cgtcaattcg tctctcgaga agccgcttca ccagctcacc       60
gaagatgaca ttgctcaggt caccgcgag gactgccgcc gttacctcaa ggaaaaaggg       120
atgaggcggc cgtcgtggaa caaatcgcag gcgattcagc aagtgataat gctgaagact      180
ctccttgagg tggcgccgga ttccgactcc ggttcgcgca gaggctccg attttcccgc       240 cctaacgaca atggtgttat cccggagagt gttaccaaag caacccacat tgagggggaa      300
acttctgtat cggctgaata tacgcgccg ttttgtggaa aggatctcga caaacctgat       360
tcttccggtg ccgctgcccg ttgtcttgct gtcaacaatg accctactct atctagaaca      420
acagcatcat taggtatgcc ggtgggacaa atgacgattt tttattgtgg caaagtaaat      480
gtgtatgaca tgttccaga agacaaggcg caatcaataa tgcatattgc tgcaagcccg      540
gtacagtttc cacaagaaca gcagccagtt gatgatacta tcattattca cccttttaacc      600
```

| | |
|---|---|
| agcctctcga aagctgtgag tgtgaaagca ggtctagatt ctcccgtcgc tctcttgcca | 660 |
| gctctacaga cagtgaaaat gagtgaaaac tctcgagcgc ttgcggatga atgtatctca | 720 |
| cttcgtgaag ggacccctgt ggagggtcca tcaaccagaa aagcatcggt gcagagatac | 780 |
| ctcgacaaga gaaaagacag gtttaagagc aagagaaagg caggaataac ctcatgcaca | 840 |
| agcttggacg tgcaattcaa ccatcaaaag aataatcaaa taccaaatga cttcttgaat | 900 |
| agaagcaaca catgctcacc accaccaatc aaaccacctt ctaccctac aagatgcagc | 960 |
| tctgtggaca atgattcatt aaggaatctt tgtggttcta ctgatctgaa taactga | 1017 |

<210> SEQ ID NO 111
<211> LENGTH: 1014
<212> TYPE: DNA
<213> ORGANISM: Mimulus guttatus

<400> SEQUENCE: 111

| | |
|---|---|
| atgcagccgg aagtcaccgc cgtcaattcg tctctcgaga agccgcttca ccagctcacc | 60 |
| gaagatgaca ttgctcaggt cacccgcgag gactgccgcc gttacctcaa ggaaaaaggg | 120 |
| atgaggcggc cgtcgtggaa caaatcgcag gcgattcagc aagtgataat gctgaagacg | 180 |
| ctcctcgagg gggcgccgga ttccgactcc ggttcgcgca gaggctccg attttcccgc | 240 |
| cctaacgaca atggtgttat cccggagagt gttcccaaag caacccacat tgagggggaa | 300 |
| acttccgtat ccgctgaata tacggcgccg ttttgtggaa aggatctcga caaacctgat | 360 |
| tcttcccgtg ccgctgcccg ttgtcttgct gtcaacaatg accctactct atctagaaca | 420 |
| acagcatcat taggtatgcc ggtgggacaa atgacgattt tttattgtgg caaagtgaat | 480 |
| gtgtatgacg atgttccgga agacaaggca caatcaataa tgcatattgc tgcaagcccg | 540 |
| gtacagtttc cacaagaaca gccagttgat gatactatca ttaatcaccc tttaaccagc | 600 |
| ctctcgaaag ctgtgagtgt gaaagcaggt ctagattctc ccgttgctct cttgccagct | 660 |
| ctacagacag tgaaaatgag tgacaactct cgagcacttg cggacgaatg tatctcactt | 720 |
| cgtgaaggga cccctgtgga gggtccatca accagaaaag catcggtgca gagatacctc | 780 |
| gacaagagaa aagacaggtt taagagcaag agaaaggcag gaataacctc aagcacaagc | 840 |
| ttggacgtgc actttaacca tcaaaagaat aatcaaatac caaatgactt cttgaataga | 900 |
| agcaacacat gctcaccacc accaatcaaa ccaccttcta cccctacaag atgcagctct | 960 |
| gtggacaatg attcattaag gaatctttgt ggttctactg atctgaataa ctga | 1014 |

<210> SEQ ID NO 112
<211> LENGTH: 1041
<212> TYPE: DNA
<213> ORGANISM: Glycine max

<400> SEQUENCE: 112

| | |
|---|---|
| atgaacggcg cgccaccac cgccaccttc cgatccatcc tcgacaagcc cctcaaccag | 60 |
| cttaccgagg atgacatttc tcagctcact cgcgaagact gtcgcagatt cctcaaagaa | 120 |
| aaagggatgc gtaggccttc ctggaacaaa tcgcaggcga tccaacaggt catttccctg | 180 |
| aaagcgctgc tggaaccttc cgacgatgat actcctcctc ctcctcctcc cgccatgcac | 240 |
| caccgtagcc atgctcaacc tcaacctcaa gtgaatttga gtgaacctcc tcctcctccg | 300 |
| cccaaggctc cgccacctga gaacccgct tttcatgctg ctgaagacat tcagaaatct | 360 |
| gcgtcgtctg ggaaaagcc tacggaaact aatgacacca acaccaacgt tgctagcccc | 420 |

| | | |
|---|---|---|
| aaagggtgtg caactagtgg atcatttggg caaatgacaa ttttctattg tggtaaggtg | 480 | |
| aatgtctatg acagagtctc gcctgataag gcacgagcaa tcatgcagct tgcaacgagt | 540 | |
| ccagtccagc ttactcagga tgatccttta aatggaaatg cagctgtttg gacttctcct | 600 | |
| tgccacttac cgatggataa ggatgtcctc gttcctgttg atactacaat ccttcaggtt | 660 | |
| gctcaagcag ataagatggt ggagtatcct ctgcaatata gggagaaagg gagcatagct | 720 | |
| cgtgatgctg atgtagaggg tcaggaacac cgaaaagtgt cattgcaacg atatcttgaa | 780 | |
| aagcgtaagg acaggggaag attgaaaggc aagaaattga ctgggataac ttcatctaac | 840 | |
| ttcgagatgt atttgaacct tccagtgaag gtccattcct caaatgggaa ttcaagccgt | 900 | |
| agcagtacta gctctccacc acaacctaga ctgcctctag tttccagtgg ttcagatcag | 960 | |
| ctaaaggttg cccttcccat tgatctcaat gacaaagtgt cttttgcagat gttcaagaat | 1020 | |
| gctaaaattc aaactagata g | 1041 | |

```
<210> SEQ ID NO 113
<211> LENGTH: 1053
<212> TYPE: DNA
<213> ORGANISM: Glycine max

<400> SEQUENCE: 113
```

| | | |
|---|---|---|
| atgaacggcg gtgccaccac cgccaccttc cgatccatcc tcgacaagcc cctcaaccag | 60 | |
| ctcaccgagg atgacatttc tcagctcact cgcgaagact gtcgcagatt cctcaaagaa | 120 | |
| aaagggatgc gcaggccttc ctggaacaaa tcgcaggcga tccaacaggt catttccctg | 180 | |
| aaagcgctgt tggaaccttc cgacgatgat actcctcctc ctaccgccat gcaccacgt | 240 | |
| agtcatgctc ctccccctcc acctcaacct caatctcaag tgaatttgac tgaacctcct | 300 | |
| cctccgccca aggctccgcc acctgaagaa tcctctttc atgctgctga agacattcag | 360 | |
| aaacctgcgt cgtctgggga aaaaccttcg gaaactaatg acaccaacac caacgttgct | 420 | |
| agccccaaag ggtgtgcaac tagtggatca tttgggcaaa tgacaatttt ctattgtggt | 480 | |
| aaggtgaatg tctatgatgg agtctcgcct gataaggcac gagcaatcat gcagcttgcg | 540 | |
| gtgagtcctg tccagtttac tcaagatgat ccttcaaatg gaaatgcagc tgtttggcct | 600 | |
| tctccttgcc acttaccaat ggataaggat gtcctcattc ctgtagatac aacaatcctt | 660 | |
| caggttgctc aatcagataa gatgatgaa tatcctctgc aatatagaga gaaaggtagc | 720 | |
| atagctcgtg atgctgatgt agagggtcag gcaagcagaa agtgtcatt gcagcgatat | 780 | |
| cttgaaaagc gtaaggacag ggggagattg aaaggcaaga aattgactgg gataacttca | 840 | |
| tctaacttcg agatgtattt gaaccttcca gtgaaggtcc atgcctcaaa tgggaattca | 900 | |
| agccgtagca gtactagctc tccaccacag cctagactgc ctctagtatc tagtggttca | 960 | |
| gctgacaacc agctaaaggt tgcccttccc attgatctca atgacaaagt gtcattgcag | 1020 | |
| atgttcaaga atgctaaaac tctaactaga tag | 1053 | |

```
<210> SEQ ID NO 114
<211> LENGTH: 951
<212> TYPE: DNA
<213> ORGANISM: Brassica rapa

<400> SEQUENCE: 114
```

| | | |
|---|---|---|
| atggaaggag gagtgtcttc ggcgaagtca atactggaga agccactgaa gctgctcacg | 60 | |
| gaagaggaca tttctcagct gacgcgcgag gattgccgca aattcctcaa ggagaaagga | 120 | |
| atgcgaagac cttcttggaa caaatcccag gcgatccagc aagttctctc cctcaaagct | 180 | |

```
ctctttgagc cggcgacga ctccggcgcc ggcatcctcc gcaagatcct cgtttctcac    240
cctccaattc cctctcgcgt cacaacaccg tcgactgagc aagcaacga cctcggagct    300 tgtggccaga ttccttttca ggaagatgat ggcccttccc tcaggagaga ttccccaga    360 tcacctgact tttctggtgg ctctgctcac tatctagccg acaaagactg ccacataaca    420
ctctctccca gaagcccagc agaaacaagt gcgctggctg ggcaattgac gatattctat    480
agtggaaaag ttaatgtata tgatggtgta ccacctgaaa aggctcggtc aattatgcac    540
tttgcagcca atcctattga ttttcctgac agtggtgttt ttccttctag tcgaatgatt    600
tccaggcccg tgagtaaaga aaagatggtg gagcatcctc attatggcct tgagaaggca    660
aatgcttctc gtgattctga tgcggagggt caggcgaaca gaaaagtgtc gttgcaaaga    720
tatcgtgaaa agcggaacga gagattgttt aagaccaaaa aggctccagg agtgggatca    780
tctagcttgg agatgtatct gaaccgtagt cagccactga tgaacgctgc tgcatattca    840
caaaacccta gtggcggcac aggaggagaa caccagtcac ctcaaaacca gacaagaagc    900
cccaattttt cagttgatct gaactgtgat ctaaacagtg aagatatcta a    951
```

```
<210> SEQ ID NO 115
<211> LENGTH: 921
<212> TYPE: DNA
<213> ORGANISM: Brassica rapa

<400> SEQUENCE: 115
atggacgcag tgtcttcggc gaagtccata ctggagaagc tctgaagct cctcacggaa     60 gatgacattt ctcagctcac ccgcgaggac tgccgcaagt tcctcaagga caaaggaatg    120
cggaggcctt cgtggaacaa atctcaggcg atccagcaag tttttatccct caaagctctc    180 tttgagcccg cgacgactc cggcgccggc atcctccgca gatcctcgt ttctcccaat      240 cccactcgcg tcacagcaac gtcgactgag ccagcgaacg aggtcggagc acggattcct    300
tttcaggaag atgacagaag agattctcca agatcggctg agttctccgg ctccgagaaa    360
gacagctaca acactctctc tcccagaagc ccagcagaaa caagtgcgct ggttgggcaa    420
atgacgatat tctatagtgg gaaagtgagt gtgtatgatg gtgtaccacc tgaaaaggcg    480
cggtctatca tgcactttgc agccaacccg attgatttgc ctgaatatgg tgtttctgct    540
tctgctagat tgacatcaag gcccatgacc atgagtaaag agaagatggt tgaacctccc    600
cactatggct atggccttga aaaggcaaat gcttctcgtg attctgatgc ggagggccag    660
gctaacagaa aagtgtcgtt gcaaagatat cttgacaagc ggaaggatag agattgtttt    720
aagaacaaaa aggcaccagg agttgcatca tctagcttgg agatgtatct gagtcgtagt    780
cagccagtga ccaacgcata ttcacaaagc cttagcggtg gtggcacagg aggagaacag    840
cacgagtcac ctgaaaatca gaggagaagt cccaatctat cagttgatct gaacagtgat    900
ttaaatagcg aagataacta a                                              921
```

```
<210> SEQ ID NO 116
<211> LENGTH: 936
<212> TYPE: DNA
<213> ORGANISM: Boechera stricta

<400> SEQUENCE: 116
atggatgttg aagtgtctcc ggcgaagtct atactggaga agcctctgaa actgttgact     60
gaagaggaca tttctcagct cactcgcgaa gattgccgca aattcctcaa agagaaagga    120
```

| | |
|---|---|
| atgcgcaggc cttcgtggaa caaatctcag gcgatccagc aagttttatc ccttaaagct | 180 |
| ctctttgagc ccggtgacga ttccggcgcc ggaatcctcc gcaagatcct cgtttctcag | 240 |
| ccggcaaatc cgcctcgcgt tgcaacaacg tcgattgagc caagcaacga gctcgaagct | 300 |
| tgtggccgga atccttttcc agaagatgaa ggtccttgcc atagaaggga ttctccaaga | 360 |
| tcagctgagt tttccggcgg ttctggtcag tttgtagctg agaaagatag cttcaagact | 420 |
| gtttccccca gaagcccagc tgaaacaagt ccgtttgttg ggcaaatgac gatattctat | 480 |
| agtggaaaag tgaatgttta tgatggagta ccacctgaaa aggcgcggtc aatcatgcac | 540 |
| tttgcagcca atccaattga tttgcctgaa aatggtcttt ttgcttctag tagaatgatt | 600 |
| tcaaacccca tgggtaaaga aagatggtg gagcttcccc aatatggctt tgaaaaggca | 660 |
| actgcttctc gtgattctga tgtggagggt caggcgaaca gaaaagtttc gttgcaaaga | 720 |
| tatcttgaaa aacggaagga cagaagattc tccaagacca aaaaggctcc aggagttgcg | 780 |
| tcaactagct tggaaatgtt tctgaatcgt ccacggatga acgctgcata ttcacaaaac | 840 |
| cttagcacag ggatctgcga gtcacctgaa aatcagacga aaagttccaa tctctcagtt | 900 |
| gatctaaaca gcgatctaaa cagtgaagat cttaa | 936 |

<210> SEQ ID NO 117
<211> LENGTH: 993
<212> TYPE: DNA
<213> ORGANISM: Medicago truncatula

<400> SEQUENCE: 117

| | |
|---|---|
| atgaacggcg gaagcaccgt ttccttccga tccatcctcg acagacctct taaccaactc | 60 |
| actgaagatg acatttctca actcactcgc gaagactgtc gcagattcct caaagataaa | 120 |
| gggatgcgca ggccttcctg gaacaaatca caggcgatcc agcaggtgat ttctctcaaa | 180 |
| gcgcttctag aacctaccga cgatgatatc ccggctaccg tcggcgttgg tgtctcctcc | 240 |
| gccattcacc accatcacca ccaccaccct cctcaacctc cgccgaaggc tttggatccc | 300 |
| gaagatactg ctttggaact acagaaatcc acttcacctg ttgctgagag acccacggaa | 360 |
| accaatgatg ccaatgttgt taacaatccc ggagggtgcg cacctagtgg gtcatttggg | 420 |
| caaatgacaa ttttctactg tggtaaggtg aatgtctatg atggagtctc gccggataag | 480 |
| gcacgatcaa tcatgcagct tgctgctgca tgtccgtcct cctttcctca ggataatcct | 540 |
| tcaaataaaa atgcagcagt ttgggcttct ccttgcaact tacctattga taaggaagtc | 600 |
| ctcttcccta ctgacacagc aatccttcaa gttgctcaaa cagataagat ggtgaaatac | 660 |
| cctctgcaat acagggagaa aggaagcaca gctcgtgatg ctgatgtaga gggtcaggca | 720 |
| agcagaaaag tgtcactgca gcgatatctt gaaaagcgaa aggacagggg aagatcgaag | 780 |
| ggcaagaaac tgactggcat aacttcatct aactttgaga tgtatttgaa ccttccagtg | 840 |
| aagctccatg cctcaaatgg gaattcaagt cgtagtagca ctgactctcc accacagcct | 900 |
| agactgcctt tagtttccag tggctcagct gaaaaccagc caaaagttac ccttcccatt | 960 |
| gatttgaatg ataaagatgt tcaagaatgc taa | 993 |

<210> SEQ ID NO 118
<211> LENGTH: 993
<212> TYPE: DNA
<213> ORGANISM: Medicago sativa

<400> SEQUENCE: 118

| | |
|---|---|
| atgaacggcg gaagcaccgt ttccttccga tccatcctcg acagacctct taaccaactc | 60 |

```
actgaagatg acatttctca actcactcgc gaagactgtc gcagattcct caaagataaa      120
gggatgcgca ggccttcctg aacaaatca caggcgatcc agcaggtgat ttctctcaaa      180
gcgcttctag aacctactga cgatgataca ccggctaccg tcggcgttgg tgtctcctcc      240
gccattcacc gccatcacca ccaccaccct cctcaacctc cgccgaaggc tttggatccc      300
gaagatactg ctttggacct tcagaaatct acttcacctg tttctgaaag acccacggaa      360
accaatgatg ccaacgttgt taaccctccc ggagggtgca cacctagtgg gtcatttggg      420
caaatgacaa ttttctactg tggtaaggtg aatgtctatg atggagtttc gccggataag      480
gcacgatcaa tcatgcagct tgctgctgca tgtccgtcct cctttcccca ggataatcct      540
tcaaataaaa atgcagcagt ttgggcttct ccttgcaact tacctattga taagaagtc      600
ctcttcccta ctgacacaac aatccttcaa gtcgctcaaa cagataaaat ggtgaaatac      660
cctctgcatt acagggagaa aggaagcaca actcgtgatg ctgatgtaga gggtcaggca      720
agcagaaaag tgtcgctgca gcgatatctt gaaaagcgaa aggacagggg aagatcgaag      780
ggcaagaaac tgactggcat aacttcatct aactttgaga tgtatttgaa ccttccagtg      840
aagctccatg cctcaaatgg gaattcaagt cgtagtagca ctgactctcc accacagcct      900
agactgcctc tagtttccag tggctcagct gaaaacctgc caaaagttac ccttcccatt      960
gatttgaatg ataaagatgt tcaagaatgc taa                                   993
```

<210> SEQ ID NO 119
<211> LENGTH: 324
<212> TYPE: PRT
<213> ORGANISM: Arabidopsis lyrata

<400> SEQUENCE: 119

```
Met Asp Val Gly Val Ser Pro Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Leu Arg Lys Ile Leu Val Ser Gln
65                  70                  75                  80

Pro Ser Asn Pro Pro Arg Val Ser Thr Thr Leu Ile Glu Pro Ser Asn
                85                  90                  95

Glu Leu Glu Ala Cys Gly Lys Ile Leu Glu Asp Asp Gly Ser Cys His
            100                 105                 110

Arg Arg Asp Ser Pro Arg Ser Ala Glu Phe Ser Gly Asn Ser Gly Gln
        115                 120                 125

Phe Val Ala Asp Lys Asp Gly His Lys Pro Val Ser Pro Ser Arg Ser
    130                 135                 140

Pro Ala Glu Thr Ser Ala Pro Val Gly Gln Met Thr Ile Phe Tyr Ser
145                 150                 155                 160

Gly Lys Val Asn Val Tyr Asp Gly Val Pro Lys Lys Ala Arg Ser
                165                 170                 175

Ile Met His Phe Ala Ala Asn Pro Ile Asp Leu Pro Glu Asn Gly Ile
            180                 185                 190

Phe Ala Ser Ser Arg Met Ile Ser Lys Pro Met Ser Lys Glu Lys Met
        195                 200                 205
```

Val Glu Pro Pro Gln Tyr Gly Leu Glu Lys Thr Ala Ala Ser Arg Asp
            210                 215                 220

Ser Asp Val Glu Gly Gln Ala Asn Arg Lys Val Ser Leu Gln Arg Tyr
225                 230                 235                 240

Leu Glu Lys Arg Lys Asp Arg Arg Phe Ser Lys Thr Lys Lys Ala Pro
                245                 250                 255

Gly Val Ala Ser Ser Ser Leu Glu Met Phe Leu Asn Arg Gln Pro Arg
            260                 265                 270

Met Asn Ala Ala Tyr Ser Gln Asn Leu Ser Gly Thr Gly Leu Cys Glu
        275                 280                 285

Ser Pro Glu Asn Gln Thr Lys Ser Pro Asn Leu Ser Val Asp Leu Asn
    290                 295                 300

Ser Asp Leu Asn Ser Glu Gly Met Asn Lys His Leu Leu Asn Gly Ser
305                 310                 315                 320

Asn Asp Leu Pro

<210> SEQ ID NO 120
<211> LENGTH: 312
<212> TYPE: PRT
<213> ORGANISM: Arabidopsis lyrata

<400> SEQUENCE: 120

Met Asp Val Gly Val Ser Ser Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Phe Glu Pro
    50                  55                  60

Gly Asp Asp Ser Gly Ala Gly Ile Leu Arg Lys Ile His Val Ser Gln
65                  70                  75                  80

Pro Ala Asn Pro Pro Arg Val Thr Thr Thr Asn Glu Leu Gly Glu Cys
                85                  90                  95

Gly Arg Asn Pro Phe Gln Glu Asp Asp Gly Pro Cys His Arg Arg Asp
            100                 105                 110

Ser Pro Lys Ser Ala Glu Phe Ser Gly Gly Ser Ala Gln Tyr Ala Ala
        115                 120                 125

Glu Lys Asp Thr Cys Arg Ser Pro Ala Glu Thr Ser Ala Leu Val Gly
    130                 135                 140

Gln Met Ala Ile Phe Tyr Ser Gly Lys Val Asn Val Tyr Asp Gly Val
145                 150                 155                 160

Pro Pro Glu Lys Ala Arg Ser Ile Met His Phe Ala Ala Asn Pro Ile
                165                 170                 175

Asp Leu Pro Glu Asn Gly Ile Phe Ala Ser Ser Arg Met Ile Ser Lys
            180                 185                 190

Arg Ile Ser Lys Glu Lys Met Val Glu Leu Pro Gln Asn Gly Leu Glu
        195                 200                 205

Lys Ala Asn Phe Ser Arg Asp Ser Asp Met Gly Gln Ala Asn Arg
    210                 215                 220

Lys Val Ser Leu Gln Arg Tyr Arg Glu Lys Arg Lys Asp Arg Lys Phe
225                 230                 235                 240

Ser Lys Ala Lys Lys Cys Pro Gly Val Ala Ser Ser Ser Leu Glu Met
                245                 250                 255

```
Phe Leu Asn Arg Gln Pro Arg Met Asn Ala Ala Tyr Ser Gln Asn Leu
            260                 265                 270

Gly Cys Thr Gly Ser Pro Leu Gln Ser Glu Ser Pro Glu Asn Gln Thr
            275                 280                 285

Lys Ser Pro Asn Leu Ser Val Asp Leu Asn Ser Glu Gly Lys Lys Arg
            290                 295                 300

Ile Ile Trp Arg Ala Leu Leu Lys
305                 310

<210> SEQ ID NO 121
<211> LENGTH: 312
<212> TYPE: PRT
<213> ORGANISM: Carica papaya

<400> SEQUENCE: 121

Met Ala Ala His Leu Thr Arg Val Val Thr Gly Met Arg Arg Pro Ser
1               5                   10                  15

Trp Asn Lys Ser Gln Ala Ile Gln Gln Val Ile Ser Leu Lys Ala Leu
            20                  25                  30

Leu Glu Thr Thr Asp Asp Ser Gly Ala Gly Ala Leu Arg Lys Ile Leu
            35                  40                  45

Val Ser Pro Glu Thr Thr Pro Arg Val Thr Ser Ser Pro Val Asp
 50                  55                  60

Ser Val Lys Glu Leu Gly Ala Gly Ala Gln Ile Ser Pro Pro Ala Asp
 65                  70                  75                  80

Glu Asn Gly Pro Tyr Arg Arg Lys Ser Pro Gln Lys Ser Ala Glu Leu
                85                  90                  95

Gly Cys Arg Pro Val Gly Glu Ala Asp Thr Lys Thr Ser Ser Pro Arg
            100                 105                 110

Ser Pro Gly Glu Ala Asn Ala Leu Val Gly Gln Met Thr Ile Phe Tyr
            115                 120                 125

Cys Gly Lys Val Asn Val Tyr Asp Gly Val Pro Pro Asp Lys Ala Gln
            130                 135                 140

Ala Ile Met His Leu Ala Ala Ser Pro Leu Asp Phe Pro Gln Asp Asp
145                 150                 155                 160

Ala Ile Gly Gly Asn Thr Val Pro Arg Ser Phe Pro Cys His Leu Gln
                165                 170                 175

Met Ser Asp Lys His Ala Phe Val Pro Pro Ser Ala Val Ile Ser Gln
            180                 185                 190

Thr Met Gln Thr Glu Lys Val Leu Glu Tyr Pro Gln Gln His Arg Glu
            195                 200                 205

Lys Gly Asn Asn Thr Arg Glu Pro Asp Leu Glu Gly Gln Ala Asn Arg
            210                 215                 220

Lys Val Leu Leu Gln Arg Tyr Leu Glu Lys Arg Lys Asp Arg Gly Arg
225                 230                 235                 240

Phe Phe Lys Val Lys Ser Thr Gly Val Thr Ser Ser Gly Leu Glu
                245                 250                 255

Met Tyr Leu Ser His Gln Val Arg Pro Asn Thr Ser Thr Gly Gln Ser
            260                 265                 270

Ser Gly Ser Gly Thr Asn Ser Pro Gln Pro Gly Leu Pro His Ile
            275                 280                 285

Ser His Ser Ser Ala Asp Asn Gln Ile Lys His Gly Ser Leu Ser Val
            290                 295                 300

Asp Leu Asn Asp Glu Gly Thr Met
```

<210> SEQ ID NO 122
<211> LENGTH: 335
<212> TYPE: PRT
<213> ORGANISM: Ricinus communis

<400> SEQUENCE: 122

Met Asp Ala Gly Val Thr Ser Phe Arg Ser Ile Leu Asp Lys Pro Leu
1               5                   10                  15

Thr Gln Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Thr
    50                  55                  60

Ser Glu Asp Ser Gly Ala Gly Ala Leu Arg Arg Ile Leu Val Ser Lys
65                  70                  75                  80

Pro Pro Val Thr Ser Asn Ser Val Asp Ser Ala Lys Glu Pro Ser Asp
                85                  90                  95

Ser Asn Asn Asn Leu Leu Asp Glu Thr Ala Pro His Asp Ser Pro
            100                 105                 110

Lys Ser Pro Pro Ala Pro Ser Leu Asp Cys Pro Leu Glu Glu Ala
        115                 120                 125

Asp Asn Lys Val Ile Ser Ser Arg Ser Pro Gly Ala Thr Asp Gly Leu
    130                 135                 140

Val Gly Gln Met Thr Ile Phe Tyr Cys Gly Lys Val Asn Val Tyr Asp
145                 150                 155                 160

Gly Val Pro Pro Asp Lys Ala Gln Ala Ile Met His Leu Ala Ala Thr
                165                 170                 175

Pro Ile His Ser Pro Leu Asp Asp Pro Ile Arg Arg Pro Val Phe Ala
            180                 185                 190

Phe Pro Tyr His Leu Gln Thr Pro Ser Asp Lys His Val Phe Val Pro
        195                 200                 205

Ser Asn Ala Ala Ile Ser Pro Thr Thr Pro Thr Glu Lys Val Thr Glu
    210                 215                 220

Tyr Ser Gln Gln Cys Arg Glu Lys Gly Asn Val Thr Tyr Asp His Asp
225                 230                 235                 240

Val Glu Gly Gln Ala Asn Arg Lys Met Ser Leu Gln Arg Tyr Leu Glu
                245                 250                 255

Lys Lys Lys Asp Arg Gly Arg Phe Lys Gly Arg Lys Asn Leu Gly Pro
            260                 265                 270

Asn Ser Ser Ser Leu Asp Ala Tyr Leu Asn His Gln Met Arg Thr His
        275                 280                 285

Ile Ser Asn Glu Gln Ser Thr Arg Ser Ser Thr Ser Ser Pro Thr Gln
    290                 295                 300

Pro Gly Val Pro His Thr Ser Ser Asn Ser Ala Glu Asp Gln Leu Lys
305                 310                 315                 320

Thr Ala Ser Phe Ala Val Asp Leu Asn Glu Asp Val Gln Glu Pro
                325                 330                 335

<210> SEQ ID NO 123
<211> LENGTH: 270
<212> TYPE: PRT
<213> ORGANISM: Ricinus communis

<400> SEQUENCE: 123

Met Ser Pro Glu Ser Lys Thr Met Gln Thr Gly Asp Ile Ile Ser Arg
1               5                   10                  15

Ser Asn Leu Asp Lys Pro Leu His Gln Leu Thr Glu Asp Asp Ile Ala
            20                  25                  30

Gln Leu Thr Arg Glu Asp Cys Arg Arg Tyr Leu Lys Asp Lys Gly Met
        35                  40                  45

Arg Arg Pro Ser Trp Asn Lys Ser Gln Ala Ile Gln Gln Val Ile Ser
    50                  55                  60

Leu Lys Ala Leu Leu Glu Thr Ala Pro Asp Ser Asn Glu Val Pro Lys
65                  70                  75                  80

Arg Arg Leu Tyr Ile Pro His Pro His Asn Val Pro Leu His His Arg
                85                  90                  95

Ile Thr Asp Trp Ser Asp His Ala Gln Ala Ile Met Gln Leu Ala Ala
            100                 105                 110

Cys Pro Leu Ser Leu Ser Gly Asp Thr Ser Ser Asp Ala Ile Pro Ala
        115                 120                 125

Leu Arg Pro Ile Pro Ser Gln Leu Glu Ala Pro Gly Val Lys Thr Ser
    130                 135                 140

Leu Ser Pro Met Phe Val Tyr Pro Thr Gln Thr Gly Lys Val Ala
145                 150                 155                 160

Glu His Cys His Leu Pro Lys Glu Glu Ser Asn Leu Phe His Glu Asp
                165                 170                 175

Asn Leu Glu Gly Arg Thr Ser Arg Lys Ala Ser Val Gln Arg Tyr Leu
            180                 185                 190

Glu Lys Arg Lys Asp Arg Phe Lys Asn Lys Arg Lys Val Ala Met Pro
        195                 200                 205

Ser Ser Asp Ile His Leu Asn His Cys Val Arg Asp Glu Phe Ser Asn
    210                 215                 220

Asp Gln Trp Asn Leu Thr Glu Ala Cys Phe Ala Thr Gln Pro Arg Pro
225                 230                 235                 240

Ser Gln Thr Pro Ile Gln Cys Ser Thr Val Ala Tyr Thr Glu Lys His
                245                 250                 255

Thr Asn Leu Ser Ala Asp Leu Asn Gly Lys Gly Asp Ile Gly
            260                 265                 270

<210> SEQ ID NO 124
<211> LENGTH: 336
<212> TYPE: PRT
<213> ORGANISM: Cucumis sativus

<400> SEQUENCE: 124

Met Ser Ala Gly Ala Thr Phe Arg Ser Ile Leu Asp Lys Pro Leu
1               5                   10                  15

Asn Gln Leu Thr Glu Asp Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
    50                  55                  60

Cys Asp Asp Ser Gly Ala Gly Ala Leu Arg Lys Val Val Ser Pro
65                  70                  75                  80

Arg Ile Asn Ser Asn Gln Gly Asp Ser Pro Lys Glu Pro Ser Asp Asp
                85                  90                  95

```
Ala Gln Val Thr Met Ser Val Asp Glu Ser Ala Tyr Ser Asn Val Glu
            100                 105                 110

Thr Ala Lys Ser Thr Pro Glu Asp Pro Val Glu Pro Glu Asn Asn
        115                 120                 125

Val Thr Ser Pro Arg Asp Gln Tyr Asp Thr Asn Gly Val Asp Gly Gln
130                 135                 140

Met Thr Ile Phe Tyr Cys Gly Lys Val Asn Val Tyr Asp Gly Val Pro
145                 150                 155                 160

Pro Asp Lys Ala Trp Ala Ile Met His Leu Ala Ala Ser Pro Ile His
                165                 170                 175

Phe Pro Gln Asn His Pro Met Ser Gly Thr Ala Ala Cys Gln Ser Pro
            180                 185                 190

Pro Cys Leu Leu Gln Thr Ser Ser Asp Arg Asp Phe Leu Pro Pro
        195                 200                 205

Ser Ala Thr Ile Tyr Arg Asn Val His Thr Glu Lys Leu Gly Glu His
210                 215                 220

Pro Gln Gln Gln Gln His Ala Lys Gly Thr Ser Met Arg Asp Ser Asp
225                 230                 235                 240

Val Glu Gly Gln Ala Ser Arg Lys Val Ser Leu Gln Arg Tyr Leu Glu
                245                 250                 255

Lys Arg Lys Asp Arg Gly Arg Leu Lys Asn Lys Lys Asn Thr Gly Leu
            260                 265                 270

Ser Ser Pro Ser Leu Glu Gly Tyr Met Asn His Gln Met Arg Thr His
        275                 280                 285

Ile Ser Asn Lys Asn Leu Gly Gln Ile Val Thr Ser Ser Leu Ser Pro
290                 295                 300

Thr Gly Val Ala Lys Ala Phe Val Gly Pro Ala Asp Asn Gln Pro Lys
305                 310                 315                 320

Leu Ala Cys Phe Ser Val Asp Leu Asn Val Lys Asp Ile Gln Glu Cys
                325                 330                 335

<210> SEQ ID NO 125
<211> LENGTH: 333
<212> TYPE: PRT
<213> ORGANISM: Prunus persica

<400> SEQUENCE: 125

Met Asn Ala Thr Thr Ser Phe Arg Ser Ile Leu Glu Lys Pro Leu
1                5                  10                  15

Asn Gln Leu Thr Glu Asp Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
    50                  55                  60

Asn Asp Asp Thr Gly Ala Gly Ala Leu Arg Arg Ile Val Val Ser Pro
65                  70                  75                  80

His Thr Thr Thr Pro Arg Ala Ala Ser Asn Ser Ala Gly Ser Ala Lys
                85                  90                  95

Glu Ala Ser Ala Asp Val Gln Val Ser Val Ser Ala Asp Glu Pro Val
            100                 105                 110

Pro Tyr Gln Lys Pro Val Gln Glu Asp Arg Pro Ala Asp Ala Asp Thr
        115                 120                 125

Lys Ala Ile Ser Pro Arg Asn Gln Cys Thr Thr Asp Ala Ser Val Arg
130                 135                 140
```

Gln Met Thr Ile Phe Tyr Cys Gly Lys Val Asn Val Tyr Asp Gly Val
145                 150                 155                 160

Pro Pro Asp Lys Ala Arg Ala Ile Met His Leu Ala Ala Arg Pro Asn
            165                 170                 175

His Leu Pro Leu Asp Asn Gln Phe Gly Gly Thr Ala Ala Leu Arg Ser
        180                 185                 190

Leu Arg Cys Gln Phe Gln Thr Ala Gly Asp Lys Asp Gly Phe Leu Pro
    195                 200                 205

Pro Ser Ala Thr Phe Ser Gln Ala Met Gln Thr Glu Lys Ile Gly Glu
210                 215                 220

Tyr Thr Gln Gln Tyr Trp Glu Lys Gly Asn Ser Thr Arg Asp Pro Asp
225                 230                 235                 240

Ala Glu Gly Gln Ala Ser Arg Lys Val Ser Leu Glu Arg Tyr Arg Glu
                245                 250                 255

Lys Arg Lys Asp Arg Gly Arg Leu Lys Ile Lys Lys Asn Ile Gly Ser
            260                 265                 270

Ser Ser Ser Leu Glu Val Phe Leu Asn His Gln Leu Arg Thr His Thr
        275                 280                 285

Ser Asn Gly Asn Ser Ser Gln Ser Gly Thr Ser Ser Pro Pro Gln Pro
    290                 295                 300

Gly Leu Leu Gln Thr Ala Asp Asn Gln Pro Lys Ser Leu Cys Leu Pro
305                 310                 315                 320

Val Asp Leu Asn Asp Lys Asp Ile Leu Glu Arg Arg Thr
                325                 330

<210> SEQ ID NO 126
<211> LENGTH: 341
<212> TYPE: PRT
<213> ORGANISM: Vitis vinifera

<400> SEQUENCE: 126

Met Ser Pro Glu Asn Ala Asn Ile Arg Ser Leu Leu Asp Lys Pro Leu
1               5                   10                  15

His Gln Leu Thr Glu Asp Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Thr Leu Leu Glu Thr
    50                  55                  60

Thr Ser Asp Cys Gly Gly Gly Asp Ala Ala Gly Ala Arg Lys Lys Leu
65                  70                  75                  80

Phe Val Pro Pro Pro Glu Asn Gln His Arg Val Pro Leu Thr Arg Ile
                85                  90                  95

Ser Val Ser Asp Glu Glu Ser Val Pro Tyr Gln Arg Gln Asp Pro Pro
            100                 105                 110

Lys Pro Asp Ile Ser Gly Asp Thr Glu Ala His Leu Leu Ala Ala Ala
        115                 120                 125

Asp Ser Asp Ser Ile Pro Pro Arg Thr Leu Asp Ala Met Asn Gly Pro
    130                 135                 140

Ala Gly Gln Met Thr Ile Phe Tyr Cys Gly Lys Val Asn Val Tyr Asp
145                 150                 155                 160

Asp Val Ser Met Asp Lys Ala Lys Ala Ile Met Gln Leu Ala Ala Ser
                165                 170                 175

Ser Leu His Leu His Gln Glu Ala Pro Cys Asp Gly Thr Pro Glu Leu

```
            180                 185                 190
Leu Pro Phe Ser Cys His Leu Arg Ala Ala Ser Val Lys Ile Gly Pro
            195                 200                 205

Ser Ser Pro Thr Val Ile Tyr Pro Thr Leu Gln Thr Val Lys Met Thr
    210                 215                 220

Glu Asn Cys Gln Leu His Arg Glu Glu Ser Asn Ile Phe Arg Glu Asp
225                 230                 235                 240

Asn His Pro Ala Ala Glu Val Pro Thr Ser Arg Lys Ala Ser Val Gln
                245                 250                 255

Arg Tyr Leu Glu Lys Arg Lys Asp Arg Phe Lys Ser Lys Lys Arg Gly
            260                 265                 270

Gly Met Pro Ser Ser Ala Gly Leu Asp Ile Tyr Leu Asn His Arg Val
            275                 280                 285

Gly Asp Gln Ile Pro Asn Asp Gln Ser Asn Gln Ser Asp Ala Cys Ser
        290                 295                 300

Leu Ser His Cys Arg Ala His His Ile Pro Thr Pro Cys Ser Leu Val
305                 310                 315                 320

Glu Asn Met Thr Lys His Thr Asn Leu Ser Ala Asp Leu Asn Ile Lys
                325                 330                 335

Asp Val Gln Glu His
            340

<210> SEQ ID NO 127
<211> LENGTH: 325
<212> TYPE: PRT
<213> ORGANISM: Vitis vinifera

<400> SEQUENCE: 127

Met Asn Pro Gly Val Thr Thr Leu Arg Ser Ile Leu Asp Lys Pro Leu
1               5                   10                  15

His Glu Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ser Leu Leu Glu Thr
    50                  55                  60

Ser Glu Gly Ser Gly Ala Gly Val Leu Arg Lys Ile Thr Asp Ser Pro
65                  70                  75                  80

Pro Ala Glu Asn Leu Pro Pro Val Thr Ser Asn Ser Ala Asp Ser Gly
                85                  90                  95

Lys Glu Leu Ser Ala Asp Ile Gln Ile Ser Val Ser Ala Asp Glu Leu
            100                 105                 110

Val Pro Leu Pro Pro Lys Asp His His Pro Glu Ser Thr Pro Ser Gly
        115                 120                 125

Glu Leu Ala Ser Arg Pro Pro Glu Ala Asp Thr Lys His Thr Cys Pro
    130                 135                 140

Arg Ser Pro Gly Ala Thr Asn Cys Leu Val Gly Gln Met Thr Ile Phe
145                 150                 155                 160

Tyr Cys Gly Lys Val Asn Val Tyr Asp Gly Val Pro Asp Asp Lys Ala
                165                 170                 175

Gln Ala Ile Met His Leu Ala Ala Ser Pro Phe His Leu Pro Ser Asp
            180                 185                 190

Asp Pro Phe Ser Gly Ala Ala Met Leu Cys Ser Ser Pro Cys His Leu
        195                 200                 205
```

His Thr Ala Asn Val Lys His Gly His Ile Pro Pro Arg Ala Met Val
         210                 215                 220

Ser Gln Thr Met Gln Thr Asp Val Glu Gly Gln Val Asp Arg Lys Leu
225                 230                 235                 240

Ser Leu Gln Arg Tyr Phe Glu Lys Arg Lys Asp Arg Phe Lys Ser Arg
                245                 250                 255

Lys Lys Ile Gly Leu Pro Ser Gly Ser Leu Glu Met Tyr Val Asn His
                260                 265                 270

Gln Ala Arg Thr Gln Pro Ser Asn Gly Gln Ser Ser Arg Ser Gly Thr
            275                 280                 285

Ser Ser Pro Pro Gln His Gly Leu Ser His Thr Leu Cys Ser Ser Ala
290                 295                 300

Asp Asn His Thr Lys Asn Phe Thr Pro Phe Val Asp Leu Asn Ser Lys
305                 310                 315                 320

Asp Ile Gln Glu Ser
                325

<210> SEQ ID NO 128
<211> LENGTH: 224
<212> TYPE: PRT
<213> ORGANISM: Manihot esculenta

<400> SEQUENCE: 128

Met Asp Ala Gly Val Thr Ala Phe Arg Ser Ile Leu Asp Lys Pro Leu
1               5                   10                  15

Thr Gln Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Thr
    50                  55                  60

Ser Glu Asp Ser Gly Ala Gly Ala Leu Arg Lys Ile Leu Val Ser Lys
65                  70                  75                  80

Pro Pro Ala Thr Ser Ile Ser Ile Asp Ser Ile Lys Glu Pro Ser Asp
                85                  90                  95

Thr Asn Asn Ile Ala Ile Ser Gly Ser Ala Asp Glu Thr Ala Pro Cys
            100                 105                 110

Arg Gln Asn Asp Ser Pro Lys Ser Pro Pro Gly Pro Leu Asp Cys
        115                 120                 125

Gln Ala Glu Glu Ala Asp Asn Lys Ala Ile Ala Ser Arg Ser Pro Gly
    130                 135                 140

Ala Thr Asp Gly Leu Val Arg Gln Met Thr Ile Phe Tyr Cys Gly Lys
145                 150                 155                 160

Val Asn Val Tyr Asp Gly Val Pro Pro Asp Lys Ala Gln Ala Ile Met
                165                 170                 175

His Leu Ala Ala Ser Pro Ile Gln Ser His Leu Asp Asp Pro Ile His
            180                 185                 190

Arg Pro Ala Phe Ser Phe Pro Cys His Phe Gln Thr Pro Ser Asp Lys
        195                 200                 205

His Gly Phe Leu His Pro Asn Ala Ala Phe Val His Ala Thr Leu Thr
    210                 215                 220

<210> SEQ ID NO 129
<211> LENGTH: 341
<212> TYPE: PRT
<213> ORGANISM: Manihot esculenta

<400> SEQUENCE: 129

Met Gln Pro Gly Glu Thr Ile Ser Arg Ser Pro Leu Asp Lys Pro Ile
1               5                   10                  15

His Gln Leu Thr Glu Asp Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Val Gln Gln Val Ile Ser Leu Lys Thr Leu Leu Glu Ala
50                  55                  60

Thr Pro Asp Thr Arg Arg Lys Leu Tyr Ile Pro Arg Pro Asp Asn Pro
65                  70                  75                  80

His Arg Ala Pro Ala Asn Ser Ser Val Ser Val Lys Glu Thr Ser Pro
                85                  90                  95

Asp Lys Gln Ile Ser Ala Ser Pro Glu Glu Pro Val Pro Phe Pro Arg
            100                 105                 110

His Asp Pro Thr Lys His Asp Ser His Val Asp Leu Pro Ala Arg Leu
        115                 120                 125

Val Ala Thr Asp Asn Asp Ser Val Ser Pro Arg Ile Lys Thr Thr Ala
130                 135                 140

Asn Glu Pro Val Gly Gln Met Thr Ile Phe Tyr Cys Gly Lys Val Asn
145                 150                 155                 160

Ile Tyr Asp Asp Val Pro Arg Asp Lys Ala Gln Ala Ile Met Gln Leu
                165                 170                 175

Ala Ala Tyr Pro Leu Ser Phe Ser Leu Glu Thr Ser Ser Asp Thr Val
            180                 185                 190

Pro Ala Leu Trp Pro Ile Pro Ser Arg Leu Glu Ser Pro Gly Val Lys
        195                 200                 205

Ala Ala Pro Ile Ser Pro Met Leu Ile Phe Pro Ala Leu Gln Thr Gly
210                 215                 220

Lys Val Ala Asp Asn Cys Glu Leu Pro Arg Glu Ser Asn Met Ser
225                 230                 235                 240

His Glu Asp Ser Leu Glu Gly Pro Ala Ser Arg Lys Ala Ser Val Gln
                245                 250                 255

Arg Tyr Leu Glu Lys Arg Lys Asp Arg Phe Lys Asn Lys Arg Lys Val
            260                 265                 270

Ala Met Pro Ser Ser Ala Ser Ser Asp Met Asn Phe Asn Tyr Arg Glu
        275                 280                 285

Gly Asp Gln Phe Ser Asn Asp Gln Trp Asn Leu Ser Gly Ala Phe Ser
290                 295                 300

Ser Pro Gln Pro Arg Pro Pro Gln Met Pro Thr Gln Cys Ser Ser Val
305                 310                 315                 320

Glu Asn Thr Ala Lys His Ser Tyr Leu Pro Ala Asp Leu Asn Gly Arg
                325                 330                 335

Asp Ile Gln Glu Cys
            340

<210> SEQ ID NO 130
<211> LENGTH: 339
<212> TYPE: PRT
<213> ORGANISM: Manihot esculenta

<400> SEQUENCE: 130

Met Asp Ala Gly Val Thr Ser Phe Arg Ser Ile Leu Glu Lys Pro Leu
1               5                   10                  15

Thr Gln Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
50                  55                  60

Ser Glu Asp Ser Gly Ala Gly Ala Leu Arg Lys Ile Leu Val Ser Lys
65                  70                  75                  80

Pro Pro Ala Thr Ser Asn Ser Val His Ser Ile Lys Glu Pro Ser Asp
                85                  90                  95

Thr Asn Asn Asn Ala Ile Ser Gly Ser Ala Asp Glu Thr Ala Pro Ser
            100                 105                 110

Arg Gln Asn Asp Ser Pro Lys Ala Thr Pro Gly Pro Leu Asp Ser
        115                 120                 125

Gln Pro Gly Glu Thr Asp Asn Lys Asp Ser Ala Thr Arg Cys Asn Asp
130                 135                 140

Ala Ala Asp Gly Leu Val Gly Gln Met Thr Ile Phe Tyr Cys Gly Lys
145                 150                 155                 160

Val Asn Val Tyr Asp Gly Ile Pro Pro Asp Lys Ala Gln Thr Ile Met
                165                 170                 175

His Leu Ala Ala Ser Arg Ile Gln Leu Pro Leu Asp Asp Pro Thr Arg
            180                 185                 190

Arg Pro Ala Phe Ser Phe Pro Cys His Phe Gln Ile Pro Ser Asp Lys
        195                 200                 205

His Gly Phe Ile Pro Pro Asn Ala Ala Val Phe Gln Ser Thr Gln Thr
    210                 215                 220

Glu Lys Met Lys Glu Tyr Ser His Pro Cys Lys Asp Lys Ala Asn Ile
225                 230                 235                 240

Ser Leu Glu Pro Asp Val Glu Gly Gln Ala Asn Arg Arg Val Ser Leu
                245                 250                 255

Gln Arg Tyr Leu Glu Lys Lys Lys Asp Arg Gly Arg Phe Lys Gly Arg
            260                 265                 270

Lys Asn Thr Gly Pro Thr Ser Ser Leu Glu Val Tyr Leu Asn His
        275                 280                 285

His Val Arg Met His Thr Ser Ser Glu Gln Thr Thr Arg Ser Ser Thr
    290                 295                 300

Ser Ser Pro Ser Gln Pro Gly Val Pro Pro Thr Leu Cys Ser Ser Ala
305                 310                 315                 320

Glu Asp Gln Ser Lys Ile Ser Cys Phe Ser Val Asp Leu Asn Glu Val
                325                 330                 335

Leu Asp Cys

<210> SEQ ID NO 131
<211> LENGTH: 326
<212> TYPE: PRT
<213> ORGANISM: Citrus sinensis

<400> SEQUENCE: 131

Met Ser Pro Gly Glu Thr Val Ser Arg Ser Leu Leu Asp Lys Pro Leu
1               5                   10                  15

His Gln Leu Thr Glu Asp Ile Ser Gln Val Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Val Ile Cys Leu Lys Thr Leu Glu Thr
    50                  55                  60

Thr Thr Asp Thr Glu Ala Thr Glu Ala Arg Arg Lys Leu Tyr Ser Val
65                  70                  75                  80

Pro Ser His Ser Ala Val Thr Val Lys Glu Thr Cys Glu Pro Ala Pro
                85                  90                  95

Cys Arg Arg Gln Asp Ala Pro Met Pro Asp Phe Ser Gly Asp Ser Ser
            100                 105                 110

Ser Arg Leu Ala Ala Asp Ser Glu Ser Ile Ser Pro Arg Thr Thr Val
        115                 120                 125

Ala Ala Lys Glu Ala Val Gly Gln Met Thr Ile Phe Tyr Ser Gly Lys
130                 135                 140

Val Asn Val Tyr Asp Asp Met Pro Ser Glu Lys Ala Gln Ala Ile Leu
145                 150                 155                 160

Gln Leu Ala Ala Ser Pro Leu Pro Leu Ser Gln Lys Ala Pro Ser Asp
                165                 170                 175

Gly Thr Thr Gly Leu Gln Ser Val Pro Cys His Leu Gln Thr Ala Gly
            180                 185                 190

Ile Asn Val Gly Pro Ser Ser Pro Val Ile Phe Pro Thr Leu Gln Thr
        195                 200                 205

Val Lys Val Val Glu Asn Cys Gln Leu Pro Trp Glu Glu Ser Asn Ile
210                 215                 220

Ser His Glu Asp Ser Phe Asp Gly Pro Thr Ser Arg Lys Ala Ser Val
225                 230                 235                 240

Gln Arg Tyr Arg Glu Lys Arg Lys Asp Arg Phe Lys Asn Lys Arg Lys
                245                 250                 255

Ile Ala Met Pro Ser Ser Ser Leu Asp Val Tyr Leu Asn Arg Trp
            260                 265                 270

Val Gly Asp Gln Phe Ala Asn Glu Gln Leu Asn Pro Ser Asp Val Cys
        275                 280                 285

Ser Thr Leu Gln Ser Arg Pro Ser Gln Thr Ser Pro Gly Cys Gly Val
290                 295                 300

Val Glu Asn Leu Ala Asn Val Ser Asn Leu Pro Val Asp Pro Asn Asp
305                 310                 315                 320

Lys Asp Val Thr Glu Asn
                325

<210> SEQ ID NO 132
<211> LENGTH: 343
<212> TYPE: PRT
<213> ORGANISM: Citrus sinensis

<400> SEQUENCE: 132

Met Asp Val Asp Gly Gly Val Thr Ser Cys Arg Ser Ile Leu Glu Lys
1               5                   10                  15

Pro Leu Ser Gln Leu Thr Glu Glu Asp Ile Thr Gln Leu Thr Arg Glu
            20                  25                  30

Asp Cys Arg Lys Phe Leu Lys Glu Lys Gly Met Arg Arg Pro Ser Trp
        35                  40                  45

Asn Lys Ser Gln Ala Ile Gln Gln Val Ile Ser Leu Lys Ala Leu Leu
    50                  55                  60

Glu Ser Ser Gly Asp Ser Gly Ser Gly Val Leu Arg Arg Val Leu Val
65                  70                  75                  80

Ser Pro Pro Glu Ser Met Pro Pro Arg Val Asn Val Thr Ser Asn Ser 85                  90                  95
Ala Asp Leu Val Lys Glu Pro Thr Ile Ser Val Ser Gly Asp Gln Asn
                100                 105                 110

Ser Ala Tyr Arg Arg Lys Tyr Pro Arg Asn Cys Ala Val Asp Ala Asp
            115                 120                 125

Asn Lys Thr Ile Ser Asn Arg Asn Pro Cys Glu Ala Asn Gly Ser Ile
130                 135                 140

Gly Gln Met Thr Ile Phe Tyr Cys Gly Lys Val Asn Val Tyr Glu Gly
145                 150                 155                 160

Val Pro Thr Asp Lys Ala Gln Glu Ile Met His Leu Ala Ala Thr Pro
                165                 170                 175

Ile Asp Phe Ser Gln Asn Gly Ser Phe Gly Gly Ile Thr Ala Tyr Arg
            180                 185                 190

Ala Ile Pro Cys His Leu Gln Val Thr Ser Asn Arg His Val Ser Leu
        195                 200                 205

Pro Leu Arg Pro Ala Ala Met Ile Ser Gln Phe Met Gln Thr Gly Lys
    210                 215                 220

Ile Ala Asp Tyr Ser Gln Glu Tyr Arg Glu Lys Ala Ile Ser Thr His
225                 230                 235                 240

Asp Ser Asp Val Asp Gly Gln Val Asn Arg Lys Val Ser Leu Gln Arg
                245                 250                 255

Tyr Leu Glu Lys Arg Lys Asp Arg Gly Arg Phe Phe Lys Gly Lys Lys
            260                 265                 270

Asn Thr Gly Pro Thr Pro Ser Leu Glu Met Tyr Leu Asn His Pro Gly
        275                 280                 285

Lys Thr His Ala Ser Asn Gly Gln Gln Ser Gln Ser Asn Thr Ser Ser
    290                 295                 300

Pro Thr Gln Pro Glu Leu Ser Asn Thr Leu Gly Thr Ser Pro Asp Asn
305                 310                 315                 320

Gln Ala Lys Thr Val Met Leu Pro Val Asp Leu Asn Asn Glu Gly Ser
                325                 330                 335

Leu Arg Ser Ser Ile His Glu
            340

<210> SEQ ID NO 133
<211> LENGTH: 313
<212> TYPE: PRT
<213> ORGANISM: Arabidopsis thaliana

<400> SEQUENCE: 133

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
            115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
    195                 200                 205

Lys Met Met Glu Leu Pro Gln Lys Gly Leu Glu Lys Ala Asn Ser Ser
210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
    275                 280                 285

Pro Leu His Ser Gln Ser Pro Glu Ser Gln Thr Lys Ser Pro Asn Leu
290                 295                 300

Ser Val Asp Leu Asn Ser Glu Gly Ile
305                 310

<210> SEQ ID NO 134
<211> LENGTH: 315
<212> TYPE: PRT
<213> ORGANISM: Arabidopsis thaliana

<400> SEQUENCE: 134

Met Asp Val Gly Val Thr Thr Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Leu Arg Lys Ile Leu Val Ser Gln
65                  70                  75                  80

Pro Pro Asn Pro Pro Arg Val Thr Thr Thr Leu Ile Glu Pro Arg Asn
                85                  90                  95

Glu Leu Glu Ala Cys Gly Arg Ile Pro Leu Gln Glu Asp Asp Gly Ala
            100                 105                 110

Cys His Arg Arg Asp Ser Pro Arg Ser Ala Glu Phe Ser Gly Ser Ser
        115                 120                 125

Gly Gln Phe Val Ala Asp Lys Asp Ser His Lys Thr Val Ser Val Ser
    130                 135                 140

Pro Arg Ser Pro Ala Glu Thr Asn Ala Val Val Gly Gln Met Thr Ile
145                 150                 155                 160

Phe Tyr Ser Gly Lys Val Asn Val Tyr Asp Gly Val Pro Pro Glu Lys
                165                 170                 175

```
Ala Arg Ser Ile Met His Phe Ala Ala Asn Pro Ile Asp Leu Pro Glu
            180                 185                 190

Asn Gly Ile Phe Ala Ser Ser Arg Met Ile Ser Lys Pro Met Ser Lys
            195                 200                 205

Glu Lys Met Val Glu Leu Pro Gln Tyr Gly Leu Glu Lys Ala Pro Ala
210                 215                 220

Ser Arg Asp Ser Asp Val Glu Gly Gln Ala Asn Arg Lys Val Ser Leu
225                 230                 235                 240

Gln Arg Tyr Leu Glu Lys Arg Lys Asp Arg Arg Phe Ser Lys Thr Lys
                245                 250                 255

Lys Ala Pro Gly Val Ala Ser Ser Leu Glu Met Phe Leu Asn Arg
            260                 265                 270

Gln Pro Arg Met Asn Ala Ala Tyr Ser Gln Asn Leu Ser Gly Thr Gly
            275                 280                 285

His Cys Glu Ser Pro Glu Asn Gln Thr Lys Ser Pro Asn Ile Ser Val
            290                 295                 300

Asp Leu Asn Ser Asp Leu Asn Ser Glu Asp Asn
305                 310                 315

<210> SEQ ID NO 135
<211> LENGTH: 322
<212> TYPE: PRT
<213> ORGANISM: Eutrema salsugineum

<400> SEQUENCE: 135

Met Asp Val Asn Val Ser Ser Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
            35                  40                  45

Ser Gln Ala Ile Gln Gln Val Leu Ser Leu Lys Ala Leu Phe Glu Pro
        50                  55                  60

Gly Asp Asp Ser Gly Ala Gly Ile Leu Arg Lys Ile Leu Val Ser Gln
65                  70                  75                  80

Pro Pro Ile Pro Pro Arg Val Ile Thr Thr Pro Pro Ile Glu Pro Ser
                85                  90                  95

Asn Asn Glu Leu Gly Ala Cys Gly Arg Ile Pro Phe Gln Glu Asp Asp
            100                 105                 110

Gly Ser Cys His Arg Arg Asp Ser Pro Arg Ser Ala Glu Phe Ser Gly
            115                 120                 125

Gly Gly Ser Gly His Phe Val Ala Glu Lys Glu Ser Tyr Lys Thr Val
        130                 135                 140

Ser Pro Ser Arg Ser Pro Ala Glu Thr Ser Ala Met Val Gly Gln Met
145                 150                 155                 160

Thr Ile Phe Tyr Ser Gly Lys Val Asn Val Tyr Asp Gly Val Pro Pro
                165                 170                 175

Glu Lys Ala Arg Ser Ile Met His Leu Ala Ala Asn Pro Met Asp Leu
            180                 185                 190

Pro Glu Asn Gly Ile Phe Ala Ser Ser Arg Met Ile Ser Arg Pro Met
            195                 200                 205

Ser Lys Glu Lys Met Val Glu His Pro His Tyr Gly Leu Glu Lys Ala
210                 215                 220

Asn Ala Ser Arg Asp Ser Asp Val Glu Ser Gln Ala Asn Arg Lys Val
```

```
                    225                 230                 235                 240
Ser Leu Gln Arg Tyr Leu Glu Lys Arg Lys Asp Arg Arg Phe Ser Lys
                245                 250                 255

Thr Lys Lys Ala Pro Gly Val Ala Ser Ser Leu Glu Met Tyr Leu
                260                 265                 270

Asn Arg Gln Pro Arg Met Asn Ala Ala Phe Ser Gln Asn Leu Gly
                275                 280                 285

Cys Thr Gly Glu Pro His Thr Phe Cys Glu Ser Glu Asn Gln Thr
                290                 295                 300

Lys Ser Pro Asn Leu Ser Val Asp Leu Asn Ser Asp Leu Asn Ser Glu
305                 310                 315                 320

Asp Ile

<210> SEQ ID NO 136
<211> LENGTH: 340
<212> TYPE: PRT
<213> ORGANISM: Citrus clementina

<400> SEQUENCE: 136

Met Asp Val Asp Gly Gly Val Thr Ser Cys Arg Ser Ile Leu Glu Lys
1               5                   10                  15

Pro Leu Ser Gln Leu Thr Glu Glu Asp Ile Thr Gln Leu Thr Arg Glu
                20                  25                  30

Asp Cys Arg Lys Phe Leu Lys Glu Lys Gly Met Arg Arg Pro Ser Trp
            35                  40                  45

Asn Lys Ser Gln Ala Ile Gln Gln Val Ile Ser Leu Lys Ala Leu Leu
    50                  55                  60

Glu Ser Ser Gly Asp Ser Gly Ser Gly Val Leu Arg Arg Val Leu Val
65                  70                  75                  80

Ser Pro Pro Glu Ser Met Pro Pro Arg Val Asn Val Thr Ser Asn Ser
                85                  90                  95

Ala Asp Leu Val Lys Glu Pro Thr Ile Ser Val Ser Gly Asp Gln Asn
                100                 105                 110

Ser Ala Tyr Arg Arg Lys Tyr Pro Arg Asn Cys Ala Val Asp Ala Asp
            115                 120                 125

Asn Lys Thr Ile Ser Asn Arg Ser Leu Asn Pro Cys Glu Ala Asn Gly
    130                 135                 140

Ser Ile Gly Gln Met Thr Ile Phe Tyr Cys Gly Lys Val Asn Val Tyr
145                 150                 155                 160

Glu Gly Val Pro Thr Asp Lys Ala Gln Glu Ile Met His Leu Ala Ala
                165                 170                 175

Thr Pro Ile Asp Phe Ser Gln Asn Gly Ser Phe Gly Gly Ile Thr Ala
                180                 185                 190

Tyr Arg Ala Ile Pro Cys His Leu Gln Val Thr Ser Asn Arg His Val
            195                 200                 205

Ser Leu Pro Leu Arg Pro Ala Ala Met Ile Ser Gln Phe Met Gln Thr
    210                 215                 220

Gly Lys Ile Ala Asp Tyr Ser Gln Glu Tyr Arg Glu Lys Ala Ile Ser
225                 230                 235                 240

Thr His Asp Ser Asp Val Asp Gly Gln Val Asn Arg Lys Val Ser Leu
                245                 250                 255

Gln Arg Tyr Leu Glu Lys Arg Lys Asp Arg Gly Arg Phe Phe Lys Gly
                260                 265                 270

Lys Lys Asn Thr Gly Pro Thr Pro Ser Leu Glu Met Tyr Leu Asn His
```

```
            275                 280                 285
Pro Gly Lys Thr His Ala Ser Asn Gly Gln Gln Ser Gln Ser Asn Thr
        290                 295                 300
Ser Ser Pro Thr Gln Pro Glu Leu Ser Asn Thr Leu Gly Thr Ser Pro
305                 310                 315                 320
Asp Asn Gln Ala Lys Thr Val Met Leu Pro Val Asp Leu Asn Asn Glu
                325                 330                 335
Asp Ile Gln Asp
            340

<210> SEQ ID NO 137
<211> LENGTH: 326
<212> TYPE: PRT
<213> ORGANISM: Citrus clementina

<400> SEQUENCE: 137

Met Ser Pro Gly Glu Thr Val Ser Arg Ser Leu Leu Asp Lys Pro Leu
1               5                   10                  15
His Gln Leu Thr Glu Asp Asp Ile Ser Gln Val Thr Arg Glu Asp Cys
            20                  25                  30
Arg Arg Tyr Leu Lys Glu Lys Gly Met Arg Arg Pro Ser Trp Asn Lys
        35                  40                  45
Ser Gln Ala Ile Gln Gln Val Ile Cys Leu Lys Thr Leu Leu Glu Thr
    50                  55                  60
Thr Thr Asp Thr Glu Ala Thr Glu Ala Arg Arg Lys Leu Tyr Ser Val
65                  70                  75                  80
Pro Ser His Ser Ala Val Thr Val Lys Glu Thr Cys Glu Pro Ala Pro
                85                  90                  95
Cys Arg Arg Gln Asp Ala Pro Met Pro Asp Phe Ser Gly Asp Ser Ser
            100                 105                 110
Ser Arg Leu Ala Ala Asp Ser Glu Ser Ile Ser Pro Arg Thr Thr Val
        115                 120                 125
Ala Ala Lys Glu Ala Val Gly Gln Met Thr Ile Phe Tyr Ser Gly Lys
    130                 135                 140
Val Asn Val Tyr Asp Asp Met Pro Ser Glu Lys Ala Gln Ala Ile Leu
145                 150                 155                 160
Gln Leu Ala Ala Ser Pro Leu Pro Leu Ser Gln Lys Ala Pro Ser Asp
                165                 170                 175
Gly Thr Thr Gly Leu Gln Ser Val Pro Cys His Leu Gln Thr Ala Gly
            180                 185                 190
Ile Asn Val Gly Pro Ser Ser Pro Val Ile Phe Pro Thr Leu Gln Thr
        195                 200                 205
Val Lys Val Val Glu Asn Cys Gln Leu Pro Trp Glu Glu Ser Asn Ile
    210                 215                 220
Ser His Glu Asp Ser Phe Asp Gly Pro Thr Ser Arg Lys Ala Ser Val
225                 230                 235                 240
Gln Arg Tyr Arg Glu Lys Arg Lys Asp Arg Phe Lys Asn Lys Arg Lys
                245                 250                 255
Ile Ala Met Pro Ser Ser Ser Ser Leu Asp Val Tyr Leu Asn Arg Trp
            260                 265                 270
Val Gly Asp Gln Phe Ala Asn Glu Gln Leu Asn Pro Ser Asp Val Cys
        275                 280                 285
Ser Thr Leu Gln Ser Arg Pro Ser Gln Thr Ser Pro Gly Cys Gly Val
    290                 295                 300
```

```
Val Glu Asn Leu Ala Asn Val Ser Asn Leu Pro Val Asp Pro Asn Asp
305                 310                 315                 320

Lys Asp Val Thr Glu Asn
                325
```

<210> SEQ ID NO 138
<211> LENGTH: 311
<212> TYPE: PRT
<213> ORGANISM: Capsella rubella

<400> SEQUENCE: 138

```
Met Glu Asp Val Gly Val Ser Thr Ala Lys Ser Ile Leu Ala Lys Pro
1               5                   10                  15

Leu Lys Leu Leu Thr Glu Asp Asp Ile Ser Gln Leu Thr Arg Glu Asp
                20                  25                  30

Cys Arg Lys Phe Leu Lys Glu Lys Gly Met Arg Arg Pro Ser Trp Asn
            35                  40                  45

Lys Ser Gln Ala Ile Gln Gln Val Leu Ser Leu Lys Ala Leu Phe Glu
        50                  55                  60

Pro Gly Asp Asp Ser Gly Ala Gly Ile Leu Arg Lys Ile Leu Val Ser
65                  70                  75                  80

Gln Pro Pro Ile Pro Pro Arg Val Thr Thr Thr Ser Thr Glu Leu Ser
                85                  90                  95

Asn Glu Leu Glu Ala Cys Gly Arg Ile Pro Pro Phe Gln Glu Asp Asp
            100                 105                 110

Gly Pro Cys His Arg Arg Asp Ser Pro Arg Ser Ala Glu Phe Ser Gly
        115                 120                 125

Gly Ser Ala His Tyr Pro Ala Glu Lys Asp Thr Asn Lys Thr Val Ser
130                 135                 140

Leu Arg Ser Pro Ala Glu Thr Asn Ala Leu Val Gly Gln Met Thr Ile
145                 150                 155                 160

Phe Tyr Ser Gly Lys Val Asn Val Tyr Asp Gly Val Pro Ser Glu Lys
                165                 170                 175

Ala Gln Ser Ile Met His Phe Ala Ala Asn Pro Val Asp Leu Pro Ala
            180                 185                 190

Asn Gly Ile Phe Ser Ser Ser Cys Met Pro Met Ser Lys Glu Lys Met
        195                 200                 205

Val Glu Leu Pro Gln Ile Gly Leu Glu Arg Val Asn Ser Ser Arg Asp
210                 215                 220

Phe Asp Met Glu Gly Gln Ala Asn Arg Lys Met Ser Leu Gln Arg Tyr
225                 230                 235                 240

Arg Glu Lys Arg Lys Asp Arg Arg Phe Leu Lys Ala Lys Lys Ser Pro
                245                 250                 255

Gly Val Ala Ser Ser Leu Glu Met Phe Leu Asn Arg Gln Pro Arg
            260                 265                 270

Met Asn Ala Ala Tyr Ser Gln Asn Leu Gly His Thr Arg Ser Ser Leu
        275                 280                 285

Gln Ser Glu Ser Pro Glu Asn Gln Arg Lys Ser Pro Asn Leu Ser Val
290                 295                 300

Asp Leu Asn Ser Glu Asp Ile
305                 310
```

<210> SEQ ID NO 139
<211> LENGTH: 270
<212> TYPE: PRT
<213> ORGANISM: Capsella rubella -continued

```
<400> SEQUENCE: 139

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Phe Glu Pro
    50                  55                  60

Gly Asp Asp Ser Gly Ala Gly Ile Leu Arg Lys Ile Leu Val Ser Gln
65                  70                  75                  80

Pro Ser Ile Pro Pro Val Thr Ser Thr Ser Ile Glu Pro Ser Ser
                85                  90                  95

Glu Leu Glu Ala Cys Gly Arg Asn Pro Phe Gln Glu Asp Glu Gly Pro
                100                 105                 110

Cys His Arg Arg Asp Ser Pro Arg Ser Ala Glu Phe Ser Gly Gly Ser
            115                 120                 125

Ala Gln Phe Val Ala Glu Lys Asp Ser Leu Lys Thr Val Ser Pro Arg
    130                 135                 140

Ser Pro Ala Glu Thr Ser Pro Leu Val Gly Gln Met Thr Ile Phe Tyr
145                 150                 155                 160

Ser Gly Lys Val Lys Val Tyr Asp Gly Val Pro Pro Glu Lys Ala Arg
                165                 170                 175

Ser Ile Met His Phe Ala Ala Asn Pro Ile Asp Phe Pro Glu Asn Gly
            180                 185                 190

Ile Phe Ala Ser Ser Arg Met Ile Ser Lys Pro Met Ser Lys Glu Lys
    195                 200                 205

Met Val Asp Leu Pro Gln Tyr Gly Leu Glu Lys Ala Thr Ala Ser Arg
210                 215                 220

Asp Ser Asp Val Glu Gly Gln Ala Asn Arg Lys Val Ser Leu Gln Arg
225                 230                 235                 240

Tyr Leu Asp Lys Arg Lys Asp Arg Cys Val Lys Gly Thr Ala Val Val
                245                 250                 255

Ala Ile Met Leu Cys Thr His Leu Arg Leu Phe Gln Asn Arg
            260                 265                 270

<210> SEQ ID NO 140
<211> LENGTH: 347
<212> TYPE: PRT
<213> ORGANISM: Aquilegia coerulea

<400> SEQUENCE: 140

Met Lys Pro Asp Glu Thr Val Ser Arg Ser Pro Leu Asp Lys Pro Leu
1               5                   10                  15

Phe Gln Leu Thr Asp Glu Asp Ile Ser Gln Leu Thr Arg Glu Asp Cys
            20                  25                  30

Arg Lys Phe Leu Arg Asp Lys Gly Met Arg Arg Pro Ser Trp Asn Lys
        35                  40                  45

Ser Gln Ala Ile Glu Gln Val Ile Ser Leu Lys Thr Leu Leu Glu Pro
    50                  55                  60

Arg Thr Glu Ser Asp Thr Asn Ala Thr Gly Ile Arg Gln Lys Leu Leu
65                  70                  75                  80

Val Ser Arg Leu Glu Asn Ser Thr Gln Val Pro Leu Asn Asp Lys Thr
                85                  90                  95
```

```
Asn Ala Ser Asn Leu Lys Thr Ser Val Gln Ala Ile Asn Ser Gly Glu
                100                 105                 110

Ala Asp Ile His Gly Asp Arg Pro Cys Arg Val Pro Val Pro Val Pro
            115                 120                 125

Asp Asp Asn Thr Ile Thr Val Pro Val Pro Asp Asn Asn Ile Thr Ser
130                 135                 140

Ser Arg Asn Leu Asn Ser Thr Asn Gly Leu Val Gly Gln Met Thr Ile
145                 150                 155                 160

Phe Tyr Cys Gly Lys Val Ile Val Tyr Asp Gly Met Pro Ala Glu Lys
                165                 170                 175

Ala His Ala Ile Met Lys Phe Ala Gly Ser His Ile Asn Val Pro Glu
            180                 185                 190

Asp Ser Ser Pro Ala Gly Ala Ala Val Ile Gln Ser Phe Ala Cys Gln
        195                 200                 205

Leu Gln Ala Ala Ser Ile Arg His Gly Leu Ala Phe Pro Ser Ala Val
    210                 215                 220

Ser Pro Pro Leu His Asn Val Val Ala Asp Thr Ser Gln His Cys Arg
225                 230                 235                 240

Glu Glu Val Thr Val Ser Arg Glu Val Glu Pro Glu Gly Pro Val Ser
                245                 250                 255

Arg Lys Ala Ser Val Gln Arg Tyr Leu Glu Lys Arg Lys Asp Arg Gly
            260                 265                 270

Arg Phe Lys Asn Lys Arg Lys Ile Glu Ser Ser Ser Leu Glu Ile
        275                 280                 285

Tyr Leu Asn His Gln Leu Gly Asp Gln Tyr Leu Asn Glu Lys Ser Ser
    290                 295                 300

Gln Ser Arg Ala Cys Ser Pro Pro Gln Pro Arg Ala Pro His Thr Pro
305                 310                 315                 320

Thr Arg Cys Ser Ser Val Glu Asn Gln Val Thr Asn Val Val Phe Ser
                325                 330                 335

Ile Asp Leu Asn Asp Asn Asp Val Arg Glu Gly
            340                 345

<210> SEQ ID NO 141
<211> LENGTH: 365
<212> TYPE: PRT
<213> ORGANISM: Malus domestica
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid

<400> SEQUENCE: 141

Met Asn Ala Ala Thr Thr Thr Phe Pro Ser Ile Leu Xaa Lys Pro Leu
1               5                   10                  15

Asn Gln Leu Thr Glu Asp Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
    50                  55                  60

Asn Glu Asp Ser Gly Ala Gly Ala Leu Arg Lys Ile Val Val Ser Ala
65                  70                  75                  80
```

```
Gln Thr Thr Thr Ala Thr Thr Gln Arg Ala Ala Ser Asn Ser Ala Asp
                85                  90                  95

Ser Ala Lys Glu Ala Ser Ala Asp Val Gln Ala Ser Val Ser Ala Asp
            100                 105                 110

Glu Pro Ala Thr His Pro Arg Asn Glu Arg Pro Lys Ser Val Pro Glu
        115                 120                 125

Asp Pro Pro Val Asp Ala Asp Thr Ala Ala Ile Ser Pro Arg Asn Gln
    130                 135                 140

Cys Thr Thr Asp Ala Leu Val Arg Gln Met Thr Ile Phe Tyr Ser Gly
145                 150                 155                 160

Lys Val Asn Val Tyr Asp Gly Val Pro Pro Asp Lys Val Asn Glu Ala
                165                 170                 175

Phe Tyr Leu Asn Gly Asp Leu Glu Ile Ser Leu Pro Met Gln Arg Tyr
            180                 185                 190

Met Asp Leu Gln Ala Arg Ala Ile Leu His Phe Ala Ala Gly Pro Asn
        195                 200                 205

His Leu Leu Asp Asn Gln Phe Gly Gly Ala Ala Ala Glu Arg Ser
    210                 215                 220

Leu Xaa Cys Gln Tyr Gln Thr Ala Gly Asp Lys Asp Gly Pro Phe Pro
225                 230                 235                 240

Pro Ser Ala Thr Ile Ser Gln Ser Met Gln Thr Gly Lys Phe Gly Glu
                245                 250                 255

Tyr Thr Gln Gln Tyr Trp Glu Lys Gly Asn Ser Thr Arg Asp Pro Asp
            260                 265                 270

Ala Glu Gly Gln Ala Ser Arg Lys Val Ser Leu Gln Arg Tyr Arg Glu
        275                 280                 285

Lys Arg Lys Asp Arg Glu Arg Leu Lys Ile Lys Lys Asn Ser Gly Ala
290                 295                 300

Asn Ser Ser Leu Glu Val Tyr Leu Asn His Gln Leu Arg Thr His Thr
305                 310                 315                 320

Ser Asn Gly Asn Ser Ser Gln Ser Gly Thr Ser Ser Pro Pro Gln Pro
                325                 330                 335

Gly Leu Leu Gln Thr Ala Glu Asn Gln Pro Lys Ile Arg Cys Leu Pro
            340                 345                 350

Val Asp Leu Asn Glu Lys Asp Ile Leu Glu Arg Gln Ala
        355                 360                 365

<210> SEQ ID NO 142
<211> LENGTH: 466
<212> TYPE: PRT
<213> ORGANISM: Malus domestica
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid

<400> SEQUENCE: 142
```

-continued

```
Met Asn Ala Pro Thr Thr Thr Phe Arg Ser Ile Leu Glu Lys Pro Leu
1               5                   10                  15

Asn Gln Leu Thr Glu Asp Asp Ile Ser Gln Leu Thr Arg Glu Asp Cys
            20                  25                  30

Arg Lys Tyr Leu Lys Glu Lys Gly Asp Pro Ala Gly Tyr Phe Ala Gln
            35                  40                  45

Gly Ala Ala Gly Ala Gln Arg Arg Phe Arg Arg Ser Ser Gln Lys
50                  55                  60

Asp Cys Arg Phe Ala Ser Tyr Asp His Arg His Pro Ala Arg Gln
65                  70                  75                  80

Tyr Phe Arg Met Cys Leu Phe Pro Glu Lys Xaa Lys Thr Gly Glu Lys
                85                  90                  95

Ile Thr Ala Ala Ser Asn Ser Ala Asp Ser Ala Lys Glu Val Ser Pro
                100                 105                 110

Asp Val Gln Ala Ser Val Ser Ala Asp Glu Leu Ala Pro His Pro Arg
            115                 120                 125

Asn Glu Pro Pro Lys Pro Ala Pro Glu Asp Pro Val Tyr Ala Asp
    130                 135                 140

Thr Thr Ala Ile Ser Leu Arg Leu Ile Phe Ser Pro Trp Val Met Ala
145                 150                 155                 160

Tyr Ala Trp Val Asp Tyr Ile Arg Ile Lys Gly Leu Thr Glu Val Thr
                165                 170                 175

Leu Arg Leu Gly Cys Ile Phe Ser Val Phe Leu Lys Thr Gly Met Lys
            180                 185                 190

Pro Lys Asn His Cys Thr Thr Asp Ala Ser Val Ser Lys Met Thr Ile
            195                 200                 205

Phe Tyr Ser Gly Lys Val Asn Val Tyr Asp Gly Val Pro Pro Asp Lys
    210                 215                 220

Val Asn Glu Ala Phe Ser Leu Asn Gly Asp Xaa Glu Ile Ser Leu Pro
225                 230                 235                 240

Met Gln Gly Tyr Met Asp Leu Gln Ala Arg Ala Ile Leu His Leu Ala
                245                 250                 255

Ala Gly Pro Asn His Leu Leu Leu Asp Asn Gln Phe Gly Gly Ala Ala
            260                 265                 270

Ala Ala Arg Ser Leu His Cys Gln Phe Gln Thr Ala Gly Asp Lys Asp
            275                 280                 285

Gly Leu Phe Leu Pro Ser Ala Thr Ile Ser Gln Ala Met Gln Thr Gly
    290                 295                 300

Asn Phe Thr Glu Lys Val Xaa Glu Tyr Thr Gln Gln Tyr Trp Glu Lys
305                 310                 315                 320

Gly Asn Asn Thr Arg Asp Pro Asp Ala Glu Gly Gln Ala Asn Arg Lys
                325                 330                 335

Val Ser Leu Gln Arg Tyr Arg Glu Lys Arg Lys Asp Arg Glu Lys Leu
            340                 345                 350

Lys Ile Lys Lys Asn Ile Gly Ser Asn Thr Ser Leu Glu Val Tyr Leu
            355                 360                 365

Asn Arg Gln Leu Arg Xaa His Thr Ser Asn Gly Asn Ser Ser Gln Tyr
    370                 375                 380

Gly Thr Ser Ser Pro Pro Gln Pro Glu Leu Leu Gln Thr Ala Glu Asn
385                 390                 395                 400

Gln Pro Arg Phe Arg Cys Leu Pro Val Asp Leu Asn Glu Lys Gly Arg
                405                 410                 415

Leu Asp Ala Glu Phe Cys Tyr Val Met Lys Asn Arg Gly Arg Gly Ser
```

```
                    420                 425                 430
Val Gly Ala Ser Glu Lys Cys Ile Thr Phe Arg Leu Thr Leu Gln Phe
            435                 440                 445

Leu Gly Phe His Phe Lys Glu Pro Leu Trp Ala Glu Leu Gln Ser Ser
        450                 455                 460

Phe Leu
465

<210> SEQ ID NO 143
<211> LENGTH: 425
<212> TYPE: PRT
<213> ORGANISM: Linum usitatissimum

<400> SEQUENCE: 143

Met Gln Pro Ala Val Gly Asp Thr Ala Ser Arg Ser Pro Leu Asp Lys
1               5                   10                  15

Pro Leu His Gln Leu Thr Glu Asp Asp Ile Ser Gln Leu Thr Arg Glu
            20                  25                  30

Asp Cys Arg Arg Phe Leu Lys Glu Lys Gly Met Arg Pro Ser Trp
        35                  40                  45

Asn Lys Ser Gln Ala Ile Gln Gln Val Ile Ser Leu Lys Thr Leu Leu
 50                  55                  60

Glu Pro Pro Pro Glu Ser Glu Asp Gly Gln Pro Pro Arg Arg Arg Tyr
65                  70                  75                  80

Ile Pro Arg Thr Ala Asn Thr Tyr Arg Ala Pro Ala Thr Pro Asn Pro
                85                  90                  95

Ala Val Ser Val Arg Val Ser Ala Val Asp Thr Pro Ile Ser Ala Pro
            100                 105                 110

Pro Asp Asp Ser Ala Pro Tyr Arg Arg His Asp Pro Pro Leu Asn Asp
        115                 120                 125

Phe Pro Ala Ser Asn Ser Leu Pro Pro Ala Pro Val Pro Ala Val His
130                 135                 140

His Ala Ala Ile Lys Glu Asn Gly Ser Val Ser Pro Arg Ser Thr Gly
145                 150                 155                 160

Gln Val Asn Glu Gln His Gly Gln Met Thr Ile Phe Tyr Cys Gly Lys
                165                 170                 175

Val Asn Val Tyr Asp Asp Met Pro Arg Asp Lys Ala Arg Val Ile Leu
            180                 185                 190

Gln Leu Ala Ala Ser Pro Val Pro Leu Thr Gln Asp Gly Thr Ser Asp
        195                 200                 205

Ala Ser Gln Pro Ala Trp Pro Phe Pro Gly Gln Thr Glu Thr His Gly
    210                 215                 220

Ala Lys Ala Ala Gln Thr Ser Ser Ala Leu Pro Phe Ser Ser Leu Gln
225                 230                 235                 240

Thr Glu Asn Cys Leu Ile Leu Arg Asp Asn Cys His Phe Thr Pro Glu
                245                 250                 255

Gly Asn Gln Glu Gly Pro Ala Ser Arg Lys Ala Ser Val Gln Arg Tyr
            260                 265                 270

Leu Glu Lys Arg Lys Asp Arg Phe Lys His Lys Arg Lys Val Ala Met
        275                 280                 285

Pro Thr Ser Ala Asn Leu Asp Ile Tyr Leu Asn Asn Arg Val Gly Asp
    290                 295                 300

Gln Val Ser Asn Glu Pro Trp Gly Ser Thr Asp Thr Cys Ser Ser Pro
305                 310                 315                 320
```

```
Gln Ser Ile His Pro Gln Arg Cys Ile Ser Ala Glu Asn Thr Ala Lys
                325                 330                 335

His Ser Ile Leu Ala Ala Asp Leu Ala Pro Lys Gly Leu Ser Val Phe
            340                 345                 350

Cys Met His Glu Asn Val Lys Arg Cys Glu Asp Lys Gly Ile Lys Gln
        355                 360                 365

Asn Ser Trp Gln Gln Phe Ser Ile Leu Gly His Val Asn Thr Leu Ser
    370                 375                 380

Pro Ile Arg Ser Glu Trp Val Arg Gly Arg Tyr Leu Val Val Gly Ser
385                 390                 395                 400

Phe Leu Val Arg Ile Pro Lys His Val Val Tyr Thr Thr Cys Cys Arg
                405                 410                 415

Ala Met Ser Arg Leu Ser Leu Leu Gly
                420                 425

<210> SEQ ID NO 144
<211> LENGTH: 377
<212> TYPE: PRT
<213> ORGANISM: Linum usitatissimum

<400> SEQUENCE: 144

Met Gln Pro Ala Val Gly Asp Thr Ala Ser Arg Ser Pro Leu Asp Lys
1               5                   10                  15

Pro Leu His Gln Leu Thr Glu Asp Asp Ile Ser Gln Leu Thr Arg Glu
            20                  25                  30

Asp Cys Arg Arg Phe Leu Lys Glu Lys Gly Met Arg Arg Pro Ser Trp
        35                  40                  45

Asn Lys Ser Gln Ala Ile Gln Gln Val Ile Ser Leu Lys Thr Leu Leu
    50                  55                  60

Glu Pro Pro Pro Glu Ser Glu Asp Gly Gln Ala Pro Arg Arg Arg Tyr
65                  70                  75                  80

Ile Pro Arg Thr Asp Asn Thr Tyr Arg Ala Pro Ala Thr Pro Asn Pro
                85                  90                  95

Ala Val Ser Val Lys Val Ser Ala Val Asp Thr Pro Ile Ser Ala Pro
                100                 105                 110

Pro Asp Asp Ser Ala Pro Tyr Arg Arg His Asp Pro Pro Leu Asn Asp
            115                 120                 125

Phe Pro Ala Ser Asn Ser Ala Leu Asp Phe Leu His Cys Pro Leu Asn
    130                 135                 140

His Leu Leu Leu Arg Met Leu Ser Met Ser Thr Gly Gln Val Asn Glu
145                 150                 155                 160

Gln His Gly Gln Met Thr Ile Phe Tyr Cys Gly Lys Val Asn Val Tyr
                165                 170                 175

Asp Asp Met Pro Arg Asp Lys Ala Arg Val Ile Leu Gln Leu Ala Ala
                180                 185                 190

Ser Pro Val Pro Leu Thr Gln Asp Gly Ala Ser Asp Ala Ser Gln Pro
            195                 200                 205

Ala Trp Pro Phe Pro Gly Gln Thr Glu Thr His Gly Ala Lys Ala Ala
    210                 215                 220

Gln Thr Ser Ser Ala Leu Pro Phe Ser Ser Leu Gln Thr Glu Gly Pro
225                 230                 235                 240

Ala Ser Arg Lys Ala Ser Val Gln Arg Tyr Leu Glu Lys Arg Lys Asp
                245                 250                 255

Arg Phe Lys His Lys Arg Lys Val Ala Met Pro Thr Ser Ala Asn Leu
                260                 265                 270
```

```
Asp Ile Tyr Leu Asn Asn Arg Val Gly Asp Gln Val Ser Asn Glu Pro
        275                 280                 285

Trp Gly Ser Thr Asp Thr Cys Ser Ser Pro Gln Ser Ile His Pro Gln
        290                 295                 300

Arg Cys Ile Ser Ala Glu Asn Thr Ala Met His Ser Ile Leu Ala Ala
305                 310                 315                 320

Asp Leu Ala Pro Lys Gly Leu Ser Val Phe Cys Val Ser Phe Ser Thr
                325                 330                 335

Cys Cys Leu Asn Lys Leu Asp Asn Ala Tyr Ser Arg Asn Pro Cys Val
                340                 345                 350

Ile Pro Ile Trp Pro Asp Glu Asp Cys Ile Phe Gln Phe Tyr Cys Phe
                355                 360                 365

Val Phe Asn Ala Glu Glu Thr Ala Tyr
        370                 375

<210> SEQ ID NO 145
<211> LENGTH: 307
<212> TYPE: PRT
<213> ORGANISM: Eucalyptus grandis

<400> SEQUENCE: 145

Met Thr Ser Leu Arg Cys Ile Leu Asp Lys Pro Leu Asn Gln Leu Thr
1               5                   10                  15

Glu Asp Asp Ile Ser Gln Leu Thr Arg Glu Asp Cys Arg Lys Phe Leu
                20                  25                  30

Lys Asp Lys Gly Met Arg Arg Pro Ser Trp Asn Lys Ser Gln Ala Ile
            35                  40                  45

Gln Gln Val Ile Ser Leu Lys Ala Leu Leu Glu Gly Pro Glu Asp Asp
        50                  55                  60

Asp Ser Gly Ala Arg Thr Leu Arg Lys Ile Val Val Ser Ser Ala Glu
65                  70                  75                  80

Asn Pro Pro Pro Arg Ala Asn Ser Asn Ser Asn Ser Pro Asp Ser Ala
                85                  90                  95

Lys Glu Val Ser Pro Gly Ala Ser Val Ser Glu Phe Ala Asp Glu Ala
            100                 105                 110

Ala Pro Tyr Arg Arg Lys Asp Pro Glu Pro Ala Pro Ala Pro His
        115                 120                 125

Gly Asp Ala Ala Ala Ser Ala Gly Ala Asp Gln Glu Arg Asn Ala Val
    130                 135                 140

Ser Pro Arg Asn Val Gly Ala Gly Glu Val Thr Leu Gly Gln Met Thr
145                 150                 155                 160

Ile Phe Tyr Cys Gly Lys Val Asn Val Tyr Asp Arg Val Ser Pro Asp
                165                 170                 175

Lys Ala Arg Thr Ile Met Gln Leu Ala Ser Gly Pro Ile Pro Leu Pro
                180                 185                 190

Leu Asp Asp Ser Ser Asn Gly Ser Ala Ala Ile Trp Ser Phe Pro Cys
            195                 200                 205

His Met Gln Ala Asn Thr Asp Asn Leu Cys Leu Leu Pro Pro Arg Ala
    210                 215                 220

Met Val Ser His Thr Thr Gln Thr Asp Met Glu Gly His Met Asn Arg
225                 230                 235                 240

Arg Val Arg Leu Gln Lys Tyr Phe Asp Lys Lys Asp Arg Gly Arg
                245                 250                 255

Phe Lys Ser Arg Lys Asp Ala Gly Pro Ala Ser Ser Gly Leu Glu Met
```

```
                260                 265                 270
Phe Leu Met Asn Gln Ile Arg Val Pro Val Pro Asp Gly Gln Leu Ser
            275                 280                 285
Lys Asn Ala Ile Thr Cys Ala Pro Gln Pro Gly Met Ala His Gly Lys
            290                 295                 300
Asn Ser Pro
305

<210> SEQ ID NO 146
<211> LENGTH: 352
<212> TYPE: PRT
<213> ORGANISM: Solanum tuberosum

<400> SEQUENCE: 146

Met Pro Pro Glu Glu Thr Val Ser Lys Ser Pro Leu Asp Lys Pro Leu
1               5                   10                  15
Asn Gln Leu Thr Asp Asp Ile Ser Gln Leu Thr Arg Glu Asp Cys
            20                  25                  30
Arg Arg Tyr Leu Lys Gln Lys Gly Met Arg Lys Pro Ser Trp Asn Lys
        35                  40                  45
Ser Gln Ala Ile Gln Val Ile Ser Leu Lys Ala Leu Leu Glu Pro
    50                  55                  60
Asp Thr Asp Ala Gly Thr Arg Lys Lys Leu His Ile Pro Arg Ala Asp
65                  70                  75                  80
Thr His Val Gln Ser Gly Lys Asn Thr Tyr Gly Glu Pro Ser Glu Pro
                85                  90                  95
Val Pro Asp Arg Arg Asn Gln Gln Asp Arg Pro Asp Leu Ser Ser His
            100                 105                 110
Ile Thr Ala Leu Pro Val Ala Val Asp Asn Ser Ala Pro Ser Arg
        115                 120                 125
Thr Ile Gly Ser Ala Asp Lys Pro Val Gly Gln Met Thr Ile Phe Tyr
    130                 135                 140
Arg Gly Lys Val Asn Val Tyr Asp Asp Val Pro Ala Asp Lys Ala Gln
145                 150                 155                 160
Lys Ile Met Cys Leu Ala Ser Ser Pro Leu Cys Val Pro Ser Glu Thr
                165                 170                 175
Pro Ser Asn Ala Thr Val Ala Ala Arg His Ser Ala Cys Cys Leu Gln
            180                 185                 190
Ala Ala Asn Ser Lys Leu Arg Leu Asp Thr Asn Ile Val Pro Thr Ile
        195                 200                 205
Gln Thr Val Lys Met Ser Glu Val Ser Arg Val Pro Ile Glu Glu Ser
    210                 215                 220
Asn Arg Leu Tyr Asn Asp Asn Pro Glu Ala Val Glu Ser Pro Ala Ser
225                 230                 235                 240
Arg Lys Ala Ser Val Gln Arg Tyr Leu Glu Lys Arg Lys Glu Arg Phe
                245                 250                 255
Lys Trp Lys Arg Lys Val Glu Thr Thr Ser Ser Ala Ser Leu Asp Ile
            260                 265                 270
Tyr Leu Ser Asp Arg Ile Gly Thr Arg Thr Pro Ser Asp Tyr Ala Ser
        275                 280                 285
Gly Ala Asp Leu Cys Phe Thr Pro His Ile Thr Pro Thr Gly Ser Gly
    290                 295                 300
Pro Ile Gln Asp Asn Ile Gln Met Asn Pro Thr Phe Ser Ser Asp Leu
305                 310                 315                 320
```

Asn Asp Arg Glu Ser Glu Cys Arg Lys Leu Asn Gly Trp Gly Cys Thr
                325                 330                 335

Pro Asp Phe Cys Phe Cys Leu Glu Met Phe Arg Gly His Ile Met Phe
            340                 345                 350

<210> SEQ ID NO 147
<211> LENGTH: 339
<212> TYPE: PRT
<213> ORGANISM: Solanum tuberosum

<400> SEQUENCE: 147

Met Ser Leu Glu Glu Thr Val Tyr Lys Ser Pro Leu Asp Lys Pro Leu
1               5                   10                  15

Tyr Leu Leu Thr Asp Asp Ile Ser Gln Leu Thr Arg Glu Asp Cys
            20                  25                  30

Arg Arg Tyr Leu Lys Ala Lys Gly Met Arg Lys Pro Ser Trp Asn Lys
            35                  40                  45

Ser Gln Ala Ile Gln Gln Val Ile Ser Leu Lys Ala Leu Leu Glu Thr
    50                  55                  60

Thr Pro Asp Ser Asp Thr Gly Gln Arg Lys Arg Arg His Ile Pro Arg
65                  70                  75                  80

Pro Asp Thr Ser Leu Gln Arg Val Gln Lys Glu Thr Gly Ile Asp Ala
                85                  90                  95

Glu Phe Ala Glu Ser Ala Glu Glu Met Val Pro Tyr Gly Arg Lys Leu
            100                 105                 110

Pro Asn Lys Pro Asp Leu Ser Gly Asn Lys Ala Ala Gly Ser Val Ala
        115                 120                 125

Val Val Asn Asn Leu Thr Pro Ser Arg Thr Thr Asp Ser Gly Asn Ala
130                 135                 140

Ser Ala Gly Gln Leu Ile Ile Phe Tyr Cys Gly Lys Val Asn Val Tyr
145                 150                 155                 160

Asp Asp Val Pro Ala Glu Lys Ala Gln Ala Ile Ile His Leu Ala Ala
                165                 170                 175

Ser Pro Leu Phe Val Pro Ser Glu Thr Pro Leu Asp Ala Thr Arg Ala
            180                 185                 190

Ala Gln His Ser Glu Cys His Leu Gln Ser Ala Asn Val Lys Met Gly
        195                 200                 205

Pro Asp Ser Pro Met Val Leu Met Pro Thr Met Gln Thr Gly Arg Ile
210                 215                 220

Thr Glu Val Thr Arg Leu His Leu Glu Gly Ser Asn Thr Phe Tyr Glu
225                 230                 235                 240

Asp Asn Ser Glu Ser Val Asn His Val Ser Arg Lys Ala Leu Leu Glu
                245                 250                 255

Arg Tyr Arg Glu Lys Arg Lys Asp Arg Phe Lys Arg Lys Met Gly Met
            260                 265                 270

Pro Ser Ser Ala Ser Leu Asp Ile Tyr Leu Asn His Arg Thr Gly Asn
        275                 280                 285

His Thr Pro Ser Glu Leu Ser Ser Arg Ser Asn Thr Cys Ser Pro Pro
290                 295                 300

Ala Ile Arg Leu Ser Val Ala Pro Ala Pro Ser Gly Ser Met Asp Asn
305                 310                 315                 320

Ile Leu Gln Met Asp Ala Asn Ala Ser Gly Phe Leu Asp Asp Lys Asp
                325                 330                 335

Gly Lys Glu

<210> SEQ ID NO 148
<211> LENGTH: 345
<212> TYPE: PRT
<213> ORGANISM: Gossypium raimondii

<400> SEQUENCE: 148

Met Ser Thr Gly Glu Met Val Ser Arg Ser Pro Leu Tyr Lys Pro Leu
1               5                   10                  15

Asn Gln Leu Thr Glu Asp Asp Ile Ser Gln Val Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Gln Val Ile Ser Leu Lys Thr Leu Leu Glu Thr
    50                  55                  60

Thr Ser Asp Ser Asp Gly Val Lys Ala Ser Lys Lys Leu His Val Pro
65                  70                  75                  80

Phe Pro His Asn Pro Pro Arg Phe Val Ser Asp Ser Thr Val Gln Pro
                85                  90                  95

Asn Glu Thr Thr Arg His Lys Gly Ile Ser Val Pro Leu Asn Glu Ser
            100                 105                 110

Val Pro Arg Ile Arg Ser Asp Pro Ser Glu Phe Lys Phe Ser Gly Gly
        115                 120                 125

Asn Ser Val Gln Thr Ala Val Ser Ala Asn Asp Ser Val Ser Pro Arg
130                 135                 140

Ser Ala Ser Val Ala Lys Glu Pro Ser Gly Gln Met Thr Ile Phe Tyr
145                 150                 155                 160

Cys Gly Lys Val Asn Val Tyr Asp Asn Ile Pro Gly Arg Lys Ala Glu
                165                 170                 175

Ala Ile Leu Gln Phe Ala Ala Ser Pro Val Ser Phe Leu Gln Glu Thr
            180                 185                 190

Leu Val Asp Gln Arg Thr Thr Pro Leu Ser Ile Pro Cys His Val Gln
        195                 200                 205

Ala Ala Gly Asp Lys Val Ser Gln Arg Ser Pro Gly Val Val Leu Ser
210                 215                 220

Ser Met Gln Ala Val Lys Val Ala Glu Asn Cys Gln Phe Pro Arg Glu
225                 230                 235                 240

Asp Cys Asn Val Ser Tyr Glu Asp Ser Leu Glu Gly Pro Thr Ser Arg
                245                 250                 255

Asn Ala Leu Leu Gln Arg Tyr Leu Glu Lys Lys Asp Arg Phe Lys
            260                 265                 270

Asn Lys Arg Lys Leu Ala Thr Ser Ser Arg Thr Leu Asp Ile Tyr
        275                 280                 285

Leu Asn Gln Met Gly Asp Gln Phe Ser Asn Glu Gln Ser Lys Gln Ser
    290                 295                 300

Glu Ser Tyr Ser Ser Thr Gln Ala Arg Pro His Thr Pro Leu Trp
305                 310                 315                 320

Cys Ser Ser Met Glu Asn Leu Pro Lys Ile Ala Asn Val Thr Thr His
                325                 330                 335

Pro Asp Gly Lys Asp Ile Phe Glu Val
            340                 345

<210> SEQ ID NO 149
<211> LENGTH: 365
<212> TYPE: PRT
<213> ORGANISM: Gossypium raimondii

<400> SEQUENCE: 149

| | | | | | | | | | | | | | | |
|---|---|---|---|---|---|---|---|---|---|---|---|---|---|---|
Met Glu Ala Gly Val Thr Thr Thr Ala Thr Thr Ala Ser Phe Ser
1               5                   10                  15

Ser Ile Leu Asp Lys Pro Leu Ser Gln Leu Thr Glu Glu Asp Ile Ser
            20                  25                  30

Gln Leu Thr Arg Glu Asp Cys Arg Lys Phe Leu Lys Glu Lys Gly Met
        35                  40                  45

Arg Arg Pro Ser Trp Asn Lys Ser Gln Ala Ile Gln Gln Val Ile Ser
    50                  55                  60

Phe Lys Ala Leu Leu Glu Ser Asn Glu Asp Ser Gly Ala Gly Ala Arg
65                  70                  75                  80

Arg Lys Ile Leu Val Cys Pro Pro Ser His Phe Pro Pro Gln Asn
                85                  90                  95

Ala Val Ala Ser Asn Ser Gly Glu Ser Val Lys Glu Ala Val Phe Gly
            100                 105                 110

Glu Glu Glu Ser Leu Tyr Gly Gln Lys Asp Leu Ser Leu Lys Ala Ala
        115                 120                 125

Pro Val Val Gln Met Asn Cys Gln Gly Gly Asp Thr Asp Asp Lys Thr
130                 135                 140

Leu Ser Pro Ser Leu Gly Ser Pro Arg Glu Tyr Ser Lys Leu Pro Gly
145                 150                 155                 160

Arg Ser Gln Cys Glu Thr Asn Glu Leu Gly Gln Met Thr Ile Phe
                165                 170                 175

Tyr Cys Gly Lys Ile Asn Val Tyr Asp Gly Val Pro Leu Ala Lys Ala
            180                 185                 190

Arg Ala Ile Met His Leu Ala Ala Ser Pro Ile Asp Phe Pro Gln Gly
        195                 200                 205

Asn Leu Cys Asn Gln Asn Gly Ala Phe Arg Ser Phe Leu Gly His Val
210                 215                 220

Gln Glu Ala Glu Asp Lys Asn Asp Leu Thr Ser Ser Ile Ala Leu Asn
225                 230                 235                 240

Leu Asn Ser His Thr Met His Thr Glu Lys Met Thr Glu Tyr Gln Gln
                245                 250                 255

Gln Phe Arg Gly Lys Ala Asn Ile Ser Arg Asp Ser Asp Val Asp Gly
            260                 265                 270

Gln Val Ser Arg Lys Glu Ser Leu Gln Arg Tyr Leu Glu Lys Arg Lys
        275                 280                 285

Asp Arg Gly Arg Phe Phe Lys Gly Arg Lys Asn Ala Gly Gln Ala Leu
    290                 295                 300

Ser Ser Ser Glu Met Tyr Leu Asn His Gln Ile Arg Ala His Tyr Leu
305                 310                 315                 320

Asn Gly Gln Thr Asn Gln Ser Arg Thr Ser Ser Pro Pro Gln Ser Gly
                325                 330                 335

Val Pro His Ala Phe Tyr Ser Ser Ala Asp Gln Glu Leu Val Asn
            340                 345                 350

Phe Ser Val Asp Leu Asn Asp Glu Gly Gly Gln Glu His
        355                 360                 365

<210> SEQ ID NO 150
<211> LENGTH: 341
<212> TYPE: PRT
<213> ORGANISM: Gossypium raimondii

<400> SEQUENCE: 150

```
Met Ser Pro Gly Glu Thr Val Ser Arg Ser Pro Leu Asp Lys Pro Leu
1               5                   10                  15

Asn Gln Leu Thr Glu Asp Asp Ile Ser Gln Val Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Gln Val Ile Ser Leu Lys Thr Leu Leu Glu Thr
50                  55                  60

Thr Ser Asp Ser Asp Ala Val Glu Ala Arg Lys Lys Leu Tyr Pro Pro
65                  70                  75                  80

Cys Pro Glu Tyr Pro Pro Arg Val Arg Val Ser Ser Ser Asn Val
                85                  90                  95

Leu Pro Arg Glu Met Thr Pro Asn Asn Gly Ile Leu Val Pro Val Ser
                100                 105                 110

Glu Ser Val Pro Cys Pro His Ser Asn Pro Ser Lys Ser Asp Phe Ser
            115                 120                 125

Gly Asp Asn Ser Gly Arg Thr Val Ile Ser Gly Asn Asp Ser Val Ser
130                 135                 140

Pro Arg Ile Ala Gly Ala Ala Lys Glu Pro Ala Gly Gln Met Thr Ile
145                 150                 155                 160

Phe Tyr Cys Gly Lys Val Asn Val Tyr Asp Asp Met Pro Gly Cys Lys
                165                 170                 175

Ala Glu Ala Ile Met Gln Leu Ala Ala Ser Pro Val Ser Phe Pro His
            180                 185                 190

Glu Ile Leu Ala Asp Gln Arg Ser Thr Pro Trp Ser Ile Pro Cys His
            195                 200                 205

Ser Gln Ala Ala Ser Val Lys Thr Ile Pro Cys Ser Gln Met Val Ile
210                 215                 220

Leu Pro Pro Gln Gln Thr Glu Asn Cys Gln Phe Pro Arg Glu Glu Ser
225                 230                 235                 240

Asn Ala Ser Leu Glu Asp Ser Leu Glu Gly Pro Thr Ser Arg Lys Ala
                245                 250                 255

Leu Val Gln Arg Tyr Leu Glu Lys Lys Lys Asp Arg Phe Lys Asn Lys
            260                 265                 270

Arg Lys Leu Ala Met Ser Ser Ser Pro Thr Leu Asp Ile Tyr Leu Asn
        275                 280                 285

Gln Val Gly Asp Gln Phe Ser Asn Glu Gln Leu Lys Gln Ser Glu Pro
290                 295                 300

Tyr Tyr Ser Pro Gln Ala Glu Val His Arg Met Pro Leu Glu Cys Ser
305                 310                 315                 320

Ser Ile Glu Asn Val Ala Lys Ile Pro Arg Leu Thr Thr Asp Gly Lys
                325                 330                 335

Asp Ala Phe Lys Ile
            340

<210> SEQ ID NO 151
<211> LENGTH: 375
<212> TYPE: PRT
<213> ORGANISM: Populus trichocarpa

<400> SEQUENCE: 151

Met Gln Pro Gly Glu Thr Val Ser Arg Ser Ala Leu Glu Lys Pro Leu
1               5                   10                  15

His Gln Leu Thr Glu Asp Asp Ile Ser Gln Leu Thr Arg Glu Asp Cys
```

```
                20                  25                  30
Arg Arg Tyr Leu Lys Glu Lys Gly Met Arg Arg Pro Ser Trp Asn Lys
            35                  40                  45

Ser Gln Ala Ile Gln Gln Val Ile Ser Leu Lys Thr Leu Leu Glu Thr
    50                  55                  60

Thr Pro Glu Thr Glu Ser Pro Arg Arg Leu Tyr Ile Pro Pro Pro
65                  70                  75                  80

Asp Asn Pro Pro Arg Ala Pro Ala Asn Ser Val Ser Val Gly Gly
                85                  90                  95

Glu Ser Ala Asp Ala Pro Ile Leu Val Ser Ala Glu Leu Val Pro
            100                 105                 110

Ser Arg Gln Pro Asp Pro Pro Asn Pro Val Val Pro Ala Asp Pro Pro
            115                 120                 125

Pro Pro Val Phe Val Ala Ala Thr Glu Asn Asp Ser Val Ser Pro Arg
        130                 135                 140

Thr Thr Gly Ala Ala Lys Glu Ser Ala Gly Gln Met Thr Ile Phe Tyr
145                 150                 155                 160

Cys Gly Lys Val Asn Val Tyr Asp Asn Val Pro Arg Asp Lys Ala Gln
                165                 170                 175

Val Ile Met His Leu Ala Ala Ser Pro Phe Ala Pro Gln Glu Ala
            180                 185                 190

Ser Ser Asn Val Ile Pro Ala Leu Trp Pro Ile Pro Cys Gln Leu Glu
        195                 200                 205

Thr Pro Gly Val Lys Ala Thr Pro Asn Ser Thr Val Val Ile Phe Pro
    210                 215                 220

Asn Leu Pro Thr Val Lys Gly Ala Asp Asp Gly Gln Leu Pro Gln Glu
225                 230                 235                 240

Glu Ser Asn Ile Ala Arg Glu Asp Asn Leu Glu Gly Ser Thr Ser Arg
                245                 250                 255

Lys Ala Ser Leu Gln Arg Tyr Leu Glu Lys Lys Asp Arg Leu Lys
            260                 265                 270

Asn Lys Arg Lys Val Ala Met Thr Ser Ala Ser Val Asp Ile Tyr Leu
        275                 280                 285

Asn His Arg Val Gly Asp Gln Ile Ser Asn Asp His Trp Asn Leu Asn
    290                 295                 300

Asp Ala Cys Ser Ser Pro Gln Pro Arg Pro Pro Gln Thr Pro Asn Arg
305                 310                 315                 320

Cys Asn Ser Ile Asp Asn Leu Ala Lys Asn Gly Ser Leu Ser Ala Asp
                325                 330                 335

Leu Asn Glu Lys Gly Tyr Ala Gln Lys Arg Leu Leu Gln Phe Ser Leu
            340                 345                 350

Trp Phe Phe Thr Glu Ser Ala Glu Trp Lys Arg Cys Asn Thr Leu Leu
        355                 360                 365

Asn Val Ile Glu Asn Thr Cys
    370                 375

<210> SEQ ID NO 152
<211> LENGTH: 454
<212> TYPE: PRT
<213> ORGANISM: Populus trichocarpa

<400> SEQUENCE: 152

Met Lys Arg Lys Ser Arg Leu Val Lys Cys Lys Leu Arg Asp Lys Val
1               5                   10                  15
```

-continued

```
Lys Phe Gln Val Arg Arg Arg Asp Thr Asn Ala Ser Pro Leu Pro Pro
             20                  25                  30

Arg Ile Ser His Ser Pro Ala His Ser Pro Arg Thr Leu Ser Pro Leu
         35                  40                  45

Glu Val Gln His Ile His Gln Asn Thr Thr Arg Arg Cys Lys Ile Thr
     50                  55                  60

Leu Asn Arg Ser Gly Asn Arg Ser Pro Asp Pro Lys Ser Asn Thr Met
 65                  70                  75                  80

Gln Pro Gly Glu Thr Val Phe Arg Ser Ala Leu Asp Lys Pro Leu His
                 85                  90                  95

Gln Leu Thr Glu Asp Asp Ile Ser Gln Val Thr Arg Glu Asp Cys Arg
            100                 105                 110

Arg Tyr Leu Lys Glu Lys Gly Met Arg Arg Pro Ser Trp Asn Lys Ser
        115                 120                 125

Gln Ala Ile Gln Gln Val Ile Ser Leu Lys Thr Leu Leu Glu Ala Thr
    130                 135                 140

Pro Glu Thr Glu Ser Pro Arg Arg Leu Tyr Ile Pro Arg Pro Pro
145                 150                 155                 160

Pro His Pro Pro Asp Asn Thr Pro Arg Val Arg Phe Ser Ala Val Pro
                165                 170                 175

Pro Asn Ser Ser Val Ser Glu Arg Gly Ala Ser Ala Glu Thr Pro Ile
            180                 185                 190

Ser Val Pro Ala Glu Glu Pro Val Pro Cys Arg Gln His Asp Pro Pro
        195                 200                 205

Asn Pro Asp Asp Pro Ala Asp Pro Leu Pro Val His Ala Ala Val
210                 215                 220

Thr Glu Asn Ala Ser Val Ser Pro Arg Thr Thr Gly Met Ala Glu Glu
225                 230                 235                 240

Ser Ala Gly Gln Met Thr Ile Phe Tyr Cys Gly Lys Val Asn Val Tyr
                245                 250                 255

Asp Asp Val Pro Gly Asp Lys Ala Gln Ala Ile Met His Leu Ala Ala
            260                 265                 270

Ser Pro Phe Ala Pro Pro Gln Asp Ala Ser Ser Asp Val Ile Pro Thr
        275                 280                 285

Leu Arg Pro Leu Gln Cys Gln Leu Asp Thr Pro Gly Val Lys Ala Ala
290                 295                 300

Pro Asn Ser Ile Val Ala Asn Phe Pro Thr Leu Pro Thr Val Lys Gly
305                 310                 315                 320

Ala Asp Ser Gly Gln Leu Leu Trp Glu Glu Ser Asn Ile Ala Arg Glu
                325                 330                 335

Asp Asn Leu Glu Gly Ser Thr Ser Arg Lys Ala Ser Leu Gln Arg Tyr
            340                 345                 350

Phe Glu Lys Lys Lys Asp Arg Phe Lys Asn Lys Arg Lys Val Ala Val
        355                 360                 365

Pro Ser Ala Ser Leu Asp Val Phe Leu Ser His Leu Val Gly Asp Gln
370                 375                 380

Ile Ser Asn Asp His Trp Asn Leu Asn Asp Ala Cys Ser Pro Ser Gln
385                 390                 395                 400

Pro Arg Pro Pro Gln Thr Pro Asn Arg Cys Asn Ser Val Asp Asn Val
                405                 410                 415

Ala Lys Asn Gly Ile Leu Lys Ala Asp Leu Asn Asn Lys Gly Asp Ala
            420                 425                 430

Asp Leu Ser Cys Cys Leu Asp Phe Ser Ser Lys Gln Ile Asn Ala Trp
```

```
                    435                 440                 445

Cys Leu Cys Leu Gly Cys
    450

<210> SEQ ID NO 153
<211> LENGTH: 335
<212> TYPE: PRT
<213> ORGANISM: Phaseolus vulgaris

<400> SEQUENCE: 153

Met Asn Ala Gly Gly Thr Ala Thr Phe Arg Ser Ile Leu Asp Lys Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Glu Lys Gly Met Arg Arg Pro Ser Trp Asn
        35                  40                  45

Lys Ser Glu Ala Ile Gln Gln Val Ile Ser Leu Lys Ala Leu Leu Glu
    50                  55                  60

Pro Ser Asp Asp Ser Pro Pro His Pro Pro Met His His His
65                  70                  75                  80

Pro His Ala Pro Gln Pro Gln Ala Asn Leu Thr Gln Pro Pro Lys
                85                  90                  95

Val Pro Pro Glu Glu Pro Ala Phe His Ala Val Asp Asp Ile Gln
            100                 105                 110

Lys Ser Ala Ser Ser Gly Glu Lys Pro Thr Glu Thr Asn Asp Thr Asn
        115                 120                 125

Thr Asn Ala Asn Val Ala Ser Pro Arg Gly Cys Ala Thr Ser Gly Ser
    130                 135                 140

Phe Gly Gln Met Thr Ile Phe Tyr Cys Gly Lys Val Asn Val Tyr Asp
145                 150                 155                 160

Gly Val Ser Pro Asp Lys Ala Arg Ala Ile Met Gln Leu Ala Ala Ser
                165                 170                 175

Pro Val His Phe Thr Gln Asp Asp Pro Leu His Gly Asn Ala Ser Val
            180                 185                 190

Trp Ser Ser Pro Cys His Leu Pro Met Asp Lys Asp Val Leu Ile Pro
        195                 200                 205

Val Asp Thr Thr Ile Leu Lys Val Ala Gln Ala Asp Lys Met Val Glu
    210                 215                 220

Tyr Pro Leu Gln Tyr Arg Asp Lys Gly Ser Leu Asn Arg Asp Ala Asp
225                 230                 235                 240

Ile Asp Gly Gln Ala Ser Arg Lys Met Ser Leu Gln Arg Tyr Arg Glu
                245                 250                 255

Lys Arg Lys Asp Arg Gly Arg Phe Lys Gly Lys Lys Leu Thr Ala Ile
            260                 265                 270

Thr Ser Ser Asn Phe Glu Met Tyr Leu Asn Leu Pro Val Lys Val His
        275                 280                 285

Ala Ser Asn Gly Asn Ser Ser Arg Ser Ser Thr Ser Ser Pro Pro Gln
    290                 295                 300

Pro Arg Leu Pro Leu Val Ser Ser Gly Ser Ala Asp Asn Gln Leu Lys
305                 310                 315                 320

Val Ala Leu Pro Ile Asp Leu Asn Asp Lys Asp Val Gln Glu Cys
                325                 330                 335

<210> SEQ ID NO 154
<211> LENGTH: 319
```

<212> TYPE: PRT
<213> ORGANISM: Solanum lycopersicum

<400> SEQUENCE: 154

```
Met Pro Pro Glu Glu Thr Val Ser Lys Ser Pro Leu Asp Lys Pro Leu
1               5                   10                  15

Asn Gln Leu Thr Asp Asp Asp Ile Ser Gln Leu Thr Arg Glu Asp Cys
            20                  25                  30

Arg Arg Tyr Leu Lys Gln Lys Gly Met Arg Lys Pro Ser Trp Asn Lys
        35                  40                  45

Ser Gln Ala Ile Gln Gln Val Ile Ser Leu Lys Ala Leu Leu Glu Pro
    50                  55                  60

Asp Thr Asp Ala Gly Ser Arg Lys Lys Leu His Ile Pro Arg Ala Asp
65                  70                  75                  80

Thr His Val Gln Arg Gly Lys Asn Thr Tyr Gly Glu Pro Ser Glu Pro
                85                  90                  95

Val Pro Asp Arg Arg Asn Gln Gln Asp Lys Pro Asp Leu Ser Asn His
            100                 105                 110

Ser Thr Ala Leu Pro Val Thr Val Asp Asn Ser Ala Pro Ser Arg
        115                 120                 125

Thr Ile Gly Ser Ala Asp Lys Pro Val Gly Gln Met Thr Ile Phe Tyr
130                 135                 140

Arg Gly Lys Val Asn Val Tyr Asp Asp Val Pro Ala Asp Lys Ala Gln
145                 150                 155                 160

Lys Ile Met Cys Leu Ala Ser Ser Pro Leu Cys Met Pro Ser Glu Thr
                165                 170                 175

Pro Ser Asn Ala Thr Ala Ala Arg His Ser Ala Tyr Cys Leu Gln
            180                 185                 190

Ala Ala Asn Ser Lys Leu Arg Leu Asp Thr Val Lys Met Ser Glu Val
        195                 200                 205

Ser Arg Val Pro Ile Glu Glu Ser Asn Arg Leu Cys Asn Asp Asn Pro
210                 215                 220

Gly Ala Val Glu Ser Pro Ala Ser Arg Lys Ala Ser Val Gln Arg Tyr
225                 230                 235                 240

Leu Glu Lys Arg Lys Glu Arg Phe Lys Trp Lys Arg Lys Val Glu Thr
                245                 250                 255

Thr Ser Ala Asn Leu Asp Ile Tyr Leu Ser Asp Arg Ile Gly Thr
            260                 265                 270

Cys Ser Pro Ser Asp Tyr Ala Ser Gly Ala Asp Leu Ser Phe Pro Pro
        275                 280                 285

His Ile Thr Pro Thr Gly Ser Gly Pro Ile Gln Asp Asn Ile Gln Met
290                 295                 300

Asn Pro Thr Phe Ser Ser Gly Leu Asn Asp Arg Asp Val Arg Lys
305                 310                 315
```

<210> SEQ ID NO 155
<211> LENGTH: 339
<212> TYPE: PRT
<213> ORGANISM: Solanum lycopersicum

<400> SEQUENCE: 155

```
Met Ser Leu Glu Gln Thr Val Tyr Lys Ser Pro Leu Asp Lys Pro Leu
1               5                   10                  15

Tyr Leu Leu Thr Asp Asp Asp Ile Ser Gln Leu Thr Arg Glu Asp Cys
            20                  25                  30
```

```
Arg Arg Phe Leu Lys Ala Lys Gly Met Arg Lys Pro Ser Trp Asn Lys
            35                  40                  45
Ser Gln Ala Ile Gln Val Ile Ser Leu Lys Ala Leu Phe Glu Thr
 50                  55                  60
Thr Pro Glu Ser Asp Thr Gly Gln Arg Lys Lys Arg His Ile Pro Arg
 65                  70                  75                  80
Pro Asp Thr Ser Leu Gln Arg Val Gln Lys Glu Thr Ser Ile Asp Ala
                 85                  90                  95
Glu Phe Ala Glu Ser Ala Glu Glu Thr Val Pro Tyr Gly Arg Lys Pro
                100                 105                 110
Pro Asn Lys Pro Asp Leu Ser Gly Asp Lys Ala Ala Ser Ala Val Ala
                115                 120                 125
Val Val Asn Asn Leu Ala Pro Ser Arg Thr Thr Asp Ser Gly Asn Ala
130                 135                 140
Ser Ser Gly Gln Leu Thr Ile Phe Tyr Cys Gly Lys Val Asn Val Tyr
145                 150                 155                 160
Asp Asp Val Pro Ala Glu Lys Ala Glu Ala Ile Met His Leu Ala Ala
                165                 170                 175
Ser Pro Leu Phe Val Pro Ser Glu Thr Pro Leu Asp Ala Asn Arg Ala
                180                 185                 190
Ala Gln His Ser Glu Cys His Leu Gln Ala Ala Asn Val Lys Leu Gly
                195                 200                 205
Gln Asp Ser Pro Met Val Phe Met Pro Thr Met Gln Thr Gly Lys Ile
                210                 215                 220
Thr Glu Val Thr Arg Leu His Leu Glu Glu Ser Asn Thr Ser Tyr Glu
225                 230                 235                 240
Asp Asn Pro Glu Ala Val Asn His Val Ser Arg Lys Ala Leu Leu Glu
                245                 250                 255
Arg Tyr Arg Glu Lys Arg Lys Asp Arg Phe Lys Arg Lys Met Gly Met
                260                 265                 270
Pro Ser Ser Ala Ser Leu Asp Ile Tyr Leu Asn His Arg Thr Ile Asn
                275                 280                 285
His Thr Gln Ser Glu Leu Ser Ser Arg Ser Asn Thr Cys Ser Pro Pro
                290                 295                 300
Ala Ile Arg Leu Ser Ala Ala Pro Ala Pro Ser Gly Ser Met Asp Asn
305                 310                 315                 320
Ile Leu Gln Met Asp Ala Asn Ala Ser Gly Phe Leu Asp Asp Lys Asp
                325                 330                 335
Gly Lys Glu

<210> SEQ ID NO 156
<211> LENGTH: 426
<212> TYPE: PRT
<213> ORGANISM: Theobroma cacao

<400> SEQUENCE: 156

Met Thr Phe Leu Arg Ser Leu Ala Lys Ile Ala Ala Val Thr Ser Lys
 1               5                  10                  15
Lys Lys Val Ser Leu Phe Leu Cys Ile Phe Leu Cys Phe Phe Cys Ile
                20                  25                  30
Phe Ser Tyr Val Lys Val Arg Thr Arg Cys Ile Ser Ser Phe Leu Phe
                35                  40                  45
Cys Cys Ser Leu Arg Val Gly Met Arg Arg Pro Ser Trp Asn Lys Ser
 50                  55                  60
```

-continued

```
Gln Ala Ile Gln Gln Val Ile Ser Leu Lys Thr Leu Leu Glu Thr Thr
 65                  70                  75                  80

Ser Asp Ser Asp Ala Val Glu Ala Cys Lys Lys Leu His Ile Pro Cys
                 85                  90                  95

Pro Glu Asn Pro Pro Arg Val Val Ser Asp Ser Thr Val Leu Val Asn
            100                 105                 110

Glu Thr Thr Gln His Asn Gly Asn Ser Ala Pro Val Asn Glu Ser Val
        115                 120                 125

Pro Cys Pro Arg Pro Asp Pro Ser Lys Ser Asp Phe Ser Gly Asp Asn
    130                 135                 140

Ser Gly Arg Asn Ala Ile Ser Gly Asn Asp Ser Val Ser Pro Arg Thr
145                 150                 155                 160

Ala Gly Ala Ala Lys Glu Gln Ala Gly Gln Met Thr Ile Phe Tyr Cys
                165                 170                 175

Gly Glu Val Asn Val Tyr Asp Asp Met Pro Gly Cys Lys Ala Gln Ala
            180                 185                 190

Ile Leu Gln Leu Ala Ala Ser Pro Leu Ser Leu Ser Gln Glu Thr Ala
        195                 200                 205

Ala Asp Gln Ser Arg Ala Pro Trp Ser Val Pro Cys Gln Leu Gln Ala
    210                 215                 220

Ala Gly Val Lys Ile Ser Pro Cys Ser Pro Met Val Ile Leu Pro Ser
225                 230                 235                 240

Pro Gln Thr Val Lys Val Ala Glu Asn Cys Gln Phe Pro Trp Glu Glu
                245                 250                 255

Ser Asn Ile Ser Arg Glu Asp Ser Leu Glu Gly Pro Ser Ser Arg Lys
            260                 265                 270

Ala Leu Val Gln Arg Tyr Leu Glu Arg Lys Lys Asp Arg Phe Lys Asn
        275                 280                 285

Lys Arg Lys Leu Ala Thr Ser Ser Ser Pro Thr Leu Asp Ile Tyr Ile
    290                 295                 300

Asn Gln Val Gly Asp Gln Phe Ala Asn Glu Gln Leu Lys Pro Ser Glu
305                 310                 315                 320

Pro Tyr Ser Ser Ser Gln Thr Arg Pro Pro Tyr Thr Pro Leu Arg Cys
                325                 330                 335

Asn Ser Ile Glu Asn Val Pro Lys Ile Ala Ser Leu Ala Thr His Pro
            340                 345                 350

Asp Ala Lys Ala Ser Asn Ser Trp Lys Gly Ser Leu Val Val Ala Ser
        355                 360                 365

Leu Ile Trp Thr Ile Phe Leu Arg Leu Tyr His Met Lys Ser Gln Thr
    370                 375                 380

Ser Tyr Ala Ser Leu Val Ile Lys Phe Pro Val Ser Phe Asn Ile Phe
385                 390                 395                 400

Gln Leu Pro Val Leu Met Thr Ser Lys Asn Ala Ser Tyr Leu Tyr Ser
                405                 410                 415

Gln Gln Val Ser Leu Asp Val Tyr Glu Ile
            420                 425

<210> SEQ ID NO 157
<211> LENGTH: 354
<212> TYPE: PRT
<213> ORGANISM: Theobroma cacao

<400> SEQUENCE: 157

Met Glu Ala Gly Val Ala Thr Thr Thr Thr Thr Glu Ser Phe Arg
 1               5                  10                  15
```

Ser Ile Leu Asp Lys Pro Leu Ser Gln Leu Thr Glu Asp Ile Ser
         20                  25                  30

Gln Leu Thr Arg Glu Asp Cys Arg Lys Phe Leu Lys Glu Lys Gly Met
         35                  40                  45

Arg Arg Pro Ser Trp Asn Lys Ser Gln Ala Ile Gln Gln Val Ile Ser
 50                  55                  60

Leu Lys Ala Leu Leu Glu Ser Asn Glu Asp Ser Gly Ala Gly Ala Ile
65                   70                  75                  80

Arg Lys Ile Leu Val Ser Pro Pro Ser Pro Ser Val Pro Pro Gln Asn
                 85                  90                  95

Ala Ala Ala Arg Val Ala Ser Asn Ser Cys Asp Ser Val Lys Glu Ala
             100                 105                 110

Val Val Gly Glu Glu Gly Ser Pro Tyr Arg Arg Lys Asp Pro Pro Leu
             115                 120                 125

Lys Pro Ser Pro Val Gly Glu Ile Asn Cys Leu Gly Gly Asp Thr Asp
130                 135                 140

Asn Lys Asn Leu Ser Pro Arg Ser Pro Cys Glu Ser Asn Glu Leu Gly
145                 150                 155                 160

Gly Gln Met Thr Ile Phe Tyr Cys Gly Lys Val Asn Val Tyr Asp Gly
                165                 170                 175

Val Pro Leu Asp Lys Ala Arg Ala Ile Met His Leu Ala Ala Thr Pro
            180                 185                 190

Ile Asp Phe Pro Gln Asp Asn Gln Cys Ser Gly Asn Ala Ala Leu Arg
        195                 200                 205

Ser Phe Met Cys His Val Gln Ala Val Gly Asp Lys Asn Gly Leu Val
    210                 215                 220

Ala Ser Thr Ala Leu Asn Ser His Thr Met Gln Thr Glu Lys Leu Thr
225                 230                 235                 240

Glu Tyr Gln His Gln Phe Arg Glu Lys Gly Asn Ile Ala Arg Asp Ala
                245                 250                 255

Asp Val Asp Gly Gln Val Asn Arg Lys Val Ser Leu Gln Arg Tyr Arg
            260                 265                 270

Glu Lys Arg Lys Asp Arg Gly Arg Phe Phe Lys Gly Arg Lys Asn Thr
        275                 280                 285

Gly Gln Ala Ser Ser Ser Leu Glu Met Tyr Leu Asn His Gln Ile Arg
    290                 295                 300

Thr His Asn Ser Asn Gly Gln Ser Ser Arg Ser Thr Gly Ser Pro
305                 310                 315                 320

Pro Gln Ser Gly Leu Pro His Ala Phe Cys Ser Ser Ala Asp Asn Gln
                325                 330                 335

Ala Lys Leu Val Asn Leu Ser Val Asp Leu Asn Asp Lys Ser Val Gln
            340                 345                 350

Glu His

<210> SEQ ID NO 158
<211> LENGTH: 312
<212> TYPE: PRT
<213> ORGANISM: Conradina grandiflora

<400> SEQUENCE: 158

Met Glu Asp Val Gly Val Ser Thr Ala Lys Ser Ile Leu Ala Lys Pro
1               5                   10                  15

Leu Lys Leu Leu Thr Glu Asp Asp Ile Ser Gln Leu Thr Arg Glu Asp
                20                  25                  30

```
Cys Arg Lys Phe Leu Lys Glu Lys Gly Met Arg Arg Pro Ser Trp Asn
            35                  40                  45

Lys Ser Gln Ala Ile Gln Val Leu Ser Leu Lys Ala Leu Phe Glu
 50                  55                  60

Pro Gly Asp Asp Ser Gly Ala Gly Ile Leu Arg Lys Ile Leu Val Ser
 65                  70                  75                  80

Gln Pro Pro Ile Pro Pro Arg Val Thr Thr Thr Ser Thr Glu Leu Ser
                 85                  90                  95

Asn Glu Leu Glu Ala Cys Gly Arg Ile Pro Pro Phe Gln Glu Asp Asp
            100                 105                 110

Gly Pro Cys His Arg Arg Asp Ser Pro Arg Ser Ala Glu Phe Ser Gly
            115                 120                 125

Gly Ser Ala His Tyr Pro Ala Glu Lys Asp Thr Asn Lys Thr Val Ser
130                 135                 140

Leu Arg Ser Pro Ala Glu Thr Asn Ala Leu Val Gly Gln Met Thr Ile
145                 150                 155                 160

Phe Tyr Ser Gly Lys Val Asn Val Tyr Asp Gly Val Pro Ser Glu Lys
                165                 170                 175

Ala Gln Ser Ile Met His Phe Ala Ala Asn Pro Val Asp Leu Pro Ala
            180                 185                 190

Asn Gly Ile Phe Ser Ser Ser Cys Met Pro Met Ser Lys Glu Lys Met
            195                 200                 205

Val Glu Leu Pro Gln Ile Gly Leu Glu Arg Val Asn Ser Ser Arg Asp
210                 215                 220

Phe Asp Met Glu Gly His Ala Asn Arg Lys Met Ser Leu Gln Arg Tyr
225                 230                 235                 240

Arg Glu Lys Arg Lys Asp Arg Arg Phe Leu Lys Ala Lys Lys Ser Pro
                245                 250                 255

Gly Val Ala Ser Ser Ser Leu Glu Met Phe Leu Asn Arg Gln Pro Arg
            260                 265                 270

Met Asn Ala Ala Tyr Ser Gln Asn Leu Gly His Thr Arg Ser Ser Leu
            275                 280                 285

Gln Ser Glu Ser Pro Glu Asn Pro Arg Lys Ser Pro Asn Leu Ser Val
            290                 295                 300

Asp Leu Asn Ser Glu Ala Asp Ile
305                 310

<210> SEQ ID NO 159
<211> LENGTH: 313
<212> TYPE: PRT
<213> ORGANISM: Conradina grandiflora

<400> SEQUENCE: 159

Met Asp Val Gly Val Ser Pro Ala Lys Ser Ile Leu Ala Lys Pro Leu
 1               5                  10                  15

Lys Leu Leu Thr Glu Glu Asp Ile Ser Gln Leu Thr Arg Glu Asp Cys
             20                  25                  30

Arg Lys Phe Leu Lys Glu Lys Gly Met Arg Arg Pro Ser Trp Asn Lys
            35                  40                  45

Ser Gln Ala Ile Gln Gln Val Leu Ser Leu Lys Ala Leu Phe Glu Pro
 50                  55                  60

Gly Asp Asp Ser Gly Ala Gly Ile Leu Arg Lys Ile Leu Val Ser Gln
 65                  70                  75                  80

Pro Ser Ile Pro Pro Val Thr Ser Thr Ser Ile Glu Pro Ser Ser
```

```
                85                  90                  95
Glu Leu Glu Ala Cys Gly Arg Asn Pro Phe Gln Glu Asp Glu Gly Pro
            100                 105                 110

Cys His Arg Arg Asp Ser Pro Arg Ser Ala Glu Phe Ser Gly Gly Ser
            115                 120                 125

Ala Gln Phe Val Ala Glu Lys Asp Ser Leu Lys Thr Val Ser Pro Arg
130                 135                 140

Ser Pro Ala Glu Thr Ser Pro Leu Val Gly Gln Met Thr Ile Phe Tyr
145                 150                 155                 160

Ser Gly Lys Val Lys Val Tyr Asp Gly Val Pro Pro Glu Lys Ala Arg
                165                 170                 175

Ser Ile Met His Phe Ala Ala Asn Pro Ile Asp Leu Pro Glu Asn Gly
                180                 185                 190

Ile Phe Ala Ser Ser Arg Met Ile Ser Lys Pro Met Ser Lys Glu Lys
                195                 200                 205

Met Val Asp Leu Pro Gln Tyr Gly Leu Glu Lys Ala Thr Ala Ser Arg
            210                 215                 220

Asp Ser Asp Val Glu Gly Gln Ala Asn Arg Lys Val Ser Leu Gln Arg
225                 230                 235                 240

Tyr Leu Asp Lys Arg Lys Asp Arg Arg Phe Ser Lys Thr Lys Lys Ala
                245                 250                 255

Pro Gly Val Ala Ser Ser Ser Leu Asp Met Phe Leu Asn Arg Gln Pro
            260                 265                 270

Arg Met Asn Ala Ala Tyr Ser Gln Asn Leu Ser Gly Ala Gly Leu Cys
            275                 280                 285

Glu Ser Pro Glu Asn Gln Thr Lys Ser Ser Asn Leu Ser Val Asp Leu
            290                 295                 300

Asn Ser Asp Leu Asn Ser Glu Asp Leu
305                 310

<210> SEQ ID NO 160
<211> LENGTH: 338
<212> TYPE: PRT
<213> ORGANISM: Mimulus guttatus

<400> SEQUENCE: 160

Met Gln Pro Glu Val Thr Ala Val Asn Ser Ser Leu Glu Lys Pro Leu
1               5                   10                  15

His Gln Leu Thr Glu Asp Asp Ile Ala Gln Val Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Gln Val Ile Met Leu Lys Thr Leu Leu Glu Val
50                  55                  60

Ala Pro Asp Ser Asp Ser Gly Ser Arg Lys Arg Leu Arg Phe Ser Arg
65                  70                  75                  80

Pro Asn Asp Asn Gly Val Ile Pro Glu Ser Val Thr Lys Ala Thr His
                85                  90                  95

Ile Glu Gly Glu Thr Ser Val Ser Ala Glu Tyr Thr Ala Pro Phe Cys
            100                 105                 110

Gly Lys Asp Leu Asp Lys Pro Asp Ser Ser Gly Ala Ala Ala Arg Cys
            115                 120                 125

Leu Ala Val Asn Asn Asp Pro Thr Leu Ser Arg Thr Thr Ala Ser Leu
        130                 135                 140
```

```
Gly Met Pro Val Gly Gln Met Thr Ile Phe Tyr Cys Gly Lys Val Asn
145                 150                 155                 160

Val Tyr Asp Asp Val Pro Glu Asp Lys Ala Gln Ser Ile Met His Ile
            165                 170                 175

Ala Ala Ser Pro Val Gln Phe Pro Gln Glu Gln Pro Val Asp Asp
        180                 185                 190

Thr Ile Ile Ile His Pro Leu Thr Ser Leu Ser Lys Ala Val Ser Val
        195                 200                 205

Lys Ala Gly Leu Asp Ser Pro Val Ala Leu Leu Pro Ala Leu Gln Thr
        210                 215                 220

Val Lys Met Ser Glu Asn Ser Arg Ala Leu Ala Asp Glu Cys Ile Ser
225                 230                 235                 240

Leu Arg Glu Gly Thr Pro Val Glu Gly Pro Ser Thr Arg Lys Ala Ser
                245                 250                 255

Val Gln Arg Tyr Leu Asp Lys Arg Lys Asp Arg Phe Lys Ser Lys Arg
            260                 265                 270

Lys Ala Gly Ile Thr Ser Cys Thr Ser Leu Asp Val Gln Phe Asn His
            275                 280                 285

Gln Lys Asn Asn Gln Ile Pro Asn Asp Phe Leu Asn Arg Ser Asn Thr
        290                 295                 300

Cys Ser Pro Pro Ile Lys Pro Pro Ser Thr Pro Thr Arg Cys Ser
305                 310                 315                 320

Ser Val Asp Asn Asp Ser Leu Arg Asn Leu Cys Gly Ser Thr Asp Leu
                325                 330                 335

Asn Asn
```

<210> SEQ ID NO 161
<211> LENGTH: 337
<212> TYPE: PRT
<213> ORGANISM: Mimulus guttatus

<400> SEQUENCE: 161

```
Met Gln Pro Glu Val Thr Ala Val Asn Ser Ser Leu Glu Lys Pro Leu
1               5                   10                  15

His Gln Leu Thr Glu Asp Asp Ile Ala Gln Val Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Gln Val Ile Met Leu Lys Thr Leu Leu Glu Gly
    50                  55                  60

Ala Pro Asp Ser Asp Ser Gly Ser Arg Lys Arg Leu Arg Phe Ser Arg
65                  70                  75                  80

Pro Asn Asp Asn Gly Val Ile Pro Glu Ser Val Pro Lys Ala Thr His
                85                  90                  95

Ile Glu Gly Glu Thr Ser Val Ser Ala Glu Tyr Thr Ala Pro Phe Cys
            100                 105                 110

Gly Lys Asp Leu Asp Lys Pro Asp Ser Ser Arg Ala Ala Ala Arg Cys
        115                 120                 125

Leu Ala Val Asn Asn Asp Pro Thr Leu Ser Arg Thr Thr Ala Ser Leu
    130                 135                 140

Gly Met Pro Val Gly Gln Met Thr Ile Phe Tyr Cys Gly Lys Val Asn
145                 150                 155                 160

Val Tyr Asp Asp Val Pro Glu Asp Lys Ala Gln Ser Ile Met His Ile
            165                 170                 175
```

```
Ala Ala Ser Pro Val Gln Phe Pro Gln Glu Gln Pro Val Asp Asp Thr
            180                 185                 190

Ile Ile Asn His Pro Leu Thr Ser Leu Ser Lys Ala Val Ser Val Lys
        195                 200                 205

Ala Gly Leu Asp Ser Pro Val Ala Leu Leu Pro Ala Leu Gln Thr Val
210                 215                 220

Lys Met Ser Asp Asn Ser Arg Ala Leu Ala Asp Glu Cys Ile Ser Leu
225                 230                 235                 240

Arg Glu Gly Thr Pro Val Glu Gly Pro Ser Thr Arg Lys Ala Ser Val
                245                 250                 255

Gln Arg Tyr Leu Asp Lys Arg Lys Asp Arg Phe Lys Ser Lys Arg Lys
            260                 265                 270

Ala Gly Ile Thr Ser Ser Thr Ser Leu Asp Val His Phe Asn His Gln
        275                 280                 285

Lys Asn Asn Gln Ile Pro Asn Asp Phe Leu Asn Arg Ser Asn Thr Cys
290                 295                 300

Ser Pro Pro Pro Ile Lys Pro Pro Ser Thr Pro Thr Arg Cys Ser Ser
305                 310                 315                 320

Val Asp Asn Asp Ser Leu Arg Asn Leu Cys Gly Ser Thr Asp Leu Asn
                325                 330                 335

Asn

<210> SEQ ID NO 162
<211> LENGTH: 346
<212> TYPE: PRT
<213> ORGANISM: Glycine max

<400> SEQUENCE: 162

Met Asn Gly Gly Ala Thr Thr Ala Thr Phe Arg Ser Ile Leu Asp Lys
1               5                   10                  15

Pro Leu Asn Gln Leu Thr Glu Asp Asp Ile Ser Gln Leu Thr Arg Glu
            20                  25                  30

Asp Cys Arg Arg Phe Leu Lys Glu Lys Gly Met Arg Arg Pro Ser Trp
        35                  40                  45

Asn Lys Ser Gln Ala Ile Gln Gln Val Ile Ser Leu Lys Ala Leu Leu
    50                  55                  60

Glu Pro Ser Asp Asp Thr Pro Pro Pro Pro Pro Ala Met His
65                  70                  75                  80

His Arg Ser His Ala Gln Pro Gln Pro Gln Val Asn Leu Ser Glu Pro
                85                  90                  95

Pro Pro Pro Pro Lys Ala Pro Pro Glu Glu Pro Ala Phe His
            100                 105                 110

Ala Ala Glu Asp Ile Gln Lys Ser Ala Ser Ser Gly Glu Lys Pro Thr
        115                 120                 125

Glu Thr Asn Asp Thr Asn Thr Asn Val Ala Ser Pro Lys Gly Cys Ala
    130                 135                 140

Thr Ser Gly Ser Phe Gly Gln Met Thr Ile Phe Tyr Cys Gly Lys Val
145                 150                 155                 160

Asn Val Tyr Asp Arg Val Ser Pro Asp Lys Ala Arg Ala Ile Met Gln
                165                 170                 175

Leu Ala Thr Ser Pro Val Gln Leu Thr Gln Asp Asp Pro Leu Asn Gly
            180                 185                 190

Asn Ala Ala Val Trp Thr Ser Pro Cys His Leu Pro Met Asp Lys Asp
        195                 200                 205
```

```
Val Leu Val Pro Val Asp Thr Thr Ile Leu Gln Val Ala Gln Ala Asp
    210                 215                 220

Lys Met Val Glu Tyr Pro Leu Gln Tyr Arg Glu Lys Gly Ser Ile Ala
225                 230                 235                 240

Arg Asp Ala Asp Val Glu Gly Gln Glu His Arg Lys Val Ser Leu Gln
                245                 250                 255

Arg Tyr Leu Glu Lys Arg Lys Asp Arg Gly Arg Leu Lys Gly Lys Lys
            260                 265                 270

Leu Thr Gly Ile Thr Ser Ser Asn Phe Glu Met Tyr Leu Asn Leu Pro
        275                 280                 285

Val Lys Val His Ser Ser Asn Gly Asn Ser Ser Arg Ser Ser Thr Ser
    290                 295                 300

Ser Pro Pro Gln Pro Arg Leu Pro Leu Val Ser Ser Gly Ser Asp Gln
305                 310                 315                 320

Leu Lys Val Ala Leu Pro Ile Asp Leu Asn Asp Lys Val Ser Leu Gln
                325                 330                 335

Met Phe Lys Asn Ala Lys Ile Gln Thr Arg
            340                 345

<210> SEQ ID NO 163
<211> LENGTH: 350
<212> TYPE: PRT
<213> ORGANISM: Glycine max

<400> SEQUENCE: 163

Met Asn Gly Gly Ala Thr Thr Ala Thr Phe Arg Ser Ile Leu Asp Lys
1               5                   10                  15

Pro Leu Asn Gln Leu Thr Glu Asp Asp Ile Ser Gln Leu Thr Arg Glu
            20                  25                  30

Asp Cys Arg Arg Phe Leu Lys Glu Lys Gly Met Arg Arg Pro Ser Trp
        35                  40                  45

Asn Lys Ser Gln Ala Ile Gln Gln Val Ile Ser Leu Lys Ala Leu Leu
    50                  55                  60

Glu Pro Ser Asp Asp Thr Pro Pro Thr Ala Met His His Arg
65                  70                  75                  80

Ser His Ala Pro Pro Pro Pro Gln Pro Gln Ser Gln Val Asn Leu
                85                  90                  95

Thr Glu Pro Pro Pro Pro Lys Ala Pro Pro Glu Glu Ser Ser
            100                 105                 110

Phe His Ala Ala Glu Asp Ile Gln Lys Pro Ala Ser Ser Gly Glu Lys
        115                 120                 125

Pro Ser Glu Thr Asn Asp Thr Asn Thr Asn Val Ala Ser Pro Lys Gly
130                 135                 140

Cys Ala Thr Ser Gly Ser Phe Gly Gln Met Thr Ile Phe Tyr Cys Gly
145                 150                 155                 160

Lys Val Asn Val Tyr Asp Gly Val Ser Pro Asp Lys Ala Arg Ala Ile
                165                 170                 175

Met Gln Leu Ala Val Ser Pro Val Gln Phe Thr Gln Asp Asp Pro Ser
            180                 185                 190

Asn Gly Asn Ala Ala Val Trp Pro Ser Pro Cys His Leu Pro Met Asp
        195                 200                 205

Lys Asp Val Leu Ile Pro Val Asp Thr Thr Ile Leu Gln Val Ala Gln
    210                 215                 220

Ser Asp Lys Met Met Glu Tyr Pro Leu Gln Tyr Arg Glu Lys Gly Ser
225                 230                 235                 240
```

```
Ile Ala Arg Asp Ala Asp Val Glu Gly Gln Ala Ser Arg Lys Val Ser
                245                 250                 255

Leu Gln Arg Tyr Leu Glu Lys Arg Lys Asp Arg Gly Arg Leu Lys Gly
            260                 265                 270

Lys Lys Leu Thr Gly Ile Thr Ser Ser Asn Phe Glu Met Tyr Leu Asn
        275                 280                 285

Leu Pro Val Lys Val His Ala Ser Asn Gly Asn Ser Ser Arg Ser Ser
    290                 295                 300

Thr Ser Ser Pro Pro Gln Pro Arg Leu Pro Leu Val Ser Ser Gly Ser
305                 310                 315                 320

Ala Asp Asn Gln Leu Lys Val Ala Leu Pro Ile Asp Leu Asn Asp Lys
                325                 330                 335

Val Ser Leu Gln Met Phe Lys Asn Ala Lys Thr Leu Thr Arg
            340                 345                 350

<210> SEQ ID NO 164
<211> LENGTH: 316
<212> TYPE: PRT
<213> ORGANISM: Brassica rapa

<400> SEQUENCE: 164

Met Glu Gly Gly Val Ser Ser Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Phe Glu Pro
    50                  55                  60

Gly Asp Asp Ser Gly Ala Gly Ile Leu Arg Lys Ile Leu Val Ser His
65                  70                  75                  80

Pro Pro Ile Pro Ser Arg Val Thr Thr Pro Ser Thr Glu Pro Ser Asn
                85                  90                  95

Asp Leu Gly Ala Cys Gly Gln Ile Pro Phe Gln Glu Asp Asp Gly Pro
            100                 105                 110

Ser Leu Arg Arg Asp Ser Pro Arg Ser Pro Asp Phe Ser Gly Gly Ser
        115                 120                 125

Ala His Tyr Leu Ala Asp Lys Asp Cys His Ile Thr Leu Ser Pro Arg
    130                 135                 140

Ser Pro Ala Glu Thr Ser Ala Leu Ala Gly Gln Leu Thr Ile Phe Tyr
145                 150                 155                 160

Ser Gly Lys Val Asn Val Tyr Asp Gly Val Pro Pro Glu Lys Ala Arg
                165                 170                 175

Ser Ile Met His Phe Ala Ala Asn Pro Ile Asp Phe Pro Asp Ser Gly
            180                 185                 190

Val Phe Pro Ser Ser Arg Met Ile Ser Arg Pro Val Ser Lys Glu Lys
        195                 200                 205

Met Val Glu His Pro His Tyr Gly Leu Glu Lys Ala Asn Ala Ser Arg
    210                 215                 220

Asp Ser Asp Ala Glu Gly Gln Ala Asn Arg Lys Val Ser Leu Gln Arg
225                 230                 235                 240

Tyr Arg Glu Lys Arg Asn Glu Arg Leu Phe Lys Thr Lys Lys Ala Pro
                245                 250                 255

Gly Val Gly Ser Ser Ser Leu Glu Met Tyr Leu Asn Arg Ser Gln Pro
```

```
                   260                 265                 270
Leu Met Asn Ala Ala Tyr Ser Gln Asn Pro Ser Gly Gly Thr Gly
                275                 280                 285

Gly Glu His Gln Ser Pro Gln Asn Gln Thr Arg Ser Pro Asn Phe Ser
            290                 295                 300

Val Asp Leu Asn Cys Asp Leu Asn Ser Glu Asp Ile
305                 310                 315

<210> SEQ ID NO 165
<211> LENGTH: 306
<212> TYPE: PRT
<213> ORGANISM: Brassica rapa

<400> SEQUENCE: 165

Met Asp Ala Val Ser Ser Ala Lys Ser Ile Leu Glu Lys Pro Leu Lys
1               5                   10                  15

Leu Leu Thr Glu Asp Asp Ile Ser Gln Leu Thr Arg Glu Asp Cys Arg
            20                  25                  30

Lys Phe Leu Lys Asp Lys Gly Met Arg Arg Pro Ser Trp Asn Lys Ser
        35                  40                  45

Gln Ala Ile Gln Gln Val Leu Ser Leu Lys Ala Leu Phe Glu Pro Gly
    50                  55                  60

Asp Asp Ser Gly Ala Gly Ile Leu Arg Lys Ile Leu Val Ser Pro Asn
65                  70                  75                  80

Pro Thr Arg Val Thr Ala Thr Ser Thr Glu Pro Ala Asn Glu Val Gly
                85                  90                  95

Ala Arg Ile Pro Phe Gln Glu Asp Arg Arg Asp Ser Pro Arg Ser
            100                 105                 110

Ala Glu Phe Ser Gly Ser Glu Lys Asp Ser Tyr Asn Thr Leu Ser Pro
        115                 120                 125

Arg Ser Pro Ala Glu Thr Ser Ala Leu Val Gly Gln Met Thr Ile Phe
    130                 135                 140

Tyr Ser Gly Lys Val Ser Val Tyr Asp Gly Val Pro Pro Glu Lys Ala
145                 150                 155                 160

Arg Ser Ile Met His Phe Ala Ala Asn Pro Ile Asp Leu Pro Glu Tyr
                165                 170                 175

Gly Val Ser Ala Ser Ala Arg Leu Thr Ser Arg Pro Met Thr Met Ser
            180                 185                 190

Lys Glu Lys Met Val Glu Pro Pro His Tyr Gly Tyr Gly Leu Glu Lys
        195                 200                 205

Ala Asn Ala Ser Arg Asp Ser Asp Ala Glu Gly Gln Ala Asn Arg Lys
    210                 215                 220

Val Ser Leu Gln Arg Tyr Leu Asp Lys Arg Lys Asp Arg Arg Leu Phe
225                 230                 235                 240

Lys Asn Lys Lys Ala Pro Gly Val Ala Ser Ser Ser Leu Glu Met Tyr
                245                 250                 255

Leu Ser Arg Ser Gln Pro Val Thr Asn Ala Tyr Ser Gln Ser Leu Ser
            260                 265                 270

Gly Gly Gly Thr Gly Gly Glu Gln His Glu Ser Pro Glu Asn Gln Arg
        275                 280                 285

Arg Ser Pro Asn Leu Ser Val Asp Leu Asn Ser Asp Leu Asn Ser Glu
    290                 295                 300

Asp Asn
305
```

<210> SEQ ID NO 166
<211> LENGTH: 311
<212> TYPE: PRT
<213> ORGANISM: Boechera stricta

<400> SEQUENCE: 166

Met Asp Val Glu Val Ser Pro Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Phe Glu Pro
    50                  55                  60

Gly Asp Asp Ser Gly Ala Gly Ile Leu Arg Lys Ile Leu Val Ser Gln
65                  70                  75                  80

Pro Ala Asn Pro Pro Arg Val Ala Thr Thr Ser Ile Glu Pro Ser Asn
                85                  90                  95

Glu Leu Glu Ala Cys Gly Arg Asn Pro Phe Pro Glu Asp Glu Gly Pro
            100                 105                 110

Cys His Arg Arg Asp Ser Pro Arg Ser Ala Glu Phe Ser Gly Gly Ser
        115                 120                 125

Gly Gln Phe Val Ala Glu Lys Asp Ser Phe Lys Thr Val Ser Pro Arg
    130                 135                 140

Ser Pro Ala Glu Thr Ser Pro Phe Val Gly Gln Met Thr Ile Phe Tyr
145                 150                 155                 160

Ser Gly Lys Val Asn Val Tyr Asp Gly Val Pro Pro Glu Lys Ala Arg
                165                 170                 175

Ser Ile Met His Phe Ala Ala Asn Pro Ile Asp Leu Pro Glu Asn Gly
            180                 185                 190

Leu Phe Ala Ser Ser Arg Met Ile Ser Lys Pro Met Gly Lys Glu Lys
        195                 200                 205

Met Val Glu Leu Pro Gln Tyr Gly Phe Glu Lys Ala Thr Ala Ser Arg
    210                 215                 220

Asp Ser Asp Val Glu Gly Gln Ala Asn Arg Lys Val Ser Leu Gln Arg
225                 230                 235                 240

Tyr Leu Glu Lys Arg Lys Asp Arg Arg Phe Ser Lys Thr Lys Lys Ala
                245                 250                 255

Pro Gly Val Ala Ser Thr Ser Leu Glu Met Phe Leu Asn Arg Pro Arg
            260                 265                 270

Met Asn Ala Ala Tyr Ser Gln Asn Leu Ser Thr Gly Ile Cys Glu Ser
        275                 280                 285

Pro Glu Asn Gln Thr Lys Ser Ser Asn Leu Ser Val Asp Leu Asn Ser
    290                 295                 300

Asp Leu Asn Ser Glu Asp Leu
305                 310

<210> SEQ ID NO 167
<211> LENGTH: 330
<212> TYPE: PRT
<213> ORGANISM: Medicago truncatula

<400> SEQUENCE: 167

Met Asn Gly Gly Ser Thr Val Ser Phe Arg Ser Ile Leu Asp Arg Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn
         35                  40                  45

Lys Ser Gln Ala Ile Gln Gln Val Ile Ser Leu Lys Ala Leu Leu Glu
 50                  55                  60

Pro Thr Asp Asp Ile Pro Ala Thr Val Gly Val Gly Val Ser Ser
 65                  70                  75                  80

Ala Ile His His His His His His Pro Gln Pro Pro Lys
                 85                  90                  95

Ala Leu Asp Pro Glu Asp Thr Ala Leu Glu Leu Gln Lys Ser Thr Ser
             100                 105                 110

Pro Val Ala Glu Arg Pro Thr Glu Thr Asn Asp Ala Asn Val Val Asn
             115                 120                 125

Asn Pro Gly Gly Cys Ala Pro Ser Gly Ser Phe Gly Gln Met Thr Ile
 130                 135                 140

Phe Tyr Cys Gly Lys Val Asn Val Tyr Asp Gly Val Ser Pro Asp Lys
145                 150                 155                 160

Ala Arg Ser Ile Met Gln Leu Ala Ala Ala Cys Pro Ser Ser Phe Pro
             165                 170                 175

Gln Asp Asn Pro Ser Asn Lys Asn Ala Ala Val Trp Ala Ser Pro Cys
             180                 185                 190

Asn Leu Pro Ile Asp Lys Glu Val Leu Phe Pro Thr Asp Thr Ala Ile
             195                 200                 205

Leu Gln Val Ala Gln Thr Asp Lys Met Val Glu Tyr Pro Leu Gln Tyr
 210                 215                 220

Arg Glu Lys Gly Ser Thr Ala Arg Asp Ala Asp Val Glu Gly Gln Ala
225                 230                 235                 240

Ser Arg Lys Val Ser Leu Gln Arg Tyr Leu Glu Lys Arg Lys Asp Arg
             245                 250                 255

Gly Arg Ser Lys Gly Lys Lys Leu Thr Gly Ile Thr Ser Ser Asn Phe
             260                 265                 270

Glu Met Tyr Leu Asn Leu Pro Val Lys Leu His Ala Ser Asn Gly Asn
             275                 280                 285

Ser Ser Arg Ser Ser Thr Asp Ser Pro Pro Gln Pro Arg Leu Pro Leu
 290                 295                 300

Val Ser Ser Gly Ser Ala Glu Asn Gln Pro Lys Val Thr Leu Pro Ile
305                 310                 315                 320

Asp Leu Asn Asp Lys Asp Val Gln Glu Cys
             325                 330

<210> SEQ ID NO 168
<211> LENGTH: 330
<212> TYPE: PRT
<213> ORGANISM: Medicago sativa

<400> SEQUENCE: 168

Met Asn Gly Gly Ser Thr Val Ser Phe Arg Ser Ile Leu Asp Arg Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn
         35                  40                  45

Lys Ser Gln Ala Ile Gln Gln Val Ile Ser Leu Lys Ala Leu Leu Glu
 50                  55                  60

Pro Thr Asp Asp Thr Pro Ala Thr Val Gly Val Gly Val Ser Ser
65                  70                  75                  80

Ala Ile His Arg His His His His Pro Gln Pro Pro Lys
            85                  90                  95

Ala Leu Asp Pro Glu Asp Thr Ala Leu Asp Leu Gln Lys Ser Thr Ser
                100                 105                 110

Pro Val Ser Glu Arg Pro Thr Glu Thr Asn Asp Ala Asn Val Val Asn
            115                 120                 125

Pro Pro Gly Gly Cys Thr Pro Ser Gly Ser Phe Gly Gln Met Thr Ile
130                 135                 140

Phe Tyr Cys Gly Lys Val Asn Val Tyr Asp Gly Val Ser Pro Asp Lys
145                 150                 155                 160

Ala Arg Ser Ile Met Gln Leu Ala Ala Ala Cys Pro Ser Ser Phe Pro
                165                 170                 175

Gln Asp Asn Pro Ser Asn Lys Asn Ala Ala Val Trp Ala Ser Pro Cys
            180                 185                 190

Asn Leu Pro Ile Asp Lys Glu Val Leu Phe Pro Thr Asp Thr Thr Ile
            195                 200                 205

Leu Gln Val Ala Gln Thr Asp Lys Met Val Glu Tyr Pro Leu His Tyr
210                 215                 220

Arg Glu Lys Gly Ser Thr Thr Arg Asp Ala Asp Val Glu Gly Gln Ala
225                 230                 235                 240

Ser Arg Lys Val Ser Leu Gln Arg Tyr Leu Glu Lys Arg Lys Asp Arg
                245                 250                 255

Gly Arg Ser Lys Gly Lys Lys Leu Thr Gly Ile Thr Ser Ser Asn Phe
            260                 265                 270

Glu Met Tyr Leu Asn Leu Pro Val Lys Leu His Ala Ser Asn Gly Asn
            275                 280                 285

Ser Ser Arg Ser Ser Thr Asp Ser Pro Pro Gln Pro Arg Leu Pro Leu
            290                 295                 300

Val Ser Ser Gly Ser Ala Glu Asn Leu Pro Lys Val Thr Leu Pro Ile
305                 310                 315                 320

Asp Leu Asn Asp Lys Asp Val Gln Glu Cys
                325                 330

<210> SEQ ID NO 169
<211> LENGTH: 5684
<212> TYPE: DNA
<213> ORGANISM: Medicago sativa

<400> SEQUENCE: 169
atgaacggcg gaagcaccgt ttccttccga tccatcctcg acagacctct taaccaactc      60
actgaagatg acatttctca actcactcgc gaagactgtc gcagattcct caaagataaa     120
ggtaacaact atccttctct ttctctttct tcttcttctt cttctttctc tttcaacatc     180
aaaaaataat aaattaatat tatttttttcg attttatcct ctcatgctcc atggtttccg     240
gctcctgaga caacttcca tttaattttt ctactccaat gcttcatact ttctatattt      300
aatattaatt taatgtaatt aaattaattg ggttgtagat ttttttttat ttaataaaat     360
aattaattaa aaaaatgagt gaagaagacg acacgtgttc gtacagggat gcgcaggcct     420
tcctggaaca atcacaggc gatccagcag gtgattctc tcaaagcgct tctagaacct      480
actgacgatg atacaccggc taccgtcggc gttggtgtct cctccgccat tcaccgccat     540
caccaccacc accctcctca acctccgccg aaggctttgg atcccgaaga tactgctttg     600

```
gaccttcaga aatctacttc acctgtttct gaaagaccca cggaaaccaa tgatgccaac    660
gttgttaacc ctcccgggtc tgttctccat ttttctttca tgttttttta aatgtcgttt    720
aattattttg ttgtgttggc aacttttgtt tgtttgtttg tttgtttgtt atcttttgtt    780
tcttgggcta cgaaacccta actccgacac cggaatgata ctgacacagt cacgtcgaca    840
ctaataaaaa aaatgaaatg atgcttgtat ttgatgtttt ctgcgaaaaa agaagtaaa     900 attctaatgt ttagtgagag tgaagggtgc ttattagatg agttgattat agcataattt    960
ggttgtttga acattaaag ttttgatttt ttttatttat ttgtttagaa ttaggttggg    1020
aaattggcac attgttttat agctttatgt gaagtgggag atgattttg gcatctgatg    1080 aatgtgtgtt gatatatgga aggtgaatct gtttgtggag tggatggaaa atatttaggg   1140
tcagtttgag ctttctcttg tcactgggat gtatgtattc tgtggcttct ttcttcctgt   1200
cattatcaaa tatctagata tctgtaactt taatatcatc tatattttgg gtttgcactg   1260
ttttactttt ctcatatttta attgttgttt acggttttct cttcatgccg tgttttagtg   1320
ccatcaaagt actgacaatc tcatgtttca ttttcaagtt ttccatttaa ttattacttt   1380
agatatcatg tttgaagtgg gtgctagata tcaactgaga gaaggaaaac cctaaatgat   1440
tatttttagg ttaagcatga tcattttgta tattaaagga ctaagaacaa gttagatgaa   1500
aaaatatacc aagcgctgtg ttggtttaat gtcaatagct catgacttca acaatgaata   1560
tggtagtaaa ttgccagttt tgttaatgtg aatttctttt cagttccaat cggtagtaat   1620
aatagtcatc tctacctgaa aaaagtgttg cgttagggct gtaattagcc tttaacatct   1680
cttgcttcca ttaaactaaa aactgcacta atgccattct tgttggaag gagtctgggg   1740 tagtggttaa gtgtgcagaa ctttcagttt atcatctgct ttcgtatgaa gagtgattta   1800
gttactcaaa atgccaaata atttaaattc aataaatttg tgtaaaatat gactgaaggt   1860
agaccaatgt tagttttgtt aattatccat tcaagttctt aacattggtt gtaaatttga   1920
tgcgagcaca gagggtgcac acctagtggg tcatttgggc aaatgacaat tttctactgt   1980
ggtaaggtga atgtctatga tggagttcg ccggataagg tgggtaaaga tgtgtcctct   2040
tgcatgaata tcttgccata catcaattaa atttcacctc ccaataatta accatacttg   2100
tatttgcagg cacgatcaat catgcagctt gctgctgcat gtccgtcctc ctttccccag   2160
gataatcctt caaataaaaa tgcagcagtt tgggcttctc cttgcaactt acctattgat   2220
aaagaagtcc tcttccctac tgacacaaca atccttcaag tcgctcaaac aggtagttag   2280
caattgggta gaaaacatgc ttaattttgc tttgaagtgt agtactctag tgtcaaacaa   2340 atcactttt tcatgcatac ttttctggaa cttaaaagaa ttcgttaatg tatgataagc   2400
acttgcagaa ggttactatt ctatttttt ttcaaaagtt cattcttcaa atttaaatcc   2460
attgactatg acatagtcac atcaatattt acaaacaaat gtattaaata tatatgtaat   2520
ttagttttga atataataaa tcagaaacac atactttcac agtttattgt taagttaaat   2580
tataattttt ttaaaagata aattataagt taaaatgtga attaaagtga gcttttgcat   2640
ttaatttttt taaatataat aaataagaag tgaacaatta tcacaatcca acacatggtt   2700
tgttggtgac ctagaacacc tattttcaat aaccacacgg gaggtcacgc cagtttgata   2760
gtttgatagc atggccgatc taatatttga cttgaaccga ttatcccttc ggttcctggt   2820
tcaaccggtc cgagccggtt tttaaatcac tgggatgtga agacattgtt ctgaccaaat   2880
tcactccgaa taccgatttt ttgaattaaa gctatttagt tcttgtgcct ataagatgaa   2940
```

```
caagctcaac atcaatgact tgtttaaaat catggtaaca tttgtaagtt aggaactgag    3000
atttttgaat taatgcaaaa atcattggat atacattgtt ttgattgtta tgattaaatt    3060
cactgcgaat actgattttt tgaattaaag ctgttgagtt ctttctagaa gatgaacaag    3120
ctcaacagct tttacttgtt taaaatcatg gcaacatcta caagttagga actgatattt    3180
ttgaattaaa gttattgagt ccatgcatct cgtagatgaa caaactcgac attttttactc   3240 gtttaaaatc atggcatcta gtcaggaagt gaagatgttt aacttcataa ttggtgttcc    3300
aaatttggtt ttacagataa aatggtggaa taccctctgc attacaggga gaaaggaagc    3360
acagctcgtg atgctggtag ggacaattaa gtgtttaaac ttttgcagtc tgctctagaa    3420
ttttatcttg tgttctcttt tggcagattt acagataatt ccaagtagat aatttgttga    3480
tagactactt gcagatttac agatgattcc attaagcggg cctttgtttt tttcttggc    3540 atcccgagtc atgctattgt gatctttaaa ataaagaaat gcaaaattca cgtacttgac    3600
tgtagagagt tgttattgaa agaacacaat acaccatttg atccctgttt cctatcttat    3660
ctagtggaaa aagcttttgc tgttattgtt actattttcc ttgtgttata aagttactgc    3720
tatttttcta ccttagtttt ggatgtcagc cccactttgg aattcacgag cttcatgcct    3780
tttttaacca tcattcatgt cttgcagtaa aattgctact tttagagtac aggagtattt    3840
ctagattttc acctctgttg caatatatgt caatgtaatt ataaattgat cacgtgtcag    3900
taccggtgct actattcagc agttacggta gttttttcccc tcaaaagatt ccatgcatgt    3960
acaaaatatg cgtgattgtg aattccagta ctcatacccg tgttgtgttt tttcacccga    4020
gattgatagt gatttatgta tttgggcagc atgttcaccc gtatattact tggctaaaag    4080
aacttgttcg taattcttaa agcaatgaaa tatgaagaaa tcttgtgggt tttactataa    4140
tgtactatag cagtagtgta tagaggaagc cttttgatgt atgtattaaa ttggtagaat    4200
ataaaatatt tgatatgtaa cttgtaatga tgcttaacct gcactgacat gatggtatga    4260
tattgaactt aagctacaag aatttctaag agctacagag aataatttct ttttaaactg    4320
aaagccctgt atcaagcttc catacctcaa attatgagaa cctaagtatc ggtaatattt    4380
atttgtttta taaagatgt agagggtcag gcaagcagaa aagtgtcgct gcagcgatat    4440
cttgaaaagc gaaaggacag gtatctgcag tactaaactg tcatctgttt attgacatca    4500
attacatccc tcgtgttacc acttttttaag ttttaaggaa tgcccgctga attattttat    4560
tactctgcct ttttagggga agatcgaagg gcaagaaact gactggcata acttcatcta    4620
actttgagat gtatttgaac cttccagtga agctccatgc ctcaaatggg aattcaagtc    4680
gtagtagcac tgactctcca ccacagccta gactgcctct agtttccagt ggctcagctg    4740
aaaacctgcc aaaagttacc cttcccattg atttgaatga taaaggtctg ttgcaatctt    4800
ttcttcaact gttaatgcaa ctaaataata acgttcattt tttgctaaca agaaagagac    4860
aataaatctc tcaaagtata ttaattagag gaccttcata ataataaat aaatcagttg    4920 tcctgcttgc tgtattgata tttattgttt agggatactt atagttatct ataccctat    4980 ataaaaagac aatacaagat ttttatatga ctttattttc ttccaatttt acccttttt    5040 agcatatact atctccggtt actgttataa gcaacaaacc acttttaggg ttaattgaat    5100
aattgatgca tcttgtcttt attattgacc agatacataa gttattcaat gaatctaaaa    5160
agtgtttttt tgcttataat agtgaccaga gaaagtaaaa ttaacaaaca aatgaaggaa    5220
gccgttgaca atttgtgcac aattccttgg tttcgatagt agttccattc caaccgtaga    5280
tgaatattag acaataaatg caataaatta gacatactaa acacagtaga aatacagaca    5340
```

```
ggcacgttag tgctgtcttt ctgctagtca atatgaaggt actcattttc ataattgatc   5400
acattataca cccaaaacca tagttgtgaa gttctccatt tgtgacaagc agcaaaggag   5460
gatcttggtt agttgacata taaacctaa gtagcagatt cttactgttt taactagtta   5520
ccagttaaca gcagatgata tttgtgatgg tgatcactaa agtgtaaacc aataattggt   5580
gatacaccag ccttattgct agattattac cagtacactg ttcaatagtt tttgtcatgt   5640
gtttatgtaa tcttgttctc ttgacagatg ttcaagaatg ctaa                    5684

<210> SEQ ID NO 170
<211> LENGTH: 6994
<212> TYPE: DNA
<213> ORGANISM: Medicago sativa

<400> SEQUENCE: 170
atgaacggcg gaagcaccgt ttccttccga tccatcctcg acagacctct taaccaactc     60
actgaagatg acatttctca actcactcgc gaagactgtc gcagattcct caagataaaa    120
ggtaacaact aaccttcttt ttctcttttct tcttcttctt cttctttctc tttcaacatc    180
aaaaaataat aaattaatat tatttttttcg atttatccct ctcatgctcc atggtttccg    240
gctcctgaga caacttcca tttaattttt ctactccaat gcttcatact ttctatattt     300
aatattaatt taatgtaatt aaattaattg ggttgtagat ttttttttat ttaataaaat    360
aattaattaa aaaaatgagt gaagaagacg acacgtgttc gtacagggat gcgcaggcct    420
tcctggaaca aatcacaggc gatccagcag gtgattctctc tcaaagcgct tctagaacct    480
actgacgatg atacaccggc taccgtcggc gttggtgtct cctccgccat tcaccgccat    540
caccaccacc ccctcctca acctccgccg aaggctttgg atcccgaaga tactgctttg    600
gaccttcaga atctacttc acctgtttct gaaagaccca cggaaaccaa tgatgccaac    660
gttgttaacc ctcccgggtc tgttctccat ttttctttca tgttttttta aatgtcgttt    720
aattattttg ttgtgttggc aacttttgtt tgtttgtttg tttgttgtt atcttttgtt    780 tcttgggcta cgaaaccta actccgacac cggaatgata ctgacacagt cacgtcgaca    840
ctaataaaaa aaatgaaatg atgcttgtat ttgatgtttt ctgcgaaaaa aagaagtaaa    900
attctaatgt ttagtgagag tgaagggtgc ttattagatg agttgattat agcataattt    960
ggttgtttga acattaaag ttttgatttt ttttttattt atttgtttag aattaggttg   1020
ggaaattggc acattgtttt atagctttat gtgaagtggg agatgatttt tggcatctga   1080
tgaatgtgtg ttgatatatg aaggtgaat ctgtttgtgg agtggatgga aaatatttag   1140
ggtcagtttg agcttttctt tgtcactggg atgtatgtat tctgtggctt ctttcttcct   1200
gtcattatca aatatctaga tatctgtaac tttaatatca tctatatttt gggtttgcac   1260 tgttttact ttctcatatt taattgttgt ttacggtttt ctcttcatgc cgtgttttag   1320
tgccatcaaa gtactacaa tctcatgttt cattttcaag ttttccattt aattattact   1380
ttagatatca tgtttgaagt gggtgctaga tatcaactga gagaaggaaa accctaaatg   1440 attatttta ggttaagcat gatcattttg tatattaaag gactaagaac aagttagatg   1500
aaaaaatata ccaagcgctg tgttggttta atgtcaatag ctcatgactt caacaatgaa   1560
tatggtagta aattgccagt tttgttaatg tggaatttct ttcagttcca atcggtagta   1620
ataatagtca tctctacctg aaaaaagtgt tgcgttaggg ctgtaattag cctttaacat   1680
ctcttgcttc cattaaacta aaaactgcac taatgccatt ctttgttgga aggagtctgg   1740
```

```
ggtagtggtt aagtgtgcag aactttcagt ttatcatctg ctttcgtatg aagagtgatt    1800
tagttactca aaatgccaaa taatttaaat tcaataaatt tgtgtaaaat atgactgaag    1860
gtagaccaat gttagttttg ttaattatcc attcaagttc ttaacattgg ttgtaaattt    1920
gatgcgagca cagagggtgc acacctagtg ggtcatttgg gcaaatgaca attttctact    1980
gtggtaaggt gaatgtctat gatggagttt cgccggataa ggtgggtaaa gatgtgtcct    2040
cttgcatgaa tatcttgcca tacatcaatt aaatttcacc tcccaataat taaccatact    2100
tgtatttgca ggcacgatca atcatgcagc ttgctgctgc atgtccgtcc tcctttcccc    2160
aggataatcc ttcaaataaa aatgcagcag tttgggcttc tccttgcaac ttacctattg    2220
ataaagaagt cctcttccct actgacacaa caatccttca agtcgctcaa acaggtagtt    2280
agcaattggg tagaaaacat gcttaatttt gctttgaagt gtagtactct agtgtcaaac    2340
aaatcacttt tttcatgcat acttttctgg aacttaaaag aattcgttga tgtatatgat    2400
aaataagcac ttgcagaagg ttgctattca gttattagt gtagcctttt tttttagctt    2460
ggataccatt caatttatta cttgatgctt gacataacag caagttacct ttctgttttt    2520
atcacaagtt cattcttcaa acttaaatcc attgactttg acatagtcac atcaatattt    2580
acaaacaaat gtattaaata tatatgtaat ttagttttga atataataaa tcagaaaaca    2640
tactttcaca gttattatt aagttaaatt atatttttt taaagataaa ttataagtta    2700
aaatgtgaat taaagtgagc ttttgcattt tgatttttt aaatatatta aataagaagt    2760
aaacaactat cacaatccaa tgcttggttt gttggtgacc tagaacacct attttcaata    2820
accacacggg agtaagatcc ctgcattatc aaatttcatt ttttcataaa atacattaaa    2880
ttgttgacca tttctataaa tggtcaagcg tggctcagct ggttttagga aaactgccga    2940
gtcgccggtt tatactgggt tcgtcgaggt cacaccagtt tgatagcttg atagcatggc    3000
cgatctaata tttgactcga accgattatc ccttcggttc aaccggtcca agccggtttt    3060
taaatcactg ggatgtgaag acattgttct gaccaaattc actccgaata ccgattttt    3120
gaattaaaag ctcaacatca atgacttgtt taaaatcatg gcaacatttg taagttagga    3180
actgagattt tgaattatg caaaaatcat tggatataca gacattgttt tgattgttat    3240
gattaaattc actgcaaata ctgatttttt gattgagttc ttcctagaag atgaacatgc    3300
tcaacatctt ttacttgttt aaaatcatgg caatatttac aagttaggaa ctgggatttt    3360
tgaattaaag ttatcgagtc catgcatcta gtaaatgaac aaactcgaca ttttactcg    3420
tttaaaatta tggcatctag tcaggaactg aagattttta acttcataat tggttttaca    3480
gataaaatgg tggaataccc tctgcattac agggagaaag gaagcacaac tcgtgatgct    3540
ggtagggaca attaagtgtt taaacttttg cagtctgctc tagaattta tcttgtgttc    3600
tcttttggca gattttgct ttgaagtgta gtactctagt gtcaaacaaa tcactttttt    3660
catgcatact tttctggaac ttaaaagaat tcgttaatgt atgataagca cttgcagaag    3720
gttactattc tatttttttt tcaaaagttc attcttcaaa tttaaatcca ttgactatga    3780
catagtcaca tcaatattta caaacaaatg tattaaatat atatgtaatt tagttttgaa    3840
tataataaat cagaaacaca tactttcaca gttattgtt aagttaaatt ataatttttt    3900
taaaagataa attataagtt aaaatgtgaa ttaaagtgag cttttgcatt taatttttt    3960
aaatataata aataagaagt gaacaattat cacaatccaa cacatggttt gttggtgacc    4020
tagaacacct attttcaata accacacggg aggtcacgcc agtttgatag tttgatagca    4080
tggccgatct aatatttgac ttgaaccgat tatcccttcg gttcctggtt caaccggtcc    4140
```

```
gagccggttt ttaaatcact gggatgtgaa gacattgttc tgaccaaatt cactccgaat    4200
accgattttt tgaattaaag ctatttagtt cttgtgccta aagatgaac  aagctcaaca    4260 tcaatgactt gtttaaaatc atggtaacat ttgtaagtta ggaactgaga ttttttgaatt   4320 aatgcaaaaa tcattggata tacattgttt tgattgttat gattaaattc actgcgaata   4380
ctgatttttt gaattaaagc tgttgagttc tttctagaag atgaacaagc tcaacagctt   4440
ttacttgttt aaaatcatgg caacatctac aagttaggaa ctgatatttt tgaattaaag   4500
ttattgagtc catgcatctc gtagatgaac aaactcgaca tttttactcg tttaaaatca   4560
tggcatctag tcaggaagtg aagatgttta acttcataat tggtgttcca aatttggttt   4620
tacagataaa atggtggaat accctctgca ttacagggag aaaggaagca cagctcgtga   4680
tgctggtagg gacaattaag tgtttaaact tttgcagtct gctctagaat tttatcttgt   4740
gttctctttt ggcagattta cagataattc caagtagata atttgttgat agactacttg   4800
cagatttaca gatgattcca ttaagcgggc ctttgttttt tttcttggca tcccgagtca   4860
tgctattgtg atctttaaaa taagaaatg  caaaattcac gtacttgact gtagagagtt   4920
gttattgaaa gaacacaata caccatttga tccctgtttc ctatcttatc tagtggaaaa   4980
agcttttgct gttattgtta ctatttttcct tgtgttataa agttactgct attttttctac  5040 cttagttttg gatgtcagcc ccactttgga attcacgagc ttcatgcttt ttttaaccat   5100
catgcatgtc ttccagtaaa attgctacta ttagagtaca tgagtatttc tagatttttca  5160 cctctgttgc aatatatgtc aatgtaatta taaattgatc atgtgtcagt accggtgcta   5220
ctattcagca gttacggtag ttttttccctt caaaagattc catgcatgta caaaatatgc  5280 gttttttgtga attccagtac tcgtacccgt gttgtgtttt ttcacccgag attgatagtg  5340
atttatgtat ttgggcagca tgtgcacccg tatattacct ggctaaaaga acttgtacat   5400
aattcttaaa gcaatgaaat atgaagaaat cttgtgggtt ttactataat gtactatagc   5460
agtagtgtat aagaggaagc cttttgatgt atgtattaaa ttggtagaat ataaaatatt   5520
tgatatgtaa cttgtaatga tgcttaacct gcactgacat gatggtatga tattgaactt   5580
aagctacaag aatttctaag agctacagag ataatttct  ttttaaactg aaagccctgt   5640
atcaagcttc catacctcaa attatgagaa cctaagtatc ggtaatattt atttgtttta   5700 taaagatgt  agagggtcag gcaagcagaa aagtgtcgct gcagcgatat cttgaaaagc   5760
gaaaggacag gtatctgcag tactaaactg tcatctgttt attgacatca attacatccc   5820
tcgtgttacc actttttaag ttttaaggaa tgcccgctga attattttat tactctgcct   5880
ttttagggga agatcgaagg gcaagaaact gactggcata acttcatcta actttgagat   5940
gtatttgaac cttccagtga agctccatgc ctcaaatggg aattcaagtc gtagtagcac   6000
tgactctcca ccacagccta gactgcctct agtttccagt ggctcagctg aaaacctgcc   6060
aaaagttacc cttcccattg atttgaatga taaaggtctg ttgcaatctt ttcttcaact   6120
gttaatgcaa ctaaataata acgttcattt tttgctaaca agaaagagac aataaatctc   6180
tcaaagtata ttaattagag gaccttcata aataataaat aaatcagttg tcctgcttgc   6240
tgtattgata tttattgttt agggatactt atagttatct atacctatat ataaaaagac   6300
aatacaagat ttttatatga ctttattttc ttccaatttt acccttttttt agcatatact   6360 atctccggtt actgttataa gcaacaaacc acttttttagg ttaattgaat aattgatgca   6420
tcttgtcttt attattgacc agatacataa gttattcaat gaatctaaaa agtgtttttt   6480
```

-continued

```
tgcttataat agtgaccaga gaaagtaaaa ttaacaaaca aatgaaggaa gccgttgaca    6540
atttgtgcac aattccttgg tttcgatagt agttccattc caaccgtaga tgaatattag    6600
acaataaatg caataaatta gacatactaa acacagtaga aatacagaca ggcacgttag    6660
tgctgtcttt ctgctagtca atatgaaggt actcattttc ataattgatc acattataca    6720
cccaaaacca tagttgtgaa gttctccatt tgtgacaagc agcaaaggag gatcttggtt    6780
agttgacata tataacctaa gtagcagatt cttactgttt taactagtta ccagttaaca    6840
gcagatgata tttgtgatgg tgatcactaa agtgtaaacc aataattggt gatacaccag    6900
ccttattgct agattattac cagtacactg ttcaatagtt tttgtcatgt gtttatgtaa    6960
tcttgttctc ttgacagatg ttcaagaatg ctaa                                6994
```

<210> SEQ ID NO 171
<211> LENGTH: 330
<212> TYPE: PRT
<213> ORGANISM: Medicago sativa

<400> SEQUENCE: 171

```
Met Asn Gly Gly Ser Thr Val Ser Phe Arg Ser Ile Leu Asp Arg Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Pro Ser Trp Asn
        35                  40                  45

Lys Ser Gln Ala Ile Gln Gln Val Ile Ser Leu Lys Ala Leu Leu Glu
    50                  55                  60

Pro Thr Asp Asp Thr Pro Ala Thr Val Gly Val Gly Val Ser Ser
65                  70                  75                  80

Ala Ile His Arg His His His His Pro Pro Gln Pro Pro Lys
                85                  90                  95

Ala Leu Asp Pro Glu Asp Thr Ala Leu Asp Leu Gln Lys Ser Thr Ser
            100                 105                 110

Pro Val Ser Glu Arg Pro Thr Glu Thr Asn Asp Ala Asn Val Val Asn
        115                 120                 125

Pro Pro Gly Gly Cys Thr Pro Ser Gly Ser Phe Gly Gln Met Thr Ile
    130                 135                 140

Phe Tyr Cys Gly Lys Val Asn Val Tyr Asp Gly Val Ser Pro Asp Lys
145                 150                 155                 160

Ala Arg Ser Ile Met Gln Leu Ala Ala Ala Cys Pro Ser Ser Phe Pro
                165                 170                 175

Gln Asp Asn Pro Ser Asn Lys Asn Ala Ala Val Trp Ala Ser Pro Cys
            180                 185                 190

Asn Leu Pro Ile Asp Lys Glu Val Leu Phe Pro Thr Asp Thr Thr Ile
        195                 200                 205

Leu Gln Val Ala Gln Thr Asp Lys Met Val Glu Tyr Pro Leu His Tyr
    210                 215                 220

Arg Glu Lys Gly Ser Thr Ala Arg Asp Ala Asp Val Glu Gly Gln Ala
225                 230                 235                 240

Ser Arg Lys Val Ser Leu Gln Tyr Leu Glu Lys Lys Asp Arg
                245                 250                 255

Gly Arg Ser Lys Gly Lys Lys Leu Thr Gly Ile Thr Ser Ser Asn Phe
            260                 265                 270

Glu Met Tyr Leu Asn Leu Pro Val Lys Leu His Ala Ser Asn Gly Asn
        275                 280                 285
```

```
Ser Ser Arg Ser Ser Thr Asp Ser Pro Gln Pro Arg Leu Pro Leu
    290                 295                 300

Val Ser Ser Gly Ser Ala Glu Asn Leu Pro Lys Val Thr Leu Pro Ile
305                 310                 315                 320

Asp Leu Asn Asp Lys Asp Val Gln Glu Cys
                325                 330

<210> SEQ ID NO 172
<211> LENGTH: 330
<212> TYPE: PRT
<213> ORGANISM: Medicago sativa

<400> SEQUENCE: 172

Met Asn Gly Gly Ser Thr Val Ser Phe Arg Ser Ile Leu Asp Arg Pro
1               5                   10                  15

Leu Asn Gln Leu Thr Glu Asp Asp Ile Ser Gln Leu Thr Arg Glu Asp
                20                  25                  30

Cys Arg Arg Phe Leu Lys Asp Lys Gly Met Arg Arg Pro Ser Trp Asn
            35                  40                  45

Lys Ser Gln Ala Ile Gln Gln Val Ile Ser Leu Lys Ala Leu Leu Glu
50                  55                  60

Pro Thr Asp Asp Thr Pro Ala Thr Val Gly Val Gly Val Ser Ser
65                  70                  75                  80

Ala Ile His Arg His His His His Pro Gln Pro Pro Pro Lys
                85                  90                  95

Ala Leu Asp Pro Glu Asp Thr Ala Leu Asp Leu Gln Lys Ser Thr Ser
            100                 105                 110

Pro Val Ser Glu Arg Pro Thr Glu Thr Asn Asp Ala Asn Val Val Asn
            115                 120                 125

Pro Pro Gly Gly Cys Thr Pro Ser Gly Ser Phe Gly Gln Met Thr Ile
130                 135                 140

Phe Tyr Cys Gly Lys Val Asn Val Tyr Asp Gly Val Ser Pro Asp Lys
145                 150                 155                 160

Ala Arg Ser Ile Met Gln Leu Ala Ala Ala Cys Pro Ser Ser Phe Pro
                165                 170                 175

Gln Asp Asn Pro Ser Asn Lys Asn Ala Ala Val Trp Ala Ser Pro Cys
            180                 185                 190

Asn Leu Pro Ile Asp Lys Glu Val Leu Phe Pro Thr Asp Thr Thr Ile
            195                 200                 205

Leu Gln Val Ala Gln Thr Asp Lys Met Val Glu Tyr Pro Leu His Tyr
210                 215                 220

Arg Glu Lys Gly Ser Thr Ala Arg Asp Ala Asp Val Glu Gly Gln Ala
225                 230                 235                 240

Ser Arg Lys Val Ser Leu Gln Arg Tyr Leu Glu Lys Arg Lys Asp Arg
                245                 250                 255

Gly Arg Ser Lys Gly Lys Leu Thr Gly Ile Thr Ser Ser Asn Phe
            260                 265                 270

Glu Met Tyr Leu Asn Leu Pro Val Lys Leu His Ala Ser Asn Gly Asn
            275                 280                 285

Ser Ser Arg Ser Ser Thr Asp Ser Pro Pro Gln Pro Arg Leu Pro Leu
            290                 295                 300

Val Ser Ser Gly Ser Ala Glu Asn Leu Pro Lys Val Thr Leu Pro Ile
305                 310                 315                 320

Asp Leu Asn Asp Lys Asp Val Gln Glu Cys
                325                 330
```

```
                    325                 330

<210> SEQ ID NO 173
<211> LENGTH: 271
<212> TYPE: PRT
<213> ORGANISM: Lotus japonicus

<400> SEQUENCE: 173

Met Asn Gly Gly Thr Thr Thr Thr Thr Ala Thr Phe Arg Ser
1               5                  10                  15

Ile Leu Asp Lys Pro Leu Lys His Leu Thr Glu Asp Ile Ser Gln
            20                  25                  30

Leu Thr Arg Glu Asp Cys Arg Arg Phe Leu Lys Glu Lys Gly Met Arg
        35                  40                  45

Arg Pro Ser Trp Asn Lys Ser Gln Ala Ile Gln Gln Val Ile Ser Leu
    50                  55                  60

Lys Ala Leu Leu Glu Pro Thr Asp Glu Asp Ser Pro Ala Ala Val His
65                  70                  75                  80

Arg His Tyr His His His Gln Gln Pro Pro His Ala Ser Ser Arg Gly
                85                  90                  95

Arg Asn Leu Asn Glu Ala Pro Ala Thr Ala Pro Val Ala Glu Glu Ala
            100                 105                 110

Gly Phe Gln Ala Ala Ala Glu Glu Pro Gln Lys Ser Pro Ser Ala Glu
        115                 120                 125

Lys Leu Pro Glu Thr Asn Asp Ala Asn Val Val Ser Pro Arg Gly Cys
130                 135                 140

Ala Ser Ser Gly Ser Phe Gly Gln Met Thr Ile Phe Tyr Cys Gly Lys
145                 150                 155                 160

Val Asn Val Tyr Asp Gly Val Ser Pro Asp Lys Ala Arg Ser Ile Met
                165                 170                 175

Gln Leu Ala Ala Ser Pro Val Gln Cys Pro Gln Asp Asp Pro Ser Asn
            180                 185                 190

Lys Asn Ala Ala Val Trp Ala Ser Thr Cys Pro Ser Leu Met Asp Lys
        195                 200                 205

Asp Ala Leu Phe Pro Val Asp Thr Ala Ile Leu Gln Val Ala Gln Thr
    210                 215                 220

Asp Lys Met Val Glu Tyr Pro Leu Gln Tyr Arg Glu Lys Val Ser Ile
225                 230                 235                 240

Pro Arg Asp Ala Asp Val Glu Gly Gln Ala Ser Arg Lys Val Ser Val
                245                 250                 255

Gln Arg Tyr Leu Glu Lys Arg Lys Asp Arg Gly Arg Leu Lys Gly
            260                 265                 270

<210> SEQ ID NO 174
<211> LENGTH: 27
<212> TYPE: RNA
<213> ORGANISM: Artificial sequence
<220> FEATURE:
<223> OTHER INFORMATION: mRNA fragment

<400> SEQUENCE: 174
gaaaaguguc auugcaacga uaucuug                                         27

<210> SEQ ID NO 175
<211> LENGTH: 21
<212> TYPE: RNA
<213> ORGANISM: Artificial sequence
<220> FEATURE:
```

```
<223> OTHER INFORMATION: mRNA fragment

<400> SEQUENCE: 175
uucacaguaa cguugcuaua u                                              21

<210> SEQ ID NO 176
<211> LENGTH: 27
<212> TYPE: RNA
<213> ORGANISM: Artificial sequence
<220> FEATURE:
<223> OTHER INFORMATION: mRNA fragment

<400> SEQUENCE: 176
gaaaaguguc auugcagcga uaucuug                                        27

<210> SEQ ID NO 177
<211> LENGTH: 21
<212> TYPE: RNA
<213> ORGANISM: Artificial sequence
<220> FEATURE:
<223> OTHER INFORMATION: mRNA fragment

<400> SEQUENCE: 177
uucacaguaa cguugcuaua u                                              21
```